(12) United States Patent (10) Patent No.: US 8,697,396 B2
Dall'Acqua et al. (45) Date of Patent: Apr. 15, 2014

(54) MODULATION OF ANTIBODY EFFECTOR FUNCTION BY HINGE DOMAIN ENGINEERING

(75) Inventors: William Dall'Acqua, Gaithersburg, MD (US); Herren Wu, Boyds, MD (US); Melissa Damschroder, Germantown, MD (US); Jose Casas-Finet, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 202 days.

(21) Appl. No.: 13/190,199

(22) Filed: Jul. 25, 2011

(65) Prior Publication Data

US 2012/0046450 A1    Feb. 23, 2012

Related U.S. Application Data

(62) Division of application No. 11/912,562, filed as application No. PCT/US2006/015393 on Apr. 25, 2006, now Pat. No. 8,008,443.

(60) Provisional application No. 60/674,674, filed on Apr. 26, 2005, provisional application No. 60/713,711, filed on Sep. 6, 2005, provisional application No. 60/735,169, filed on Nov. 10, 2005.

(51) Int. Cl.
*C12P 21/04* (2006.01)
*C12N 15/00* (2006.01)
*C07K 16/00* (2006.01)

(52) U.S. Cl.
USPC .......................................... 435/69.6; 435/440

(58) Field of Classification Search
None
See application file for complete search history.

(56) References Cited

U.S. PATENT DOCUMENTS

| | | | |
|---|---|---|---|
| 5,624,821 A | 4/1997 | Winter et al. | |
| 5,677,425 A | 10/1997 | Bodmer et al. | |
| 5,869,046 A | 2/1999 | Presta et al. | |
| 5,885,573 A | 3/1999 | Bluestone et al. | |
| 6,165,745 A | 12/2000 | Ward et al. | |
| 6,194,551 B1 | 2/2001 | Idusogie et al. | |
| 6,277,375 B1 | 8/2001 | Ward et al. | |
| 6,737,056 B1 | 5/2004 | Presta et al. | |
| 7,276,585 B2 * | 10/2007 | Lazar et al. | 530/387.1 |
| 7,659,374 B2 | 2/2010 | Wu et al. | |
| 8,008,443 B2 * | 8/2011 | Dall'Acqua et al. | 530/387.1 |
| 2001/0036459 A1 | 11/2001 | Ravetch | |
| 2002/0147311 A1 | 10/2002 | Gilles et al. | |
| 2003/0157108 A1 | 8/2003 | Presta | |
| 2003/0190311 A1 | 10/2003 | Dall'Acqua et al. | |
| 2004/0002587 A1 | 1/2004 | Watkins et al. | |
| 2004/0121415 A1 | 6/2004 | King et al. | |
| 2004/0132101 A1 | 7/2004 | Lazar et al. | |
| 2005/0032114 A1 | 2/2005 | Hinton | |
| 2005/0037000 A1 | 2/2005 | Stavenhagen | |
| 2005/0054832 A1 | 3/2005 | Lazar et al. | |
| 2005/0064514 A1 | 3/2005 | Stavenhagen | |
| 2005/0215768 A1 | 9/2005 | Armour | |
| 2005/0244403 A1 | 11/2005 | Lazar et al. | |
| 2006/0275283 A1 | 12/2006 | van Vlijmen et al. | |
| 2007/0148164 A1 | 6/2007 | Farrington et al. | |
| 2007/0275460 A1 | 11/2007 | Desjarlais et al. | |
| 2009/0053240 A1 | 2/2009 | Lazar et al. | |

FOREIGN PATENT DOCUMENTS

| | | |
|---|---|---|
| WO | WO-91-01335 | 2/1991 |
| WO | WO-94-29351 | 12/1994 |
| WO | WO-98-05787 | 2/1998 |
| WO | WO-98-23289 | 6/1998 |
| WO | WO-99-15549 | 4/1999 |
| WO | WO-99-58572 | 11/1999 |
| WO | WO-03-074679 | 9/2003 |
| WO | WO-2004-099249 | 11/2004 |
| WO | WO-2005-000899 | 1/2005 |
| WO | WO 2005-047327 | 5/2005 |
| WO | WO-2005-070963 | 8/2005 |
| WO | WO-2005-092925 | 10/2005 |
| WO | WO-2006-076594 | 7/2006 |
| WO | WO-2006-116260 A3 | 11/2006 |

OTHER PUBLICATIONS

Alegre, M. L., et al. "A Non-Activating "Humanized" Anti-CD3 Monoclonal Antibody Retains Immunosuppressive Properties in Vivo." *Transplantation* (1994) 57: 1537-43.
Armour, K. L., et al. "Recombinant Human IgG Molecules Lacking Fcgamma Receptor I Binding and Monocyte Triggering Activities." *Eur.J.Immunol.* (1999) 29: 2613-24.
Bastida-Corcuera et al., "Differential complement activation by bovine IgG2 allotypes." *Vet Immunol Immunopathol* (1999) 71:115-123.
Brekke et al., "Activation of complement by an IgG molecule without a genetic hinge." *Nature* (1993) 363:628-30.
Brekke et al., "The structural requirements for complement activation by IgG: does it hinge on the hinge?" *Immunol. Today* (1995) 16:85-90.
Bruggemann, M., et al. "Comparison of the Effector Functions of Human Immunoglobulins using a Matched Set of Chimeric Antibodies." *J.Exp.Med.* (1987) 166: 1351-61.
Clynes, R., et al. "Fc Receptors are Required in Passive and Active Immunity to Melanoma." *Proc.Natl.Acad.Sci.U.S.A.* (1998) 95: 652-6.

(Continued)

*Primary Examiner* — Chun Dahle

(57) ABSTRACT

The present invention relates to novel molecules (Fc variants) comprising at least one antigen binding region and an Fc region that further comprises a modified hinge which alters the binding of Fc to one or more Fc ligand (e.g., FcγRs) and/or modulates effector function. More specifically, this invention provides Fc variants that have modified binding affinity to one or more FcγR and/or C1q. Additionally, the Fc variants have altered antibody-dependent cell-mediated cytotoxicity (ADCC) and/or complement dependent cytotoxicity (CDC) activity. The invention further provides methods and protocols for the application of said Fc variants particularly for therapeutic purposes.

10 Claims, 31 Drawing Sheets

(56) References Cited

OTHER PUBLICATIONS

Coloma et al., "The Hinge as a Is Required for Spacer Contributes Function of IgG" *J. Immunol.* (1997)158:733-40.

Dall'Acqua, W. F., et al. "Modulation of the Effector Functions of a Human IgG1 through Engineering of its Hinge Region." *J.Immunol.* (2006) 177: 1129-38.

Dangl et al., "Segmental flexibility and complement fixation of genetically engineered chimeric human, rabbit and mouse antibodies."*EMBO* (1988) 71989-94.

Duncan, A. R., et al. "Localization of the Binding Site for the Human High-Affinity Fc Receptor on IgG." *Nature* (1988) 332: 563-4.

Ghetie, V., et al. "Increasing the Serum Persistence of an IgG Fragment by Random Mutagenesis." *Nat.Biotechnol.* (1997) 15: 637-40.

Gillies and Wesolowsi, "Antigen binding and biological activities of engineered mutant chimeric antibodies with human tumor speciicities." *Hum. Antibod. Hybridomas* (1990) 1: 47-54.

Hutchins, J. T., et al. "Improved Biodistribution, Tumor Targeting, and Reduced Immunogenicity in Mice with a Gamma 4 Variant of Campath-1H." *Proc.Natl.Acad.Sci.U.S.A.* (1995) 92: 11980-4.

Idusogie, E. E., et al. "Engineered Antibodies with Increased Activity to Recruit Complement." *J.Immunol.* (2001) 166: 2571-5.

Idusogie, E. E., et al. "Mapping of the C1q Binding Site on Rituxan, a Chimeric Antibody with a Human IgG1 Fc." *J.Immunol.* (2000) 164: 4178-84.

Jefferis, R., et al. "Interaction Sites on Human IgG—Fc for FcgammaR: Current Models." *Immunol.Lett.* (2002) 82: 57-65.

Jefferis, R., et al. "Modulation of Fc(Gamma)R and Human Complement Activation by IgG3-Core Oligosaccharide Interactions." *Immunol.Lett.* (1996) 54: 101-4.

Jefferis, R., et al. "Recognition Sites on Human IgG for Fc Gamma Receptors: The Role of Glycosylation." *Immunol.Lett.* (1995) 44: 111-7.

Klein et al., "Expression of biological effector functions by immunoglobulin G molecules lacking the hinge region." *Proc Natl Acad Sci USA* (1981) 78: 524-8.

Lund, J., et al. "Multiple Interactions of IgG with its Core Oligosaccharide can Modulate Recognition by Complement and Human Fc Gamma Receptor I and Influence the Synthesis of its Oligosaccharide Chains." *J.Immunol.* (1996) 157: 4963-9.

Lund, J., et al. "Oligosaccharide-Protein Interactions in IgG can Modulate Recognition by Fc Gamma Receptors." *FASEB J.* (1995) 9: 115-9.

Lund, J., et al. "Multiple Binding Sites on the CH2 Domain of IgG for Mouse Fc Gamma R11." *Mol.Immunol.* (1992) 29: 53-9.

Lund, J., et al. "Human Fc Gamma RI and Fc Gamma RII Interact with Distinct but Overlapping Sites on Human IgG." *J.Immunol.* (1991) 147: 2657-62.

Oi, T., et al. "Correlation between segmental flexibility and effector function of antibodies." *Nature* (1984) 307: 136-40.

Patel, A. K., et al. "An Improved Assay for Antibody Dependent Cellular Cytotoxicity Based on Time Resolved Fluorometry." *J.Immunol.Methods* (1995) 184: 29-38.

Presta, L. G., et al. "Engineering Therapeutic Antibodies for Improved Function." *Biochem.Soc.Trans.* (2002) 30: 487-90.

Radaev, S., et al. "Recognition of immunoglobulins by Fcγ receptors." Mol. Immunol. (2001) 38:1073-83.

Reddy, M. P., et al. "Elimination of Fc Receptor-Dependent Effector Functions of a Modified IgG4 Monoclonal Antibody to Human CD4." *J.Immunol.* (2000) 164: 1925-33.

Redpath, S., et al. "Activation of complement by human IgG1 and IgG3 antibodies against the human leucocyte antigen CD52." Immunology (1998) 93:595-600.

Redpath, S., et al. "The Influence of the Hinge Region Length in Binding of Human IgG to Human Fcγ Receptors." Human Immunol. (1998) 59:720-27.

Shields, R. L., et al. "Lack of Fucose on Human IgG1 N-Linked Oligosaccharide Improves Binding to Human Fcgamma RIII and Antibody-Dependent Cellular Toxicity." *J.Biol.Chem.* (2002) 277: 26733-40.

Shields, R. L., et al. "High Resolution Mapping of the Binding Site on Human IgG1 for Fc Gamma RI, Fc Gamma RII, Fc Gamma RIII, and FcRn and Design of IgG1 Variants with Improved Binding to the Fc Gamma R." *J.Biol.Chem.* (2001) 276: 6591-604.

Shopes, B., "A Genetically engineered human IgG with limited flexibility full initiates cytolysis via complement." *Mol. Immunol.* (1993) 30: 603-09.

Stevenson G., et al. "Conjugation of Human Fcγ in Closed-Hinge or Open Hinge Configuration to Fab' γ and Analogous Ligands." *J. Immunol.* (1997) 158:2242-50.

Tan, L., et al. "Influence of the hinge region on complement activation, C1q binding, and segmental flexibility in chimeric human immunoglobulins." *Proc.Natl.Acad.Sci.U.S.A.* (1990) 87:162-66.

Wilkinson, R. W., et al. "Antibody-Dependent Cell-Mediated Cytotoxicity: A Flow Cytometry-Based Assay using Fluorophores." *J.Immunol.Methods* (2001) 258: 183-91.

Wisecarver, J., et al. "A Method for Determination of Antibody-Dependent Cellular Cytotoxicity (ADCC) of Human Peripheral Mononuclear Cells." *J.Immunol.Methods* (1985) 79:277-82.

Xu, D., et al. "In Vitro Characterization of Five Humanized OKT3 Effector Function Variant Antibodies." *Cell.Immunol.* (2000) 200: 16-26.

MedImmune Inc. "International Preliminary Report on Patentability and Written Opinion of the International Searching Authority for PCT/US2006/015393.": 1-5, Nov., 2, 2006.

MedImmune, Inc. "Supplementary European Search Report for EP 06 75 1192" 1-11, Jul. 22, 2010.

* cited by examiner

V_L Sequence:

DIQMTQSPSSLSASVGDRVTITC RASQSISNNLH WYQQKPGKAPKLLIK YAFQSIS GVPSRFSGSGSGTDFTFTISSLQPEDFATYYC QQANSWPLI FGGGTKVEIK (SEQ ID NO: 1)

V_H Sequence:

QMQLVQSGPEVKKPGTSVKVSCKASGFTFL DYSMN WVRQARGQRLEWIG FIRNKANDYTTEYADSVKG RVTITRDMSTSTAYMELSSLRSE DTAVYYCAR YPRHHAMDS WGQGTSVTVSS (SEQ ID NO: 2)

Boxed: CDRs (Kabat definition).

Fig. 1

MODULATION OF ANTIBODY EFFECTOR FUNCTION BY HINGE DOMAIN ENGINEERING

1. CROSS REFERENCE TO RELATED APPLICATIONS

This application is a divisional and claims benefit under 35 U.S.C. §120 of U.S. National Phase application Ser. No. 11/912,562 filed on Apr. 24, 2008 (now U.S. Pat. No. 8,008,443), said application Ser. No. 11/912,562 claims benefit under 35 U.S.C. §365(c) of International Application No. PCT/US2006/015393, filed Apr. 25, 2006, said International Application No. PCT/US2006/015393 claims benefit under 35 U.S.C. §119(c) of the following U.S. Provisional Application Nos. 60/674,674, filed on Apr. 26, 2005, 60/713,711, filed on Sep. 6, 2005 and 60/735,169, filed on Nov. 10, 2005. Each of the above listed applications is incorporated by reference herein in its entirety for all purposes.

2. REFERENCE TO THE SEQUENCE LISTING

This application incorporates by reference a Sequence Listing submitted with this application as text file entitled AE705_PCTseqST25.txt created on Apr. 24, 2006 and having a size of 32 kilobytes.

3. FIELD OF THE INVENTION

The present invention provides molecules, in particular polypeptides, more specifically binding proteins including but not limited to immunoglobulins (e.g., antibodies) comprising an Fc region that further comprises a modified hinge which alters the binding of the Fc region to one or more Fc ligand (e.g., FcγRs) and/or modulates Fc mediated effector function. The present invention also relates to novel fusion polypeptides comprising a binding domain, or fragments thereof, which specifically bind a molecule (e.g., antigen) and an Fc region that further comprises a modified hinge. Collectively, molecules incorporating Fc regions comprising or incorporating a modified hinge are referred to herein as "Fc variants of the invention" or "Fc variants." In one embodiment, the Fc variants of the invention have altered binding affinity to one or more Fc ligands (e.g., FcγRs). In another embodiment the Fc variants of the invention have altered effector function. In one embodiment, the Fc variants of the invention have enhanced binding to FcγRIIIA and increased ability to mediate antibody dependent cell-mediated cytotoxicity (ADCC). In another embodiment, the Fc variants have reduced binding to FcγRIIIA and decreased ability to mediate ADCC (referred to herein as "ADCC activity"). In still another embodiment, the Fc variants have enhanced binding to C1q and increased complement dependent cytotoxicity (CDC). In yet another embodiment, the Fc variants have reduced binding to C1q and decreased CDC activity. In addition, the present invention provides methods and protocols for the application or use of Fc variants, particularly for therapeutic purposes. Specifically, the methods and protocols involve the administration of a prophylactically or therapeutically effective amount of one or more Fc variants alone or in combination with the administration of one or more other therapies useful for the treatment, prevention, and amelioration of one or more symptoms associated with a disease, disorder or infection, including but not limited to cancer, inflammatory and autoimmune diseases. The Fc variants utilized for therapeutic purposes may or may not be conjugated or fused to a moiety (e.g., a therapeutic agent or drug). The invention also provides methods for generating Fc variant fusion proteins that comprise a polypeptide fused to an Fc variant. Further, the invention provides pharmaceutical compositions and kits for use in preventing, managing, treating or ameliorating diseases and disorders.

4. BACKGROUND OF THE INVENTION

Antibodies are immunological proteins that bind a specific antigen. In most mammals, including humans and mice, antibodies are constructed from paired heavy and light polypeptide chains. Each chain is made up of two distinct regions, referred to as the variable (Fv) and constant (Fc) regions. The light and heavy chain Fv regions contain the antigen binding determinants of the molecule and are responsible for binding the target antigen. The Fc regions define the class (or isotype) of antibody (IgG for example) and are responsible for binding a number of natural proteins to elicit important biochemical events. The constant region of the heavy chain may be further divided into four smaller domains called: CH1, hinge, CH2 and CH3. A portion of the constant region, the Fc region, is involved in a number of important cellular functions. Generally the Fc region is defined as only comprising CH2 and CH3 and may encompass a portion of the hinge. Given the critical role that the hinge region plays in these cellular functions it will be clear that as used herein, "Fc region" includes the hinge region or portions thereof.

The Fc region of an antibody interacts with a number of Fc receptors and other Fc ligands, imparting an array of important functional capabilities referred to as effector functions. An important family of Fc receptors for the IgG class are the Fc gamma receptors (FcγRs). These receptors mediate communication between antibodies and the cellular arm of the immune system (Raghavan et al., 1996, *Annu Rev Cell Dev Biol* 12:181-220; Ravetch et al., 2001, *Annu Rev Immunol* 19:275-290). In humans this protein family includes FcγRI (CID64), including isoforms FcγRIA, FcγRIB, and FcγRIC; FcγRII (CD32), including isoforms FcγRIIA, FcγRIIB, and FcγRIIC; and FcγRIII (CID16), including isoforms FcγRIIIA and FcγRIIIB (Jefferis et al., 2002, *Immunol Lett* 82:57-65). These receptors typically have an extracellular domain that mediates binding to Fc, a membrane spanning region, and an intracellular domain that may mediate some signaling event within the cell. These different FcγR subtypes are expressed on different cell types (reviewed in Ravetch et al., 1991, *Annu Rev Immunol* 9:457-492). For example, in humans, FcγRIIIB is found only on neutrophils, whereas FcγRIIIA is found on macrophages, monocytes, natural killer (NK) cells, and a subpopulation of T-cells.

Formation of the Fc/FcγR complex recruits effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, *Annu Rev Cell Dev Biol* 12:181-220; Ghetie et al., 2000, *Annu Rev Immunol* 18:739-766; Ravetch et al., 2001, *Annu Rev Immunol* 19:275-290). Notably, the primary cells for mediating ADCC, NK cells, express only FcγRIIIA only, whereas monocytes express FcγRI, FcγRII and FcγRIII (Ravetch et al., 1991, supra). Table 1 summarizes several features of the Fc Receptors.

TABLE 1

Fc Receptor Characteristics

| Receptor | FcγRI (CD64) | FcγRII-A (CD32) | FcγRII-B2 (CD32) | FcγRII-B1 (CD32) | FcγRIII (CD16) | FcεRI | FcαRI (CD89) |
|---|---|---|---|---|---|---|---|
| Binding | IgG1 $10^8 M^{-1}$ | IgG1 $2 \times 10^6 M^{-1}$ | IgG1 $2 \times 10^6 M^{-1}$ | IgG1 $2 \times 10^6 M^{-1}$ | IgG1 $5 \times 10^5 M^{-1}$ | IgE $10^{10} M^{-1}$ | IgA1, IgA2 $10^7 M^{-1}$ |
| Cell Type | Macrophage Neutrophil Eosinophil Dendritic cell | Macrophage Neutrophil Eosinophil Dendritic cell Platelet Langerhan cell | Macrophage Neutrophils Eosinophils | B cell Mast cell | NK cell Eosinophil Macrophage Neutrophil Mast cell | Mast cell Eosinophil Basophil | Macrophage Neutrophil Eosinophil |
| Effect of Ligation | Uptake Stimulation Activation of respiratory burst Induction of killing | Uptake Granule release | Uptake Inhibition of Stimulation | No uptake Inhibition of Stimulation | Induction of Killing | Secretion of granules | Uptake Induction of killing |

Another important Fc ligand is the complement protein C1q. Fc binding to C1q mediates a process called complement dependent cytotoxicity (CDC) (reviewed in Ward et al., 1995, *Ther Immunol* 2:77-94). C1q is capable of binding six antibodies, although binding to two IgGs is sufficient to activate the complement cascade. C1q forms a complex with the C1r and C1s serine proteases to form the C1 complex of the complement pathway.

Several key features of antibodies including but not limited to, specificity for target, ability to mediate immune effector mechanisms, and long half-life in serum, make antibodies and related immunoglobulin molecules powerful therapeutics. Numerous monoclonal antibodies are currently in development or are being used therapeutically for the treatment of a variety of conditions including cancer. For example Vitaxin® (MedImmune), a humanized Integrin α$_v$β$_3$ antibody (e.g., PCT publication WO 2003/075957), Herceptin® (Genentech), a humanized anti-Her2/neu antibody approved to treat breast cancer (e.g., U.S. Pat. No. 5,677,171), CNTO 95 (Centocor), a human Integrin α$_v$ antibody (PCT publication WO 02/12501), Rituxan® (IDEC/Genentech/Roche), a chimeric anti-CD20 antibody approved to treat Non-Hodgkin's lymphoma (e.g., U.S. Pat. No. 5,736,137) and Erbitux® (ImClone), a chimeric anti-EGFR antibody (e.g., U.S. Pat. No. 4,943,533).

There are a number of possible mechanisms by which antibodies destroy tumor cells, including anti-proliferation via blockage of needed growth pathways, intracellular signaling leading to apoptosis, enhanced down regulation and/or turnover of receptors, ADCC, CDC, and promotion of an adaptive immune response (Cragg et al., 1999, *Curr Opin Immunol* 11:541-547; Glennie et al., 2000, *Immunol Today* 21:403-410). However, despite widespread use, antibodies are not optimized for clinic use and many have suboptimal anticancer potency. Thus, there is a significant need to enhance the capacity of antibodies to destroy targeted cancer cells. Methods for enhancing the anti-tumor-potency of antibodies via enhancement of their ability to mediate cytotoxic effector functions such as ADCC and CDC are particularly promising. The importance of FcγR-mediated effector functions for the anti-cancer activity of antibodies has been demonstrated in mice (Clynes et al., 1998, *Proc Natl Acad Sci USA* 95:652-656; Clynes et al., 2000, *Nat Med* 6:443-446), and the affinity of the interaction between Fc and certain FcγRs correlates with targeted cytotoxicity in cell-based assays (Shields et al., 2001, *J Biol Chem* 276:6591-6604; Presta et al., 2002, *Biochem Soc Trans* 30:487-490; Shields et al., 2002, *J Biol Chem* 277:26733-26740). Together these data suggest that manipulating the binding ability of the Fc region of an IgG1 antibody to certain FcγRs may enhance effector functions resulting in more effective destruction of cancer cells in patients. Furthermore, because FcγRs can mediate antigen uptake and processing by antigen presenting cells, enhanced Fc/FcγR affinity may also improve the capacity of antibody therapeutics to elicit an adaptive immune response.

While enhancing effector function can increase the capacity of antibodies to destroy target cells, for some antibody therapies reduced or eliminated effector function may be more desirable. This is particularly true for those antibodies designed to deliver a drug (e.g., toxins and isotopes) to the target cell where the Fc/FcγR mediated effector functions bring healthy immune cells into the proximity of the deadly payload, resulting in depletion of normal lymphoid tissue along with the target cells (Hutchins et al., 1995, *PNAS USA* 92:11980-11984; White et al., 2001, *Annu Rev Med* 52:125-145). In these cases the use of Fc variants that poorly recruit complement or effector cells would be of tremendous benefit (see for example, Wu et al., 2000, *Cell Immunol* 200:16-26; Shields et al., 2001, *J. Biol Chem* 276:6591-6604; U.S. Pat. No. 6,194,551; U.S. Pat. No. 5,885,573 and PCT publication WO 04/029207).

All FcγRs bind the Fc region of the IgG subclass, but with different affinities (e.g., FcγRI is a high affinity while FcγRII and FcγRIII are low affinity binders. Other differences between the FcγRs are mechanistic. For example, FcγRI, FcγRIIA/C, and FcγRIIIA are positive regulators of immune complex triggered activation, characterized by having an immunoreceptor tyrosine-based activation motif (ITAM) while FcγRIIB has an immunoreceptor tyrosine-based inhibition motif (ITIM) and is therefore inhibitory. Thus, the balance between activating and inhibiting receptors is an important consideration. For example, enhancing Fc binding to the positive regulators (e.g., FcγRIIIA) while leaving unchanged or even reducing Fc binding to the negative regulator FcγRIIB could result in optimized effector function such as enhanced ADCC mediated destruction of tumor cells. Another critical consideration is that Fc variants should be engineered such that the binding to FcγRs and/or C1q is modulated in the desired manner but so that they maintain their stability, solubility, structural integrity as well as their ability to interact with other important Fc ligands such as FcRn and staphylococcal protein A, streptococcal protein G.

Antibodies of the IgG isotype are exceptionally flexible molecules. The structure primarily responsible for the internal flexibility of IgG molecules is located between the first (CH1) and second (CH2) domains of the constant region, and is termed the hinge. The hinge can be divided into three peptide regions; upper, middle and lower hinge respectively Brekke et al., 1995, *Immunol Today* 16: 85-90. Several studies indicate that the hinge region is essential for activation of the complement cascade by IgGs (Klein et al., 1981 *Proc Natl Acad Sci USA* 78: 524-8; Mechaelsen et al., 1990, *Scand J Immunol.* 32: 517-28). In other studies one group has demonstrated that the lower hinge region is also involved in contact with FcγRs (Radaev and Sun, 2001, *Immunology* 38:1073-1083). Likewise, the nature of the hinge region also influences binding to FcγRs as well as ADCC activity (Redpath et al., 1998, *Human Immunology;* 59: 720-7; Gillies and Wesolowsi, 1990, *Hum. Antibod. Hybridomas* 1: 47-54).

Numerous mutagenesis studies have been carried out on the hinge domain however there is little consensus as to how alterations of the hinge region affect function. For example, some studies indicate that, generally speaking, reducing the hinge flexibility or length results in a decrease in complement fixation/activation (Oi et al., 1984, *Nature* 307:136-40; Dangl et al., 1988, *EMBO* 71989-94). Conversely, other studies suggest that a reduction in hinge flexibility or length directly correlates with an increase in complement activation (Brekke et al., 1993, *Nature* 363:628-30; Bastida-Corcuera et al., 1999, *Vet Immunol Immunopathol* 71:115-123; Redpath et al., 1998, *Human Immunol.* 59:720-7; Sandlie et al., 1989, *Eur J Immunol* 19:1599-603; Michaelsen et al., 1994, U.S. Pat. No. 5,348,876; Norderhaug et al., 1991, *Eur J Immunol* 21:2379-3284) whereas a third set of studies indicates the lack of such a simple correlation (Shopes et al., 1993, *Mol. Immunol.* 30:603-9; Brekke et al., 1993, *Nature* 363:628-30; Brekke et al., 1995, *Immunol. Today* 16:85-90; Tan et al., 1990, *PNAS USA* 87:162-166; Tan et al., 1991, *PNAS USA* 88:5066; Coloma et al., 1997, *J. Immunol.* 158:733-40). One set of studies suggest that the "openness" status of the hinge region may play a role (Schauenstein et al., 1986, *Int Arch Allergy Appl Immunol* 80:174-9; Schauenstein et al., 1996, *Biochem Mol Biol Int* 40:433-446; Stevenson et al., 1997, *J Immunol* 158:2242-50). Although many of the previous studies appear to give contradictory interpretations of the relationship between the structure and function of the hinge, it is important to recognize that many of the previous studies were performed using disparate techniques and in many cases on molecules of different IgG subtypes. Thus, interpretation and extrapolation of previous studies is difficult. Given the importance of the hinge region in mediating antibody function the ability to specifically modify the hinge in order to modulate Fc function would be a useful tool in developing therapeutics for the treatment and prevention of numerous diseases and disorders. The present invention provides a detailed analysis of the hinge region and the identification of specific classes of modifications useful for the modulation of Fc ligand binding and effector function.

4.1 Diseases of Relevance

Several key features of antibodies including but not limited to, specificity for target, ability to mediate immune effector mechanisms, and long half-life in serum, make antibodies powerful therapeutics. Numerous monoclonal antibodies are currently in development or are being used therapeutically for the treatment of a variety of conditions including cancer. The ability to modulate the effector binding and function of any particular antibody would be of tremendous benefit in adapting an antibody for the treatment of a disease or disorder. Diseases for which antibody therapeutics are particularly well suited are described below.

4.1.1 Cancer

A neoplasm, or tumor, is a neoplastic mass resulting from abnormal uncontrolled cell growth, which can be benign or malignant. Benign tumors generally remain localized. Malignant tumors are collectively termed cancers. The term "malignant" generally means that the tumor can invade and destroy neighboring body structures and spread to distant sites to cause death (for review, see Robbins and Angell, 1976, *Basic Pathology,* 2d Ed., W.B. Saunders Co., Philadelphia, pp. 68-122). Cancer can arise in many sites of the body and behave differently depending upon its origin. Cancerous cells destroy the part of the body in which they originate and then spread to other part(s) of the body where they start new growth and cause more destruction.

More than 1.2 million Americans develop cancer each year. Cancer is the second leading case of death in the United States and if current trends continue, cancer is expected to be the leading cause of the death by the year 2010. Lung and prostate cancer are the top cancer killers for men in the United States. Lung and breast cancer are the top cancer killers for women in the United States. One in two men in the United States will be diagnosed with cancer at some time during his lifetime. One in three women in the United States will be diagnosed with cancer at some time during her lifetime.

Currently, cancer therapy may involve surgery, chemotherapy, hormonal therapy and/or radiation treatment to eradicate neoplastic cells in a patient (See, for example, Stockdale, 1998, "Principles of Cancer Patient Management", in *Scientific American: Medicine,* vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of the patient or may be unacceptable to the patient. Additionally, surgery may not completely remove the neoplastic tissue. Radiation therapy is only effective when the neoplastic tissue exhibits a higher sensitivity to radiation than normal tissue, and radiation therapy can also often elicit serious side effects. Hormonal therapy is rarely given as a single agent and although can be effective, is often used to prevent or delay recurrence of cancer after other treatments have removed the majority of the cancer cells. Biological therapies/immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A significant majority of cancer chemotherapeutics act by inhibiting DNA synthesis, either directly, or indirectly by inhibiting the biosynthesis of the deoxyribonucleotide triphosphate precursors, to prevent DNA replication and concomitant cell division (See, for example, Gilman et al., Goodman and Gilman's: *The Pharmacological Basis of Therapeutics,* Eighth Ed. (Pergamom Press, New York, 1990)). These agents, which include alkylating agents, such as nitrosourea, anti-metabolites, such as methotrexate and hydroxyurea, and other agents, such as etoposides, campathecins, bleomycin, doxorubicin, daunorubicin, etc., although not necessarily cell cycle specific, kill cells during S phase because of their effect on DNA replication. Other agents, specifically colchicine and the vinca alkaloids, such as vinblastine and vincristine, interfere with microtubule assembly resulting in mitotic arrest.

Chemotherapy protocols generally involve administration of a combination of chemotherapeutic agents to increase the efficacy of treatment.

Despite the availability of a variety of chemotherapeutic agents, chemotherapy has many drawbacks (See, for example, Stockdale, 1998, "Principles Of Cancer Patient Management" in *Scientific American Medicine*, vol. 3, Rubenstein and Federman, eds., ch. 12, sect. 10). Almost all chemotherapeutic agents are toxic, and chemotherapy causes significant, and often dangerous, side effects, including severe nausea, bone marrow depression, immunosuppression, etc. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even those agents that act by mechanisms different from the mechanisms of action of the drugs used in the specific treatment; this phenomenon is termed pleiotropic drug or multidrug resistance. Thus, because of drug resistance, many cancers prove refractory to standard chemotherapeutic treatment protocols.

There is a significant need for alternative cancer treatments, particularly for treatment of cancer that has proved refractory to standard cancer treatments, such as surgery, radiation therapy, chemotherapy, and hormonal therapy. A promising alternative is immunotherapy, in which cancer cells are specifically targeted by cancer antigen-specific antibodies. Major efforts have been directed at harnessing the specificity of the immune response, for example, hybridoma technology has enabled the development of tumor selective monoclonal antibodies (See Green M. C. et al., 2000 *Cancer Treat Rev.*, 26: 269-286; Weiner L M, 1999 *Semin Oncol.* 26(suppl. 14): 43-51), and in the past few years, the Food and Drug Administration has approved the first MAbs for cancer therapy: Rituxin (anti-CD20) for non-Hodgkin's Lymphoma and Herceptin [anti-(c-erb-2/HER-2)] for metastatic breast cancer (Suzanne A. Eccles, 2001, *Breast Cancer Res.*, 3: 86-90). However, the potency of antibody effector function, e.g., to mediate antibody dependent cellular cytotoxicity ("ADCC") is an obstacle to such treatment. Methods to improve the efficacy of such immunotherapy are thus needed.

4.1.2 Inflammatory Diseases and Autoimmune Diseases

Inflammation is a process by which the body's white blood cells and chemicals protect our bodies from infection by foreign substances, such as bacteria and viruses. It is usually characterized by pain, swelling, warmth and redness of the affected area. Chemicals known as cytokines and prostaglandins control this process, and are released in an ordered and self-limiting cascade into the blood or affected tissues. This release of chemicals increases the blood flow to the area of injury or infection, and may result in the redness and warmth. Some of the chemicals cause a leak of fluid into the tissues, resulting in swelling. This protective process may stimulate nerves and cause pain. These changes, when occurring for a limited period in the relevant area, work to the benefit of the body.

In autoimmune and/or inflammatory disorders, the immune system triggers an inflammatory response when there are no foreign substances to fight and the body's normally protective immune system causes damage to its own tissues by mistakenly attacking self. There are many different autoimmune disorders that affect the body in different ways. For example, the brain is affected in individuals with multiple sclerosis, the gut is affected in individuals with Crohn's disease, and the synovium, bone and cartilage of various joints are affected in individuals with rheumatoid arthritis. As autoimmune disorders progress destruction of one or more types of body tissues, abnormal growth of an organ, or changes in organ function may result. The autoimmune disorder may affect only one organ or tissue type or may affect multiple organs and tissues. Organs and tissues commonly affected by autoimmune disorders include red blood cells, blood vessels, connective tissues, endocrine glands (e.g., the thyroid or pancreas), muscles, joints, and skin. Examples of autoimmune disorders include, but are not limited to, Hashimoto's thyroiditis, pernicious anemia, Addison's disease, type 1 diabetes, rheumatoid arthritis, systemic lupus erythematosus, dermatomyositis, Sjogren's syndrome, dermatomyositis, lupus erythematosus, multiple sclerosis, autoimmune inner ear disease myasthenia gravis, Reiter's syndrome, Graves disease, autoimmune hepatitis, familial adenomatous polyposis and ulcerative colitis.

Rheumatoid arthritis (RA) and juvenile rheumatoid arthritis are types of inflammatory arthritis. Arthritis is a general term that describes inflammation in joints. Some, but not all, types of arthritis are the result of misdirected inflammation. Besides rheumatoid arthritis, other types of arthritis associated with inflammation include the following: psoriatic arthritis, Reiter's syndrome, ankylosing spondylitis arthritis, and gouty arthritis. Rheumatoid arthritis is a type of chronic arthritis that occurs in joints on both sides of the body (such as both hands, wrists or knees). This symmetry helps distinguish rheumatoid arthritis from other types of arthritis. In addition to affecting the joints, rheumatoid arthritis may occasionally affect the skin, eyes, lungs, heart, blood or nerves.

Rheumatoid arthritis affects about 1% of the world's population and is potentially disabling. There are approximately 2.9 million incidences of rheumatoid arthritis in the United States. Two to three times more women are affected than men. The typical age that rheumatoid arthritis occurs is between 25 and 50. Juvenile rheumatoid arthritis affects 71,000 young Americans (aged eighteen and under), affecting six times as many girls as boys.

Rheumatoid arthritis is an autoimmune disorder where the body's immune system improperly identifies the synovial membranes that secrete the lubricating fluid in the joints as foreign. Inflammation results, and the cartilage and tissues in and around the joints are damaged or destroyed. In severe cases, this inflammation extends to other joint tissues and surrounding cartilage, where it may erode or destroy bone and cartilage and lead to joint deformities. The body replaces damaged tissue with scar tissue, causing the normal spaces within the joints to become narrow and the bones to fuse together. Rheumatoid arthritis creates stiffness, swelling, fatigue, anemia, weight loss, fever, and often, crippling pain. Some common symptoms of rheumatoid arthritis include joint stiffness upon awakening that lasts an hour or longer; swelling in a specific finger or wrist joints; swelling in the soft tissue around the joints; and swelling on both sides of the joint. Swelling can occur with or without pain, and can worsen progressively or remain the same for years before progressing.

The diagnosis of rheumatoid arthritis is based on a combination of factors, including: the specific location and symmetry of painful joints, the presence of joint stiffness in the morning, the presence of bumps and nodules under the skin (rheumatoid nodules), results of X-ray tests that suggest rheumatoid arthritis, and/or positive results of a blood test called the rheumatoid factor. Many, but not all, people with rheumatoid arthritis have the rheumatoid-factor antibody in their blood. The rheumatoid factor may be present in people who do not have rheumatoid arthritis. Other diseases can also cause the rheumatoid factor to be produced in the blood. That is why the diagnosis of rheumatoid arthritis is based on a combination of several factors and not just the presence of the rheumatoid factor in the blood.

The typical course of the disease is one of persistent but fluctuating joint symptoms, and after about 10 years, 90% of sufferers will show structural damage to bone and cartilage. A small percentage will have a short illness that clears up completely, and another small percentage will have very severe disease with many joint deformities, and occasionally other manifestations of the disease. The inflammatory process causes erosion or destruction of bone and cartilage in the joints. In rheumatoid arthritis, there is an autoimmune cycle of persistent antigen presentation, T-cell stimulation, cytokine secretion, synovial cell activation, and joint destruction. The disease has a major impact on both the individual and society, causing significant pain, impaired function and disability, as well as costing millions of dollars in healthcare expenses and lost wages. (See, for example, the NIH website and the NIAID website).

Currently available therapy for arthritis focuses on reducing inflammation of the joints with anti-inflammatory or immunosuppressive medications. The first line of treatment of any arthritis is usually anti-inflammatories, such as aspirin, ibuprofen and Cox-2 inhibitors such as celecoxib and rofecoxib. "Second line drugs" include gold, methotrexate and steroids. Although these are well-established treatments for arthritis, very few patients remit on these lines of treatment alone. Recent advances in the understanding of the pathogenesis of rheumatoid arthritis have led to the use of methotrexate in combination with antibodies to cytokines or recombinant soluble receptors. For example, recombinant soluble receptors for tumor necrosis factor (TNF)-α have been used in combination with methotrexate in the treatment of arthritis. However, only about 50% of the patients treated with a combination of methotrexate and anti-TNF-α agents such as recombinant soluble receptors for TNF-α show clinically significant improvement. Many patients remain refractory despite treatment. Difficult treatment issues still remain for patients with rheumatoid arthritis. Many current treatments have a high incidence of side effects or cannot completely prevent disease progression. So far, no treatment is ideal, and there is no cure. Novel therapeutics are needed that more effectively treat rheumatoid arthritis and other autoimmune disorders.

4.1.3 Infectious Diseases

Infectious agents that cause disease fall into five groups: viruses, bacteria, fungi, protozoa, and helminths (worms). The remarkable variety of these pathogens has caused the natural selection of two crucial features of adaptive immunity. First, the advantage of being able to recognize a wide range of different pathogens has driven the development of receptors on B and T cells of equal or greater diversity. Second, the distinct habitats and life cycles of pathogens have to be countered by a range of distinct effector mechanisms. The characteristic features of each pathogen are its mode of transmission, its mechanism of replication, its pathogenesis or the means by which it causes disease, and the response it elicits.

The record of human suffering and death caused by smallpox, cholera, typhus, dysentery, malaria, etc. establishes the eminence of the infectious diseases. Despite the outstanding successes in control afforded by improved sanitation, immunization, and antimicrobial therapy, the infectious diseases continue to be a common and significant problem of modern medicine. The most common disease of mankind, the common cold, is an infectious disease, as is the feared modem disease AIDS. Some chronic neurological diseases that were thought formerly to be degenerative diseases have proven to be infectious. There is little doubt that the future will continue to reveal the infectious diseases as major medical problems.

An enormous number of human and animal diseases result from virulent and opportunistic infections from any of the above mentioned infectious agents (see Belshe (Ed.) 1984 *Textbook of Human Virology*, PSG Publishing, Littleton, Mass.).

One category of infectious diseases are viral infections for example. Viral diseases of a wide array of tissues, including the respiratory tract, CNS, skin, genitourinary tract, eyes, ears, immune system, gastrointestinal tract, and musculoskeletal system, affect a vast number of humans of all ages (see Table 328-2 In: Wyngaarden and Smith, 1988, *Cecil Textbook of Medicine*, $18^{th}$ Ed., W.B. Saunders Co., Philadelphia, pp. 1750-1753). Although considerable effort has been invested in the design of effective anti-viral therapies, viral infections continue to threaten the lives of millions of people worldwide. In general, attempts to develop anti-viral drugs have focused on several stages of viral life cycle (See e.g., Mitsuya et al., 1991, *FASEB J.* 5:2369-2381, discussing HIV). However, a common drawback associated with using of many current anti-viral drugs is their deleterious side effects, such as toxicity to the host or resistance by certain viral strains.

Citation or discussion of a reference herein shall not be construed as an admission that such is prior art to the present invention.

5. SUMMARY OF THE INVENTION

The present invention provides a detailed characterization of polypeptides comprising a modified hinge. The modified hinge region may exhibit alterations in one or more of the characteristics of the hinge, including, but not limited to, flexibility, length, conformation, charge and hydrophobicity relative to a wild type hinge. The modified hinge regions disclosed herein may be generated by methods well know in the art, such as, for example introducing a modification into a wild type hinge. Modifications which may be utilized to generate a modified hinge region include, but are not limited to, amino acid insertions, deletions, substitutions, and rearrangements. Said modifications of the hinge and the modified hinge regions disclosed are referred to herein jointly as "hinge modifications of the invention", "modified hinge(s) of the invention" or simply "hinge modifications" or "modified hinge(s)." The modified hinge regions disclosed herein may be incorporated into a molecule of choice including, but not limited to, antibodies and fragments thereof. As demonstrated herein, molecules comprising a modified hinge may exhibit altered binding to one or more Fc ligands (e.g., FcγRs, C1q) and/or altered effector function when compared to a molecule having the same amino acid sequence except for the modified hinge such as, for example, a molecule having the same amino acid sequence except comprising a wild type hinge.

Accordingly, the present invention relates to molecules, in particular polypeptides, more specifically immunoglobulins (e.g., antibodies) and other binding proteins, comprising an Fc region (as used herein "Fc region" and similar terms encompasses any heavy chain constant region domain comprising all or at least a portion of the hinge region) incorporating a modified hinge of the invention, where said modified hinge alters the binding of the Fc region to one or more Fc ligands (e.g., FcγRs, C1q) and/or modulates Fc mediated effector function when compared to a molecule having the same amino acid sequence except for the modified hinge. These modified hinge regions may be incorporated into a molecule of choice. Molecules comprising an Fc region comprising a modified hinge of the invention are referred to herein as "Fc variants of the invention" or "Fc variants." It is specifically contemplated that an Fc variant may be generated by methods well known to one skilled in the art. Briefly, such methods include but are not limited to, combining a variable region or other binding domain with the desired specificity (e.g., a variable region isolated from a phage display or expression library or derived from a human or non-human antibody or a ligand binding domain of a receptor) with an Fc region comprising a modified hinge of the invention. Alternatively, one skilled in the art may generate an Fc variant by modifying the hinge (e.g., introducing amino acid insertions, deletions, substitutions, or rearrangements) of a molecule comprising an Fc region, using methods well known in the art, to generate an Fc variant of the invention.

The present invention provides Fc variants that have altered binding affinity for at least one Fc ligand (e.g., FcγRs, C1q) when compared to a molecule having the same amino acid sequence as the Fc variant except for the modified hinge (also referred to herein as a "comparable molecule") such as, for example, an Fc variant comprising a wild type hinge. In one embodiment, the Fc variants of the invention have higher binding affinity to activating FcγRs (e.g., FcγRIIIA) and/or unchanged or lower binding affinity to inhibitory FcγRs (e.g., FcγRIIB) relative to a comparable molecule (e.g., an antibody having an unmodified or wild type hinge region). The present invention further provides Fc variants with enhanced ability to mediated ADCC (referred to herein as "ADCC activity"), relative to a comparable molecule. In another embodiment, the Fc variants of the invention have enhanced ADCC activity in addition to the above changes in FcγR affinities, relative to a comparable molecule (e.g., an antibody having an unmodified or wild type hinge region). In other embodiments, Fc variants that have higher binding affinity to their FcγRs do not have significantly altered antigen binding specificity, relative to a comparable molecule.

The present invention also provides Fc variants that have lower binding affinity to activating FcγRs (e.g., FcγRIIIA) and/or increased binding affinity to inhibitory FcγRs (e.g., FcγRIIB), relative to a comparable molecule (e.g., an antibody having an unmodified or wild type hinge region). The present invention further provides Fc variants with decreased ADCC function, relative to a comparable molecule. In a specific embodiment, the Fc variants of the invention exhibit decreased ADCC activity in addition to the above changes in FcγR affinities, relative to a comparable molecule. In other embodiments, Fc variants that have lower binding affinity to activating FcγRs do not have significantly altered antigen binding specificity, relative to a comparable molecule.

The present invention additionally provides Fc variants that have altered binding affinity to the complement protein C1q, relative to a comparable molecule (e.g., an antibody having an unmodified or wild type hinge region). In one embodiment, the Fc variants have enhanced binding affinity to C1q and more effectively mediate CDC (also referred to herein as "CDC activity"). In another embodiment, the Fc variants have reduced binding affinity to C1q and less effectively mediate CDC. In still other embodiments, Fc variants with altered binding affinity to the complement protein C1q do not have significantly altered antigen binding specificity relative to a comparable molecule.

It is an object of the present invention to provide Fc variants that bind with greater affinity to one or more Fc ligand (e.g., FcγRs, C1q). In one embodiment, said Fc variants have an affinity for one or more Fc ligand (e.g., FcγRs, C1q) that is at least 2 fold greater than that of a comparable molecule. In another embodiment, the Fc variants of the invention have affinity for one or more Fc ligand (e.g., FcγR, C1q) that is between about 2 fold and about 50 fold greater than that of a comparable molecule. In other embodiments, the Fc variants of the invention have an affinity for one or more Fc ligand (e.g., FcγRs, C1q) that is increased between about 10% and about 200%, relative to a comparable molecule. In one specific embodiment, an Fc variant of the invention has a greater affinity for FcγRIIIA and/or C1q. In another specific embodiment, an Fc variant of the invention has a greater affinity for FcγRIIB.

It is a further object of the present invention to provide Fc variants that bind with reduced affinity to one or more FcγRs and/or C1q. In a one embodiment, the Fc variants of the invention have affinity for one or more FcγRs and/or C1q that is between about 2 fold and about 50 fold lower than that of a comparable molecule. In other embodiments, the Fc variants of the invention have an affinity for one or more FcγRs and/or C1q that is reduced between about 10% and about 200%, relative to a comparable molecule. In a specific embodiment, the Fc variants of the invention have an affinity for FcγRIIB that is either unchanged, or reduced, relative to a comparable molecule. In another specific embodiment, the Fc variants of the invention have an affinity for FcγRIIIA and/or C1q that is reduced, relative to a comparable molecule.

In a specific embodiment, an Fc variant of the invention has an equilibrium dissociation constant ($K_D$) for an Fc ligand (e.g., FcγRs, C1q) that is decreased between about 2 fold and 10 fold, or between about 5 fold and 50 fold, or between about 25 fold and 250 fold, or between about 100 fold and 500 fold, relative to a comparable molecule. In another specific embodiment, an Fc variant of the invention has an equilibrium dissociation constant ($K_D$) for an Fc ligand (e.g., FcγRs, C1q) that is decreased between about 10% and 200%, or between about 10% and 50%, or between about 50% and 100%, or between about 100% and 200%, relative to a comparable molecule. In still another specific embodiment, an Fc variant of the invention has a ratio of FcγRIIIA/FcγRIIB equilibrium dissociation constants ($K_D$) that is decreased and enhanced ADCC activity, relative to a comparable molecule.

In another embodiment, an Fc variant of the invention has a decreased affinity for FcγRIIIA, an affinity for FcγRIIB that is increased and reduced ADCC activity relative to a comparable molecule (e.g., an antibody comprising a wild type hinge). In still another embodiment, an Fc variant of the invention has a ratio of FcγRIIIA/FcγRIIB equilibrium dissociation constants ($K_D$) that is increased and reduced ADCC activity relative to a comparable molecule.

It is a further object of the present invention to provide Fc variants that have enhanced ADCC and/or CDC activity relative to a comparable molecule. In one embodiment, Fc variants of the invention have ADCC and/or CDC activity that is at least about 2 fold greater then that of a comparable molecule. In one embodiment, Fc variants of the invention have ADCC and/or CDC activity that is between about 2 fold and about 100 fold greater then that of a comparable molecule. In other embodiments, the Fc variants of the invention have ADCC and/or CDC activity that is increased between about 10% and about 200%, relative to a comparable molecule.

It is a further object of the present invention to provide Fc variants that have reduced ADCC and/or CDC activity, relative to a comparable molecule. In one embodiment, Fc variants of the invention have ADCC and/or CDC activity that is at least about 2 fold lower then that of a comparable molecule. In another embodiment, the Fc variants of the invention have ADCC and/or CDC activity that is between about 2 fold and about 100 fold lower then that of a comparable molecule. In other embodiments, the Fc variants of the invention have ADCC and/or CDC activity that is reduced between about 10% and about 200%, relative to a comparable molecule. In certain embodiments, Fc variants of the invention have little or no ADCC and/or CDC activity, relative to a comparable molecule.

In one specific embodiment, an Fc variant of the invention has an increased affinity for FcγRIIIA and an affinity for FcγRIIB that is unchanged or reduced and enhanced ADCC activity, relative to a comparable molecule. In another specific embodiment, an Fc variant of the invention has a decreased affinity for FcγRIIIA and an affinity for FcγRIIB that is increased and reduced ADCC activity, relative to a comparable molecule.

In some embodiments, an Fc variant of the invention does not bind any Fc ligand (e.g., FcγR, C1q) or binds with a reduced affinity, relative to a comparable molecule, as determined by standard assays (e.g., in vitro assays) known to one skilled in the art. In a specific embodiment, the invention encompasses Fc variants which only bind one FcγR, wherein said FcγR is FcγRIIIA. In yet another embodiment, the invention encompasses Fc variants which only bind one FcγR, wherein said FcγR is FcγRIIB. In still another embodiment, an Fc variant of the invention does not bind C1q or binds with a reduced affinity, relative to a comparable molecule.

The binding properties of a receptor for its ligand, may be determined by a variety of methods well-known in the art, including but not limited to, equilibrium methods (e.g., enzyme-linked immunoabsorbent assay (ELISA) or radioimmunoassay (RIA)), or kinetics (e.g., BIACORE® analysis), and other methods such as indirect binding assays, competitive inhibition assays, fluorescence resonance energy transfer (FRET), gel electrophoresis and chromatography (e.g., gel filtration). These and other well-known methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4$^{th}$ Ed., Lippincott-Raven, Philadelphia (1999), which focuses on antibody-immunogen interactions.

In a specific embodiment, the invention encompasses an Fc variant, wherein said Fc variant comprises a modified hinge having altered (e.g., increases or decreases) flexibility of the hinge relative to a wild type hinge. A modified hinge having altered flexibility may be generated by incorporating certain modifications into a wild type hinge. Modifications which increase the flexibility of the hinge include but are not limited to, the substitution of one or more amino acids residues with one or more glycine residues, the substitution of a cysteine involved in the formation of a disulfide bond with an amino acid residue which can not form a disulfide bond (e.g. serine, alanine, glycine). Modifications which decrease the flexibility of the hinge include but are not limited to the substitution of one or more amino acids residues with one or more proline residues, the substitution of an amino acid residue which can not form a disulfide bond (e.g. serine, alanine, glycine) with an amino acid residue capable of forming a disulfide bond (e.g. cysteine).

In a specific embodiment, the invention encompasses an Fc variant, wherein said Fc variant comprises a modified hinge having altered (e.g., increased or decreased) hinge length relative to a wild type hinge. A modified hinge having altered hinge length may be generated by incorporating certain modifications into a wild type hinge. Modifications which increase the length of the hinge include but are not limited to, the addition of one or more amino acids residues within the hinge. Modifications which decrease the length of the hinge include but are not limited to the deletion of one or more amino acids residues within the hinge.

In a specific embodiment, the invention encompasses an Fc variant, wherein said Fc variant comprises a modified hinge having altered the hinge conformation, relative to a wild type hinge. A modified hinge having altered hinge conformation may be generated by incorporating certain modifications into a wild type hinge. Modifications which alter the conformation of the hinge include but are not limited to, the substitution of one or more amino acids residues with small side chains (e.g., alanine, glycine) for those with larger more bulky side chains (e.g., tryptophan, proline) or the inversion of two or more amino acid resides within the hinge.

It is contemplated that a hinge modification which alters one or more characteristics (e.g., flexibility, length, conformation, charge, hydrophobicity) of the hinge may be present one or more defined regions of the modified hinge including but not limited to the upper hinge, the middle hinge and the lower hinge. It will be apparent to one skilled in the art that such hinge modifications may be made such that they overlap one or more defined regions of the hinge and that a hinge may be modified in more then one region.

The present invention further encompasses an Fc variant, wherein said Fc variant comprises a modified hinge having more then one characteristic of the hinge altered including but not limited to flexibility, length, conformation, charge, hydrophobicity.

The Fc variants of the present invention may be combined with other Fc modifications, including but not limited to modifications that alter Fc ligand binding and/or effector function. The invention encompasses combining an Fc variant of the invention with other Fc modifications to provide additive, synergistic, or novel properties in antibodies or Fc fusions. It is contemplated that the Fc variants of the invention enhance the phenotype of the modified hinge with which they are combined. For example, if an Fc variant (i.e., incorporating a hinge modification of the invention) is combined with a mutant known to bind FcγRIIIA with a higher affinity than a comparable molecule comprising a wild type Fc region; the combination results in a greater fold enhancement in FcγRIIIA affinity.

The invention encompasses molecules that comprise homodimers or heterodimers of Fc regions wherein at least one Fc region incorporates a modified hinge of the invention. Heterodimers comprising Fc regions refer to molecules where the two Fc chains have different sequences. In some embodiments, in the heterodimeric molecules comprising an Fc region incorporating a modified hinge and/or other Fc modification, each chain has one or more different modifications from the other chain. In other embodiments, in the heterodimeric molecules comprising an Fc region incorporating a modified hinge, one chain contains the wild-type Fc region and the other chains comprises one or more modifications. Methods of engineering heterodimeric Fc containing molecules are known in the art and encompassed within the invention.

The present invention also encompasses Fc variants conjugated or fused to a moiety (e.g., therapeutic agent or drug).

In a specific embodiment, the invention provides antibodies which are Fc variants with an altered affinity for one or more Fc ligand (e.g., FcγR, C1q). Such antibodies include IgG molecules that naturally comprise an Fc region comprising a hinge which can be modified to generate an Fc variant, or antibody derivatives that have been engineered to contain an Fc region comprising a modified hinge. Antibodies which are Fc variants include any antibody molecule that binds, preferably, specifically (e.g., competes off non-specific binding as determined by immunoassays well known in the art for assaying specific antigen-antibody binding) binds an antigen and contains an Fc region or fragment thereof incorporating a modified hinge. Such antibodies include, but are not limited to, polyclonal, monoclonal, bi-specific, multi-specific, human, humanized, chimeric antibodies, single chain antibodies, Fab fragments, F(ab')$_2$ fragments, disulfide-linked Fvs, and fragments containing either a VL or VH domain or even a complementary determining region (CDR) that specifically binds an antigen, in certain cases, engineered to contain or fused to an Fc region or portion thereof incorporating at least one modified hinge of the present invention.

The present invention also provides methods for altering the affinity of a polypeptide comprising an Fc region (e.g., antibody, Fc fusion) for one or more Fc ligand (e.g., FcγR, C1q). Further, the present invention provides methods for altering the effector function (e.g., ADCC, CDC) of a polypeptide comprising an Fc region (e.g., antibody, Fc fusion).

The invention encompasses engineering human or humanized therapeutic antibodies (e.g., tumor specific monoclonal antibodies) by modification (e.g., insertion, deletion, substitution, inversion) of one or more amino acid residues of the hinge, wherein said modifications modulate the binding affinity of the therapeutic for one or more Fc ligand (e.g., FcγR, C1q). In one embodiment, the invention relates to engineering human or humanized therapeutic antibodies (e.g., tumor specific monoclonal antibodies) by modification of the hinge, which modifications increase the affinity of the Fc region for activating FcγR (e.g., FcγRIIIA). In another embodiment, the invention relates to engineering human or humanized therapeutic antibodies (e.g., tumor specific monoclonal antibodies) in the hinge region by modification of one or more amino acid residues, wherein said modification increases the affinity of the Fc region for activating FcγRs (e.g., FcγRIIIA) and further decreases the affinity of the Fc region for inhibitory FcγRs (e.g., FcγRIIB). In still another embodiment, the invention relates to engineering human or humanized therapeutic antibodies in the hinge region by modification of one or more amino acid residues, wherein said modification increases the affinity of the Fc region for C1q. The engineered therapeutic antibodies may further have an enhanced effector function, e.g., enhanced ADCC activity, CDC activity, phagocytosis activity, etc., as determined by standard assays known to those skilled in the art.

The present invention also encompasses the use of Fc variants of the invention for the prevention, management, treatment or amelioration of one or more symptoms associated with diseases, disorders or infection, including but not limited to cancer, inflammatory and autoimmune diseases either alone or in combination with other therapies.

The invention also encompasses the use of the Fc variants of the invention conjugated or fused to a moiety (e.g., therapeutic agent or drug) for prevention, management, treatment or amelioration of one or more symptoms associated with diseases, disorders or infection, including but not limited to cancer, inflammatory and autoimmune diseases either alone or in combination with other therapies. The antibodies (or other molecules) comprising the Fc variants of the present invention can be used for the prevention, management, treatment or amelioration of one or more symptoms associated with diseases, disorders or infection, including but not limited to infection, cancer, inflammatory and autoimmune diseases either alone or in combination with other therapies. Accordingly, the invention further encompasses treatment protocols that enhance the prophylactic or therapeutic effect of the Fc variants with altered binding affinity to at least one Fc ligand (e.g., FcγRs, C1q).

The present invention provides kits comprising molecules, wherein said molecules comprise one or more Fc variants with modified binding affinity to one or more Fc ligand (e.g., FcγRs, C1q) conjugated or fused to a detectable agent, therapeutic agent or drug, in one or more containers, for use in the prevention, treatment, management, detection, monitoring, diagnosis or amelioration of one or more symptoms associated of diseases and disorders including but not limited to infection, cancer, inflammatory and autoimmune diseases.

6. BRIEF DESCRIPTION OF THE FIGURES

FIG. 1 shows the amino acid sequences of the variable light ($V_L$) and heavy ($V_H$) chains (SEQ ID NOS. 1 and 2, respectively) of the anti-human EphA2 antibody 12G3H11. Boxed regions are the CDRs (as defined by Kabat).

FIG. 2 shows the binding curves for C1q binding to purified IgGs comprising Fc variants with modifications that may increase the flexibility of the hinge region. Plotted as the ratio of the optical density versus concentration of IgG for the Fc variant over the wild type Fc. All of these variants show reduced C1q binding with variant 9 and 10 having a small reduction and variants 3, 4, 7 and 8 having a larger reduction in binding.

FIG. 3 shows the binding curves for C1q binding to purified IgGs comprising Fc variants with modifications that may decrease the flexibility of the hinge region. Plotted as the ratio of the optical density versus concentration of IgG for the Fc variant over the wild type Fc. Variant 14 had no change in binding; variant 21 showed a slight decrease while variants 17 and 18 had slightly improved binding to C1q.

FIG. 4 shows the binding curves for C1q binding to purified IgGs comprising Fc variants with modifications that may increase the length and flexibility of the hinge region. Plotted as the ratio of the optical density versus concentration of IgG for the Fc variant over the wild type Fc. Both variants 5 and 6 show a decrease in C1q binding with variant 5 having a larger reduction in binding.

FIG. 5 shows the binding curves for C1q binding to purified IgGs comprising Fc variants with modifications that may increase the length and decrease the flexibility of the hinge region, plotted as the ratio of the optical density versus concentration of IgG for the Fc variant over the wild type Fc. Variants 15 and 16 are virtually unchanged in their binding to C1q by this assay.

FIG. 6 shows the binding curves for C1q binding to purified IgGs comprising Fc variants with modifications that may decrease the length of the hinge region. Plotted as the ratio of the optical density versus concentration of IgG for the Fc variant over the wild type Fc. The binding of variant 13 was unchanged while variants 11 and 12 had greatly reduced binding to C1q.

FIG. 7 shows the binding curves for C1q binding to purified IgGs comprising Fc variants with modifications that may alter the overall conformation of the hinge region. Plotted as the ratio of the optical density versus concentration of IgG for the Fc variant over the wild type Fc. The C1q binding of variant 2 was virtually unchanged while the binding of variant 19 was reduced. Variants 1 and 20 showed an increase in binding.

FIG. 8 shows the binding curves for FcγRIIIA binding to purified IgGs comprising Fc variants with modifications that may increase the flexibility of the hinge region. Plotted as the ratio of the optical density versus concentration of IgG for the Fc variant over the wild type Fc. No change in FcγRIII binding was seen for variants 3, 9 and 10 and only a slight reduction in FcγRIII binding was seen for variants 4, 7 and 8.

FIG. 9 shows the binding curves for FcγRIIIA binding to purified IgGs comprising Fc variants with modifications that may decrease the flexibility of the hinge region. Plotted as the ratio of the optical density versus concentration of IgG for the Fc variant over the wild type Fc. None of these variants, 14, 17, 18 and 21, showed a significant difference in FcγRIII binding.

FIG. 10 shows the binding curves for FcγRIIIA binding to purified IgGs comprising Fc variants with modifications that may increase the length and flexibility of the hinge region. Plotted as the ratio of the optical density versus concentration of IgG for the Fc variant over the wild type Fc. Variant 5 exhibited a significant decrease in FcγRIII binding while variant 6 was virtually unchanged.

FIG. 11 shows the binding curves for FcγRIIIA binding to purified IgGs comprising Fc variants with modifications that may increase the length and decrease the flexibility of the hinge region. Plotted as the ratio of the optical density versus concentration of IgG for the Fc variant over the wild type Fc. Neither of these Fc variants showed a difference in FcγRIII binding in these assays.

FIG. 12 shows the binding curves for FcγRIIIA binding to purified IgGs comprising Fc variants with modifications that may decrease the length of the hinge region. Plotted as the ratio of the optical density versus concentration of IgG for the Fc variant over the wild type Fc. These Fc variants showed FcγRIII binding curves that ranged from virtually unchanged, variant 13, to slightly reduced, Fc variants 11 and 12.

FIG. 13 shows the binding curves for FcγRIIIA binding to purified IgGs comprising Fc variants with modifications that may alter the overall conformation of the hinge region. Plotted as the ratio of the optical density versus concentration of IgG for the Fc variant over the wild type Fc. Fc variants 1, 2 and 20 have virtually unchanged FcγRIII binding while Fc variant 19 had reduced FcγRIII binding.

FIG. 14 shows the ADCC activity of the wild type 12G3H11 antibody and the Fc variant 5 against A549 (human lung carcinoma) target cells. The E:T ratio was 25:1, effector cells from donor 139. The ADCC activity of Fc variant 5 was significantly reduced. The same result was seen for effector cells derived from several other donors (see FIGS. 15 and 16).

FIG. 15 shows the ADCC activity of the wild type 12G3H11 antibody and the Fc variant 5 against A549 (human lung carcinoma) target cells. The E:T ratio was 50:1, effector cells from donor 168. The ADCC activity of Fc variant 5 was significantly reduced. The same result was seen for effector cells derived from several other donors (see FIGS. 14 and 16).

FIG. 16 shows the ADCC activity of the wild type 12G3H11 antibody and the Fc variant 5 against A549 (human lung carcinoma) target cells. The E:T ratio was 25:1, effector cells from donor 103. The ADCC activity of Fc variant 5 was significantly reduced. The same result was seen for effector cells derived from several other donors (see FIGS. 14 and 15).

Figure 22:
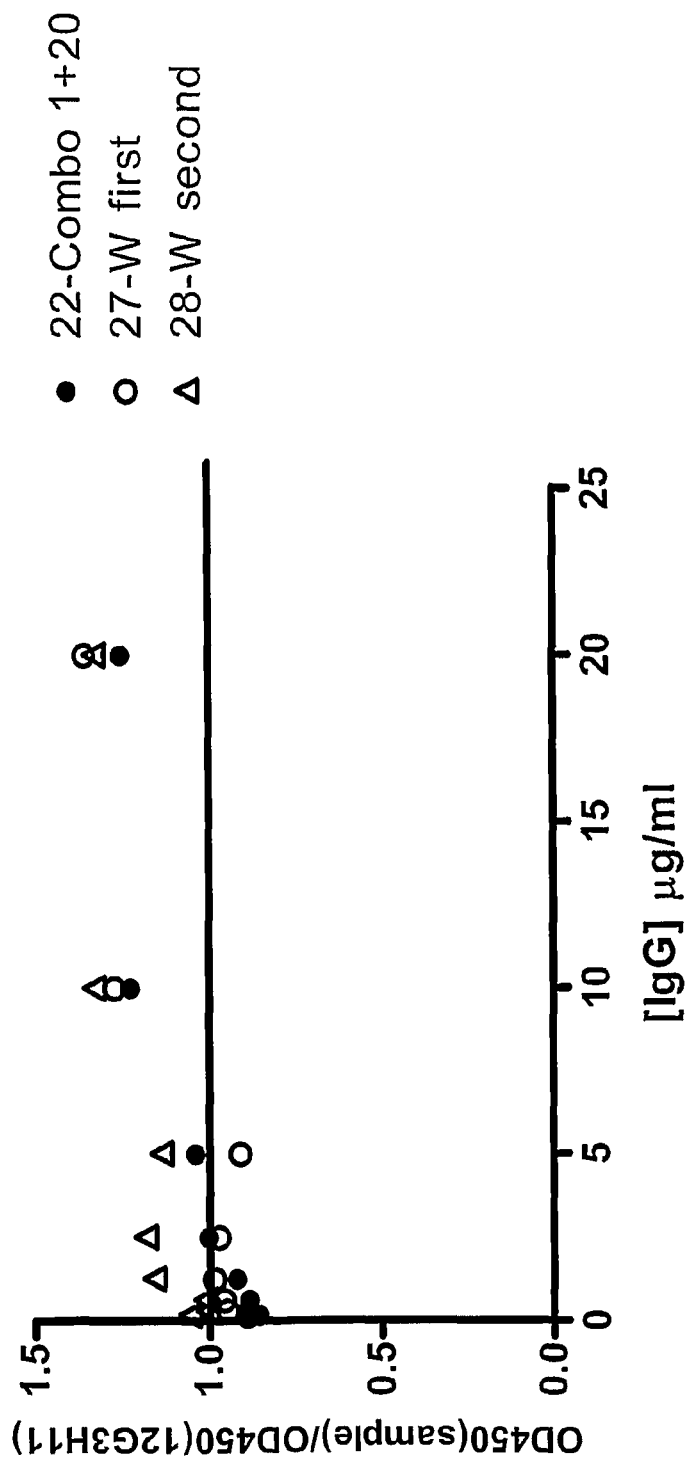

FIG. 22 shows the binding curves for C1q binding to purified IgGs comprising Fc variants with combinatorial and alternative modifications. Plotted as the ratio of the optical density versus concentration of IgG for the Fc variant over the wild type Fc. Fc variants "22-Combo 1+20", 27 and 28 exhibited enhanced binding to C1q.

Figure 23:
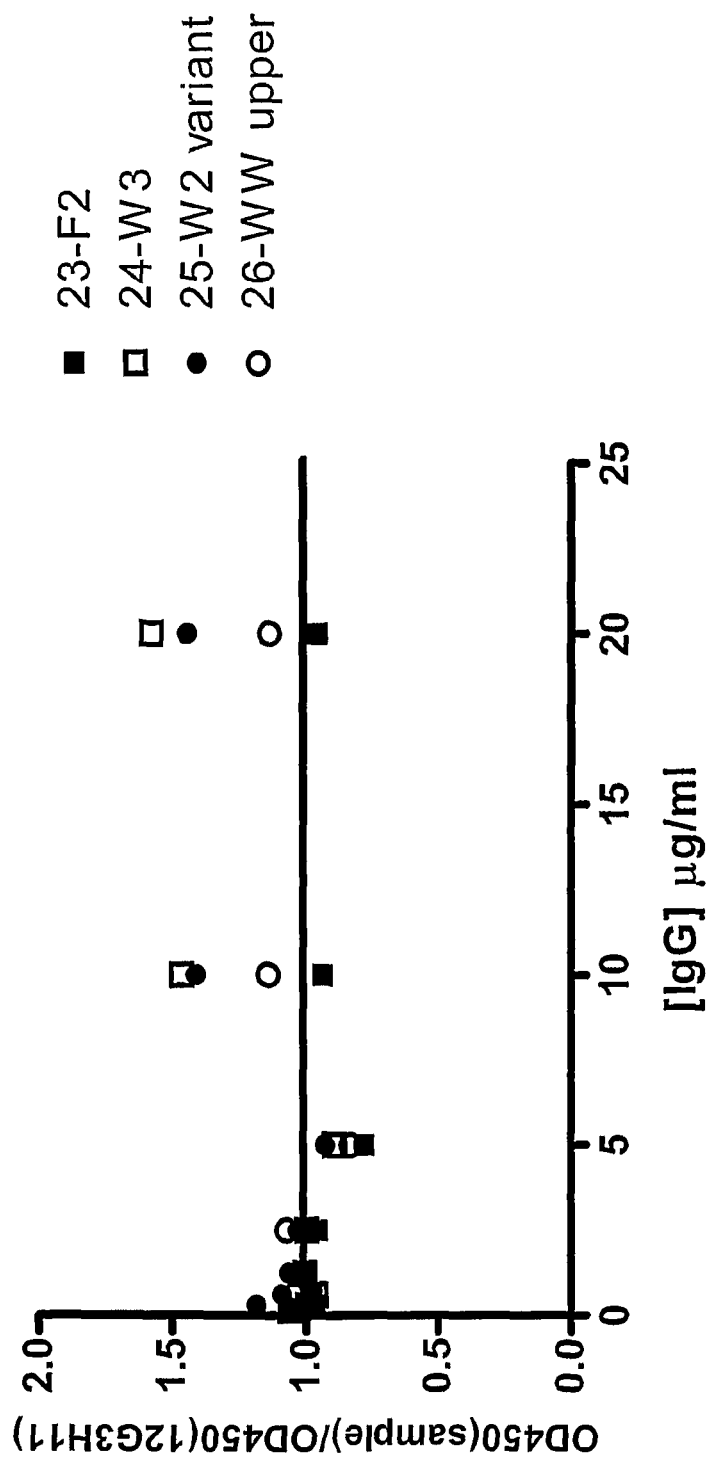

FIG. 23 shows the binding curves for C1q binding to purified IgGs comprising Fc variants with combinatorial and alternative modifications. Plotted as the ratio of the optical density versus concentration of IgG for the Fc variant over the wild type Fc. Fc variants 24 and 25 exhibited enhanced binding to C1q while 26 and 23 were relatively unaltered.

Figure 24:
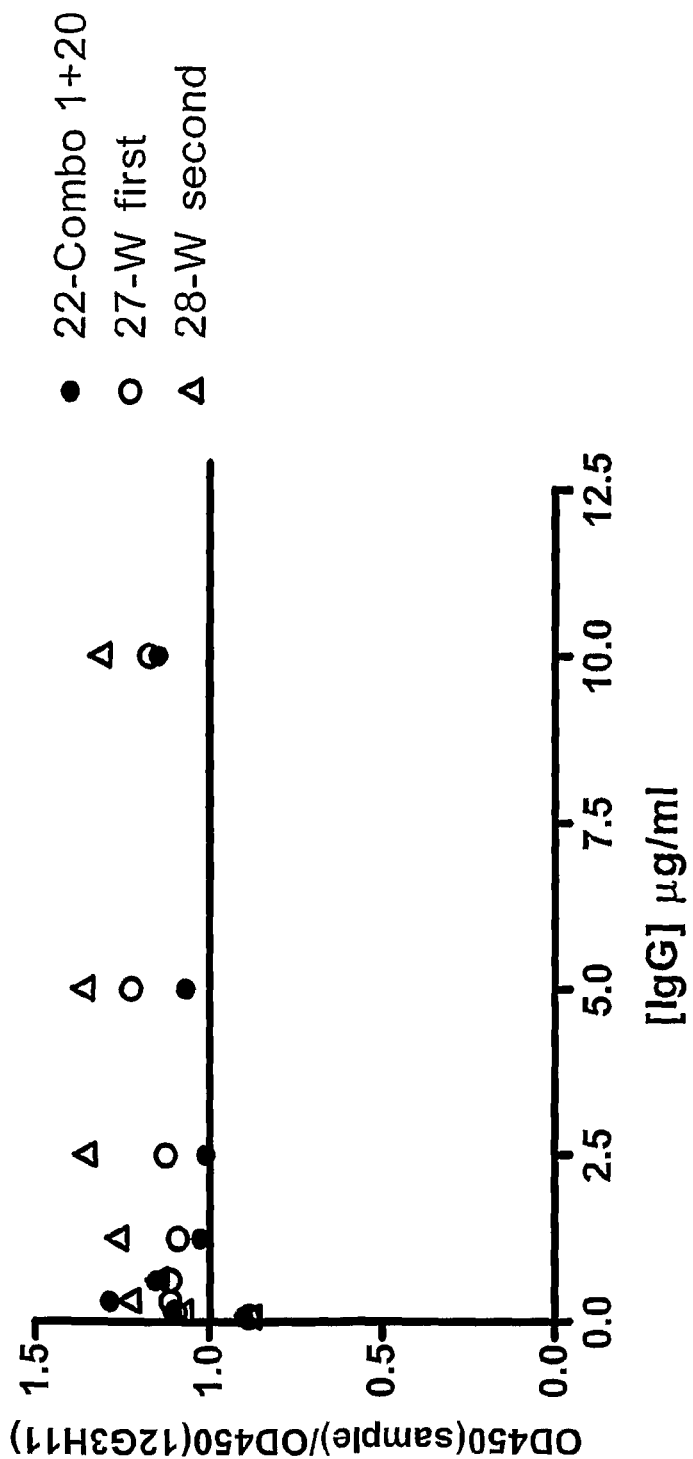

FIG. 24 shows the binding curves for FcγRIIIA binding to purified IgGs comprising Fc variants with combinatorial and alternative modifications. Plotted as the ratio of the optical density versus concentration of IgG for the Fc variant over the wild type Fc. Fc variants 27 and 28 exhibited a slight increase in binding to FcγRIIIA while Fc variant 22 was relatively unaltered.

Figure 25:
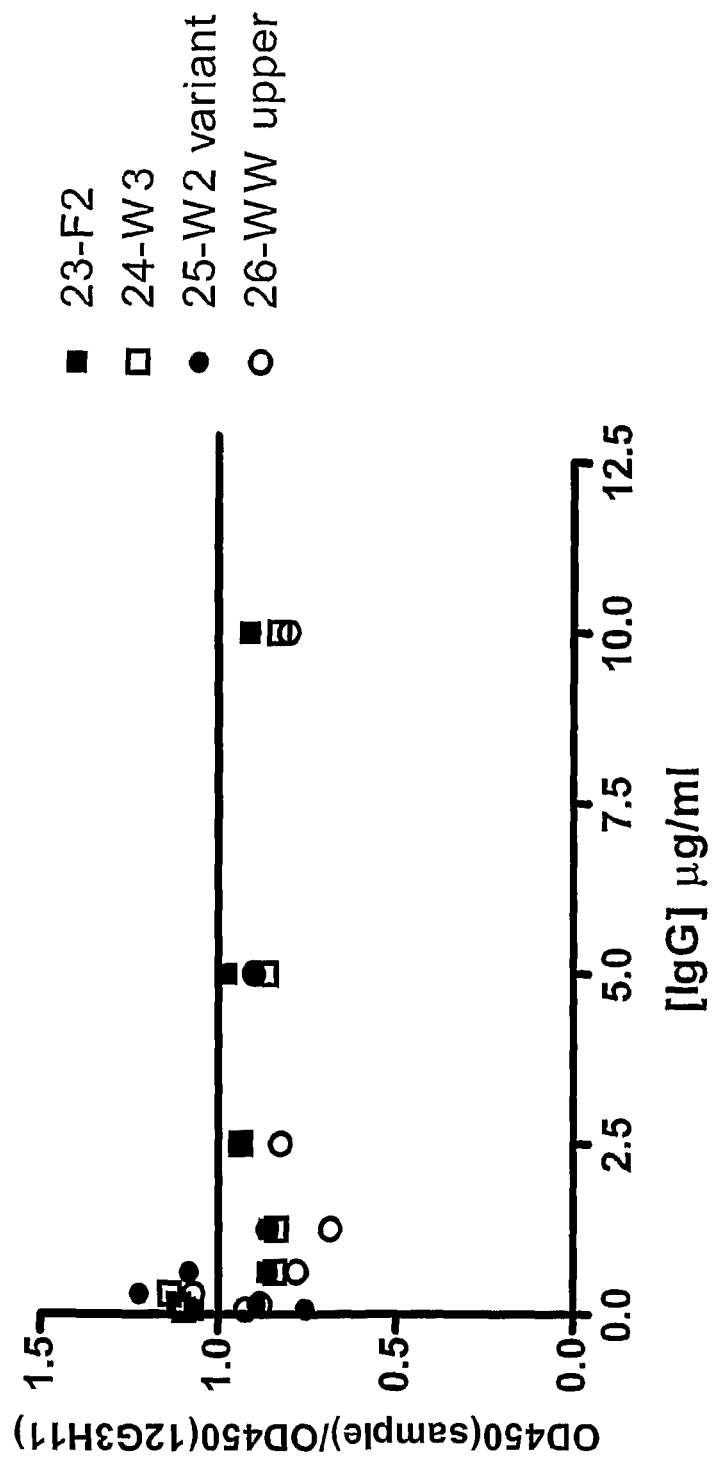

FIG. 25 shows the binding curves for FcγRIIIA binding to purified IgGs comprising Fc variants with combinatorial and alternative modifications. Plotted as the ratio of the optical density versus concentration of IgG for the Fc variant over the wild type Fc. The binding of Fc variants 23 and 25 to FcγRIIIA were relatively unaltered while variants 24 and 26 shows a slight reduction in binding.

Figure 26:
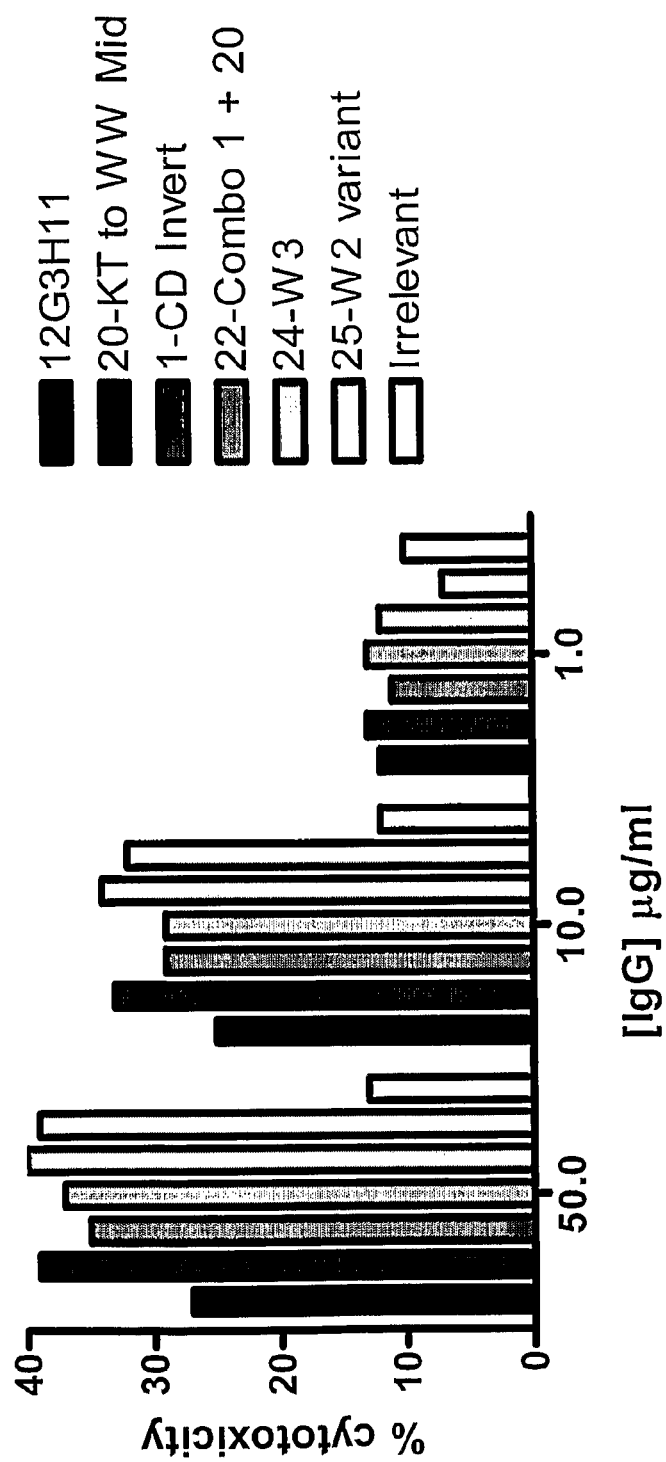

FIG. 26 shows the CDC activity against untransfected KATOIII cells of wild type 12G3H11 antibody, an irrelevant control antibody, Fc variants with combinatorial and alternative modifications (21, 24 and 25) and two previously analyzed Fc variants (1 and 20) which show significantly increased CDC activity. As was previously seen Fc variants 1 and 20 showed increased CDC activity in addition, the Fc variants 22, 24 and 25 showed increased CDC activity. The same result was seen for EphA2-transfected KATOIII, CT26 and CHO cells (see FIGS. 27-30).

Figure 27:
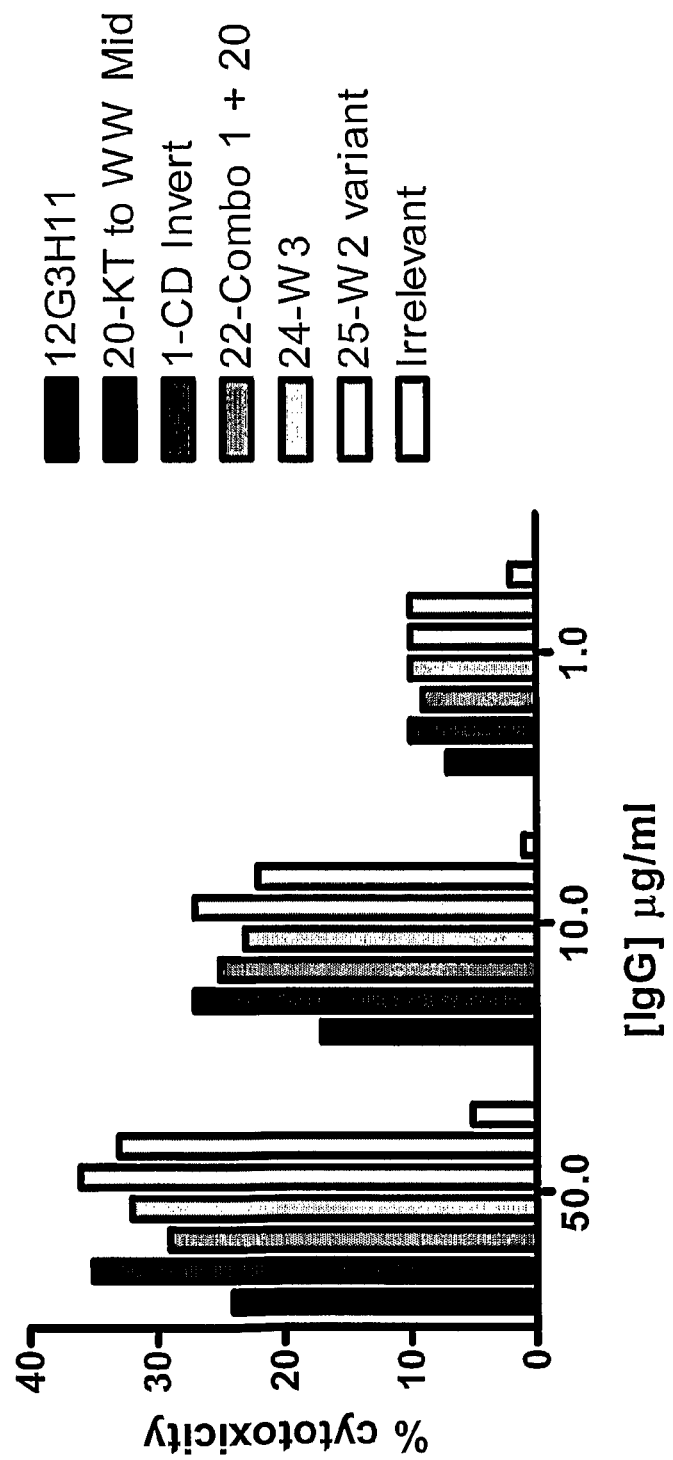

FIG. 27 shows the CDC activity against human EphA2-transfected CT26 cells of wild type 12G3H11 antibody, an irrelevant control antibody, Fc variants with combinatorial and alternative modifications (21, 24 and 25) and two previously analyzed Fc variants (1 and 20) which show significantly increased CDC activity. As was previously seen Fc variants 1 and 20 showed increased CDC activity in addition, the Fc variants 22, 24 and 25 showed increased CDC activity. The same result was seen for untransfected KATOIII cells, EphA2-transfected KATOIII and CHO cells (see FIGS. 26, 28-30).

Figure 28:
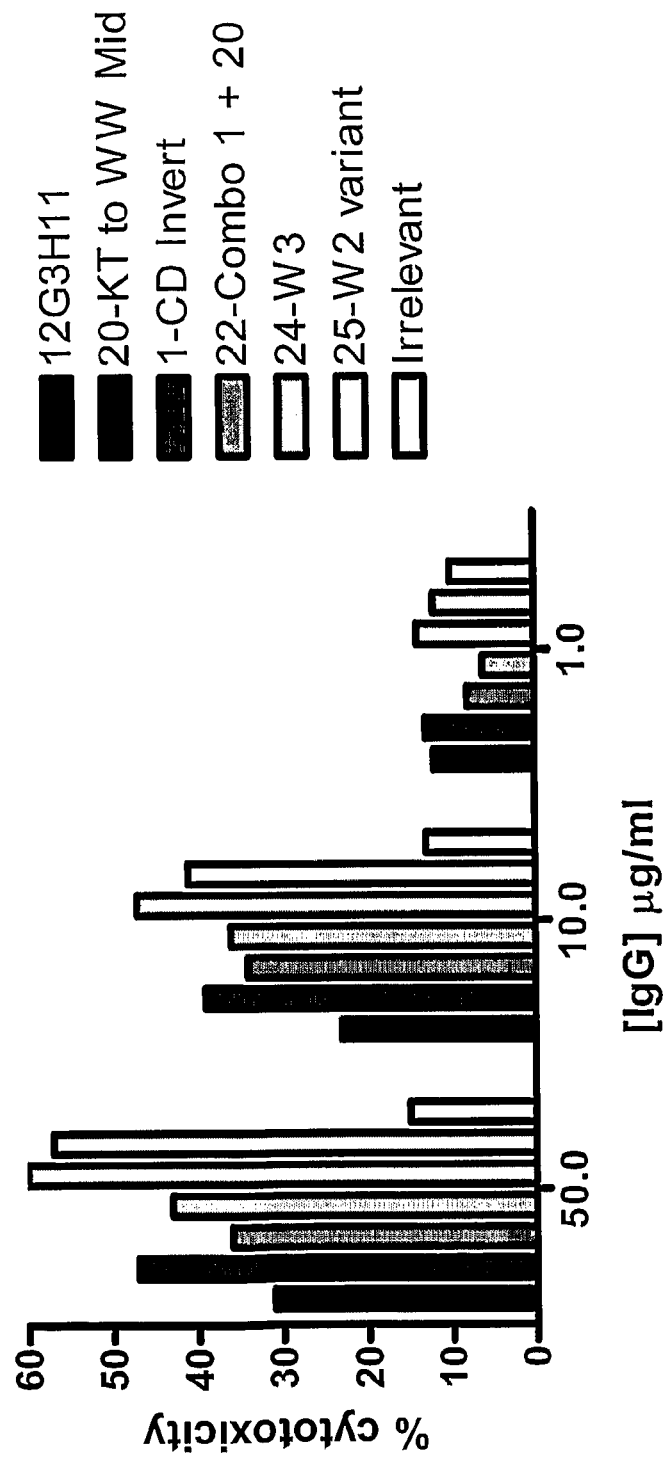

FIG. 28 shows the CDC activity against cynomolgous EphA2-transfected CHO cells of wild type 12G3H11 antibody, an irrelevant control antibody, Fc variants with combinatorial and alternative modifications (22, 24 and 25) and two previously analyzed Fc variants (1 and 20) which show significantly increased CDC activity. As was previously seen Fc variants 1 and 20 showed increased CDC activity in addition, the Fc variants 22, 24 and 25 showed increased CDC activity. The same result was seen for untransfected KATOIII cells, EphA2-transfected KATOIII, CT26 and CHO cells (see FIGS. 26, 27, 29-30).

Figure 29:
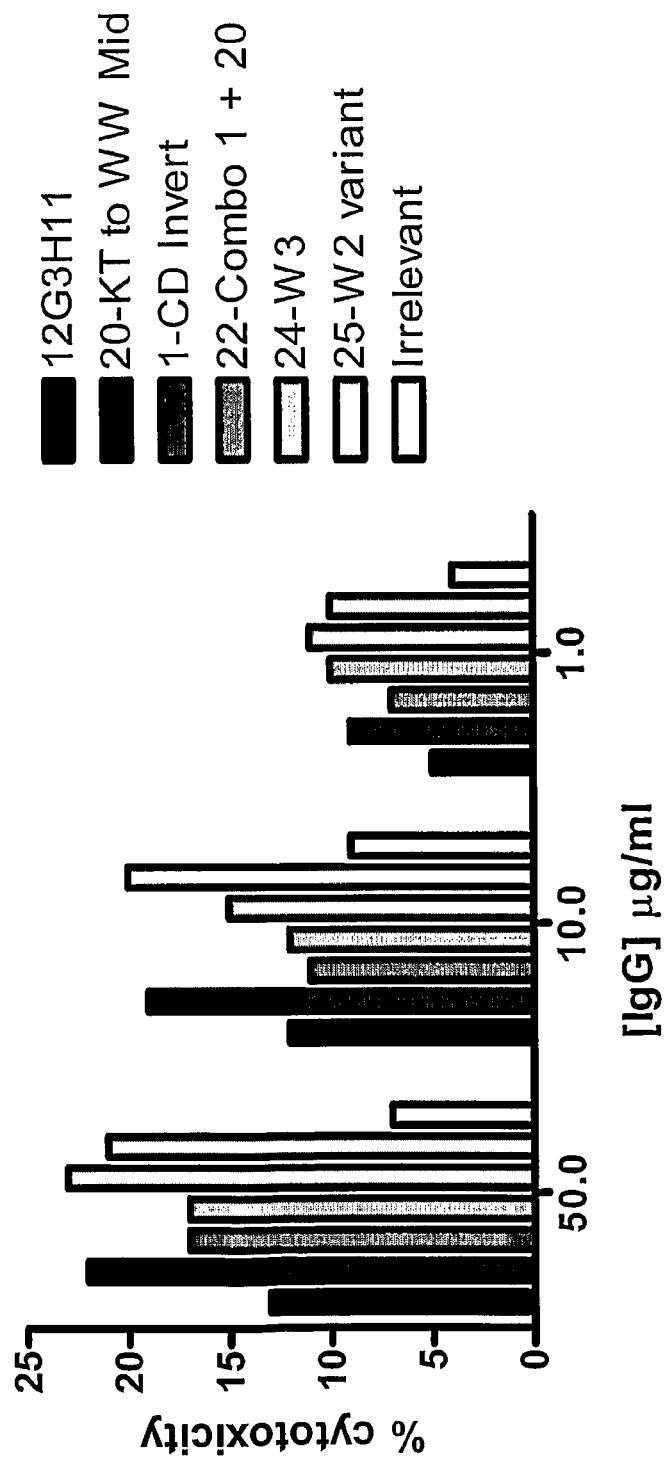

FIG. 29 shows the CDC activity against human EphA2-transfected KATOIII cells of wild type 12G3H11 antibody, an irrelevant control antibody, Fc variants with combinatorial and alternative modifications (22, 24 and 25) and two previously analyzed Fc variants (1 and 20) which show significantly increased CDC activity. As was previously seen Fc variants 1 and 20 showed increased CDC activity in addition the Fc variants 22, 24 and 25 showed increased CDC activity. The same result was seen for untransfected KATOIII cells, EphA2-transfected CT26 and CHO cells (see FIGS. 26, 27-28, 30).

Figure 30:
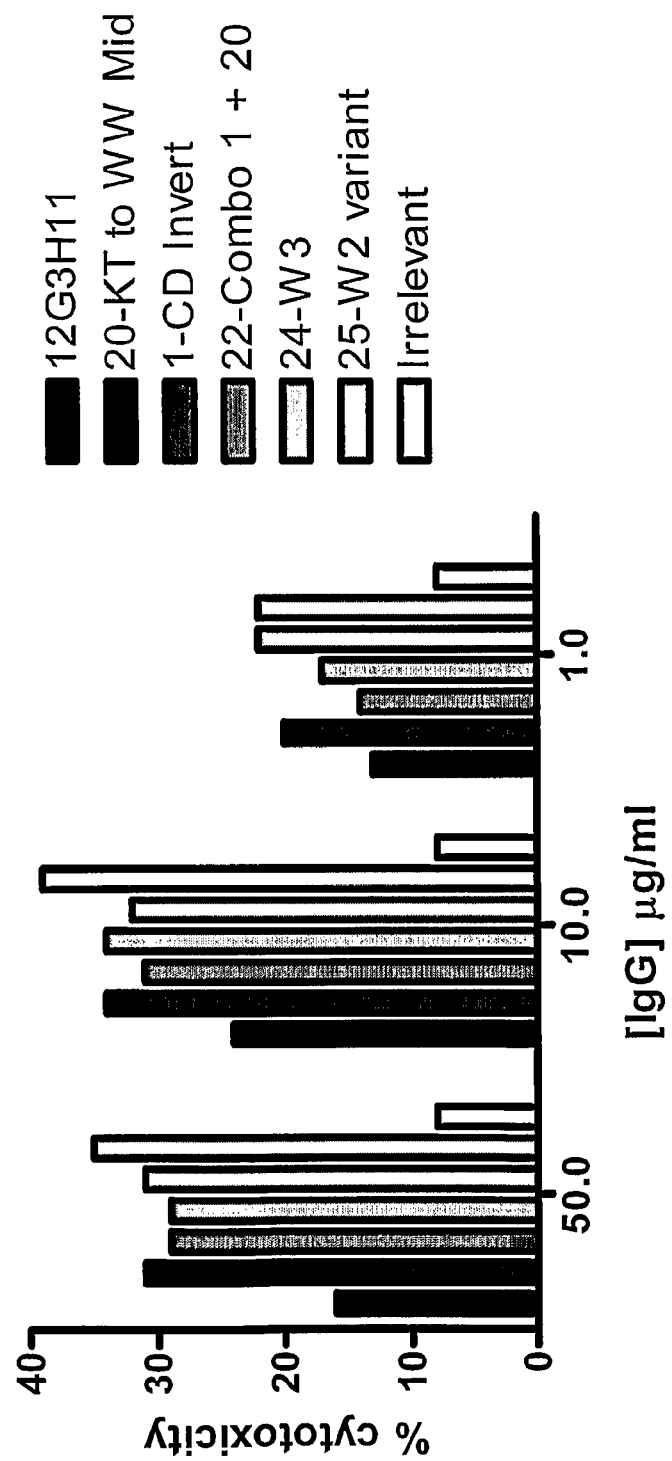

FIG. 30 shows the CDC activity against human EphA2-transfected CHO cells of wild type 12G3H11 antibody, an irrelevant control antibody, Fc variants with combinatorial and alternative modifications (22, 24 and 25) and two previously analyzed Fc variants (1 and 20) which show significantly increased CDC activity. As was previously seen Fc variants 1 and 20 showed increased CDC activity in addition the Fc variants 22, 24 and 25 showed increased CDC activity. The same result was seen for untransfected KATOIII cells, EphA2-transfected CT26, CHO and KATO cells (see FIGS. 26-29).

Figure 10:
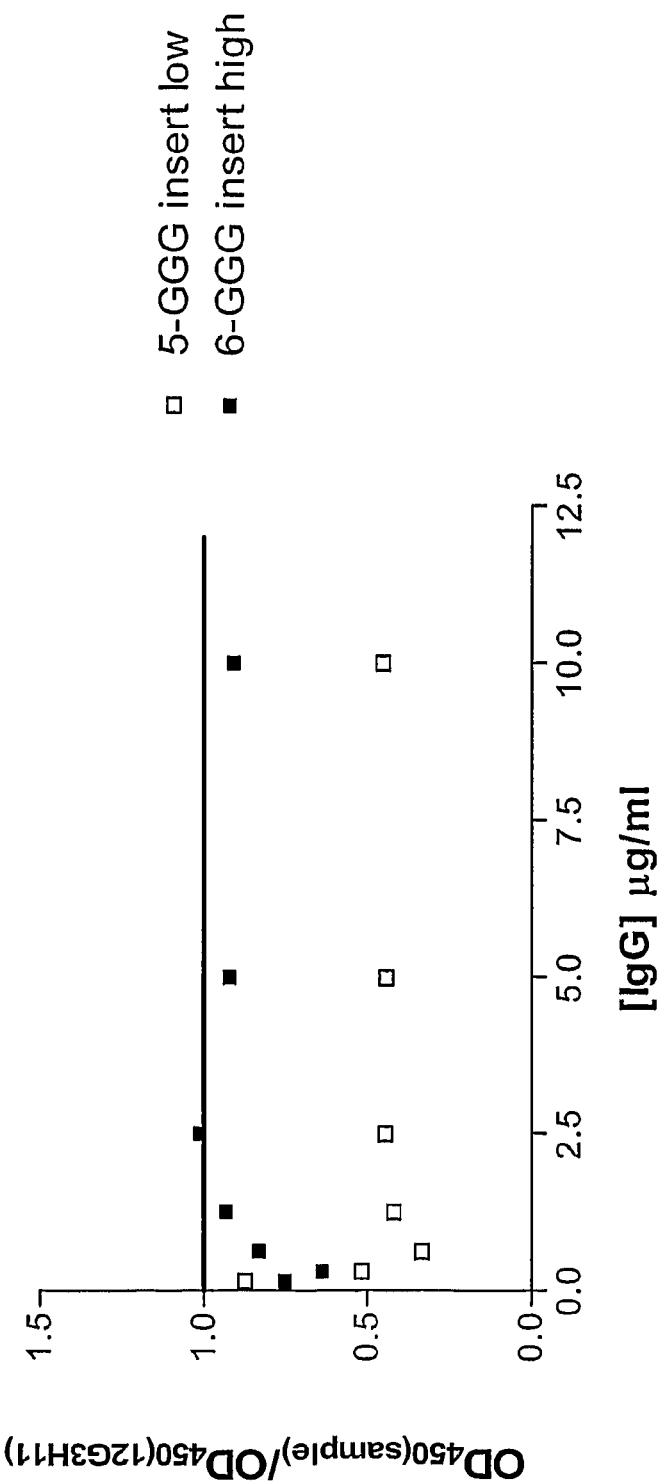
Figure 11:
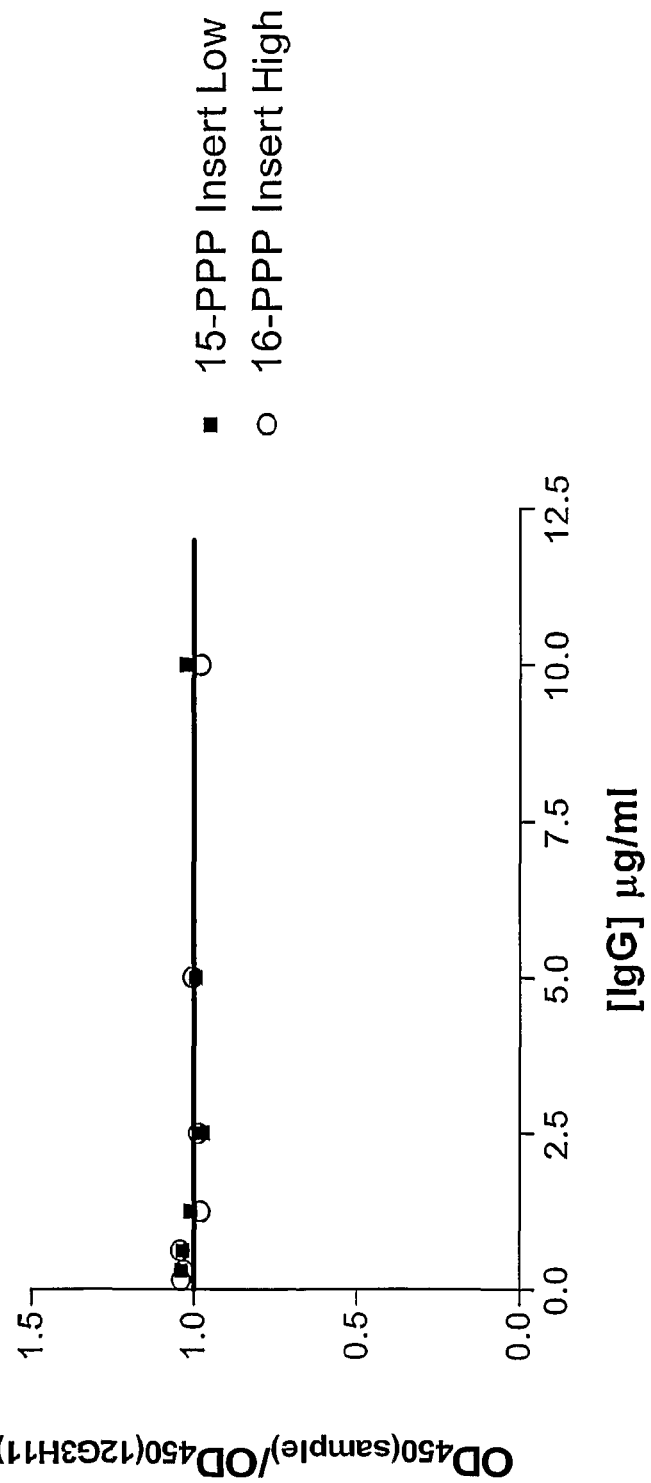
Figure 12:
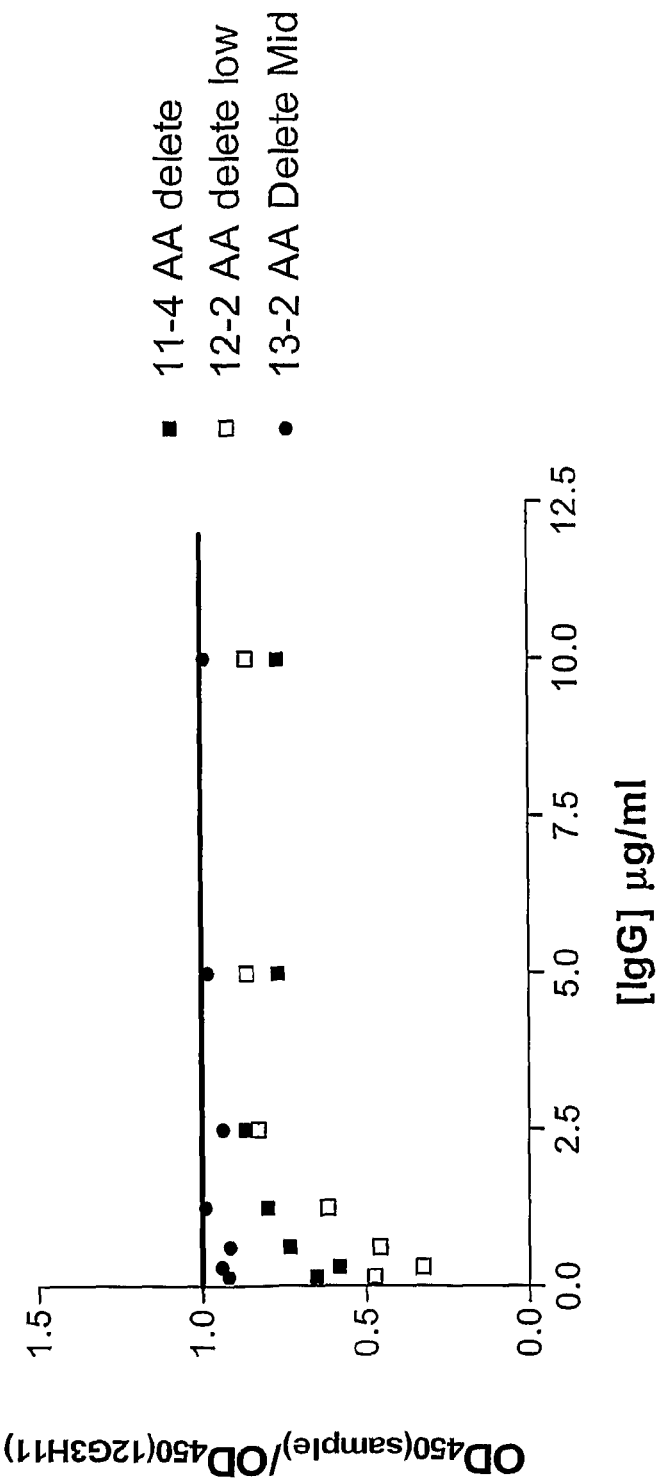
Figure 13:
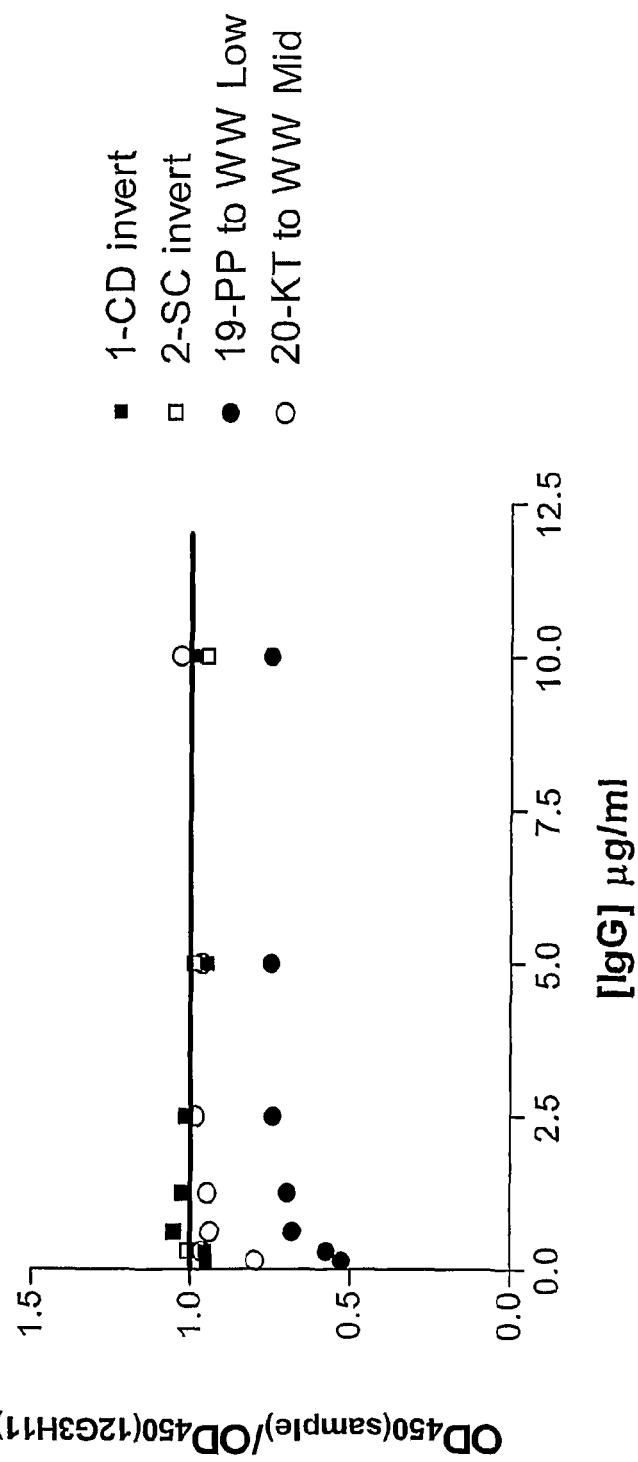
Figure 31:
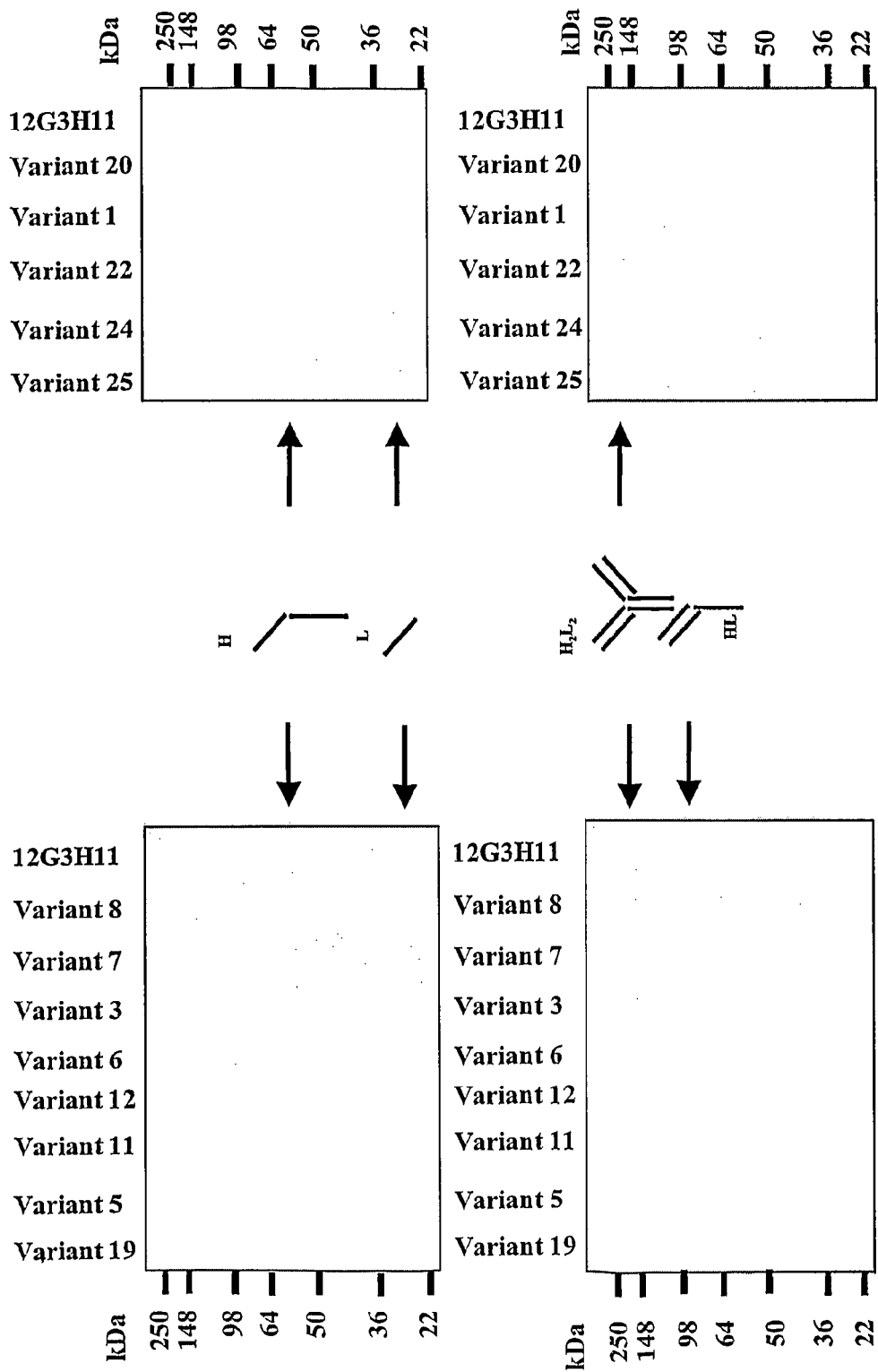

FIG. 31 10% SDS-PAGE profile of purified 12G3H11 and select hinge variants under reducing (top panels) and non reducing (bottom panels) conditions. Lanes 6 and 12, molecular mass standards (SeeBlue Plus 2, Invitrogen, CA) the variants are indicated along the top. H=heavy chain. L=light chain.

7. DETAILED DESCRIPTION OF THE INVENTION

The present invention provides modified hinge regions comprising specific amino acid residues and/or lacking specific amino acid residues. The present invention also provides modified hinge regions which exhibit alterations in one or more characteristics including, but not limited to, flexibility, length, conformation, charge and hydrophobicity, relative to a wild type hinge. Modifications which may be utilized to generate a modified hinge of the invention include, but are not limited to, amino acid insertions, deletions, substitutions, and rearrangements). Said modifications of the hinge and the modified hinges are referred to herein jointly as "hinge modifications of the invention", "modified hinge(s) of the invention" or simply "hinge modifications" or "modified hinge(s)." These modified hinges may be incorporated into a molecule of choice. Accordingly, the present invention further provides molecules, in particular polypeptides, more specifically immunoglobulins (e.g., antibodies) and other binding proteins, comprising an Fc region (as used herein "Fc region" and similar terms encompass any heavy chain constant region domain comprising at least a portion of the hinge region) incorporating a modified hinge. Molecules comprising Fc regions comprising a modified hinge (e.g., a hinge region comprising one or more amino acid insertions, deletions, substitutions, or rearrangements) are referred to herein as "Fc variants of the invention" or "Fc variants." In particular, the present invention provides modified hinges that alter Fc binding to one or more Fc ligand (e.g., FcγRs, C1q) and/or Fc mediated effector function when compared to to the same molecule comprising an Fc region without said modified hinge (e.g., the same molecule comprising an Fc region having a wild type hinge). In addition, the present invention provides certain modified hinge regions that alter the binding of the Fc regions comprising them to one or more Fc ligands (e.g., FcγRs, C1q) and/or modulate effector function when compared to an Fc region comprising a wild type hinge.

Fc ligands for which the Fc variants of the invention may have altered binding affinity for include, but are not limited to, FcγRs, FcRn, C1q, C3, staphylococcal protein A, streptococcal protein G, viral FcγR and undiscovered molecules that bind Fc.

Fc binding interactions are essential for a variety of effector functions and downstream signaling events such as antibody dependent cell-mediated cytotoxicity (ADCC) activity and complement dependent cytotoxicity (CDC). Accordingly, the invention provides Fc variants comprising modified hinges that exhibit altered binding affinity for at least one Fc ligand (e.g., FcγRIIIA, C1q) relative to an molecule having the same amino acid sequence as the Fc variant of the invention except for the modified hinge (referred to herein as a "comparable molecule"). A specific example of a comparable molecule would be an Fc variant having an unmodified or wild type hinge region. In one embodiment, the invention encompasses Fc variants with altered binding to C1q. In another embodiment, the invention encompasses Fc variants with altered binding to FcγRIIIA. In some embodiments, the Fc variant with altered binding to FcγRIIIA does not have concomitant change in binding the FcγRIIB receptor. In other embodiments, the presence of a modified hinge results in Fc variants with altered antibody dependent cell-mediated cytotoxicity (ADCC) activity. In still other embodiments, the Fc variants of the invention have altered complement dependent cytotoxicity (CDC).

The present invention further provides Fc variants that specifically bind to at least one antigen, said Fc variants comprising an Fc region incorporating a modified hinge. The present invention also relates to antibodies comprising Fc regions incorporating a modified hinge that have altered binding affinity for Fc ligands when compared to that of the original antibodies (i.e. antibodies prior to modification of the hinge, referred to herein as "comparable molecule(s)") or counterpart antibodies (i.e. antibodies containing naturally occurring amino acid residues at the corresponding position in the hinge, also referred to herein as "comparable molecule(s)").

The Fc variants of the present invention may be produced "de novo" by combining a variable domain, or fragment thereof, that specifically binds at least one antigen with an Fc region comprising a modified hinge as disclosed herein. Alternatively, or optionally, the Fc variants of the invention may be produced by modifying the hinge of an Fc region-containing antibody that binds an antigen.

In one embodiment, the Fc variants have higher binding affinity to activating FcγRs (e.g., FcγRIIIA), relative to a comparable molecule. In another embodiment the Fc variants have higher binding affinity to activating FcγRs and unchanged or lower binding affinity to inhibitory FcγRs (e.g., FcγRIIB), relative to a comparable molecule. In still another embodiment, the Fc variants of the invention also exhibit increased ADCC activity, relative to a comparable molecule in addition to the above changes in FcγR affinities. In yet another embodiment, the Fc variants of the invention specifically bind to at least one antigen.

The present invention also relates to Fc variants with a higher binding affinity to inhibitory FcγRs and a lower binding affinity to activating FcγRs compared to that of comparable molecules. It is contemplated that the Fc variants will also exhibit a reduced ability to mediate ADCC activity, relative to a comparable molecule. In one embodiment, the Fc variants of the invention specifically bind to at least one antigen.

In addition, the present invention further provides novel Fc variants with altered binding to C1q, relative to comparable molecules. In one embodiment, the Fc variants of the invention may exhibit a higher binding affinity for C1q and increased CDC activity. Alternatively, the Fc variants of the invention may exhibit a lower binding affinity for C1q and reduced CDC activity. It is specifically contemplated that the Fc variants with alterations in C1q binding and CDC activity may also exhibit alterations in binding to one or more FcγRs and/or ADCC activity. In a specific embodiment, the Fc variants of the invention specifically bind to at least one antigen.

As used herein, the terms "antibody" and "antibodies" refer to monoclonal antibodies, multispecific antibodies, human antibodies, humanized antibodies, camelised antibodies, chimeric antibodies, single-chain Fvs (scFv), disulfide-linked Fvs (sdFv), Fab fragments, F (ab') fragments, and anti-idiotypic (anti-Id) antibodies (including, e.g., anti-Id antibodies to antibodies of the invention), and epitope-binding fragments of any of the above. In particular, antibodies include immunoglobulin molecules and immunologically active fragments of immunoglobulin molecules, i.e., molecules that contain an antigen binding site, these fragments may or may not be fused to another immunoglobulin domain including but not limited to, an Fc region or fragment thereof. As outlined herein, the terms "antibody" and "antibodies" specifically include the Fc variants described herein, full length antibodies and Fc variant-fusions comprising Fc regions, or fragments thereof, comprising a modified hinge of the invention described herein fused to an immunologically active fragment of an immunoglobulin or to other proteins as described herein. Such Fc variant-fusions include but are not limited to, scFv-Fc fusions, variable region (e.g., VL and VH)-Fc fusions, scFv-scFv-Fc fusions. Immunoglobulin molecules can be of any type (e.g., IgG, IgE, IgM, IgD, IgA and IgY), class (e.g., IgG1, IgG2, IgG3, IgG4, IgA1 and IgA2) or subclass.

As used herein, the term "specifically binds" and analogous terms refer to peptides, polypeptides, proteins, fusion proteins and antibodies or fragments thereof that specifically bind to a molecule or a fragment thereof (e.g., antigen). A peptide, polypeptide, protein, or antibody that specifically binds a molecule or a fragment thereof may bind to other molecules with lower affinity as determined by, e.g., immunoassays, BIAcore, or other assays known in the art. Antibodies or fragments that specifically bind to at least one molecule or a fragment thereof may be cross-reactive with related molecules. In particular, antibodies or fragments that specifically bind to at least one molecule or a fragment thereof can compete off molecules that bind non-specifically. The present invention specifically encompasses antibodies with multiple specificities (e.g., an antibody with specificity for two or more discrete antigens (reviewed in Cao et al., 2003, *Adv Drug Deliv Rev* 55:171; Hudson et al., 2003, *Nat Med* 1:129)) in the definition of specifically binds. For example, bispecific antibodies contain two different binding specificities fused together. In the simplest case a bispecific antibody would bind to two adjacent epitopes on a single target antigen, such an antibody would not cross-react with other antigens (as described supra). Alternatively, bispecific antibodies can bind to two different antigens, such an antibody specifically binds to two different molecules but not to other unrelated molecules.

Peptides, polypeptides, proteins, fusion proteins and in particular antibodies or fragments thereof that specifically bind to a molecule with higher affinity than to any cross-reactive molecules can be identified by numerous techniques known to those of skill in the art including. See, e.g., Paul, ed., 1989, Fundamental Immunology Second Edition, Raven Press, New York at pages 332-336 for a discussion regarding antibody specificity. Immunoassays which can be used to analyze specific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Current Protocols in Molecular Biology, Vol. 1, John Wiley & Sons, Inc., New York).

Without wishing to be bound by any particular theory, the modified hinges of the invention can alter the affinity of an Fc region for one or more Fc ligands (e.g., FcγRs, C1q) by modulating one or more of the factors that regulate protein-protein interactions (e.g., receptor-ligand and antibody-antigen interactions). Such factors include but are not limited to, factors affecting protein folding or three dimensional configuration such as hydrogen bonds, hydrophobic interactions, ionic interactions, Von der Waals forces and/or disulfide bonds as well as factors affecting allosteric interactions, solubility and covalent modifications.

Without wishing to be bound by any particular theory, the modified hinges of the invention can modulate the ADCC and/or CDC activity of an antibody by altering one more of the factors that influence downstream effector function including but not limited to, the affinity of the Fc region for its FcγRs and/or to C1q, ability to mediate cytotoxic effector and/or complement cascade functions, protein stability, antibody half life and recruitment of effector cells and/or molecules.

The constant region of the heavy chain of IgG may be divided into four smaller domains, CH1, hinge, CH2 and CH3. As used herein "Fc region" and similar terms encompasses any heavy chain constant region domain comprising at least a portion of the hinge region and may include the entire hinge region. Accordingly, Fc region as defined herein comprises a hinge region or fragment thereof, and may additionally comprise one or more addition constant region domains, or fragments thereof, including CH1, CH2 CH3. It will be understood that the numbering of the Fc amino acid residues is that of the EU index as in Kabat et al., 1991, NIH Publication 91-3242, National Technical Information Service, Springfield, Va. The "EU index as set forth in Kabat" refers to the EU index numbering of the human IgG1 Kabat antibody. The "Kabat index as set forth in Kabat" refers to the Kabat index numbering of the IgG1 Kabat antibody. For informational purposes the normal hinge region of human IgG1 using the Kabat index (see Kabat ibid) is presented in Table 2 along with the same region numbered using the EU index. Furthmore, the Kabat numbers may be provided in addition to the EU numbers when referring to particular amino acid residues for clarity.

The "hinge region" is generally defined as stretching from 216-238 (EU numbering) or 226-251 (Kabat numbering) of human IgG1. The hinge may be further divided into three distinct regions, the upper, middle and lower hinge. In a human IgG1 antibody these regions are generally defined as follows:

Upper hinge: 216-225 (EU numbering) or 226-238 (Kabat numbering).

Middle hinge: 226-230 (EU numbering) or 239-243 (Kabat numbering).

Lower hinge: 231-238 (EU numbering) or 244-251 (Kabat numbering).

Hinge regions of other IgG isotypes may be aligned with the IgG 1 sequence by placing the first and last cysteine residues forming inter-heavy chain S-S binds in the same positions (see for example Table 1 of Brekke et al., 1995, *Immunol. Today* 16: 85-90).

It will be understood that the complementarity determining regions (CDRs) residue numbers referred to herein are those of Kabat et al. (1991, NIH Publication 91-3242, National Technical Information Service, Springfield, Va.). Specifically, residues 24-34 (CDR1), 50-56 (CDR2) and 89-97 (CDR3) in the light chain variable domain and 31-35 (CDR1), 50-65 (CDR2) and 95-102 (CDR3) in the heavy chain variable domain. Note that CDRs vary considerably from antibody to antibody (and by definition will not exhibit homology with the Kabat consensus sequences). Maximal alignment of framework residues frequently requires the insertion of "spacer" residues in the numbering system, to be used for the Fv region. It will be understood that the CDRs referred to herein are those of Kabat et al. supra. In addition, the identity of certain individual residues at any given Kabat site number may vary from antibody chain to antibody chain due to interspecies or allelic divergence.

In one embodiment, Fc variants of the invention comprise a modified hinge of the present invention. The amino acid sequence of several modified hinges are detailed in Table 2. It is specifically contemplated that an Fc variant of the invention may comprise and/or lack specific amino acid residues from more then one of the modified hinges detailed in Table 2.

In a specific embodiment, an Fc variant of the invention comprises at least one amino acid residue selected from those detailed in Table 3. In another specific embodiment, and Fc variant comprises more then one amino acid residue selected from those detailed in Table 3. In another specific embodiment, an Fc variant of the invention is lacking at least one amino acid normally present in a wild type hinge. Specific amino acids which may be absent from an Fc variant of the invention are detailed in Table 3.

In one embodiment, the present invention provides methods of altering the binding affinity for an Fc ligand and/or the effector function of a polypeptide comprising an Fc region, wherein said Fc region comprises a hinge region, said method comprising introducing a modification into the hinge region. In a specific embodiment, the hinge is modified as detailed in Table 2. In certain embodiments, the hinge is modified by a combination of the modifications detailed in Table 2. In another specific embodiment, the hinge is modified to incorporate at least one amino acid residue selected from those detailed in Table 3. In still another specific embodiment, the hinge is modified to remove at least one amino acid normally present in a wild type hinge. Specific amino acids which may be removed from a hinge region are detailed in Table 3. In other embodiments, the hinge is modified to incorporate at least one amino acid residue selected from those detailed in Table 3 and to remove at least one amino acid selected from those detailed in Table 3. In still other embodiments, a hinge is modified as detailed in Table 2 and further modified to add and/or remove at least one additional amino acid residue selected from those detailed in Table 3.

In certain embodiments, the methods of altering the binding affinity for an Fc ligand of a polypeptide comprising an Fc region improve the binding affinity for an Fc ligand. In a specific embodiment the binding affinity for FcγRIIIA is improved. In another specific embodiment, the binding affinity for C1q is improved. In other embodiments, the methods of altering the binding affinity for an Fc ligand of a polypeptide comprising an Fc region decrease the binding affinity for an Fc ligand. In a specific embodiment the binding affinity for FcγRIIIA is decreased. In another specific embodiment, the binding affinity for C1q is decreased.

In certain embodiments, the methods of altering the effector function of a polypeptide comprising an Fc region, wherein said Fc region comprises a hinge region improve the effection fuction. In a specific embodiment, the ADCC activity is improved. In another specific embodiment, the CDC activity is improved. In other embodiments, the methods of altering the effector function of a polypeptide comprising an Fc region, wherein said Fc region comprises a hinge region reduce the effection fuction. In a specific embodiment, the ADCC activity is decreased. In another specific embodiment, the CDC activity is decreased.

TABLE 2

Hinge Modifications/Modified Hinges<sup>a</sup>:

The numbering of the hinge residues according to the EU (bold) index or Kabat (italics) index are shown at the top and bottom, respectively.

| Upper Hinge (216-225) | | | | | | | | | | Middle Hinge (226-230) | | | | | |
|---|---|---|---|---|---|---|---|---|---|---|---|---|---|---|---|
| E (216) | P (217) | K (218) | S (221) | C<sup>b</sup> | D<sup>b</sup> | K (222) | T (223) | H (224) | T (225) | C (226) | P (227) | P (228) | C (229) | P (230) | EU |
| Modifications that may increase the flexibility of the human IgG1 hinge region: | | | | | | | | | | | | | | | |
| <u>G</u> | <u>G</u> | <u>G</u> | <u>G</u> | C | D | K | T | H | T | C | P | P | C | P | "10-EPKS to GGGG" |
| E | P | K | S | C | <u>G</u> | <u>G</u> | <u>G</u> | <u>G</u> | <u>G</u> | C | P | P | C | P | "9-DKTHT to GGGGG" |
| E | P | K | S | C | D | K | T | H | T | C | <u>G</u> | <u>G</u> | C | P | "8-PP to GG Low" |
| E | P | K | S | C | D | K | T | H | T | C | P | P | C | <u>G</u> | "7-P to G Low" |
| E | P | K | S | C | D | K | T | H | T | C | P | P | <u>S</u> | P | "3-C to S low" |
| E | P | K | S | C | D | K | T | H | T | <u>S</u> | P | P | C | P | "4-C to S Middle" |
| Modifications that may decrease the flexibility of the human IgG1 hinge region: | | | | | | | | | | | | | | | |
| E | P | K | S | C | D | K | <u>C</u> | H | T | C | P | P | C | P | "14-T to C Middle" |
| E | P | K | S | C | D | K | T | <u>C</u> | <u>C</u> | C | P | P | C | P | "21-HT to CC Middle" |

TABLE 2-continued

Hinge Modifications/Modified Hinges[a]:

The numbering of the hinge residues according to the EU (bold) index or Kabat (italics) index are shown at the top and bottom, respectively.

| Upper Hinge (216-225) | | | | | | | | | | Middle Hinge (226-230) | | | | | |
|---|---|---|---|---|---|---|---|---|---|---|---|---|---|---|---|
| E | P | K | S | | | K | T | H | T | C | P | P | C | P | EU |
| (216) | (217) | (218) | (221) | C[b] | D[b] | (222) | (223) | (224) | (225) | (226) | (227) | (228) | (229) | (230) | |
| E | P | K | S | C | *P* | *P* | *P* | *P* | *P* | C | P | P | C | P | "17-DKTHT to PPPPP" |
| *P* | P | *P* | *P* | C | D | K | T | H | T | C | P | P | C | P | "18-EPKS to PPPP" |

Modifications that will decrease the length of the human IgG1 hinge region:

| E | P | K | S | C | D | K | T | H | T | C | — | — | C | P | "12-2 AA Delete Low" |
| E | P | K | S | C | D | K | — | — | T | C | P | P | C | P | "13-2 AA Delete Mid" |
| E | P | K | S | C | D | K | — | — | T | C | — | — | C | P | "11-4 AA Delete" |

Modifications that will increase the length and may increase the flexibility of the human IgG1 hinge region:

| E | P | K | S | C | D | K | T | H | T | C | P | *GGG* | P | C | P | "5-GGG Insert Low" |
| E | P | K | S | C | *DGGG* | K | T | H | T | C | P | P | C | P | "6-GGG Insert High" |

Modifications that will increase the length and may decrease the flexibility of the human IgG1 hinge region:

| E | P | K | S | C | *DPPP* | K | T | H | T | C | P | P | C | P | "16-PPP Insert High" |
| E | P | K | S | C | D | K | T | H | T | C | P | *PPP* | P | C | P | "15-PPP Insert Low" |

Modifications that may alter the overall conformation of the human IgG1 hinge region:

| E | P | K | S | C | D | K | T | H | T | C | *W* | *W* | C | P | "19-PP to WW Low" |
| E | P | K | S | C | D | *W* | *W* | H | T | C | P | P | C | P | "20-KT to WW Mid" |
| E | P | K | *C* | *S* | D | K | T | H | T | C | P | P | C | P | "2-SC Invert" |
| E | P | K | S | *D* | *C* | K | T | H | T | C | P | P | C | P | "1-CD Invert" |

Combinatorial and Alternative Modifications:

| E | P | K | S | *D* | *C* | *W* | *W* | H | T | C | P | P | C | P | "22-Combo 1 + 20" |
| E | P | K | S | C | D | *W* | T | H | T | C | P | P | C | P | "27-W first" |
| E | P | K | S | C | D | K | *W* | H | T | C | P | P | C | P | "28-W second" |
| E | P | K | S | C | D | *F* | *F* | H | T | C | P | P | C | P | "23-F2" |
| E | P | K | S | C | D | *W* | *W* | *W* | T | C | P | P | C | P | "24-W3" |
| E | P | K | S | *W* | *W* | T | H | T | C | P | P | C | P | "25-W2 variant" |
| E | P | *W* | *W* | C | D | K | T | H | T | C | P | P | C | P | "26-WW upper" |

| E | P | K | S | C | D | K | T | H | T | C | P | P | C | P | *Kabat* |
| (226) | (227) | (228) | (232) | (233) | (234) | (235) | (236) | (237) | (238) | (239) | (240) | (241) | (242) | (243) | |

[a]The names listed to the right designate Fc variants comprising the modified hinge, these Fc variants may also be referred to simply by the number indicated above.
[b]these residues have no EU number.

TABLE 3

Specific Hinge Residues

| Specific Amino Acid Residue[a] | EU number | Kabat number |
|---|---|---|
| G, P | 216 | 226 |
| G | 217 | 227 |
| G, P, W | 218 | 228 |
| G, P, C, W | 221 | 232 |
| S, D | no EU number | 233 |
| G, P, C, W | no EU number | 234 |
| G, P, W, F | 222 | 235 |
| G, C, P, W, F, — | 223 | 236 |
| G, C, P, W, — | 224 | 237 |
| G, C, P | 225 | 238 |
| S | 226 | 239 |
| G, W, — | 227 | 240 |
| G, W, — | 228 | 241 |
| S | 229 | 242 |
| G | 230 | 243 |
| GGG | prior[b] to 222 | prior[b] to 235 |
| PPP | prior[b] to 222 | prior[b] to 235 |
| GGG | prior[b] to 228 | prior[b] to 241 |
| PPP | prior[b] to 228 | prior[b] to 241 |

[a]Each amino acid listed may be present at the indicated position, a dashed line indicates that no amino acid residue may also be present in this position.
[b]The specific amino acids residues indicated are located immediately adjacent and just prior to this position.

In one embodiment, Fc variants of the invention will have at least a modified hinge (e.g., a hinge region comprising one or more amino acid insertions, deletions, substitutions, or rearrangements) wherein said Fc variant has an altered binding affinity for one or more Fc ligand (e.g., FcγRs, C1q), relative to a comparable molecule.

The present invention encompasses Fc variants comprising an Fc region incorporating a hinge modification, said modification altering one or more characteristics of the hinge including, but not limited to, flexibility, length, conformation, charge and hydrophobicity. The present invention also encompasses Fc variants comprising a modified hinge, said modified hinge exhibiting one or more altered characteristics relative to a wild type hinge including, but not limited to, flexibility, length, conformation, charge and hydrophobicity. The modified hinges of the invention may be generated by methods well know in the art, such as, for example, introducing a modification into a wild type hinge. Hinge modifications which may be utilized in generating a modified hinge include, but are not limited to, insertions, deletions, inversions and substitutions of one or more amino acid residues. It will be appreciated by one skilled in the art that combinations of insertions and/or deletions and/or substitutions may also be used to generate a modified hinge of the invention.

In certain embodiments, the invention encompasses hinge modifications which are the insertion of at least one amino acid residue in the hinge. In one embodiment, at least one, or at least two, or at least three, or at least four, or at least five, or at least ten, or at least 15 amino acid residues are inserted in the hinge. In one embodiment, the insertion is made in the upper hinge. In another embodiment, the insertion is made in the middle hinge. In another embodiment, the insertion is made in the lower hinge. In still another embodiment, insertions are made in more the one position including, but not limited to, the upper hinge, the middle hinge and the lower hinge.

In other embodiments, the invention encompasses hinge modifications which are the deletion of at least one amino acid residues in the hinge. In one embodiment, at least one, or at least two, or at least three, or at least four, or at least five, or at least ten, or at least fifteen amino acid residues are deleted in the hinge. In one embodiment, the deletion is made in the upper hinge. In another embodiment, the deletion is made in the middle hinge. In another embodiment, the deletion is made in the lower hinge. In still another embodiment, deletions are made in more the one position including, but not limited to, the upper hinge, the middle hinge and the lower hinge.

In still other embodiments, the invention encompasses hinge modifications which are the substitution of at least one amino acid residues in the hinge. In one embodiment, at least one, or at least two, or at least three, or at least four, or at least five, or at least ten, or at least fifteen amino acid residues are substituted in the hinge. In one embodiment, the substitution is made in the upper hinge. In another embodiment, the substitution is made in the middle hinge. In another embodiment, the substitution is made in the lower hinge. In still another embodiment, substitutions are made in more the one position including, but not limited to, the upper hinge, the middle hinge and the lower hinge. In a specific embodiment, an Fc variant of the invention comprises at least one substitution in the middle hinge region, wherein the substitution is selected from the group consisting of: P227W and P228W, wherein the numbering system is that of the EU index as set forth in Kabat, or the substitution is selected from the group consisting of: P240W and P241W, wherein the numbering system is that of the Kabat index as set forth in Kabat. Additional specific substitutions are described in Table 2. Fc variants comprising any combination of the hinge modifications set forth in Tables 2 and 3 are specifically contemplated as embodiments of the invention.

In one embodiment, the invention encompasses a molecule comprising an Fc variant, wherein said Fc variant comprises a modified hinge that has altered (e.g., increased or decreased) flexibility of the hinge, relative to a wild type hinge. A modified hinge having altered flexibility of the hinge may be generated by incorporating certain modifications into a wild type hinge. Hinge modifications which increase the flexibility of the hinge include but are not limited to, the substitution of one or more amino acids residues with one or more amino acid residues which increase the flexibility (e.g., Glycine), the substitution of a cysteine involved in the formation of a disulfide bond with an amino acid residue which can not form a disulfide bond (e.g. Serine, Alanine, Glycine), the insertion of one or more amino acid residues which allow for a high degree of local flexibility (e.g., Glycine) and the deletion of one or more amino acid residues which increase the rigidity of a polypeptide (e.g., Proline). Hinge modifications which decrease the flexibility of the hinge include but are not limited to the substitution of one or more amino acids residues with one or more amino acid residues which increase the rigidity of the polypeptide (e.g., Proline), the substitution of an amino acid residue which can not form a disulfide bond (e.g. Serine, Alanine, Glycine) with an amino acid residue capable of forming a disulfide bond (e.g. cysteine), the insertion of one or more amino acid residues which increase the rigidity of the polypeptide (e.g., Proline) and the deletion of one or more amino acid residues which increase the flexibility (e.g., Glycine).

It is contemplated that a hinge modification that alters (e.g., increases or decreases) the flexibility of the hinge may be present in one or more defined regions of the hinge including, but not limited to, the upper hinge, the middle hinge and the lower hinge. A hinge modification that alters the flexibility of the hinge may also overlap one or more defined regions of the hinge. In one embodiment, the hinge modification that alters (e.g., increases or decreases) the flexibility of the hinge is made in the upper hinge. In another embodiment, the modification that alters (e.g., increases or decreases) the flexibility of the hinge is made in the middle hinge. In another embodiment, the hinge modification that alters the flexibility of the hinge is made in the lower hinge. In still another embodiment, hinge modifications that alter the flexibility of the hinge are made in more the one position including, but not limited to, the upper hinge, the middle hinge and the lower hinge. In a specific embodiment, an Fc variant of the invention comprises at least one substitution in the middle hinge region, wherein the substitution is selected from the group consisting of: P227G and P228G wherein the numbering system is that of the EU index as set forth in Kabat, or the substitution is selected from the group consisting of: P240G and P241G, wherein the numbering system is that of the Kabat index as set forth in Kabat. Additional specific hinge modifications that alter (e.g., increase or decrease) the flexibility of the hinge are listed in Table 2. Fc variants comprising any combination of the hinge modifications set forth in Tables 2 and 3 are specifically contemplated as embodiments of the invention.

In a specific embodiment, the invention encompasses a molecule comprising an Fc variant, wherein said Fc variant comprises a modified hinge having altered (e.g., increased or decreased) hinge length relative to a wild type hinge. A modified hinge having altered hinge length may be generated by incorporating certain modifications into a wild type hinge. Hinge modifications which increase the length of the hinge include but are not limited to, the addition of one or more amino acids residues within the hinge. Hinge modifications which decrease the length of the hinge include but are not limited to the deletion of one or more amino acids residues within the hinge.

It is contemplated that a hinge modification that alters (e.g., increases or decreases) the length of the hinge may be present in one or more defined regions of the hinge including, but not limited to, the upper hinge, the middle hinge and the lower hinge. A hinge modification that alters the length of the hinge may also overlap one or more defined regions of the hinge. In one embodiment, the hinge modification that alters (e.g., increases or decreases) the length of the hinge is made in the upper hinge. In another embodiment, the hinge modification that alters (e.g., increases or decreases) the length of the hinge is made in the middle hinge. In another embodiment, the hinge modification that alters the length of the hinge is made in the lower hinge. In still another embodiment, hinge modifications that alter the length of the hinge are made in more the one position including, but not limited to, the upper hinge, the middle hinge and the lower hinge. In a specific embodiment, at least one glycine residue is inserted in the middle hinge between residues 227 and 228 wherein the numbering system is that of the EU index as set forth in Kabat, or at least one glycine residue is inserted in the middle hinge between residues 240 and 241, wherein the numbering system is that of the Kabat index as set forth in Kabat. In another specific embodiment, at least one proline residue in the middle hinge is deleted. Additional specific hinge modifications that alter (e.g., increase or decrease) the length of the hinge are listed in Table 2. Fc variants comprising any combination of the hinge modifications set forth in Tables 2 and 3 are specifically contemplated as embodiments of the invention.

In a specific embodiment, the invention encompasses a molecule comprising an Fc variant, wherein said Fc variant comprises a modified hinge having altered the hinge conformation relative to a wild type hinge. A modified hinge having altered hinge conformation may be generated by incorporating certain modifications into a wild type hinge. Hinge modifications which alter the conformation of the hinge include but are not limited to, the substitution of one or more amino acids residues with small side chains (e.g., alanine, glycine) for those with larger more bulky side chains (e.g., tryptophan, proline), the substitution of one or more amino acids residues with larger more bulky side chains (e.g., tryptophan, proline) for those with small side chains (e.g., alanine, glycine), the inversion of two or more amino acid resides within the hinge, the insertion or deletion of one or more amino acid residues with large or bulky side chains (e.g., tryptophan, proline). In addition, hinge modifications which alter the length and/or flexibility of the hinge (see above) may also result in an alteration of the conformation.

It is contemplated that a hinge modification that alters the conformation of the hinge may be present in one or more defined regions of the hinge including, but not limited to, the upper hinge, the middle hinge and the lower hinge. A hinge modification that alters the conformation of the hinge may also overlap one or more defined regions of the hinge. In one embodiment, the hinge modification that alters the conformation of the hinge is made in the upper hinge. In another embodiment, the hinge modification that alters the conformation of the hinge is made in the middle hinge. In another embodiment, the hinge modification that alters the conformation of the hinge is made in the lower hinge. In still another embodiment, hinge modifications that alter the conformation of the hinge are made in more the one position including, but not limited to, the upper hinge, the middle hinge and the lower hinge. In a specific embodiment, an Fc variant of the invention comprises at least one substitution in the upper hinge region, wherein the substitution is selected from the group consisting of: K222W and T223W, wherein the numbering system is that of the EU index as set forth in Kabat, or the substitution is selected from the group consisting of: K235W and T236W, wherein the numbering system is that of the Kabat index as set forth in Kabat. In another specific embodiment, an Fc variant of the invention comprises at least one substitution in the upper hinge region, wherein the substitution is selected from the group consisting of: C(no EU number)D and D(no EU number)C, wherein the substitution occurs between hinge residues 221 and 222, and wherein the numbering system is that of the EU index as set forth in Kabat, or the substitution is selected from the group consisting of: C233D and D234C, wherein the substitution occurs between hinge residues 232 and 235, and wherein the numbering system is that of the Kabat index as set forth in Kabat. Additional specific hinge modifications that may alter the conformation of the hinge are listed in Table 2. Fc variants comprising any combination of the hinge modifications set forth in Tables 2 and 3 are specifically contemplated as embodiments of the invention.

In another specific embodiments, the invention encompasses a molecule comprising an Fc variant, wherein said Fc variant comprises a modified hinge having altered charge relative to a wild type hinge. A modified hinge having altered charge may be generated by incorporating certain modifications into a wild type hinge. Hinge modifications which alter the charge of the hinge include but are not limited to, the substitution of one or more amino acids residues with a neutral charge (e.g., valine, threonine) for those with a charge (e.g., aspartate, glutamate, lysine, arginine), the substitution of one or more amino acid residues with a positive charge (e.g., lysine, arginine) for those with a neutral (e.g., valine, threonine) or negative charge (e.g., aspartate, glutamate), the substitution of one or more amino acid residues with a negative charge (e.g., aspartate, glutamate) for those with a neutral (e.g., valine, threonine) or positive charge (e.g., lysine, arginine) and the insertion or deletion of one or more charged amino acid residues (e.g., aspartate, glutamate, lysine, arginine).

It is contemplated that a hinge modification that alters the charge of the hinge may be present in one or more defined regions of the hinge including, but not limited to, the upper hinge, the middle hinge and the lower hinge. A hinge modification that alters the charge of the hinge may also overlap one or more defined regions of the hinge. In one embodiment, the hinge modification that alters the charge of the hinge is made in the upper hinge. In another embodiment, the hinge modification that alters the charge of the hinge is made in the middle hinge. In another embodiment, the hinge modification that alters the charge of the hinge is made in the lower hinge. In still another embodiment, hinge modifications that alter the charge of the hinge are made in more the one position including, but not limited to, the upper hinge, the middle hinge and the lower hinge. In a specific embodiment, an Fc variant of the invention comprises at least one substitution in the upper hinge region, wherein the substitution is selected from the group consisting of: D(no EU number)P and K222P wherein the numbering system is that of the EU index as set forth in Kabat, or the substitution is selected from the group consisting of: D234P and K235P, wherein the numbering system is that of the Kabat index as set forth in Kabat. Additional specific hinge modifications that may alter the conformation of the hinge are listed in Table 2. Fc variants comprising any combination of the hinge modifications set forth in Tables 2 and 3 are specifically contemplated as embodiments of the invention.

In another specific embodiments, the invention encompasses a molecule comprising an Fc variant, wherein said Fc variant comprises a modified hinge having altered (e.g., increased or decreased) hydrophobicity relative to a wild type hinge. A modified hinge having altered hydrophobicity may be generated by incorporating certain modifications into a wild type hinge. Hinge modifications which alter the hydrophobicity of the hinge include but are not limited to, the substitution of one or more hydrophobic amino acids residues (e.g., valine, leucine) for hydrophilic amino acid residues (e.g., serine, threonine, tyrosine), the substitution of one or more hydrophilic amino acid (e.g., serine, threonine, tyrosine), for hydrophobic amino acids residues (e.g., valine, leucine), and the insertion or deletion of one or more hydrophobic or hydrophilic amino acid residues (e.g., valine, leucine, serine, threonine, tyrosine).

It is contemplated that a modification that alters (e.g., increases or decreases) the hydrophobicity of the hinge may be present in one or more defined regions of the hinge including, but not limited to, the upper hinge, the middle hinge and the lower hinge. A hinge modification that alters the hydrophobicity of the hinge may also overlap one or more defined regions of the hinge. In one embodiment, the hinge modification that alters the hydrophobicity of the hinge is made in the upper hinge. In another embodiment, the hinge modification that alters the hydrophobicity of the hinge is made in the middle hinge. In another embodiment, the hinge modification that alters the hydrophobicity of the hinge is made in the lower hinge. In still another embodiment, hinge modifications that alter the hydrophobicity of the hinge are made in more the one position including, but not limited to, the upper hinge, the middle hinge and the lower hinge.

It will be recognized by one of skill in the art that any given hinge modification may alter more than one characteristic of the hinge. For example the addition of one or more proline residue into the hinge results in a hinge modification that increases the length of the hinge while at the same time potentially decreasing the flexibility. Likewise the substitution of a glycine residue with an aspartate can alter both the charge and the hydrophobicity of the hinge. Other combinations are described above and still others will be apparent to one skilled in the art.

It is specifically contemplated that one may choose to analyze the nature of the amino acid residues present in the hinge prior to making any hinge modifications.

One skilled in the art will appreciate that in some cases an antibody of interest will already have the appropriate amino acid sequence within the hinge such that one or more characteristic (e.g., flexibility, length, conformation, charge and hydrophobicity) of the hinge is altered compared to a wild type hinge. In this situation, additional hinge modifications will only be introduced if further modification is desirable.

The Fc variants of the present invention may be combined with other Fc modifications, including but not limited to modifications that alter effector function. The invention encompasses combining an Fc variant of the invention with other Fc modifications to provide additive, synergistic, or novel properties in antibodies or Fc fusions. It is contemplated that the Fc variants of the invention enhance the phenotype of the modification with which they are combined. For example, if an Fc variant of the invention is combined with a mutant known to bind FcγRIIIA with a higher affinity than a comparable molecule comprising a wild type Fc region; the combination with an Fc variant of the invention likely results in a greater fold enhancement in FcγRIIIA affinity.

In one embodiment, the Fc variants of the present invention may be combined with other known Fc variants such as those disclosed in Duncan et al, 1988, *Nature* 332:563-564; Lund et al., 1991, *J. Immunol.* 147:2657-2662; Lund et al, 1992, *Mol Immunol* 29:53-59; Alegre et al, 1994, *Transplantation* 57:1537-1543; Hutchins et al., 1995, *Proc Natl. Acad Sci USA* 92:11980-11984; Jefferis et al, 1995, *Immunol Lett.* 44:111-117; Lund et al., 1995, *Faseb J* 9:115-119; Jefferis et al, 1996, *Immunol Lett* 54:101-104; Lund et al, 1996, *J Immunol* 157:4963-4969; Armour et al., 1999, *Eur J Immunol* 29:2613-2624; Idusogie et al, 2000, *J Immunol* 164:4178-4184; Reddy et al, 2000, *J Immunol* 164:1925-1933; Xu et al., 2000, *Cell Immunol* 200:16-26; Idusogie et al, 2001, *J Immunol* 166:2571-2575; Shields et al., 2001, *J Biol Chem* 276: 6591-6604; Jefferis et al, 2002, *Immunol Lett* 82:57-65; Presta et al., 2002, *Biochem Soc Trans* 30:487-490); U.S. Pat. Nos. 5,624,821; 5,885,573; 6,194,551; U.S. Pat. App. Publication No. 2005/0064514; International Patent PCT Publication Nos. WO 00/42072 and WO 99/58572.

It will be apparent to one skilled in the art that in addition to the specific amino acid residues described above and listed in Tables 2 and 3, a number of additional amino acid residues may be inserted, deleted and/or substituted in the hinge to change the characteristics of the hinge. Families of amino acid residues having similar properties have been defined in the art and several examples are shown in Table 4.

TABLE 4

Properties of Amino Acid Residues

| Family | Amino Acids |
|---|---|
| non-polar (hydrophobic) | Trp, Phe, Met, Leu, Ile, Val, Ala, Pro, Gly, |
| uncharged polar (hydrophilic) | Ser, Thr, Asn, Gln, Tyr, Cys |
| acidic/negatively charged | Asp, Glu |
| basic/positively charged | Arg, Lys, His |
| Beta-branched | Thr, Val, Ile |
| residues that influence chain orientation | Gly, Pro |
| aromatic | Trp, Tyr, Phe, His |

It is specifically contemplated that conservative amino acid substitutions may be made for said modifications of the hinge, described supra. It is well known in the art that "conservative amino acid substitution" refers to amino acid substitutions that substitute functionally equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. Substitutions that are charge neutral and which replace a residue with a smaller residue may also be considered "conservative substitutions" even if the residues are in different groups (e.g., replacement of phenylalanine with the smaller isoleucine). Families of amino acid residues having similar side chains have been defined in the art. Several families of conservative amino acid substitutions are shown in Table 4 (supra).

The term "conservative amino acid substitution" also refers to the use of amino acid analogs or variants. Guidance concerning how to make phenotypically silent amino acid substitutions is provided in Bowie et al., "Deciphering the Message in Protein Sequences: Tolerance to Amino Acid Substitutions," (1990, Science 247:1306-1310).

The invention further encompasses incorporation of unnatural amino acids in the modification of the hinge to generate the Fc variants of the invention. Such methods are known to those skilled in the art such as those using the natural biosynthetic machinery to allow incorporation of unnatural amino acids into proteins, see, e.g., Wang et al., 2002 *Chem. Comm.* 1:1-11; Wang et al., 2001, *Science*, 292: 498-500; van Hest et al., 2001. *Chem. Comm.* 19: 1897-1904. Alternative strategies focus on the enzymes responsible for the biosynthesis of amino acyl-tRNA, see, e.g., Tang et al., 2001, *J. Am. Chem.* 123(44): 11089-11090; Kiick et al., 2001, *FEBS Lett.* 505(3): 465.

One skilled in the art will understand that the Fc variants of the invention may have altered Fc ligand (e.g., FcγR, C1q)

binding properties (examples of binding properties include but are not limited to, binding specificity, equilibrium dissociation constant ($K_D$), dissociation and association rates ($K_{off}$ and $K_{on}$ respectively), binding affinity and/or avidity) and that certain alterations are more or less desirable. It is well known in the art that the equilibrium dissociation constant ($K_D$) is defined as $k_{off}/k_{on}$. It is generally understood that a binding molecule (e.g., and antibody) with a low $K_D$ is preferable to a binding molecule (e.g., and antibody) with a high $K_D$. However, in some instances the value of the $k_{on}$ or $k_{off}$ may be more relevant than the value of the $K_D$. One skilled in the art can determine which kinetic parameter is most important for a given antibody application. For example a modified hinge that enhances Fc binding to one or more positive regulators (e.g., FcγRIIIA) while leaving unchanged or even reducing Fc binding to the negative regulator FcγRIIB would be more advantageous for enhancing ADCC activity. Alternatively, a modified hinge that reduced binding to one or more positive regulator and/or enhanced binding to FcγRIIB would be advantageous for reducing ADCC activity. Accordingly, the ratio of binding affinities (e.g., equilibrium dissociation constants ($K_D$)) can indicate if the ADCC activity of an Fc variant is enhanced or decreased. For example a decrease in the ratio of FcγRIIIA/FcγRIIB equilibrium dissociation constants ($K_D$), will correlate with improved ADCC activity, while an increase in the ratio will correlate with a decrease in ADCC activity. Additionally, modified hinges that enhanced binding to C1q would be advantageous for enhancing CDC activity while modified hinges that reduced binding to C1q would be advantageous for reducing or eliminating CDC activity.

It will also be appreciated by one skilled in the art that the Fc variants of the invention may have altered immunogenicity when administered to a subject. Accordingly, it is contemplated that the modified hinge which minimize the immunogenicity of the Fc variant are generally more desirable for therapeutic applications.

The affinities and binding properties of the Fc variants of the invention for an FcγR are initially determined using in vitro assays (biochemical or immunological based assays) known in the art for determining Fc-FcγR interactions, i.e., specific binding of an Fc region to an FcγR including but not limited to ELISA assay, surface plasmon resonance assay, immunoprecipitation assays (See section entitled "Characterization and Functional Assays" infra) and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4$^{th}$ Ed., Lippincott-Raven, Philadelphia (1999), which focuses on antibody-immunogen interactions.

It is contemplated that the binding properties of the molecules of the invention are also characterized by in vitro functional assays for determining one or more FcγR mediator effector cell functions (See section entitled "Characterization and Functional Assays" infra). In certain embodiments, the molecules of the invention have similar binding properties in in vivo models (such as those described and disclosed herein) as those in in vitro based assays. However, the present invention does not exclude molecules of the invention that do not exhibit the desired phenotype in in vitro based assays but do exhibit the desired phenotype in vivo.

The invention encompasses Fc variants which bind FcγRIIIA with increased affinity, relative to a comparable molecule. In a specific embodiment, the Fc variants of the invention bind FcγRIIIA with increased affinity and bind FcγRIIB with a binding affinity that is either unchanged or reduced, relative to a comparable molecule. In yet another embodiment, the Fc variants of the invention have a ratio of FcγRIIIA/FcγRIIB equilibrium dissociation constants ($K_D$) that is decreased relative to a comparable molecule.

Also encompassed by the present invention are Fc variants which bind FcγRIIIA with decreased affinity, relative to a comparable molecule. In a specific embodiment, the Fc variants of the invention bind FcγRIIIA with decreased affinity, relative to a comparable molecule and bind FcγRIIB with a binding affinity that is unchanged or increased, relative to a comparable molecule.

The invention further encompasses, Fc variants which bind C1q with an altered affinity, relative to a comparable molecule. In a particular embodiment, the Fc variants of the invention bind C1q with an increased affinity, relative to a comparable molecule. In another embodiment, the Fc variants of the invention bind C1q with a decreased affinity, relative to a comparable molecule.

In one embodiment, said Fc variants bind with increased affinity to FcγRIIIA. In a specific embodiment, said Fc variants have affinity for FcγRIIIA that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold greater than that of a comparable molecule. In other embodiments, said Fc variants have an affinity for FcγRIIIA that is increased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In another embodiment, an Fc variant of the invention has an equilibrium dissociation constant ($K_D$) for an Fc ligand (e.g., FcγR, C1q) that is decreased between about 2 fold and 10 fold, or between about 5 fold and 50 fold, or between about 25 fold and 250 fold, or between about 100 fold and 500 fold, or between about 250 fold and 1000 fold relative to a comparable molecule.

In a specific embodiment, said Fc variants have an equilibrium dissociation constant ($K_D$) for FcγRIIIA that is reduced by at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, or at least 400 fold, or at least 600 fold, relative to a comparable molecule. In another specific embodiment, said Fc variants have an equilibrium dissociation constant ($K_D$) for FcγRIIIA that is reduced by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In one embodiment, said Fc variant binds to FcγRIIB with an affinity that is unchanged or reduced. In a specific embodiment, said Fc variants have affinity for FcγRIIB that is unchanged or reduced by at least 1 fold, or by at least 3 fold, or by at least 5 fold, or by at least 10 fold, or by at least 20 fold, or by at least 50 fold, or by at least 100 fold, relative to a comparable molecule. In other embodiments, said Fc variants have an affinity for FcγRIIB that is unchanged or reduced by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In another embodiment, said Fc variants have an equilibrium dissociation constant ($K_D$) for FcγRIIB that is unchanged or increased by at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold relative to a comparable molecule. In another specific embodiment, said Fc variants have an equilibrium dissociation constant ($K_D$) for FcγRIIB that is unchanged or increased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In still another embodiment, the Fc variants of the invention bind FcγRIIIA with increased affinity, relative to a comparable molecule and bind FcγRIIB with an affinity that is unchanged or reduced, relative to a comparable molecule. In a specific embodiment, said Fc variants have affinity for FcγRIIIA that is increased by at least 1 fold, or by at least 3 fold, or by at least 5 fold, or by at least 10 fold, or by at least 20 fold, or by at least 50 fold, or by at least 100 fold, relative to a comparable molecule. In another specific embodiment, said Fc variants have affinity for FcγRIIB that is either unchanged or is reduced by at least 2 fold, or at least 3 fold, or at least 5 fold, or at least 7 fold, or a least 10 fold, or at least 20 fold, or at least 50 fold, or at least 100 fold, relative to a comparable molecule. In other embodiments, said Fc variants have an affinity for FcγRIIIA that is increased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule and said Fc variants have an affinity for FcγRIIB that is either unchanged or is increased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In yet another embodiment, the Fc variants of the invention have a ratio of FcγRIIIA/FcγRIIB equilibrium dissociation constants ($K_D$) that is decreased relative to a comparable molecule. In a specific embodiment, the Fc variants of the invention have a ratio of FcγRIIIA/FcγRIIB equilibrium dissociation constants ($K_D$) that is decreased by at least 1 fold, or by at least 3 fold, or by at least 5 fold, or by at least 10 fold, or by at least 20 fold, or by at least 50 fold, or by at least 100 fold, relative to a comparable molecule. In another specific embodiment, the Fc variants of the invention have a ratio of FcγRIIIA/FcγRIIB equilibrium dissociation constants ($K_D$) that is decreased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In another embodiment, the Fc variants of the invention bind FcγIIIA with a decreased affinity, relative to a comparable molecule. In a specific embodiment, said Fc variants have affinity for FcγRIIIA that is reduced by at least 1 fold, or by at least 3 fold, or by at least 5 fold, or by at least 10 fold, or by at least 20 fold, or by at least 50 fold, or by at least 100 fold, relative to a comparable molecule. In other embodiments, said Fc variants have an affinity for FcγRIIIA that is decreased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In still another embodiment, the Fc variants of the invention bind FcγRIIIA with decreased affinity and bind FcγRIIB with an affinity that is either unchanged or increased, relative to a comparable molecule. In a specific embodiment, said Fc variants have affinity for FcγRIIIA that is reduced by at least 1 fold, or by at least 3 fold, or by at least 5 fold, or by at least 10 fold, or by at least 20 fold, or by at least 50 fold, or by at least 100 fold relative to a comparable molecule. In another specific embodiment, said Fc variants have affinity for FcγRIIB that is at least 2 fold, or at least 3 fold, or at least 5 fold, or at least 7 fold, or a least 10 fold, or at least 20 fold, or at least 50 fold, or at least 100 fold, greater than that of a comparable molecule. In other embodiments, said Fc variants have an affinity for FcγRIIIA that is decreased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule and said Fc variants have an affinity for FcγRIIB that is increased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In still another embodiment, the Fc variants have an equilibrium dissociation constant ($K_D$) for FcγRIIIA that are increased by at least 1 fold, or by at least 3 fold, or by at least 5 fold or by at least 10 or by at least 20 fold, or by at least 50 fold when compared to that of a comparable molecule. In a specific embodiment, said Fc variants have equilibrium dissociation constant ($K_D$) for FcγRIIB that are decreased at least 2 fold, or at least 3 fold, or at least 5 fold, or at least 7 fold, or a least 10 fold, or at least 20 fold, or at least 50 fold or at least 100 fold, relative to a comparable molecule.

In one embodiment, said Fc variants bind with increased affinity to C1q. In a specific embodiment, said Fc variants have affinity for C1q that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold greater than that of a comparable molecule. In other embodiments, said Fc variants have an affinity for C1q that is increased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule. In a specific embodiment, said Fc variants have an equilibrium dissociation constant ($K_D$) for C1q that is reduced by at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, or at least 400 fold, or at least 600 fold, relative to a comparable molecule. In another specific embodiment, said Fc variants have an equilibrium dissociation constant ($K_D$) for C1q that is reduced by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In another embodiment, said Fc variant binds to C1q with an affinity that is reduced. In certain embodiments, said Fc variants have affinity for C1q that is unchanged or reduced by at least 1 fold, or by at least 3 fold, or by at least 5 fold, or by at least 10 fold, or by at least 20 fold, or by at least 50 fold, or by at least 100 fold, relative to a comparable molecule. In other embodiments, said Fc variants have an affinity for C1q that is unchanged or reduced by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule. In another embodiment, said Fc variants have an equilibrium dissociation constant ($K_D$) for C1q that is unchanged or increased by at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold relative to a comparable molecule. In another specific embodiment, said Fc variants have an equilibrium dissociation constant ($K_D$) for C1q that is unchanged or increased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

The present invention also relates to fusion polypeptides comprising a binding domain fused to an Fc region comprising a modified hinge, wherein said modified hinge alters the affinity for one or more Fc ligand (e.g., FcγRIIA, FcγRIIB, C1q) relative to a comparable molecule. It is specifically contemplated that molecules comprising a modified hinge of the invention may be generated by methods well known to one skilled in the art. Briefly, such methods include but are not limited to, combining a variable region or binding domain with the desired specificity (e.g., a variable region isolated from a phage display or expression library or derived from a human or non-human antibody or a binding domain of a receptor) with an Fc region incorporating a modified hinge. Alternatively, one skilled in the art may generate an Fc variant by modifying the hinge in the Fc region of a molecule comprising an Fc region (e.g., an antibody).

In one embodiment, the Fc variants of the present invention are antibodies or Fc fusion proteins. In a specific embodiment, the invention provides antibodies comprising an Fc region comprising a modified hinge, wherein said modified hinge alters the affinity for one or more Fc ligand (e.g., FcγRIIA, FcγRIIB, C1q) relative to a comparable molecule. Such antibodies include IgG molecules that naturally comprise an Fc region containing a hinge which can be modified to generate an Fc variant, or antibodies derivatives that have been engineered to contain an Fc region comprising a modified hinge. Fc variants of the invention includes any antibody molecule that binds, preferably, specifically (i.e., competes off non-specific binding as determined by immunoassays well known in the art for assaying specific antigen-antibody binding) an antigen which comprises an Fc region incorporating a modified hinge. Such antibodies include, but are not limited to, polyclonal, monoclonal, bi-specific, multi-specific, human, humanized, chimeric antibodies, single chain antibodies, Fab fragments, F(ab')$_2$ fragments, disulfide-linked Fvs, and fragments containing either a VL or VH domain or even a complementary determining region (CDR) that specifically binds an antigen, in certain cases, engineered to contain or fused to an Fc region.

"Antibody-dependent cell-mediated cytotoxicity" or "ADCC" refers to a form of cytotoxicity in which secreted antibody bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the surface of target cells "arm" the cytotoxic cells and are absolutely required for such killing. Lysis of the target cell is extracellular, requires direct cell-to-cell contact, and does not involve complement.

The ability of any particular antibody to mediate lysis of the target cell by ADCC can be assayed. To assess ADCC activity an antibody of interest is added to target cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., 1985, 79:277; Bruggemann et al., 1987, *J Exp Med* 166:1351; Wilkinson et al., 2001, *J Immunol Methods* 258:183; Patel et al., 1995 *J Immunol Methods* 184:29 and herein (see section entitled "Characterization and Functional Assays" infra). Alternatively, or additionally, ADCC activity of the antibody of interest may be assessed in vivo, e.g., in an animal model such as that disclosed in Clynes et al., 1998, *PNAS USA* 95:652.

It is contemplated that the Fc variants of the invention are characterized by in vitro functional assays for determining one or more FcγR mediator effector cell functions (See section entitled "Effector Function of Fc Variants" infra). In specific embodiments, the molecules of the invention have similar binding properties and effector cell functions in in vivo models (such as those described and disclosed herein) as those in in vitro based assays However, the present invention does not exclude molecules of the invention that do not exhibit the desired phenotype in in vitro based assays but do exhibit the desired phenotype in vivo.

The present invention further provides Fc variants with enhanced ADCC function, relative to a comparable molecule. In one embodiment, the Fc variants of the invention have increased ADCC activity, relative to a comparable molecule. In another embodiment, the Fc variants have ADCC activity that is at least 2 fold, or at least 3 fold, or at least 5 fold, or at least 10 fold, or at least 50 fold, or at least 100 fold greater than that of a comparable molecule. In another embodiment, the Fc variants have ADCC activity that is increased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule. In a specific embodiment, the Fc variants of the invention bind FcγRIIIA with increased affinity, bind FcγRIIB with an unchanged or decreased affinity and have enhanced ADCC activity.

In a specific embodiment, the Fc variants of the invention have enhanced ADCC activity and specifically bind to at least one antigen. Also contemplated are Fc variants of the invention that have enhanced ADCC activity and have a ratio of FcγRIIIA/FcγRIIB equilibrium dissociation constants ($K_D$) that is decreased relative to a comparable molecule. It is further contemplated that the Fc variants of the invention have enhanced ADCC activity, bind activating FcγRs (e.g., FcγRIIIA) with higher affinity and bind inhibitory FcγRs (e.g., FcγRIIB) with unchanged or lower affinity and specifically bind to at least one antigen.

The present invention also provides Fc variants with reduced ADCC function, relative to a comparable molecule. In one embodiment, the Fc variants of the invention have reduced ADCC activity, relative to a comparable molecule. In another embodiment, the Fc variants have ADCC activity that is at least 2 fold, or at least 3 fold, or at least 5 fold, or at least 10 fold, or at least 50 fold, or at least 100 fold less than that of a comparable molecule. In a specific embodiment, Fc variants of the invention bind FcγRIIIA with decreased affinity, bind FcγRIIB with an unchanged or increased affinity and have reduced ADCC activity. In another embodiment, the Fc variants have ADCC activity that is decreased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule.

In a specific embodiment, the Fc variants of the invention have reduced ADCC activity and specifically bind to at least one antigen. In another specific embodiment, the Fc variants of the invention have reduced ADCC activity, bind activating FcγRs (e.g., FcγRIIIA) with lower affinity, bind inhibitory FcγRs (e.g., FcγRIIB) with an unchanged or increased affinity and specifically bind to at least one antigen.

"Complement dependent cytotoxicity" and "CDC" refer to the lysing of a target cell in the presence of complement. The complement activation pathway is initiated by the binding of the first component of the complement system (C1q) to a molecule, an antibody for example, complexed with a cognate antigen. To assess complement activation, a CDC assay, e.g. as described in Gazzano-Santoro et al., 1996, *J. Immunol. Methods*, 202:163, may be performed.

The present invention further provides Fc variants with enhanced CDC function. In one embodiment, the Fc variants of the invention have increased CDC activity. In one embodiment, the Fc variants have CDC activity that is at least 2 fold, or at least 3 fold, or at least 5 fold, or at least 10 fold, or at least 50 fold, or at least 100 fold greater than that of a comparable molecule. In another embodiment, the Fc variants of the invention bind C1q with an affinity that is at least 2 fold, or at least 3 fold, or at least 5 fold, or at least 7 fold, or a least 10 fold, or at least 20 fold, or at least 50 fold, or at least 100 fold, greater than that of a comparable molecule. In yet another embodiment, the Fc variants have CDC activity that is increased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule. In a specific embodiment, the Fc variants of the invention bind C1q with increased affinity; have enhanced CDC activity and specifically bind to at least one antigen.

The present invention also provides Fc variants with reduced CDC function. In one embodiment, the Fc variants of the invention have reduced CDC activity. In one embodiment, said Fc variants have CDC activity that is at least 2 fold, or at least 3 fold, or at least 5 fold or at least 10 fold or at least 50 fold or at least 100 fold less than that of a comparable molecule. In another embodiment, an Fc variant of the invention binds C1q with an affinity that is reduced by at least 1 fold, or by at least 3 fold, or by at least 5 fold, or by at least 10 fold, or by at least 20 fold, or by at least 50 fold, or by at least 100 fold, relative to a comparable molecule. In another embodiment, the Fc variants have CDC activity that is decreased by at least 10%, or at least 20%, or at least 30%, or at least 40%, or at least 50%, or at least 60%, or at least 70%, or at least 80%, or at least 90%, or at least 100%, or at least 150%, or at least 200%, relative to a comparable molecule. In a specific embodiment, Fc variants of the invention bind to C1q with decreased affinity have reduced CDC activity and specifically bind to at least one antigen.

It is contemplated that the Fc variants of the invention may have other altered characteristics including increased in vivo half-lives (e.g., serum half-lives) in a mammal; in particular a human, increased stability in vivo (e.g., serum half-lives) and/or in vitro (e.g., shelf-life) and/or increased melting temperature (Tm), relative to a comparable molecule. In one embodiment, an Fc variant of the invention has an in vivo half-life of greater then 15 days, greater than 20 days, greater than 25 days, greater than 30 days, greater than 35 days, greater than 40 days, greater than 45 days, greater than 2 months, greater than 3 months, greater than 4 months, or greater than 5 months. In another embodiment, an Fc variant of the invention has an in vitro half-live (e.g, liquid or powder formulation) of greater then then 15 days, greater than 30 days, greater than 2 months, greater than 3 months, greater than 6 months, or greater than 12 months, or greater than 24 months, or greater than 36 months, or greater than 60 months. In still another embodiment, an Fc variant of the invention has a Tm value higher than about 60° C., 65° C., 70° C., 75° C., 80° C., 85° C., 90° C. or 95° C.

It is also specifically contemplated that the Fc variants of the invention may contain inter alia one or more additional amino acid residue substitutions, mutations and/or modifications which result in an antibody with preferred characteristics including but not limited to: increased serum half life, increase binding affinity, reduced immunogenicity, increased production, enhanced or reduced ADCC or CDC activity, altered glycosylation and/or disulfide bonds and modified binding specificity.

The Fc variants of the present invention may be combined with other Fc modifications, including but not limited to modifications that alter effector function. The invention encompasses combining an Fc variant of the invention with other Fc modifications to provide additive, synergistic, or novel properties in antibodies or Fc fusions. Such modifications may be in the CH1, CH2, or CH3 domains or a combination thereof. It is contemplated that the Fc variants of the invention enhance the property of the modification with which they are combined. For example, if an Fc variant of the invention is combined with a mutant known to bind FcγRIIIA with a higher affinity than a comparable molecule comprising a wild type Fc region; the combination with a mutant of the invention results in a greater fold enhancement in FcγRIIIA affinity.

In one embodiment, the Fc variants of the present invention may be combined with other known Fc variants such as those disclosed in Duncan et al, 1988, *Nature* 332:563-564; Lund et al., 1991, *J. Immunol.* 147:2657-2662; Lund et al, 1992, *Mol Immunol* 29:53-59; Alegre et al, 1994, *Transplantation* 57:1537-1543; Hutchins et al., 1995, *Proc Natl. Acad Sci USA* 92:11980-11984; Jefferis et al, 1995, *Immunol Lett.* 44:111-117; Lund et al., 1995, *Faseb J* 9:115-119; Jefferis et al, 1996, *Immunol Lett* 54:101-104; Lund et al, 1996, *Immunol* 157:4963-4969; Armour et al., 1999, *Eur J Immunol* 29:2613-2624; Idusogie et al, 2000, *J Immunol* 164:4178-4184; Reddy et al, 2000, *J Immunol* 164:1925-1933; Xu et al., 2000, *Cell Immunol* 200:16-26; Idusogie et al, 2001, *J Immunol* 166:2571-2575; Shields et al., 2001, *J Biol Chem* 276: 6591-6604; Jefferis et al, 2002, *Immunol Lett* 82:57-65; Presta et al., 2002, *Biochem Soc Trans* 30:487-490); U.S. Pat. Nos. 5,624,821; 5,885,573; 6,194,551; U.S. Patent Application Nos. 60/601,634 and 60/608,852; PCT Publication Nos. WO 00/42072 and WO 99/58572.

In some embodiments, the Fc variants of the present invention comprises one or more engineered glycoforms, i.e., a carbohydrate composition that is covalently attached to a molecule comprising an Fc region. Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example β(1,4)—N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, *Nat. Biotechnol* 17:176-180; Davies et al., 20017 *Biotechnol Bioeng* 74:288-294; Shields et al, 2002, *J Biol Chem* 277:26733-26740; Shinkawa et al., 2003, *J Biol Chem* 278: 3466-3473) U.S. Pat. No. 6,602,684; U.S. Ser. No. 10/277, 370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland). See, e.g., WO 00061739; EA01229125; US 20030115614; Okazaki et al., 2004, JMB, 336: 1239-49. Additional methods are described in the section entitled "Antibodies of the Invention" below.

7.1 Antibodies of the Invention

It is contemplated that Fc variants of the invention includes antibodies comprising a variable region and an Fc region incorporating a modified hinge of the invention. The Fc variants which are antibodies may be produced "de novo" by combing a variable domain, of fragment thereof, that specifically binds at least one antigen with an Fc region incorporating a modified hinge of the invention. Alternatively, Fc variants may be produced by modifying the hinge of an Fc region containing antibody that binds an antigen. Fc variants which are antibodies may be referred to herein more generically as "Fc variants" or more specifically as "antibodies of the invention."

Antibodies of the invention may include, but are not limited to, synthetic antibodies, monoclonal antibodies, recombinantly produced antibodies, intrabodies, multispecific antibodies, bispecific antibodies, human antibodies, humanized antibodies, chimeric antibodies, synthetic antibodies, single-chain FvFcs (scFvFc), single-chain Fvs (scFv), and anti-idiotypic (anti-Id) antibodies. In particular, antibodies used in the methods of the present invention include immunoglobulin molecules and immunologically active portions of immunoglobulin molecules. The immunoglobulin molecules of the invention can be of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass of immunoglobulin molecule.

Antibodies of the invention may be from any animal origin including birds and mammals (e.g., human, murine, donkey, sheep, rabbit, goat, guinea pig, camel, horse, or chicken). In a specific embodiment, the antibodies are human or humanized monoclonal antibodies. As used herein, "human" antibodies include antibodies having the amino acid sequence of a human immunoglobulin and include antibodies isolated from human immunoglobulin libraries or from mice that express antibodies from human genes.

Antibodies like all polypeptides have an Isoelectric Point (pI), which is generally defined as the pH at which a polypeptide carries no net charge. It is known in the art that protein solubility is typically lowest when the pH of the solution is equal to the isoelectric point (pI) of the protein. It is possible to optimize solubility by altering the number and location of ionizable residues in the antibody to adjust the pI. For example the pI of a polypeptide can be manipulated by making the appropriate amino acid substitutions (e.g., by substituting a charged amino acid such as a lysine, for an uncharged residue such as alanine). Without wishing to be bound by any particular theory, amino acid substitutions of an antibody that result in changes of the pI of said antibody may improve solubility and/or the stability of the antibody. One skilled in the art would understand which amino acid substitutions would be most appropriate for a particular antibody to achieve a desired pI. The pI of a protein may be determined by a variety of methods including but not limited to, isoelectric focusing and various computer algorithms (see for example Bjellqvist et al., 1993, *Electrophoresis* 14:1023). In one embodiment, the pI of the Fc variants of the invention is between pH 6.2 and pH 8.0. In another embodiment, the pI of the antibodies of the invention is between pH 6.8 and pH 7.4. In one embodiment, substitutions resulting in alterations in the pI of the Fc variant of the invention will not significantly diminish its binding affinity for an antigen. It is specifically contemplated that the modified hinge that alters binding to at least one Fc ligand (described supra) may also result in a change in the pI. In a specific embodiments, modified hinges are specifically chosen to effect both the desired alteration in Fc ligand binding and any desired change in pI.

Antibodies of the invention may be monospecific, bispecific, trispecific or have greater multispecificity. Multispecific antibodies may specifically bind to different epitopes of desired target molecule or may specifically bind to both the target molecule as well as a heterologous epitope, such as a heterologous polypeptide or solid support material. See, e.g., International Publication Nos. WO 94/04690; WO 93/17715; WO 92/08802; WO 91/00360; and WO 92/05793; Tutt, et al., 1991, *J. Immunol.* 147:60-69; U.S. Pat. Nos. 4,474,893, 4,714,681, 4,925,648, 5,573,920, and 5,601,819; and Kostelny et al., 1992, *J. Immunol.* 148:1547).

Multispecific antibodies have binding specificities for at least two different antigens. While such molecules normally will only bind two antigens (i.e. bispecific antibodies, BsAbs), antibodies with additional specificities such as trispecific antibodies are encompassed by the instant invention. Examples of BsAbs include without limitation those with one arm directed against a tumor cell antigen and the other arm directed against a cytotoxic molecule. Methods for making bispecific antibodies are known in the art. Traditional production of full-length bispecific antibodies is based on the coexpression of two immunoglobulin heavy chain-light chain pairs, where the two chains have different specificities (Millstein et al., 1983, *Nature*, 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., 1991, *EMBO J.*, 10:3655-3659.

According to a different approach, antibody variable domains with the desired binding specificities (antibody-antigen combining sites) are fused to immunoglobulin constant domain sequences. The fusion may be with an immunoglobulin heavy chain constant domain, comprising at least part of the hinge, CH2, and CH3 regions. It is contemplated that the first heavy-chain constant region (CH1) containing the site necessary for light chain binding is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when, the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., 1986, *Methods in Enzymology*, 121:210. According to another approach described in WO96/27011, a pair of antibody molecules can be engineered to maximize the percentage of heterodimers which are recovered from recombinant cell culture. One interface contemplated comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Antibodies with more than two valencies incorporating modified hinge of the invention are contemplated. For example, trispecific antibodies can be prepared. See, e.g., Tutt et al. *J. Immunol.* 147: 60 (1991).

Antibodies of the invention encompass single domain antibodies, including camelized single domain antibodies (see e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231:25; International Publication Nos. WO 94/04678 and WO 94/25591; U.S. Pat. No. 6,005,079).

Antibodies of the invention further encompasses antibody-like and antibody-domain fusion proteins. An antibody-like molecule is any molecule that has been generated with a desired binding property, see, e.g., PCT Publication Nos. WO 04/044011; WO 04/058821; WO 04/003019 and WO 03/002609. Antibody-domain fusion proteins may incorporate one or more antibody domains such as the Fc domain or the variable domain. For example, the heterologous polypeptides may be fused or conjugated to a Fab fragment, Fd fragment, Fv fragment, F(ab)$_2$ fragment, a VH domain, a VL domain, a VH CDR, a VL CDR, or fragment thereof A large number of antibody-domain molecules are known in the art including, but not limited to, diabodies (dsFv)$_2$ (Bera et al., 1998, *J. Mol. Biol.* 281:475-83); minibodies (homodimers of scFv-CH$_3$ fusion proteins) (Pessi et al., 1993, *Nature* 362: 367-9), tetravalent di-diabody (Lu et al., 2003 *J. Immunol. Methods* 279:219-32), tetravalent bi-specific antibodies called Bs(scFv)$_4$-IgG (Zuo et al., 2000, *Protein Eng.* 13:361-367). Fc domain fusions combine the Fc region of an immunoglobulin, specifically an Fc region comprising a modified hinge of the invention, with a fusion partner which in general can be an protein, including, but not limited to, a ligand, an enzyme, the ligand portion of a receptor, an adhesion protein, or some other protein or domain. See, e.g., Chamow et al., 1996, *Trends Biotechnol* 14:52-60; Ashkenazi et al., 1997, *Curr Opin Immunol* 9:195-200; Heidaran et al., 1995, *FASEB J.* 9:140-5. Methods for fusing or conjugating polypeptides to antibody portions are well known in the art. See, e.g., U.S. Pat. Nos. 5,336,603, 5,622,929, 5,359,046, 5,349,053, 5,447, 851, and 5,112,946; European Patent Nos. EP 307,434 and EP 367,166; PCT Publication Nos. WO 96/04388 and WO 91/06570; Ashkenazi et al., 1991, *Proc. Natl. Acad. Sci. USA* 88: 10535-10539; Zheng et al., 1995, *J. Immunol.* 154:5590-5600; and Vil et al., 1992, *Proc. Natl. Acad. Sci. USA* 89:11337-11341.

Other molecules specifically contemplated are small, engineered protein domains such as, for example, immuno-domains and/or monomer domains (see for example, U.S. Patent Publication Nos. 2003082630 and 2003157561). Immuno-domains contain at least one complementarity determining region (CDR) of an antibody while monomer domains are based upon known naturally-occurring, non-antibody domain families, specifically protein extracellular domains, which contain conserved scaffold and variable binding sites, an example is the LDL receptor A domain which is involved in ligand binding. Such protein domains can correctly fold independently or with limited assistance from, for example, a chaperonin or the presence of a metal ion. This ability avoids mis-folding of the domain when it is inserted into a new protein environment, thereby preserving the protein domain's binding affinity for a particular target. The variable binding sites of the protein domains are randomized using various diversity generation methods such as, for example, random mutagenesis, site-specific mutagenesis, as well as by directed evolution methods, such as, for example, recursive error-prone PCR, recursive recombination and the like. For details of various diversity generation methods see U.S. Pat. Nos. 5,811,238; 5,830,721; 5,834,252; PCT Publication Nos. WO 95/22625; WO 96/33207; WO 97/20078; WO 97/35966; WO 99/41368; WO 99/23107; WO 00/00632; WO 00/42561; and WO 01/23401. The mutagenized protein domains are then expressed using a display system such as, for example, phage display, which can generate a library of at least $10^{10}$ variants and facilitate isolation of those protein domains with improved affinity and potency for an intended target by subsequent panning and screening. Such methods are described in PCT publication Nos. WO 91/17271; WO 91/18980; WO 91/19818; WO 93/08278. Examples of additional display systems are described in U.S. Pat. Nos. 6,281, 344; 6,194,550; 6,207,446; 6,214,553 and 6,258,558. Utilizing these methods a high diversity of engineered protein domains having sub-nM binding affinidty (Kd) and blocking function (IC50) can be rapidly generated. Once identified two to ten such engineered protein domains can be linked together, using natural protein linkers of about 4-15 amino acids in length, to form a binding protein. The individual domains can target a single type of protein or several, depending upon the use/disease indication. The engineered protein domains can then be linked to an Fc region comprising a modified hinge of the present invention.

In some embodiments, the antibodies of the present invention comprises one or more engineered glycoforms, i.e., a carbohydrate composition that is covalently attached to a molecule comprising an Fc region, wherein said carbohydrate composition differs chemically from that of a parent molecule comprising an Fc region. Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example β(1,4)—N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, Nat. Biotechnol 17:176-180; Davies et al., 20017 Biotechnol Bioeng 74:288-294; Shields et al, 2002, J Biol Chem 277:26733-26740; Shinkawa et al., 2003, J Biol Chem 278: 3466-3473) U.S. Pat. No. 6,602,684; U.S. Ser. No. 10/277, 370; U.S. Ser. No. 10/113,929; PCT WO 00/61739A1; PCT WO 01/292246A1; PCT WO 02/311140A1; PCT WO 02/30954A1; Potelligent™ technology (Biowa, Inc. Princeton, N.J.); GlycoMAb™ glycosylation engineering technology (GLYCART biotechnology AG, Zurich, Switzerland). See, e.g., WO 00061739; EA01229125; US 20030115614; Okazaki et al., 2004, JMB, 336: 1239-49.

Antibodies of the present invention also encompass those that have half-lives (e.g., serum half-lives) in a mammal, (e.g., a human), of greater than 15 days, greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present invention in a mammal, (e.g., a human), results in a higher serum titer of said antibodies or antibody fragments in the mammal, and thus, reduces the frequency of the administration of said antibodies or antibody fragments and/or reduces the concentration of said antibodies or antibody fragments to be administered. Antibodies having increased in vivo half-lives can be generated by techniques known to those of skill in the art. For example, antibodies with increased in vivo half-lives can be generated by modifying (e.g., substituting, deleting or adding) amino acid residues identified as involved in the interaction between the Fc domain and the FcRn receptor (see, e.g., International Publication Nos. WO 97/34631; WO 04/029207; U.S. Pat. No. 6,737,056 and U.S. Patent Publication No. 2003/0190311).

The introduction of a modified hinge into an antibody already described in the art is also contemplated. Antibodies into which a modified hinge of the invention is introduced may specifically bind a cancer or tumor antigen for example, including, but not limited to, KS 1/4 pan-carcinoma antigen (Perez and Walker, 1990, J. Immunol. 142: 3662-3667; Bumal, 1988, Hybridoma 7(4): 407-415), ovarian carcinoma antigen (CA125) (Yu et al., 1991, Cancer Res. 51(2): 468-475), prostatic acid phosphate (Tailor et al., 1990, Nucl. Acids Res. 18(16): 4928), prostate specific antigen (Henttu and Vihko, 1989, Biochem. Biophys. Res. Comm. 160(2): 903-910; Israeli et al., 1993, Cancer Res. 53: 227-230), melanoma-associated antigen p97 (Estin et al., 1989, J. Natl. Cancer Instil. 81(6): 445-446), melanoma antigen gp75 (Vijayasardahl et al., 1990, J. Exp. Med. 171(4): 1375-1380), high molecular weight melanoma antigen (HMW-MAA) (Natali et al., 1987, Cancer 59: 55-63; Mittelman et al., 1990, J. Clin. Invest. 86: 2136-2144), prostate specific membrane antigen, carcinoembryonic antigen (CEA) (Foon et al., 1994, Proc. Am. Soc. Clin. Oncol. 13: 294), polymorphic epithelial mucin antigen, human milk fat globule antigen, colorectal tumor-associated antigens such as: CEA, TAG-72 (Yokata et al., 1992, Cancer Res. 52: 3402-3408), CO17-1A (Ragnhammar et al., 1993, Int. J. Cancer 53: 751-758); GICA 19-9 (Herlyn et al., 1982, J. Clin. Immunol. 2: 135), CTA-1 and LEA, Burkitt's lymphoma antigen-38.13, CD19 (Ghetie et al., 1994, Blood 83: 1329-1336), human B-lymphoma antigen-CD20 (Reff et al., 1994, Blood 83:435-445), CD33 (Sgouros et al., 1993, J. Nucl. Med. 34:422-430), melanoma specific antigens such as ganglioside GD2 (Saleh et al., 1993, J. Immunol., 151, 3390-3398), ganglioside GD3 (Shitara et al., 1993, Cancer Immunol. Immunother. 36:373-380), ganglioside GM2 (Livingston et al., 1994, J. Clin. Oncol. 12: 1036-1044), ganglioside GM3 (Hoon et al., 1993, Cancer Res. 53: 5244-5250), tumor-specific transplantation type of cell-surface antigen (TSTA) such as virally-induced tumor antigens including T-antigen DNA tumor viruses and Envelope antigens of RNA tumor viruses, oncofetal antigen-alpha-fetoprotein such as CEA of colon, bladder tumor oncofetal antigen (Hellstrom et al., 1985, Cancer. Res. 45:2210-2188), differentiation antigen such as human lung carcinoma antigen L6, L20 (Hellstrom et al., 1986, Cancer Res. 46: 3917-3923), antigens of fibrosarcoma, human leukemia T cell antigen-Gp37 (Bhattacharya-Chatterjee et al., 1988, J. of Immun. 141:1398-1403), neoglycoprotein, sphingolipids, breast cancer antigen such as EGFR (Epidermal growth factor receptor), HER2 antigen (p185$^{HER2}$), polymorphic epithelial mucin (PEM) (Hilkens et al., 1992, Trends in Bio. Chem. Sci. 17:359), malignant human lymphocyte antigen-APO-1 (Bernhard et al., 1989, Science 245: 301-304), differentiation antigen (Feizi, 1985, Nature 314: 53-57) such as I antigen found in fetal erythrocytes, primary endoderm I antigen found in adult erythrocytes, preimplantation embryos, I(Ma) found in gastric adenocarcinomas, M18, M39 found in breast epithelium, SSEA-1 found in myeloid cells, VEP8, VEP9, Myl, VIM-D5, $D_1$56-22 found in colorectal cancer, TRA-1-85 (blood group H), C14 found in colonic adenocarcinoma, F3 found in lung adenocarcinoma, AH6 found in gastric cancer, Y hapten, Le found in embryonal carcinoma cells, TL5 (blood group A), EGF receptor found in A431 cells, $E_1$ series (blood group B) found in pancreatic cancer, FC 10.2 found in embryonal carcinoma cells, gastric adenocarcinoma antigen, CO-514 (blood group Le$^a$) found in Adenocarcinoma, NS-10 found in adenocarcinomas, CO-43 (blood group Le$^b$), G49 found in EGF receptor of A431 cells, MH2 (blood group ALe$^b$/LeY) found in colonic adenocarcinoma, 19.9 found in colon cancer, gastric cancer mucins, $T_5A_7$ found in myeloid cells, $R_{24}$ found in melanoma, 4.2, $G_{D3}$, D1.1, OFA-1, $G_{M2}$, OFA-2, $G_{D2}$, and M1:22:25:8 found in embryonal carcinoma cells, and SSEA-3 and SSEA-4 found in 4 to 8-cell stage embryos. In one embodiment, the antigen is a T cell receptor derived peptide from a Cutaneous Tcell Lymphoma (see, Edelson, 1998, The Cancer Journal 4:62).

In some embodiments, a modified hinge of the invention is introduced into an anti-fluoresceine monoclonal antibody, 4-4-20 (Kranz et al., 1982 J. Biol. Chem. 257(12): 6987-6995). In other embodiments, a modified hinge of the invention is introduced into a mouse-human chimeric anti-CD20 monoclonal antibody 2H7, which recognizes the CD20 cell surface phosphoprotein on B cells (Liu et al., 1987, Journal of Immunology, 139: 3521-6). In yet other embodiments, a modified hinge of the invention is introduced into a humanized antibody (Ab4D5) against the human epidermal growth factor receptor 2 (p185 HER2) as described by Carter et al.

(1992, *Proc. Natl. Acad. Sci. USA* 89: 4285-9). In yet other embodiments a modified hinge of the invention is introduced into a humanized anti-TAG72 antibody (CC49) (Sha et al., 1994 *Cancer Biother.* 9(4): 341-9). In other embodiments, modified hinge of the invention is introduced into Rituxan which is used for treating lymphomas.

In certain embodiments, the invention encompasses engineering a modified hinge of the invention into an antibody including but not limited to any of the antibodies that specifically bind an Eph Receptor. The Eph receptors encompasses a family of polypeptides comprising proteins that are defined by a certain degree of homology to the known Eph receptor tyrosine kinases (RTKs). Eph receptors include, but are not limited to EphA1 (also known as ephrin type-A receptor 1, erythropoietin-producing hepatoma amplified sequence and exemplified by GenBank Acc. No. NP_005223.2), EphA2 (also known as epithelial cell receptor protein tyrosine kinase and exemplified by GenBank Acc. No. NP_004422.2), EphA3 (also known as human embryo kinase 1, eph-like tyrosine kinase 1, TYRO4 protein tyrosine kinase and exemplified by GenBank Acc. Nos. N_005224.2 and NP_872585.1, isoforms 3a and 3b respectively), EphA4 (also known as ephrin type-A receptor 4, TYROL protein tyrosine kinase, tyrosine-protein kinase receptor SEK, receptor protein-tyrosine kinase HEK8 and exemplified by GenBank Acc. No. NP_004429.1), EphA5 (also known as Eph homology kinase-1, ephrin type-A receptor 5, receptor protein-tyrosine kinase HEK7, tyrosine-protein kinase receptor EHK-1 and exemplified by GenBank Acc. Nos. NP_004430.2 and NP_872272 isoforms 5a and 5b respectively), EphA6 (exemplified by GenBank Acc. No. XP_114973.4), EphA7 (also known as Eph homology kinase-3, ephrin type-A receptor 7, receptor protein-tyrosine kinase HEK11, tyrosine-protein kinase receptor EHK-3 and exemplified by GenBank Acc. No. NP_004431.1), EphA8 (also known as tyrosylprotein kinase, protein-tyrosine kinase, hydroxyaryl-protein kinase, ephrin type-A receptor 8 precursor, eph- and elk-related tyrosine kinase, tyrosine-protein kinase receptor eek and exemplified by GenBank Acc. No. NP_065387.1), EphB1 (also known as eph tyrosine kinase 2 and exemplified by GenBank Acc. No. NP_004432.1), EphB2 (also known as eph tyrosine kinase 3, elk-related tyrosine kinase, developmentally-regulated eph-related tyrosine kinase and exemplified by GenBank Acc. Nos. NP_059145.1 and NP_004433.2 isoforms 2a and 2b respectively), EphB3 (also known as human embryo kinase 2, EPH-like tyrosine kinase-2 and exemplified by GenBank Acc. No. NP_004434.2), EphB4 (also known as hepatoma transmembrane kinase and exemplified by GenBank Acc. No. NP_004435.3) and B6 (exemplified by GenBank Acc. No. NM_004445.1).

In a specific embodiment, the invention encompasses engineering a modified hinge of the invention into an antibody including but not limited to antibodies that specifically bind EphA2 and/or EphA4, their derivatives, analogs and epitope-binding fragments thereof, such as but not limited to, those disclosed herein and in PCT Publication Nos. WO 04/014292, WO 03/094859 and U.S. patent application Ser. No. 10/863,729, and any of the antibodies listed in Table 5. In a specific embodiment, the Fc variants of the invention are antibodies that specifically bind EphA2 and/or EphA4 which comprise all or a portion of the variable region (e.g., one or more CDR) from 12G3H11 and/or any of the antibodies listed in Table 5.

TABLE 5

Specific anti-Eph receptor antibodies

| Antibody/Hybridoma | EphR | ATCC No. | Date of deposit | Patent App. No. |
|---|---|---|---|---|
| Eph099B-102.147 | EphA2 | PTA-4572 | Aug. 7, 2002 | WO 03/094859 |
| Eph099B208.261 | EphA2 | PTA-4573 | Aug. 7, 2002 | WO 03/094859 |
| Eph099B-210.248 | EphA2 | PTA-4574 | Aug. 7, 2002 | WO 03/094859 |
| Eph099B-233.152 | EphA2 | PTA-5194 | May 12, 2003 | WO 03/094859 |
| EA2 | EphA2 | PTA-4380 | May 22, 2002 | WO 04/014292 |
| EA5 | EphA2 | PTA-4381 | May 22, 2002 | WO 04/014292 |
| EA44 | EphA4 | PTA-6044 | Jun. 4, 2004 | 10/863,729 |

In a specific embodiment, the invention encompasses engineering a modified hinge of the invention into an antibody including but not limited to antibodies that specifically bind Integrin $\alpha_v\beta_3$ including, but not limited to, LM609 (Scripps), the murine monoclonal LM609 (PCT Publication WO 89/015155 and U.S. Pat. No. 5,753,230); the humanized monoclonal antibody MEDI-522 (a.k.a. VITAXIN®, MedImmune, Inc., Gaithersburg, Md.; Wu et al., 1998, *PNAS USA* 95(11): 6037-6042; PCT Publications WO 90/33919 and WO 00/78815); D12 (PCT Publication WO 98/40488); anti-Integrin $\alpha_v\beta_3$ antibody PDE 117-706 (ATCC access No. HB-12224), P112-4C1 (ATCC access No. HB-12225), P113-12A6 (ATCC access No. HB-12226), P112-11D2 (ATCC access No. HB-12227), P112-10D4 (ATCC access No. HB-12228) and P113-1F3 (ATCC access No. HB-12229). (G.D, Searle & Co., PCT Publication WO 98/46264); 17661-37E and 17661-37E1-5 (USBiological), MON 2032 and 2033 (CalTag), ab7166 (BV3) and ab 7167 (BV4) (Abcam), WOW-1 (Kiosses et al., 2001, *Nature Cell Biology*, 3:316-320), CNTO 95 (Centocor, PCT publication WO 02/12501) and analogs, derivatives, or fragments thereof.

In some embodiments, a modified hinge of the invention is introduced into a therapeutic monoclonal antibody specific for a cancer antigen or cell surface receptor including but not limited to, Erbitux™ (also known as IMC-C225) (ImClone Systems Inc.), a chimerized monoclonal antibody against EGFR; HERCEPTIN® (Trastuzumab) (Genentech, CA) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection. Other examples are a humanized anti-CD18 F(ab')$_2$ (Genentech); CDP860 which is a humanized anti-CD18 F(ab')$_2$ (Celltech, UK); PRO542 which is an anti-HIV gp120 antibody fused with CD4 (Progenics/Genzyme Transgenics); C14 which is an anti-CD14 antibody (ICOS Pharm); a humanized anti-VEGF IgG1 antibody (Genentech); OVAREX™ which is a murine anti-CA 125 antibody (Altarex); PANOREX™ which is a murine anti-17-IA cell surface antigen IgG2a antibody (Glaxo Wellcome/Centocor); IMC-C225 which is a chimeric anti-EGFR IgG antibody (ImClone System); VITAXIN™ which is a humanized anti-$\alpha$V$\beta$3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); Smart ID10 which is a humanized anti-HLA antibody (Protein Design Lab); ONCOLYM™ (Lym-1) is a radiolabelled murine anti-HLA DR antibody (Techniclone); anti-CD11a is a humanized IgG1 antibody (Genetech/Xoma); ICM3 is a humanized anti-ICAM3 antibody (ICOS Pharm); IDEC-114 is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); Ortho-Clone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); MDX-33 is a human anti-CD64 (FcγR) antibody (Medarex/Centeon); rhuMab-E25 is a humanized anti-IgE IgG1 antibody (Genentech/Norvartis/Tanox Biosystems); IDEC-152 is a primatized anti-CD23 antibody (IDEC Pharm); ABX-CBL is a murine anti CD-147 IgM antibody (Abgenix); BTI-322 is a rat anti-CD2 IgG antibody (Medimmune/Bio Transplant); Orthoclone/OKT3 is a murine anti-CD3 IgG2a antibody (ortho Biotech); SIMULECT™ is a chimeric anti-CD25 IgG1 antibody (Novartis Pharm); LDP-01 is a humanized anti-β$_2$-integrin IgG antibody (LeukoSite); Anti-LFA-1 is a murine anti CD18 F(ab')$_2$ (Pasteur-Merieux/Immunotech); CAT-152 is a human anti-TGF-β$_2$ antibody (Cambridge Ab Tech); and Corsevin M is a chimeric anti-Factor VII antibody (Centocor).

In still another embodiment, antibodies of the invention specifically bind to the same antigen as a known therapeutic antibody including, but not limited to those listed supra, provided that the variable region of the antibodies of the invention is not that of said therapeutic antibody.

In yet another embodiment, antibodies of the invention include the known therapeutic antibodies listed above, wherein the Fc region of the antibodies is modified in the hinge region according to the teachings of the present invention such that 1) the binding of the Fc to one or more Fc ligands (e.g., FcγRs) is increased or decreased; and/or 2) the Fc is modified such that effector function is increased or decreased 7.1.1 Specific Antigens and Fusion Partners of the Invention Generally, when the Fc variant is an antibody (referred to herein as an antibody of the invention), the antibody of the invention specifically binds an antigen of interest. In one embodiment, an antibody of the invention specifically binds a polypeptide antigen. In another embodiment, an antibody of the invention specifically binds a nonpolypeptide antigen. In yet another embodiment, administration of an antibody of the invention to a mammal suffering from a disease or disorder can result in a therapeutic benefit in that mammal.

Virtually any molecule may be targeted by and/or incorporated into an Fc variant protein (e.g., antibodies, Fc fusion proteins) including, but not limited to, the following list of proteins, as well as subunits, domains, motifs and epitopes belonging to the following list of proteins: renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VII, factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors such as, for example, EGFR, VEGFR; interferons such as alpha interferon (α-IFN), beta interferon (β-IFN) and gamma interferon (γ-IFN); protein A or D; rheumatoid factors; a neurotrophic factor such as bone-derived neurotrophic factor (BDNF), neurotrophin-3,-4,-5, or -6 (NT-3, NT-4, NT-5, or NT-6), or a nerve growth factor; platelet-derived growth factor (PDGF); fibroblast growth factor such as αFGF and βFGF; epidermal growth factor (EGF); transforming growth factor (TGF) such as TGF-alpha and TGF-beta, including TGF-1, TGF-2, TGF-3, TGF-4, or TGF-5; insulin-like growth factor-I and-II (IGF-I and IGF-II); des (1-3)-IGF-I (brain IGF-I), insulin-like growth factor binding proteins; CD proteins such as CD2, CD3, CD4, CD 8, CD11a, CD14, CD18, CD19, CD20, CD22, CD23, CD25, CD33, CD34, CD40, CD40L, CD52, CD63, CD64, CD80 and CD147; erythropoietin; osteoinductive factors; immunotoxins; a bone morphogenetic protein (BMP); an interferon such as interferon-alpha,-beta, and -gamma; colony stimulating factors (CSFs), such as M-CSF, GM-CSF, and G-CSF; interleukins (ILs), e.g., IL-1 to IL-13; TNFα, superoxide dismutase; T-cell receptors; surface membrane proteins; decay accelerating factor; viral antigen such as, for example, a portion of the AIDS envelope, e.g., gp120; transport proteins; homing receptors; addressins; regulatory proteins; cell adhesion molecules such as LFA-1, Mac 1, p150.95, VLA-4, ICAM-1, ICAM-3 and VCAM, a4/p7 integrin, and (Xv/p3 integrin including either a or subunits thereof, integrin alpha subunits such as CD49a, CD49b, CD49c, CD49d, CD49e, CD49f, alpha7, alpha8, alpha9, alphaD, CD11a, CD11b, CD51, CD11c, CD41, alphaIIb, alphaIELb; integrin beta subunits such as, CD29, CD18, CD61, CD104, beta5, beta6, beta7 and beta8; Integrin subunit combinations including but not limited to, αVβ3, αVβ5 and α4β7; a member of an apoptosis pathway; IgE; blood group antigens; flk2/flt3 receptor; obesity (OB) receptor; mpl receptor; CTLA-4; protein C; an Eph receptor such as EphA2, EphA4, EphB2, etc.; a Human Leukocyte Antigen (HLA) such as HLA-DR; complement proteins such as complement receptor CR1, C1Rq and other complement factors such as C3, and C5; a glycoprotein receptor such as GpIbα, GPIIb/IIIa and CD200; and fragments of any of the above-listed polypeptides.

Also contemplated are antibodies of the invention that specifically bind cancer antigens including, but not limited to, ALK receptor (pleiotrophin receptor), pleiotrophin, KS ¼ pan-carcinoma antigen; ovarian carcinoma antigen (CA125); prostatic acid phosphate; prostate specific antigen (PSA); melanoma-associated antigen p97; melanoma antigen gp75; high molecular weight melanoma antigen (HMW-MAA); prostate specific membrane antigen; carcinoembryonic antigen (CEA); polymorphic epithelial mucin antigen; human milk fat globule antigen; colorectal tumor-associated antigens such as: CEA, TAG-72, C017-1A, GICA 19-9, CTA-1 and LEA; Burkitt's lymphoma antigen-38.13; CD19; human B-lymphoma antigen-CD20; CD33; melanoma specific antigens such as ganglioside GD2, ganglioside GD3, ganglioside GM2 and ganglioside GM3; tumor-specific transplantation type cell-surface antigen (TSTA); virally-induced tumor antigens including T-antigen, DNA tumor viruses and Envelope antigens of RNA tumor viruses; oncofetal antigen-alpha-fetoprotein such as CEA of colon, 5T4 oncofetal trophoblast glycoprotein and bladder tumor oncofetal antigen; differentiation antigen such as human lung carcinoma antigens L6 and L20; antigens of fibrosarcoma; human leukemia T cell antigen-Gp37; neoglycoprotein; sphingolipids; breast cancer antigens such as EGFR (Epidermal growth factor receptor); NY-BR-16; NY-BR-16 and HER2 antigen (p185$^{HER2}$); polymorphic epithelial mucin (PEM); malignant human lymphocyte antigen-APO-1; differentiation antigen such as I antigen found in fetal erythrocytes; primary endoderm I antigen found in adult erythrocytes; preimplantation embryos; I(Ma) found in gastric adenocarcinomas; M18, M39 found in breast epithelium; SSEA-1 found in myeloid cells; VEP8; VEP9; Myl; VIM-D5; $D_1$56-22 found in colorectal cancer; TRA-1-85 (blood group H); SCP-1 found in testis and ovarian cancer; C14 found in colonic adenocarcinoma; F3 found in lung adenocarcinoma; AH6 found in gastric cancer; Y hapten; Le$^y$ found in embryonal carcinoma cells; TL5 (blood group A); EGF receptor found in A431 cells; $E_1$ series (blood group B) found in pancreatic cancer; FC10.2 found in embryonal carcinoma cells; gastric adenocarcinoma antigen; CO-514 (blood group Le$^a$) found in Adenocarcinoma; NS-10 found in adenocarcinomas; CO-43 (blood group Le$^b$); G49 found in EGF receptor of A431 cells; MH2 (blood group ALe$^b$/Le$^y$) found in colonic adenocarcinoma; 19.9 found in colon cancer; gastric cancer mucins; $T_5A_7$ found in myeloid cells; $R_{24}$ found in melanoma; 4.2, $G_{D3}$, D1.1, OFA-1, $G_{m2}$, OFA-2, $G_{D2}$, and M1:22:25:8 found in embryonal carcinoma cells and SSEA-3 and SSEA-4 found in 4 to 8-cell stage embryos; Cutaneous Tcell Lymphoma antigen; MART-1 antigen; Sialy Tn (STn) antigen; Colon cancer antigen NY—CO-45; Lung cancer antigen NY-LU-12 variant A; Adenocarcinoma antigen ART1; Paraneoplastic associated brain-testis-cancer antigen (onconeuronal antigen MA2; paraneoplastic neuronal antigen); Neuro-oncological ventral antigen 2 (NOVA2); Hepatocellular carcinoma antigen gene 520; TUMOR-ASSOCIATED ANTIGEN CO-029; Tumor-associated antigens MAGE-C1 (cancer/testis antigen CT7), MAGE-B1 (MAGE-XP antigen), MAGE-B2 (DAM6), MAGE-2, MAGE-4-a, MAGE-4-b and MAGE-X2; Cancer-Testis Antigen (NY-EOS-1) and fragments of any of the above-listed polypeptides.

7.1.2 Antibody Conjugates and Derivatives

Antibodies of the invention include derivatives that are modified (i.e., by the covalent attachment of any type of molecule to the antibody such that covalent attachment). For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

Further, antibodies can be conjugated to albumin in order to make the antibody or antibody fragment more stable in vivo or have a longer half life in vivo. The techniques are well known in the art, see e.g., International Publication Nos. WO 93/15199, WO 93/15200, and WO 01/77137; and European Patent No. EP 413, 622. The present invention encompasses the use of antibodies or fragments thereof conjugated or fused to one or more moieties, including but not limited to, peptides, polypeptides, proteins, fusion proteins, nucleic acid molecules, small molecules, mimetic agents, synthetic drugs, inorganic molecules, and organic molecules.

The present invention encompasses the use of antibodies or fragments thereof recombinantly fused or chemically conjugated (including both covalent and non-covalent conjugations) to a heterologous protein or polypeptide (or fragment thereof, for example, to a polypeptide of at least 10, at least 20, at least 30, at least 40, at least 50, at least 60, at least 70, at least 80, at least 90 or at least 100 amino acids) to generate fusion proteins. The fusion does not necessarily need to be direct, but may occur through linker sequences. For example, antibodies may be used to target heterologous polypeptides to particular cell types, either in vitro or in vivo, by fusing or conjugating the antibodies to antibodies specific for particular cell surface receptors. Antibodies fused or conjugated to heterologous polypeptides may also be used in in vitro immunoassays and purification methods using methods known in the art. See e.g., International publication No. WO 93/21232; European Patent No. EP 439,095; Naramura et al., 1994, Immunol. Lett. 39:91-99; U.S. Pat. No. 5,474,981; Gillies et al., 1992, PNAS 89:1428-1432; and Fell et al., 1991, J. Immunol. 146:2446-2452.

The present invention further includes compositions comprising heterologous proteins, peptides or polypeptides fused or conjugated to antibody fragments. For example, the heterologous polypeptides may be fused or conjugated to a Fab fragment, Fd fragment, Fv fragment, F(ab)$_2$ fragment, a VH domain, a VL domain, a VH CDR, a VL CDR, or fragment thereof. Methods for fusing or conjugating polypeptides to antibody portions are well known in the art. See, e.g., U.S. Pat. Nos. 5,336,603, 5,622,929, 5,359,046, 5,349,053, 5,447, 851, and 5,112,946; European Patent Nos. EP 307,434 and EP 367,166; International publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins, e.g., of antibodies that specifically bind an antigen (e.g., supra), may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S.

Pat. Nos. 5,605,793; 5,811,238; 5,830,721; 5,834,252; and 5,837,458, and Patten et al., 1997, Curr. Opinion Biotechnol. 8:724-33; Harayama, 1998, Trends Biotechnol. 16(2): 76-82; Hansson, et al., 1999, J. Mol. Biol. 287:265-76; and Lorenzo and Blasco, 1998, Biotechniques 24(2): 308-313. Antibodies or fragments thereof, or the encoded antibodies or fragments thereof, may be altered by being subjected to random mutagenesis by error-prone PCR, random nucleotide insertion or other methods prior to recombination. One or more portions of a polynucleotide encoding an antibody or antibody fragment, which portions specifically bind to an Antigen may be recombined with one or more components, motifs, sections, parts, domains, fragments, etc. of one or more heterologous molecules.

Moreover, the antibodies or fragments thereof can be fused to marker sequences, such as a peptide to facilitate purification. In certain embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexahistidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag.

In other embodiments, Fc variants of the present invention or analogs or derivatives thereof are conjugated to a diagnostic or detectable agent. Such antibodies can be useful for monitoring or prognosing the development or progression of a cancer as part of a clinical testing procedure, such as determining the efficacy of a particular therapy. Such diagnosis and detection can be accomplished by coupling the antibody to detectable substances including, but not limited to various enzymes, such as but not limited to horseradish peroxidase, alkaline phosphatase, beta-galactosidase, or acetylcholinesterase; prosthetic groups, such as but not limited to streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbon ($_{14}$C), (sulfur ($^{35}$S), tritium ($^{3}$H), indium $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, noradioactive paramagnetic metal ions, and molecules that are radiolabelled or conjugated to specific radioisotopes.

The present invention further encompasses uses of Fc variants of the invention or fragments thereof conjugated to a therapeutic agent.

An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Examples include ribonuclease, monomethylauristatin E and F, paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). A more extensive list of therapeutic moieties can be found in PCT publications WO 03/075957.

Further, an antibody or fragment thereof may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, Onconase (or another cytotoxic RNase), pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, J. Immunol., 6:1567), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

Moreover, an antibody can be conjugated to therapeutic moieties such as a radioactive materials or macrocyclic chelators useful for conjugating radiometal ions (see above for examples of radioactive materials). In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4:2483; Peterson et al., 1999, Bioconjug. Chem. 10:553; and Zimmerman et al., 1999, Nucl. Med. Biol. 26:943.

Techniques for conjugating therapeutic moieties to antibodies are well known. Moieties can be conjugated to antibodies by any method known in the art, including, but not limited to aldehyde/Schiff linkage, sulphydryl linkage, acid-labile linkage, cis-aconityl linkage, hydrazone linkage, enzymatically degradable linkage (see generally Garnett, 2002, Adv Drug Deliv Rev 53:171). Techniques for conjugating therapeutic moieties to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy:

A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, *Immunol. Rev.* 62:119.

Methods for fusing or conjugating antibodies to polypeptide moieties are known in the art. See, e.g., U.S. Pat. Nos. 5,336,603; 5,622,929; 5,359,046; 5,349,053; 5,447,851, and 5,112,946; EP 307,434; EP 367,166; PCT Publications WO 96/04388 and WO 91/06570; Ashkenazi et al., 1991, *PNAS USA* 88:10535; Zheng et al., 1995, *J Immunol* 154:5590; and Vil et al., 1992, *PNAS USA* 89:11337. The fusion of an antibody to a moiety does not necessarily need to be direct, but may occur through linker sequences. Such linker molecules are commonly known in the art and described in Denardo et al., 1998, *Clin Cancer Res* 4:2483; Peterson et al., 1999, *Bioconjug Chem* 10:553; Zimmerman et al., 1999, *Nucl Med Biol* 26:943; Garnett, 2002, *Adv Drug Deliv Rev* 53:171.

Alternatively, an antibody can be conjugated to a second antibody to form an antibody heteroconjugate as described by Segal in U.S. Pat. No. 4,676,980.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

The therapeutic moiety or drug conjugated to an Fc variant of the invention should be chosen to achieve the desired prophylactic or therapeutic effect(s) for a particular disorder in a subject. A clinician or other medical personnel should consider the following when deciding on which therapeutic moiety or drug to conjugate to an Fc variant of the invention: the nature of the disease, the severity of the disease, and the condition of the subject.

7.1.3 Methods of Generating Antibodies

Antibodies of the invention (i.e., antibodies incorporating a modified hinge of the invention) can be produced by any method known in the art for the synthesis of antibodies, in particular, by chemical synthesis or by recombinant expression techniques.

Polyclonal antibodies recognizing a particular antigen can be produced by various procedures well known in the art. For example, an antigen or immunogenic fragments thereof can be administered to various host animals including, but not limited to, rabbits, mice, rats, etc. to induce the production of sera containing polyclonal antibodies specific for an antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas* 563-681 (Elsevier, N.Y., 1981). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with an antigen or immunogenic fragment thereof and once an immune response is detected, e.g., antibodies specific for the administered antigen are detected in the mouse serum, the mouse spleen is harvested and splenocytes isolated. The splenocytes are then fused by well known techniques to any suitable myeloma cells, for example cells from cell line SP20 available from the ATCC. Additionally, a RIMMS (repetitive immunization, multiple sites) technique can be used to immunize an animal (Kilpatrick et al., 1997, *Hybridoma* 16:381-9). Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, monoclonal antibodies can be generated by culturing a hybridoma cell secreting an antibody wherein, the hybridoma may be generated by fusing splenocytes isolated from a mouse immunized with an antigen or immunogenic fragments thereof, with myeloma cells and then screening the hybridomas resulting from the fusion for hybridoma clones that secrete an antibody able to bind the administered antigen.

The antibodies of the invention (i.e., Fc variants) contain novel amino acid residues in their hinge regions. Fc variants can be generated by numerous methods well known to one skilled in the art. Non-limiting examples include, isolating antibody coding regions (e.g., from hybridoma) and introducing one or more hinge modifications of the invention into the isolated antibody coding region. Alternatively, the variable regions may be subcloned into a vector encoding an Fc region comprising a modified hinge of the invention. Additional methods and details are provided below.

Antibody fragments that recognize specific an antigen may be generated by any technique known to those of skill in the art. For example, Fab and F(ab')$_2$ fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles that carry the polynucleotide sequences encoding them. In particular, DNA sequences encoding VH and VL domains are amplified from animal cDNA libraries (e.g., human or murine cDNA libraries of lymphoid tissues). The DNA encoding the VH and VL domains are recombined together with an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to the an Antigen epitope of interest can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in International Publication No. WO 92/22324; Mullinax et al., 1992, BioTechniques 12(6): 864-869; Sawai et al., 1995, AJRI 34:26-34; and Better et al., 1988, Science 240:1041-1043.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma constant, and the PCR amplified VL domains can be cloned into vectors expressing a VL constant region, e.g., human kappa or lamba constant regions. It is contemplated that the constant region comprises a modified hinge of the invention. In certain embodiments, the vectors for expressing the VH or VL domains comprise a promoter, a secretion signal, a cloning site for both the variable and constant domains, as well as a selection marker such as neomycin. The VH and VL domains may also be cloned into one vector expressing the desired constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. Methods for producing chimeric antibodies are known in the art. See e.g., Morrison, 1985, Science 229: 1202; Oi et al., 1986, BioTechniques 4:214; Gillies et al., 1989, J. Immunol. Methods 125:191-202; and U.S. Pat. Nos. 5,807,715, 4,816,567, 4,8 16397, and 6,311,415.

For some uses, including in vivo use of antibodies in humans and in vitro detection assays, it may be preferable to use human or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and PCT Publication Nos. WO 98/46645, WO 98/50433, WO 98/24893, WO98/16654, WO 96/34096, WO 96/33735, and WO 91/10741.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab')$_2$, Fabc, Fv) in which all or substantially all of the CDR regions correspond to those of a non-human immunoglobulin (i.e., donor antibody) and all or substantially all of the framework regions are those of a human immunoglobulin consensus sequence. In a specific embodiment, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG.sub.1. Where such cytotoxic activity is not desirable, the constant domain may be of the IgG.sub.2 class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework region (FR) and CDR sequences, more often 90%, or greater than 95%. Humanized antibody can be produced using variety of techniques known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5): 489-498; Studnicka et al., 1994, Protein Engineering 7(6): 805-814; and Roguska et al., 1994, PNAS 91:969-973), chain shuffling (U.S. Pat. No. 5,565,332), and techniques disclosed in, e.g., U.S. Pat. No. 6,407,213, U.S. Pat. No. 5,766,886, WO 9317105, Tan et al., J. Immunol. 169:1119-25 (2002), Caldas et al., Protein Eng. 13(5): 353-60 (2000), Morea et al., Methods 20(3): 267-79 (2000), Baca et al., J. Biol. Chem. 272(16): 10678-84 (1997), Roguska et al., Protein Eng. 9(10): 895-904 (1996), Couto et al., Cancer Res. 55 (23 Supp): 5973s-5977s (1995), Couto et al., Cancer Res. 55(8): 1717-22 (1995), Sandhu J S, Gene 150(2): 409-10 (1994), and Pedersen et al., J. Mol. Biol. 235(3): 959-73 (1994). Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323).

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen or immunogenic fragments thereof. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569, 825, 5,661,016, 5,545,806, 5,814,318, and 5,939,598. In addition, companies such as Abgenix, Inc. (Freemont, Calif.), Genpharm (San Jose, Calif.) and Medarex (Princeton, N.J.) can be engaged to provide human antibodies directed against a selected antigen using technology similar to that described above.

Further, the antibodies of the invention can, in turn, be utilized to generate anti-idiotype antibodies that "mimic" a receptor using techniques well known to those skilled in the art. (See, e.g., Greenspan & Bona, 1989, FASEB J. 7(5): 437-444; and Nissinoff, 1991, J. Immunol. 147(8): 2429-2438). For example, antibodies of the invention which bind to and competitively inhibit the binding of an receptor (as determined by assays well known in the art and disclosed infra) to its ligands can be used to generate anti-idiotypes that "mimic" the ligand and, as a consequence, bind to and neutralize the receptor and/or its ligands. Such neutralizing anti-idiotypes or Fab fragments of such anti-idiotypes can be used in therapeutic regimens to neutralize a ligand and/or its receptor. The invention provides methods employing the use of polynucleotides comprising a nucleotide sequence encoding an antibody of the invention or a fragment thereof.

In one embodiment, the nucleotide sequence encoding an antibody that specifically binds an antigen is obtained and used to generate the Fc variants of the invention. The nucleotide sequence can be obtained from sequencing hybridoma clone DNA. If a clone containing a nucleic acid encoding a particular antibody or an epitope-binding fragment thereof is not available, but the sequence of the antibody molecule or epitope-binding fragment thereof is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from any tissue or cells expressing the antibody, such as hybridoma cells selected to express an antibody) by PCR amplification using synthetic primers that hybridize to the 3' and 5'ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in *Current Protocols in Molecular Biology*, F. M. Ausubel et al., ed., John Wiley & Sons (Chichester, England, 1998); *Molecular Cloning: A Laboratory Manual,* 3rd Edition, J. Sambrook et al., ed., Cold Spring Harbor Laboratory Press (Cold Spring Harbor, N.Y., 2001); *Antibodies: A Laboratory Manual*, E. Harlow and D. Lane, ed., Cold Spring Harbor Laboratory Press (Cold Spring Harbor, N.Y., 1988); and *Using Antibodies: A Laboratory Manual*, E. Harlow and D. Lane, ed., Cold Spring Harbor Laboratory (Cold Spring Harbor, N.Y., 1999)), to generate antibodies having a different amino acid sequence by, for example, introducing deletions, and/or insertions into desired regions of the antibodies.

In one embodiment, one or more hinge modification of the invention is made within the hinge of an antibody able to specifically bind an antigen. It is specifically contemplated that the hinge modification modifies binding to at least one Fc ligand (e.g., FcγRs and/or C1q) and alters ADCC and/or CDC function.

In a specific embodiment, one or more of the CDRs is inserted within framework regions using routine recombinant DNA techniques. The framework regions may be naturally occurring or consensus framework regions, including, but not limited to, human framework regions (see, e.g., Chothia et al., 1998, J. Mol. Biol. 278: 457-479 for a listing of human framework regions). It is contemplated that the polynucleotide generated by the combination of the framework regions and CDRs encodes an antibody that specifically binds to an Antigen. In one embodiment, as discussed supra, one or more amino acid substitutions may be made within the framework regions, and, in certain embodiments, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

The hinge of antibodies identified from such screening methods can be modified as described supra to generate an antibody incorporating a modified hinge of the invention. It is further contemplated that the Fc variants of the newly identified antibodies are useful for the prevention, management and treatment of a disease, disorder, infection, including but not limited to inflammatory diseases, autoimmune diseases, bone metabolism related disorders, angiogenic related disorders, infection, and cancer. Such antibodies can be used in the methods and compositions of the present invention.

7.2 Fusion Proteins Comprising Hinge Modifications

An Fc fusion protein combines an Fc region of an immunoglobulin or fragment thereof, with a fusion partner, which in general can be any protein, polypeptide, peptide, or small molecule. The role of the non-Fc part of the Fc fusion protein, i.e., the fusion partner, is often but not always to mediate target binding, and thus is functionally analogous to the variable regions of an antibody. Accordingly, the present invention encompasses Fc variants comprising polypeptides that specifically bind to a molecule (e.g., a cell surface receptor, chemokine, etc) and an Fc region incorporating a hinge modification of the present invention. In certain embodiments, Fc variants specifically bind to and/or incorporate one or more of the antigens described above (see, section entitled "Antibodies of the Invention," supra). In other embodiments, Fc variants specifically bind to and/or incorporate one or more of the molecules described above (see, section entitled "Specific Antigens and Fusion Partners of the Invention," supra).

In a one embodiment, an Fc variant that specifically binds to a molecule may comprise, for example, a ligand, a receptor or a fragment thereof, which specifically binds to a molecule, fused to an Fc region. It is specifically contemplated that the Fc region of said fusion protein comprises a modified hinge of the invention as described supra.

In another embodiment, an Fc variant that specifically binds to a molecule comprises a bioactive molecule fused to an Fc region incorporating at least one hinge modification of the present invention. In accordance with these embodiments, the bioactive molecule specifically binds to a molecule. Bioactive molecules that may be fused to an Fc region incorporating at least one hinge modification of the present invention, but are not limited to, peptides, polypeptides, proteins, small molecules, mimetic agents, synthetic drugs, inorganic molecules, and organic molecules. In one embodiment, a bioactive molecule is a polypeptide comprising at least 5, at least 10, at least 20, at least 30, at least 40, at least 50, at least 60, at least 70, at least 80, at least 90 or at least 100 contiguous amino acid residues, and is heterologous to the amino acid sequence of the Fc region incorporating at least one hinge modification of the present invention.

The present invention also encompasses Fc variants comprising polypeptides and an Fc region incorporating at least one hinge modification of the present invention that specifically bind to a molecule, fused to marker sequences, such as but not limited to, a peptide, to facilitate purification. In other embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. Other peptide tags useful for purification include, but are not limited to, the hemagglutinin"HA" tag, which corresponds to an epitope derived from the influenza hemagglutinin protein (Wilson et al., 1984, Cell 37:767) and the "flag" tag.

The present invention further encompasses Fc variants comprising polypeptides and an Fc region incorporating at least one hinge modification of the present invention that specifically bind to a molecule which are further conjugated to a therapeutic moiety such as a cytotoxin, e.g., a cytostatic or cytocidal agent, an agent which has a potential therapeutic benefit, or a radioactive metal ion, e.g., alpha-emitters. A cytotoxin or cytotoxic agent includes any agent that is detrimental to cells. Examples of a therapeutic moieties and cytotoxin or cytotoxic agents are listed supra (see section entitled "Antibody Conjugates and Derivatives" supra).

A variety of linkers, defined and described herein, may be used to covalent link and Fc region to a fusion partner to generate an Fc fusion protein. Alternatively, polypeptides, proteins and fusion proteins can be produced by standard recombinant DNA techniques or by protein synthetic techniques, e.g., by use of a peptide synthesizer. For example, a nucleic acid molecule encoding a peptide, polypeptide, protein or a fusion protein can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., *Current Protocols in Molecular Biology*, Ausubel et al., eds., John Wiley & Sons, 1992). Moreover, a nucleic acid encoding a bioactive molecule can be cloned into an expression vector containing an Fc region incorporating a hinge modification or a fragment thereof such that the bioactive molecule is linked in-frame to the Fc region incorporating a hinge modification.

Methods for fusing or conjugating polypeptides to the constant regions of antibodies are known in the art. See, e.g., U.S. Pat. Nos. 5,336,603, 5,622,929, 5,359,046, 5,349,053, 5,447, 851, 5,723,125, 5,783,181, 5,908,626, 5,844,095, and 5,112, 946; EP 307,434; EP 367,166; EP 394,827; International Publication Nos. WO 91/06570, WO 96/04388, WO 96/22024, WO 97/34631, and WO 99/04813; Ashkenazi et al., 1991, Proc. Natl. Acad. Sci. USA 88: 10535-10539; Traunecker et al., 1988, Nature, 331:84-86; Zheng et al., 1995, J. Immunol. 154:5590-5600; and Vil et al., 1992, Proc. Natl. Acad. Sci. USA 89:11337-11341.

The nucleotide sequences encoding a bioactive molecule and an Fc domain or fragment thereof may be obtained from any information available to those of skill in the art (i.e., from Genbank, the literature, or by routine cloning). The nucleotide sequences encoding Integrin ligands may be obtained from any available information, e.g., from Genbank, the literature or by routine cloning. See, e.g., Xiong et al., Science, 12; 294(5541): 339-45 (2001). The Fc region or a fragment thereof may be a naturally occurring domain or may comprise a modified hinge including, but not limited to, those described herein. In the event that a naturally occurring Fc region is utilized, the hinge region is modified using methods known in the art including but not limited to those disclosed herein to generate an Fc variant of the invention. The nucleotide sequence coding for a polypeptide a fusion protein can be inserted into an appropriate expression vector, i.e., a vector that contains the necessary elements for the transcription and translation of the inserted protein-coding sequence. A variety of host-vector systems may be utilized in the present invention to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

7.3 Recombinant Expression of Fc Variants

Recombinant expression of an Fc variant, derivative, analog or fragment thereof, (e.g., an antibody or fusion protein of the invention), requires construction of an expression vector containing a polynucleotide that encodes the Fc variant (e.g., antibody, or fusion protein). Once a polynucleotide encoding an Fc variant (e.g., antibody, or fusion protein) has been obtained, the vector for the production of the Fc variant (e.g., antibody, or fusion protein) may be produced by recombinant DNA technology using techniques well known in the art. Thus, methods for preparing a protein by expressing a polynucleotide containing an Fc variant (e.g., antibody, or fusion protein) encoding nucleotide sequence are described herein. Methods that are well known to those skilled in the art can be used to construct expression vectors containing Fc variant (e.g., antibody, or fusion protein) coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an Fc variant of the invention, operably linked to a promoter. Such vectors may include the nucleotide sequence encoding the constant region of the antibody molecule (see, e.g., International Publication No. WO 86/05807; International Publication No. WO 89/01036; and U.S. Pat. No. 5,122,464) and the variable domain of the antibody, or a polypeptide for generating an Fc variant may be cloned into such a vector for expression of the full length antibody chain (e.g. heavy or light chain), or complete Fc variant comprising a fusion of a non-antibody derived polypeptide and an Fc region incorporating at least one hinge modification of the invention.

The expression vector is transferred to a host cell by conventional techniques and the transfected cells are then cultured by conventional techniques to produce an Fc variant of the invention. Thus, the invention includes host cells containing a polynucleotide encoding an Fc variant of the invention, operably linked to a heterologous promoter. In specific embodiments for the expression of Fc variants comprising double-chained antibodies, vectors encoding both the heavy and light chains may be co-expressed in the host cell for expression of the entire immunoglobulin molecule, as detailed below.

A variety of host-expression vector systems may be utilized to express the Fc variants of the invention (e.g., antibody or fusion protein molecules) (see, e.g., U.S. Pat. No. 5,807, 715). Such host-expression systems represent vehicles by which the coding sequences of interest may be produced and subsequently purified, but also represent cells which may, when transformed or transfected with the appropriate nucleotide coding sequences, express an Fc variant of the invention in situ. These include but are not limited to microorganisms such as bacteria (e.g., *E. coli* and *B. subtilis*) transformed with recombinant bacteriophage DNA, plasmid DNA or cosmid DNA expression vectors containing Fc variant coding sequences; yeast (e.g., *Saccharomyces Pichia*) transformed with recombinant yeast expression vectors containing Fc variant coding sequences; insect cell systems infected with recombinant virus expression vectors (e.g., baculovirus) containing Fc variant coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing Fc variant coding sequences; or mammalian cell systems (e.g., COS, CHO, BHK, 293, NSO, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In certain embodiments, bacterial cells such as *Escherichia coli*, or eukaryotic cells, are used for the expression of an Fc variant which is a recombinant antibody or fusion protein molecules. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In a specific embodiment, the expression of nucleotide sequences encoding an Fc variant of the invention (e.g., antibody or fusion protein) is regulated by a constitutive promoter, inducible promoter or tissue specific promoter.

In bacterial systems, a number of expression vectors may be advantageously selected depending upon the use intended for the Fc variant (e.g., antibody or fusion protein) being expressed. For example, when a large quantity of such a protein is to be produced, for the generation of pharmaceutical compositions of an Fc variant, vectors that direct the expression of high levels of fusion protein products that are readily purified may be desirable. Such vectors include, but are not limited to, the *E. coli* expression vector pUR278 (Ruther et al., 1983, EMBO 12:1791), in which the Fc variant coding sequence may be ligated individually into the vector in frame with the lac Z coding region so that a lac Z-fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The Fc variant (e.g., antibody or fusion protein) coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the Fc variant (e.g., antibody or fusion protein) coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the Fc variant (e.g., antibody or fusion protein) in infected hosts (e.g., see Logan & Shenk, 1984, Proc. Natl. Acad. Sci. USA 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:516-544).

The expression of an Fc variant (e.g., antibody or fusion protein) may be controlled by any promoter or enhancer element known in the art. Promoters which may be used to control the expression of the gene encoding an Fc variant (e.g., antibody or fusion protein) include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), the tetracycline (Tet) promoter (Gossen et al., 1995, Proc. Nat. Acad. Sci. USA 89:5547-5551); prokaryotic expression vectors such as the β-lactamase promoter (VIIIa-Kamaroff et al., 1978, Proc. Natl. Acad. Sci. U.S.A. 75:3727-3731), or the tac promoter (DeBoer et al., 1983, Proc. Natl. Acad. Sci. U.S.A. 80:21-25; see also "Useful proteins from recombinant bacteria" in Scientific American, 1980, 242:74-94); plant expression vectors comprising the nopaline synthetase promoter region (Herrera-Estrella et al., Nature 303:209-213) or the cauliflower mosaic virus $^{35}$S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94); myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286); neuronal-specific enolase (NSE) which is active in neuronal cells (Morelli et al., 1999, Gen. Virol. 80:571-83); brain-derived neurotrophic factor (BDNF) gene control region which is active in neuronal cells (Tabuchi et al., 1998, Biochem. Biophysic. Res. Com. 253:818-823); glial fibrillary acidic protein (GFAP) promoter which is active in astrocytes (Gomes et al., 1999, Braz J Med Biol Res 32(5): 619-631; Morelli et al., 1999, Gen. Virol. 80:571-83) and gonadotropic releasing hormone gene control region which is active in the hypothalamus (Mason et al., 1986, Science 234:1372-1378).

Expression vectors containing inserts of a gene encoding an Fc variant of the invention (e.g., antibody or fusion protein) can be identified by three general approaches: (a) nucleic acid hybridization, (b) presence or absence of "marker" gene functions, and (c) expression of inserted sequences. In the first approach, the presence of a gene encoding a peptide, polypeptide, protein or a fusion protein in an expression vector can be detected by nucleic acid hybridization using probes comprising sequences that are homologous to an inserted gene encoding the peptide, polypeptide, protein or the fusion protein, respectively. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleotide sequence encoding an antibody or fusion protein in the vector. For example, if the nucleotide sequence encoding the Fc variant (e.g., antibody or fusion protein) is inserted within the marker gene sequence of the vector, recombinants containing the gene encoding the antibody or fusion protein insert can be identified by the absence of the marker gene function. In the third approach, recombinant expression vectors can be identified by assaying the gene product (e.g., antibody or fusion protein) expressed by the recombinant. Such assays can be based, for example, on the physical or functional properties of the fusion protein in in vitro assay systems, e.g., binding with anti-bioactive molecule antibody.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered fusion protein may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells that possess the cellular machinery for proper processing of the primary transcript (e.g., glycosylation, and phosphorylation) of the gene product may be used. Such mammalian host cells include, but are not limited to, CHO, VERY, BHK, Hela, COS, MDCK, 293, 3T3, WI38, NSO, and in particular, neuronal cell lines such as, for example, SK-N-AS, SK-N-FI, SK-N-DZ human neuroblastomas (Sugimoto et al., 1984, J. Natl. Cancer Inst. 73: 51-57), SK-N—SH human neuroblastoma (Biochim. Biophys. Acta, 1982, 704: 450-460), Daoy human cerebellar medulloblastoma (He et al., 1992, Cancer Res. 52: 1144-1148) DBTRG-05MG glioblastoma cells (Kruse et al., 1992, In Vitro Cell. Dev. Biol. 28A: 609-614), IMR-32 human neuroblastoma (Cancer Res., 1970, 30: 2110-2118), 1321N1 human astrocytoma (Proc. Natl. Acad. Sci. USA, 1977, 74: 4816), MOG-G-CCM human astrocytoma (Br. J. Cancer, 1984, 49: 269), U87MG human glioblastoma-astrocytoma (Acta Pathol. Microbiol. Scand., 1968, 74: 465-486), A172 human glioblastoma (Olopade et al., 1992, Cancer Res. 52: 2523-2529), C6 rat glioma cells (Benda et al., 1968, Science 161: 370-371), Neuro-2a mouse neuroblastoma (Proc. Natl. Acad. Sci. USA, 1970, 65: 129-136), NB41A3 mouse neuroblastoma (Proc. Natl. Acad. Sci. USA, 1962, 48: 1184-1190), SCP sheep choroid plexus (Bolin et al., 1994, J. Virol. Methods 48: 211-221), G355-5, PG-4 Cat normal astrocyte (Haapala et al., 1985, J. Virol. 53: 827-833), Mpf ferret brain (Trowbridge et al., 1982, In Vitro 18: 952-960), and normal cell lines such as, for example, CTX TNA2 rat normal cortex brain (Radany et al., 1992, Proc. Natl. Acad. Sci. USA 89: 6467-6471) such as, for example, CRL7030 and Hs578Bst. Furthermore, different vector/host expression systems may effect processing reactions to different extents.

For long-term, high-yield production of recombinant proteins, stable expression is often preferred. For example, cell lines which stably express an Fc variant of the invention (e.g., antibody or fusion protein) may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express an Fc variant that specifically binds to an Antigen. Such engineered cell lines may be particularly useful in screening and evaluation of compounds that affect the activity of an Fc variant (e.g., a polypeptide or a fusion protein) that specifically binds to an antigen.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk–, hgprt– or aprt– cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes.

Once an Fc variant (e.g., antibody, or a fusion protein) of the invention has been produced by recombinant expression, it may be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins.

The expression levels of an Fc variant (e.g., antibody or fusion protein) can be increased by vector amplification (for a review, see Bebbington and Hentschel, The use of vectors based on gene amplification for the expression of cloned genes in mammalian cells in DNA cloning, Vol. 3. (Academic Press, New York, 1987)). For example, when a marker in the vector system expressing an antibody or fusion protein is amplifiable, increase in the level of inhibitor present in culture of host cell will increase the number of copies of the marker gene. Since the amplified region is associated with the antibody gene, production of the antibody or fusion protein will also increase (Crouse et al., 1983, Mol. Cell. Biol. 3:257).

The host cell may be co-transfected with two expression vectors of the invention. For example, the first vector encoding a heavy chain derived polypeptide and the second vector encoding a light chain derived polypeptide. The two vectors may contain identical selectable markers, which enable equal expression of heavy and light chain polypeptides. Alternatively, a single vector may be used which encodes, and is capable of expressing, a fusion protein or both heavy and light chain polypeptides. The coding sequences for the fusion protein or heavy and light chains may comprise cDNA or genomic DNA.

7.4 Characterization and Functional Assays

Fc variants (e.g., antibodies or fusion proteins) of the present invention may be characterized in a variety of ways. In particular, Fc variants of the present invention may be assayed for the ability to specifically bind to a ligand, (e.g., FcγRIIIA, FcγRIIB, C1q). Such an assay may be performed in solution (e.g., Houghten, *Bio/Techniques*, 13:412-421, 1992), on beads (Lam, *Nature*, 354:82-84, 1991, on chips (Fodor, *Nature*, 364:555-556, 1993), on bacteria (U.S. Pat. No. 5,223,409), on plasmids (Cull et al., *Proc. Natl. Acad. Sci. USA*, 89:1865-1869, 1992) or on phage (Scott and Smith, *Science*, 249:386-390, 1990; Devlin, *Science*, 249:404-406, 1990; Cwirla et al., *Proc. Natl. Acad. Sci. USA*, 87:6378-6382, 1990; and Felici, *J. Mol. Biol.*, 222:301-310, 1991). Molecules that have been identified to specifically bind to a ligand, (e.g., FcγRIIIA, FcγRIIB, C1q or to an antigen) can then be assayed for their affinity for the ligand.

Fc variants of the invention may be assayed for specific binding to a molecule such as an antigen (e.g., cancer antigen and cross-reactivity with other antigens) or a ligand (e.g., FcγR) by any method known in the art. Immunoassays which can be used to analyze specific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Current Protocols in Molecular Biology, Vol. 1, John Wiley & Sons, Inc., New York).

The binding affinity of the Fc variants of the present invention to a molecule such as an antigen or a ligand, (e.g., FcγR) and the off-rate of the interaction can be determined by competitive binding assays. One example of a competitive binding assay is a radioimmunoassay comprising the incubation of labeled ligand, such as FcγR (e.g., $^3$H or $^{125}$I) with a molecule of interest (e.g., Fc variants of the present invention) in the presence of increasing amounts of unlabeled ligand, such as FcγR, and the detection of the molecule bound to the labeled ligand. The affinity of the molecule of the present invention for the ligand and the binding off-rates can be determined from the saturation data by scatchard analysis.

The kinetic parameters of an Fc variant may also be determined using any surface plasmon resonance (SPR) based assays known in the art (e.g., BIAcore kinetic analysis). For a review of SPR-based technology see Mullet et al., 2000, *Methods* 22: 77-91; Dong et al., 2002*l*, *Review in Mol. Biotech.*, 82: 303-23; Fivash et al., 1998, *Current Opinion in Biotechnology* 9: 97-101; Rich et al., 2000, *Current Opinion in Biotechnology* 11: 54-61. Additionally, any of the SPR instruments and SPR based methods for measuring protein-protein interactions described in U.S. Pat. Nos. 6,373,577; 6,289,286; 5,322,798; 5,341,215; 6,268,125 are contemplated in the methods of the invention.

Fluorescence activated cell sorting (FACS), using any of the techniques known to those skilled in the art, can be used for characterizing the binding of Fc variants to a molecule expressed on the cell surface (e.g., FcγRIIIA, FcγRIIB). Flow sorters are capable of rapidly examining a large number of individual cells that contain library inserts (e.g., 10-100 million cells per hour) (Shapiro et al., *Practical Flow Cytometry*, 1995). Flow cytometers for sorting and examining biological cells are well known in the art. Known flow cytometers are described, for example, in U.S. Pat. Nos. 4,347,935; 5,464, 581; 5,483,469; 5,602,039; 5,643,796; and 6,211,477. Other known flow cytometers are the FACS Vantage™ system manufactured by Becton Dickinson and Company, and the COPAS™ system manufactured by Union Biometrica.

The Fc variants of the invention can be characterized by their ability to mediate FcγR-mediated effector cell function. Examples of effector cell functions that can be assayed include, but are not limited to, antibody-dependent cell mediated cytotoxicity (ADCC), phagocytosis, opsonization, opsonophagocytosis, C1q binding, and complement dependent cell mediated cytotoxicity (CDC). Any cell-based or cell free assay known to those skilled in the art for determining effector cell function activity can be used (For effector cell assays, see Perussia et al., 2000, *Methods Mol. Biol.* 121: 179-92; Baggiolini et al., 1998 *Experientia*, 44(10): 841-8; Lehmann et al., 2000 *J. Immunol. Methods*, 243(1-2): 229-42; Brown E J. 1994, *Methods Cell Biol.*, 45: 147-64; Munn et al., 1990 *J. Exp. Med.*, 172: 231-237, Abdul-Majid et al., 2002 *Scand. J. Immunol.* 55: 70-81; Ding et al., 1998, *Immunity* 8:403-411).

In particular, the Fc variants of the invention can be assayed for FcγR-mediated ADCC activity in effector cells, (e.g., natural killer cells) using any of the standard methods known to those skilled in the art (See e.g., Perussia et al., 2000, *Methods Mol. Biol.* 121: 179-92). An exemplary assay for determining ADCC activity of the molecules of the invention is based on a $^{51}$Cr release assay comprising of: labeling target cells with [$^{51}$Cr]Na$_2$CrO$_4$ (this cell-membrane permeable molecule is commonly used for labeling since it binds cytoplasmic proteins and although spontaneously released from the cells with slow kinetics, it is released massively following target cell necrosis); osponizing the target cells with the Fc variants of the invention; combining the opsonized radiolabeled target cells with effector cells in a microtitre plate at an appropriate ratio of target cells to effector cells; incubating the mixture of cells for 16-18 hours at 37° C.; collecting supernatants; and analyzing radioactivity. The cytotoxicity of the molecules of the invention can then be determined, for example using the following formula: % lysis=(experimental cpm−target leak cpm)/(detergent lysis cpm−target leak cpm)×100%. Alternatively, % lysis=(ADCC−AICC)/(maximum release−spontaneous release). Specific lysis can be calculated using the formula: specific lysis=% lysis with the molecules of the invention−% lysis in the absence of the molecules of the invention. A graph can be generated by varying either the target: effector cell ratio or antibody concentration. Specific methods are also disclosed in the section entitled "Examples," infra.

Method to characterize the ability of the Fc variants to bind C1q and mediate complement dependent cytotoxicity (CDC) are well known in the art. For example, to determine C1q binding, a C1q binding ELISA may be performed. An exemplary assay may comprise the following: assay plates may be coated overnight at 4C with polypeptide variant or starting polypeptide (control) in coating buffer. The plates may then be washed and blocked. Following washing, an aliquot of human C1q may be added to each well and incubated for 2 hrs at room temperature. Following a further wash, 100 uL of a sheep anti-complement C1q peroxidase conjugated antibody may be added to each well and incubated for 1 hour at room temperature. The plate may again be washed with wash buffer and 100 ul of substrate buffer containing OPD (O-phenylenediamine dihydrochloride (Sigma)) may be added to each well. The oxidation reaction, observed by the appearance of a yellow color, may be allowed to proceed for 30 minutes and stopped by the addition of 100 ul of 4.5 NH2 SO4. The absorbance may then read at (492-405) nm. Specific methods are also disclosed in the section entitled "Examples," infra.

To assess complement activation, a complement dependent cytotoxicity (CDC) assay may be performed, (e.g. as described in Gazzano-Santoro et al., 1996, J. Immunol. Methods 202:163). Briefly, various concentrations of Fc variant and human complement may be diluted with buffer. Cells which express the antigen to which the Fc variant binds may be diluted to a density of about 1×10$^6$ cells/ml. Mixtures of the Fc variant, diluted human complement and cells expressing the antigen may be added to a flat bottom tissue culture 96 well plate and allowed to incubate for 2 hrs at 37C. and 5% CO2 to facilitate complement mediated cell lysis. 50 uL of alamar blue (Accumed International) may then be added to each well and incubated overnight at 37 C. The absorbance is measured using a 96-well fluorometer with excitation at 530 nm and emission at 590 nm. The results may be expressed in relative fluorescence units (RFU). The sample concentrations may be computed from a standard curve and the percent activity, relative to a comparable molecule (i.e., a molecule comprising an Fc region with an unmodified or wild type hinge) is reported for the variant of interest.

Complement assays may be performed with guinea pig, rabbit or human serum. Complement lysis of target cells may be detected by monitoring the release of intracellular enzymes such as lactate dehydrogenase (LDH), as described in Korzeniewski et al., 1983, *Immunol. Methods* 64(3): 313-20; and Decker et al., 1988, *J. Immunol. Methods* 115(1): 61-9; or the release of an intracellular label such as europium, chromium 51 or indium 111 in which target cells are labeled.

7.5 Methods of Treatment

The present invention encompasses administering one or more Fc variant of the invention (e.g., antibodies) to an animal, in particular a mammal, specifically, a human, for preventing, treating, or ameliorating one or more symptoms associated with a disease, disorder, or infection. The Fc variants of the invention are particularly useful for the treatment or prevention of a disease or disorder where an altered efficacy of effector cell function (e.g., ADCC, CDC) is desired. The Fc variants and compositions thereof are particularly useful for the treatment or prevention of primary or metastatic neoplastic disease (i.e., cancer), and infectious diseases. Molecules of the invention may be provided in pharmaceutically acceptable compositions as known in the art or as described herein. As detailed below, the molecules of the invention can be used in methods of treating or preventing cancer (particularly in passive immunotherapy), autoimmune disease, inflammatory disorders or infectious diseases.

The Fc variants of the invention may also be advantageously utilized in combination with other therapeutic agents known in the art for the treatment or prevention of a cancer, autoimmune disease, inflammatory disorders or infectious diseases. In a specific embodiment, Fc variants of the invention may be used in combination with monoclonal or chimeric antibodies, lymphokines, or hematopoietic growth factors (such as, e.g., IL-2, IL-3 and IL-7), which, for example, serve to increase the number or activity of effector cells which interact with the molecules and, increase immune response. The Fc variants of the invention may also be advantageously utilized in combination with one or more drugs used to treat a disease, disorder, or infection such as, for example anti-cancer agents, anti-inflammatory agents or anti-viral agents.

Accordingly, the present invention provides methods for preventing, treating, or ameliorating one or more symptoms associated with cancer and related conditions by administering one or more Fc variants of the invention. Although not intending to be bound by any mechanism of actions, an Fc variant of the invention that binds FcγRIIIA and/or FcγRIIA with a greater affinity than a comparable molecule, and further binds FcγRIIB with a lower affinity than a comparable molecule, and/or said Fc variant has an enhanced effector function, e.g., ADCC, CDC, phagocytosis, opsonization, etc. will result in the selective targeting and efficient destruction of cancer cells.

The invention further encompasses administering one or more Fc variants of the invention in combination with other therapies known to those skilled in the art for the treatment or prevention of cancer, including but not limited to, current standard and experimental chemotherapies, hormonal therapies, biological therapies, immunotherapies, radiation therapies, or surgery. In some embodiments, the molecules of the invention may be administered in combination with a therapeutically or prophylactically effective amount of one or more anti-cancer agents, therapeutic antibodies or other agents known to those skilled in the art for the treatment and/or prevention of cancer. Examples of dosing regimes and therapies which can be used in combination with the Fc variants of the invention are well known in the art and have been described in detail elsewhere (see for example, PCT publications WO 02/070007 and WO 03/075957).

Cancers and related disorders that can be treated or prevented by methods and compositions of the present invention include, but are not limited to, the following: Leukemias, lymphomas, multiple myelomas, bone and connective tissue sarcomas, brain tumors, breast cancer, adrenal cancer, thyroid cancer, pancreatic cancer, pituitary cancers, eye cancers, vaginal cancers, vulvar cancer, cervical cancers, uterine cancers, ovarian cancers, esophageal cancers, stomach cancers, colon cancers, rectal cancers, liver cancers, gallbladder cancers, cholangiocarcinomas, lung cancers, testicular cancers, prostate cancers, penal cancers; oral cancers, salivary gland cancers pharynx cancers, skin cancers, kidney cancers, bladder cancers (for a review of such disorders, see Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

The invention further contemplates engineering any of the antibodies known in the art (see for example the antibodies listed in section entitled "Antibodies of the Invention" supra) for the treatment and/or prevention of cancer and related disorders, so that the antibodies comprise an Fc region incorporating a hinge modification of the invention.

In a specific embodiment, a molecule of the invention (e.g., an antibody comprising an Fc region incorporating a hinge modification of the invention, or a therapeutic monoclonal antibody engineered according to the methods of the invention to have a hinge modification of the invention) inhibits or reduces the growth of primary tumor or metastasis of cancerous cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth of primary tumor or metastasis in the absence of said molecule of the invention.

The present invention encompasses the use of one or more Fc variants of the invention for preventing, treating, or managing one or more symptoms associated with an inflammatory disorder in a subject. Although not intending to be bound by any mechanism of actions, Fc variants with enhanced affinity for FcγRIIB will lead to a dampening of the activating receptors and thus a dampening of the immune response and have therapeutic efficacy for treating and/or preventing an autoimmune disorder.

The invention further encompasses administering the Fc variants of the invention in combination with a therapeutically or prophylactically effective amount of one or more anti-inflammatory agents. The invention also provides methods for preventing, treating, or managing one or more symptoms associated with an autoimmune disease further comprising, administering to said subject an Fc variant of the invention in combination with a therapeutically or prophylactically effective amount of one or more immunomodulatory agents. Examples of autoimmune disorders that may be treated by administering the Fc variants of the invention include, but are not limited to, alopecia greata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, and chronic inflammation resulting from chronic viral or bacteria infections. Some autoimmune disorders are associated with an inflammatory condition, thus, there is overlap between what is considered an autoimmune disorder and an inflammatory disorder. Therefore, some autoimmune disorders may also be characterized as inflammatory disorders. Examples of inflammatory disorders which can be prevented, treated or managed in accordance with the methods of the invention include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, and chronic inflammation resulting from chronic viral or bacteria infections.

Fc variants of the invention can also be used to reduce the inflammation experienced by animals, particularly mammals, with inflammatory disorders. In a specific embodiment, an Fc of the invention reduces the inflammation in an animal by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the inflammation in an animal, which is not administered the said molecule.

The invention further contemplates engineering any of the antibodies known in the art (see for example the antibodies listed in section entitled "Antibodies of the Invention" supra) for the treatment and/or prevention of autoimmune disease or inflammatory disease, so that the antibodies comprise an Fc region incorporating a hinge modification of the invention.

The invention also encompasses methods for treating or preventing an infectious disease in a subject comprising administering a therapeutically or prophylatically effective amount of one or more Fc variants of the invention. Infectious diseases that can be treated or prevented by the Fc variants of the invention are caused by infectious agents including but not limited to viruses, bacteria, fungi, protozae, and viruses.

Viral diseases that can be treated or prevented using the Fc variants of the invention in conjunction with the methods of the present invention include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral miningitis, encephalitis, dengue or small pox.

Bacterial diseases that can be treated or prevented using the Fc variants of the invention in conjunction with the methods of the present invention, that are caused by bacteria include, but are not limited to, mycobacteria *rickettsia*, mycoplasma, *neisseria, S. pneumonia, Borrelia burgdorferi* (Lyme disease), *Bacillus antracis* (anthrax), tetanus, *streptococcus, staphylococcus*, mycobacterium, tetanus, pertissus, cholera, plague, diptheria, chlamydia, *S. aureus* and *legionella*. Protozoal diseases that can be treated or prevented using the molecules of the invention in conjunction with the methods of the present invention, that are caused by protozoa include, but are not limited to, *leishmania*, kokzidioa, *trypanosoma* or malaria. Parasitic diseases that can be treated or prevented using the molecules of the invention in conjunction with the methods of the present invention, that are caused by parasites include, but are not limited to, chlamydia and *rickettsia*.

In some embodiments, the Fc variants of the invention may be administered in combination with a therapeutically or prophylactically effective amount of one or additional therapeutic agents known to those skilled in the art for the treatment and/or prevention of an infectious disease. The invention contemplates the use of the molecules of the invention in combination with other molecules known to those skilled in the art for the treatment and or prevention of an infectious disease including, but not limited to, antibiotics, antifungal agents and anti-viral agents.

7.6 Compositions and Methods of Administering

The invention provides methods and pharmaceutical compositions comprising Fc variants of the invention (e.g., antibodies, polypeptides). The invention also provides methods of treatment, prophylaxis, and amelioration of one or more symptoms associated with a disease, disorder or infection by administering to a subject an effective amount of at least one Fc variant of the invention, or a pharmaceutical composition comprising at least one Fc variant of the invention. In a one aspect, the Fc variant, is substantially purified (i.e., substantially free from substances that limit its effect or produce undesired side-effects). In a specific embodiment, the subject is an animal, such as a mammal including non-primates (e.g., cows, pigs, horses, cats, dogs, rats etc.) and primates (e.g., monkey such as, a cynomolgous monkey and a human). In a specific embodiment, the subject is a human. In yet another specific embodiment, the antibody of the invention is from the same species as the subject.

The route of administration of the composition depends on the condition to be treated. For example, intravenous injection may be preferred for treatment of a systemic disorder such as a lymphatic cancer or a tumor which has metastasized. The dosage of the compositions to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. Depending on the condition, the composition can be administered orally, parenterally, intranasally, vaginally, rectally, lingually, sublingually, buccally, intrabuccally and/or transdermally to the patient.

Accordingly, compositions designed for oral, lingual, sublingual, buccal and intrabuccal administration can be made without undue experimentation by means well known in the art, for example, with an inert diluent or with an edible carrier. The composition may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums, and the like.

Tablets, pills, capsules, troches and the like may also contain binders, recipients, disintegrating agent, lubricants, sweetening agents, and/or flavoring agents. Some examples of binders include microcrystalline cellulose, gum tragacanth and gelatin. Examples of excipients include starch and lactose. Some examples of disintegrating agents include alginic acid, cornstarch, and the like. Examples of lubricants include magnesium stearate and potassium stearate. An example of a glidant is colloidal silicon dioxide. Some examples of sweetening agents include sucrose, saccharin, and the like. Examples of flavoring agents include peppermint, methyl salicylate, orange flavoring, and the like. Materials used in preparing these various compositions should be pharmaceutically pure and non-toxic in the amounts used.

The pharmaceutical compositions of the present invention can be administered parenterally, such as, for example, by intravenous, intramuscular, intrathecal and/or subcutaneous injection. Parenteral administration can be accomplished by incorporating the compositions of the present invention into a solution or suspension. Such solutions or suspensions may also include sterile diluents, such as water for injection, saline solution, fixed oils, polyethylene glycols, glycerine, propylene glycol and/or other synthetic solvents. Parenteral formulations may also include antibacterial agents, such as, for example, benzyl alcohol and/or methyl parabens, antioxidants, such as, for example, ascorbic acid and/or sodium bisulfite, and chelating agents, such as EDTA. Buffers, such as acetates, citrates and phosphates, and agents for the adjustment of tonicity, such as sodium chloride and dextrose, may also be added. The parenteral preparation can be enclosed in ampules, disposable syringes and/or multiple dose vials made of glass or plastic. Rectal administration includes administering the composition into the rectum and/or large intestine. This can be accomplished using suppositories and/or enemas. Suppository formulations can be made by methods known in the art. Transdermal administration includes percutaneous absorption of the composition through the skin. Transdermal formulations include patches, ointments, creams, gels, salves, and the like. The compositions of the present invention can be administered nasally to a patient. As used herein, nasally administering or nasal administration includes administering the compositions to the mucous membranes of the nasal passage and/or nasal cavity of the patient.

The pharmaceutical compositions of the invention may be used in accordance with the methods of the invention for preventing, treating, or ameliorating one or more symptoms associated with a disease, disorder, or infection. It is contemplated that the pharmaceutical compositions of the invention are sterile and in suitable form for administration to a subject.

In one embodiment the compositions of the invention are pyrogen-free formulations which are substantially free of endotoxins and/or related pyrogenic substances. Endotoxins include toxins that are confined inside a microorganism and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with monoclonal antibodies, it is advantageous to remove even trace amounts of endotoxin. In a specific embodiment, endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg.

The invention provides methods for preventing, treating, or ameliorating one or more symptoms associated with a disease, disorder, or infection, said method comprising: (a) administering to a subject in need thereof a dose of a prophylactically or therapeutically effective amount of a composition comprising one or more Fc variants and (b) administering one or more subsequent doses of said Fc variants, to maintain a plasma concentration of the Fc variant at a desirable level (e.g., about 0.1 to about 100 µg/ml), which continuously binds to an antigen. In a specific embodiment, the plasma concentration of the Fc variant is maintained at 10 µg/ml, 15 µg/ml, 20 µg/ml, 25 µg/ml, 30 µg/ml, 35 µg/ml, 40 µg/ml, 45 µg/ml or 50 µg/ml. In a specific embodiment, said effective amount of Fc variant to be administered is between at least 1 mg/kg and 8 mg/kg per dose. In another specific embodiment, said effective amount of Fc variant to be administered is between at least 4 mg/kg and 8 mg/kg per dose. In yet another specific embodiment, said effective amount of Fc variant to be administered is between 50 mg and 250 mg per dose. In still another specific embodiment, said effective amount of Fc variant to be administered is between 100 mg and 200 mg per dose.

The present invention also encompasses protocols for preventing, treating, or ameliorating one or more symptoms associated with a disease, disorder, or infection which an Fc variant is used in combination with a therapy (e.g., prophylactic or therapeutic agent) other than an Fc variant and/or variant fusion protein. The invention is based, in part, on the recognition that the Fc variants of the invention potentiate and synergize with, enhance the effectiveness of, improve the tolerance of, and/or reduce the side effects caused by, other cancer therapies, including current standard and experimental chemotherapies. The combination therapies of the invention have additive potency, an additive therapeutic effect or a synergistic effect. The combination therapies of the invention enable lower dosages of the therapy (e.g., prophylactic or therapeutic agents) utilized in conjunction with Fc variants for preventing, treating, or ameliorating one or more symptoms associated with a disease, disorder, or infection and/or less frequent administration of such prophylactic or therapeutic agents to a subject with a disease disorder, or infection to improve the quality of life of said subject and/or to achieve a prophylactic or therapeutic effect. Further, the combination therapies of the invention reduce or avoid unwanted or adverse side effects associated with the administration of current single agent therapies and/or existing combination therapies, which in turn improves patient compliance with the treatment protocol. Numerous molecules which can be utilized in combination with the Fc variants of the invention are well known in the art. See for example, PCT publications WO 02/070007; WO 03/075957 and U.S. Patent Publication 2005/064514.

The present invention provides kits comprising one or more Fc variants with altered binding affinity to FcγRs and/or C1q and altered ADCC and/or CDC activity that specifically bind to an antigen conjugated or fused to a detectable agent, therapeutic agent or drug, in one or more containers, for use in monitoring, diagnosis, preventing, treating, or ameliorating one or more symptoms associated with a disease, disorder, or infection.

The invention also provides kits comprising one or more Fc variants with altered binding affinity to FcγRs and/or C1q and altered ADCC and/or CDC activity that specifically bind to an antigen in a first vial and one or more prophylactic or therapeutic agents, other than Fc variant, in a second vial for use in monitoring, diagnosis, preventing, treating, or ameliorating one or more symptoms associated with a disease, disorder, or infection. The invention also provides kits comprising one or more Fc variants with altered binding affinity to FcγRs and/or C1q and altered ADCC and/or CDC activity that specifically bind to an antigen conjugated or fused to a therapeutic agent or drug in a first vial and one or more prophylactic or therapeutic agents, other than an Fc variant, in a second vial for use in monitoring, diagnosis, preventing, treating, or ameliorating one or more symptoms associated with a disease, disorder, or infection. The kits may further comprise packaging materials and/or instructions.

8. SPECIFIC EMBODIMENTS

1. A polypeptide comprising an Fc region, said Fc region comprising a modified hinge, wherein said polypeptide binds at least one Fc ligand with an altered affinity relative to a polypeptide having the same amino acid sequence except having a wild type hinge.

2. The polypeptide of embodiment 1, wherein the modified hinge has increased flexibility, relative to a polypeptide having the same amino acid sequence except having a wild type hinge.

3. The polypeptide of embodiment 1 or 2, wherein the modified hinge comprises at least one amino acid substitution.

4. The polypeptide of embodiment 3, wherein the modified hinge comprises at least one amino acid substitution at one or more positions selected from the group consisting of: E216, P217, K218, S221, D(no EU number, Kabat number 234), K222, T223, H224, T225, C226, P227, P228, C229 and P230, utilizing the EU index numbering system set forth in Kabat except where indicated.

5. The polypeptide of embodiment 3, wherein the modified hinge comprises at least one amino acid substitution selected from the group consisting of: E216G, E216A, P217G, P217A, K218G, K218A, S221G, S221A, D(no EU number, Kabat number 234)G, D(no EU number, Kabat number 234)A, K222G, K222A, T223G, T223A, H224G, H224A, T225G, T225A, C226S, C226T, P227G, P227A, P228G, P228A, C229S, C229T, P230G and P230A, utilizing the EU index numbering system set forth in Kabat except where indicated.

6. The polypeptide of embodiment 3, 4 or 5, wherein the modified hinge comprises at least one amino acid substitution selected from the group consisting of:
 (a) E216, P217, K218 and S221, wherein each residue is substituted with A or G;
 (b) D (no EU number, Kabat number 234), K222, T223, H224 and T225, wherein each residue is substituted with A or G;
 (c) P227 and P228, wherein each residue is substituted with A or G;
 (d) P230G or P230A;
 (e) C229S or C229T; and
 (f) C226S or C226T, utilizing the EU index numbering system set forth in Kabat except where indicated.

7. The polypeptide of embodiment 3, 4 or 5, wherein the modified hinge comprises at least one amino acid substitution selected from the group consisting of:
 (a) E216G, P217G, K218G and S221G;
 (b) D (no EU number, Kabat number 234)G, K222G, T223G, H224G and T225G;
 (c) P227G and P228G;
 (d) P230G;
 (e) C229S; and
 (f) C226S,
utilizing the EU index numbering system set forth in Kabat except where indicated.

8. The polypeptide of embodiment 1, wherein the modified hinge has decreased flexibility, relative to a polypeptide having the same amino acid sequence except having a wild type hinge.

9. The polypeptide of embodiment 1 or 8, wherein the modified hinge comprises at least one amino acid substitution.

10. The polypeptide of embodiment 9, wherein the modified hinge comprises at least one amino acid substitution at one or more positions selected from the group consisting of: E216, K218, S221, D(no EU number, Kabat number 234), K222, T223, H224, and T225,
utilizing the EU index numbering system set forth in Kabat except where indicated.

11. The polypeptide of embodiment 9, wherein the modified hinge comprises at least one amino acid substitution selected from the group consisting of: E216P, K218P, S221P, D(no EU number, Kabat number 234)P, K222P, T223P, T223C, H224P, H224C and T225P, T225C, utilizing the EU index numbering system set forth in Kabat except where indicated.

12. The polypeptide of embodiment 9, wherein the modified hinge comprises at least one amino acid substitution selected from the group consisting of:
 (a) T223C;
 (b) H224C and T225C;
 (c) D(no EU number, Kabat number 234)P, K222P, T223P, H224P and T225P; and
 (d) E216P, K218P and S221P, utilizing the EU index numbering system set forth in Kabat except where indicated.

13. The polypeptide of embodiment 1, wherein the modified hinge has decreased length, relative to a polypeptide having the same amino acid sequence except having a wild type hinge.

14. The polypeptide of embodiment 1 or 13, wherein the modified hinge comprises at least one amino acid deletion.

15. The polypeptide of embodiment 14, wherein the modified hinge comprises at least one amino acid deletion at one or more positions selected from the group consisting of: T223, H224, P227 and P228, utilizing the EU index numbering system set forth in Kabat.

16. The polypeptide of embodiment 14 or 15, wherein the modified hinge comprises at least one amino acid deletion selected from the group consisting of:
 (a) P227 and P228;
 (b) T223 and H224; and
 (c) T223, H224, P227 and P228, utilizing the EU index numbering system set forth in Kabat.

17. The polypeptide of embodiment 1, wherein the modified hinge has increased length and increased flexibility, relative to a polypeptide having the same amino acid sequence except having a wild type hinge.

18. The polypeptide of embodiment 1 or 17, wherein the modified hinge comprises at least one amino acid insertion.

19. The polypeptide of embodiment 18, wherein the modified hinge comprises at least one amino acid insertion selected from the group consisting of:
 (a) at least one A residue;
 (b) at least one G residue; and
 (c) at least one A residues and at least one G residue.

20. The polypeptide of embodiment 18 or 19, wherein at least one amino acid insertion is the insertion of between 1 and 5 amino acid residues.

21. The polypeptide of embodiment 18, 19 or 20, wherein at least one amino acid insertion is inserted between the amino acid residues selected from the group consisting of:
 (a) P227 and P228; and
 (b) D(no EU number, Kabat number 234) and K222, utilizing the EU index numbering system set forth in Kabat except where indicated.

22. The polypeptide of embodiment 18, 19, 20 or 21, wherein at least one amino acid insertion is selected from the group consisting of:
 (a) "GGG" between P227 and P228; and
 (b) "GGG" between D(no EU number, Kabat number 234) and K222, utilizing the EU index numbering system set forth in Kabat except where indicated.

23. The polypeptide of embodiment 1, wherein the modified hinge has increased length and decreased flexibility, relative to a polypeptide having the same amino acid sequence except having a wild type hinge.

24. The polypeptide of embodiment 1 or 23, wherein the modification of the hinge comprises at least one amino acid insertion.

25. The polypeptide of embodiment 24, wherein at least one amino acid insertion comprises at least one P residue.

26. The polypeptide of embodiment 24 or 25, wherein at least one amino acid insertion is the insertion of between 1 and 5 amino acid residues.

27. The polypeptide of embodiment 24, 25 or 26, wherein at least one amino acid insertion is inserted between the amino acid residues selected from the group consisting of:
 (a) P227 and P228; and
 (b) D(no EU number, Kabat number 234) and K222, utilizing the EU index numbering system set forth in Kabat except where indicated.

28. The polypeptide of embodiment 24, 25, 26 or 27, wherein at least one amino acid insertion is selected from the group consisting of:
   (a) "PPP" between P227 and P228; and
   (b) "PPP" between D(no EU number, Kabat number 234) and K222, utilizing the EU index numbering system set forth in Kabat except where indicated.

29. The polypeptide of embodiment 1, wherein the modification of the hinge alters the overall conformation of the hinge, relative to a polypeptide having the same amino acid sequence except having a wild type hinge.

30. The polypeptide of embodiment 1 or 29, wherein the modification of the hinge comprises at least one amino acid substitution.

31. The polypeptide of embodiment 30, wherein the modified hinge comprises at least one amino acid substitution at a position selected from the group consisting of: K218, S221, C(no EU number, Kabat number 233), D(no EU number, Kabat number 234), K222, T223, H224, P227 and P228, utilizing the EU index numbering system set forth in Kabat except where indicated.

32. The polypeptide of embodiment 30, wherein the modified hinge comprises at least one amino acid substitution selected from the group consisting of: K218W, K218F, S221C, S221W, S221F, C(no EU number, Kabat number 233)S, C(no EU number, Kabat number 233)T, C(no EU number, Kabat number 233)D, C(no EU number, Kabat number 233)E, D(no EU number, Kabat number 234)C, K222W, K222F, T223W, T223F, H224W, H224F, P227W, P227F, P228W and P228F, utilizing the EU index numbering system set forth in Kabat except where indicated.

33. The polypeptide of embodiment 30, wherein the modified hinge comprises at least one amino acid substitution is selected from the group consisting of:
   (a) P227 and P228, wherein each residue is substituted with W or F;
   (b) K222 and T223, wherein each residue is substituted with W or F;
   (c) 5221C and C(no EU number, Kabat number 233), wherein C(no EU number, Kabat number 233) is substituted with S or T;
   (d) C(no EU number, Kabat number 233) and D(no EU number, Kabat number 234)C, wherein C(no EU number, Kabat number 233) is substituted with D or E;
   (e) C(no EU number, Kabat number 233), D(no EU number, Kabat number 234)C, K222 and T223, wherein C(no EU number, Kabat number 233) is substituted with D or E and wherein K222 and T222 are substituted with either W or F;
   (f) K222W or K222F;
   (g) T223W or K222F;
   (h) K222 and T223, wherein each residue is substituted with W or F;
   (i) K222, T223 and H224 wherein each residue is substituted with W or F;
   (j) D(no EU number, Kabat number 234) and K222, wherein each residue is substituted with W or F; and
   (k) K218 and 5221, wherein each residue is substituted with W or F, utilizing the EU index numbering system set forth in Kabat except where indicated.

34. The polypeptide of embodiment 30, wherein the modified hinge comprises at least one amino acid substitution is selected from the group consisting of:
   (a) P227W and P228W;
   (b) K222W and T223W;
   (c) 5221C and C(no EU number, Kabat number 233)S;
   (d) C(no EU number, Kabat number 233)D and D(no EU number, Kabat number 234)C;
   (e) C(no EU number, Kabat number 233)D, D(no EU number, Kabat number 234)C, K222W and T223W;
   (f) K222W;
   (g) T223W;
   (h) K222F and T223F;
   (i) K222W, T223W and H224W;
   (j) D(no EU number, Kabat number 234)W and K222W; and
   (k) K218W and S221W, utilizing the EU index numbering system set forth in Kabat except where indicated.

35. A polypeptide comprising an Fc region, said Fc region comprising a modified hinge, wherein said polypeptide binds at least one FcγR with an altered affinity relative to a polypeptide having the same amino acid sequence except having a wild type hinge.

36. The polypeptide of embodiment 35, wherein the altered affinity is increased affinity.

37. The polypeptide of embodiment 36, wherein the FcγR is FcγRIIIA.

38. The polypeptide of embodiment 37, wherein the affinity is increased between about 10% and 100%.

39. The polypeptide of embodiment 37, wherein the affinity is increased between about 2-fold and 100-fold.

40. The polypeptide of embodiment 37, 38 or 39, wherein said polypeptide has ADCC activity which is increased between about 2-fold and 100-fold, relative to a polypeptide having the same amino acid sequence except having a wild type hinge.

41. The polypeptide of embodiment 35, wherein the altered affinity is decreased affinity.

42. The polypeptide of embodiment 41, wherein the FcγR is FcγRIIIA.

43. The polypeptide of embodiment 42, wherein the affinity is decreased between about 10% and 100%.

44. The polypeptide of embodiment 42, wherein the affinity is decreased between about 2-fold and 100-fold, relative to a polypeptide having the same amino acid sequence except having a wild type hinge.

45. The polypeptide of embodiment 42, 43 or 44, wherein the polypeptide has ADCC activity which is decreased between about 2-fold and 100-fold.

46. The polypeptide of embodiment 42, 43, 44, or 45, wherein said modified hinge comprises at least one modification selected from the group consisting of:
   (a) insertion of at least one G or A between P227 and P228;
   (b) deletion of P227 and/or P228; and
   (c) substitution of P227 and P228, wherein each residue is substituted with either a W or an F,
utilizing the EU index numbering system set forth in Kabat.

47. The polypeptide of embodiment 42, 43, 44, or 45, wherein said modified hinge comprises at least one modification selected from the group consisting of:
   (a) insertion of at least one G between P227 and P228;
   (b) deletion of P227 and P228; and
   (c) substitution of P227W and P228W, utilizing the EU index numbering system set forth in Kabat.

48. A polypeptide comprising an Fc region, said Fc region having a modified hinge, wherein said polypeptide binds at least C1q with an altered affinity relative to a polypeptide having the same amino acid sequence except having a wild type hinge.

49. The polypeptide of embodiment 48, wherein the altered affinity for C1q is increased affinity.

50. The polypeptide of embodiment 49, wherein the affinity is increased between about 10% and 100%.

51. The polypeptide of embodiment 49, wherein the affinity is increased between about 2-fold and 100-fold.

52. The polypeptide of embodiment 49, 50 or 51, wherein said modified hinge comprises at least one amino acid substitution.

53. The polypeptide of embodiment 52, wherein the modified hinge comprises at least one amino acid substitution at a position selected from the group consisting of: C(no EU number, Kabat number 233), D(no EU number, Kabat number 234), K222, T223 and H224, utilizing the EU index numbering system set forth in Kabat except where indicated.

54. The polypeptide of embodiment 52, wherein the modified hinge comprises at least one amino acid substitution selected from the group consisting of: C(no EU number, Kabat number 233)D, C(no EU number, Kabat number 233) E, D(no EU number, Kabat number 234)C, D(no EU number, Kabat number 234)W, D(no EU number, Kabat number 234) F, K222W, K222F, T223W, T223F, H224W and H224F, utilizing the EU index numbering system set forth in Kabat except where indicated.

55. The polypeptide of embodiment 52, wherein the modified hinge comprises at least one amino acid substitution is selected from the group consisting of:
  (a) C(no EU number, Kabat number 233)D and D(no EU number, Kabat number 234)C or C(no EU number, Kabat number 233)E and D(no EU number, Kabat number 234)C;
  (b) K222 and T223, wherein each residue is substituted with W or F;
  (c) C(no EU number, Kabat number 233), D(no EU number, Kabat number 234)C, K222 and T223, wherein C(no EU number, Kabat number 233) is substituted with D or E and wherein K222 and T223 are each substituted with W or F;
  (d) K222W or K222F;
  (e) T223W or T223F;
  (f) K222, T223 and H224, wherein each residue is substituted with W or F; and
  (g) D(no EU number, Kabat number 234) and K222, wherein each residue is substituted with W or F,
utilizing the EU index numbering system set forth in Kabat except where noted.

56. The polypeptide of claim 52, wherein the modified hinge comprises at least one amino acid substitution is selected from the group consisting of:
  (a) C(no EU number, Kabat number 233)D and D(no EU number, Kabat number 234)C;
  (b) K222W and T223W
  (c) C(no EU number, Kabat number 233)D, D(no EU number, Kabat number 234)C, K222W and T223W;
  (d) K222W;
  (e) T223W;
  (f) K222W, T223W and H224W; and
  (g) D(no EU number, Kabat number 234)W and K222W, utilizing the EU index numbering system set forth in Kabat except where noted.

57. The polypeptide of embodiment 49, 50, 51, 52, 53, 54, 55 or 56, wherein said polypeptide has CDC activity that is increased between about 2-fold and 100-fold, relative to a polypeptide having the same amino acid sequence except having a wild type hinge.

58. The polypeptide of embodiment 48, wherein the altered affinity is decreased affinity.

59. The polypeptide of embodiment 58, wherein the affinity is decreased between about 10% and 100%.

60. The polypeptide of embodiment 58, wherein the affinity is decreased between about 2-fold and 100-fold.

61. The polypeptide of embodiment 58, 59 or 60, wherein said polypeptide has CDC activity which is decreased between about 2-fold and 100-fold, relative to a polypeptide having the same amino acid sequence except having a wild type hinge.

62. The polypeptide of embodiment 58, 59, 60 or 61, wherein said modified hinge comprises at least one modification selected from the group consisting of:
  (a) substitution of at least one amino acid residue at position(s) C226, P227 P228, C229, P230;
  (b) insertion of at least one amino acid between P227 and P228; and
  (c) deletion of at least one amino acid residue at positions P227 and/or P228; utilizing the EU index numbering system set forth in Kabat.

63. The polypeptide of embodiment 62, wherein said substitution is the substitution of at least one amino acid residue selected from the group consisting of: C226S, C226T, P227G, P227A, P227W, P227F, P228G, P228A, P228W, P228F, C229S, C229T, P230G and P230A, utilizing the EU index numbering system set forth in Kabat.

64. The polypeptide of embodiment 62, wherein the amino acid insertion is the insertion of between 1 and 5 amino acid residues.

65. The polypeptide of embodiment 62 or 63, wherein the amino acid insertion is selected from the group consisting of: at least one A residue; at least one G residue and at least one A residues and at least one G residue.

66. The polypeptide of embodiment 62, 63 or 64, wherein the amino acid insertion is inserted between P227 and P228, utilizing the EU index numbering system set forth in Kabat.

67. The polypeptide of embodiment 58, 59, 60 or 61, wherein said modified hinge comprises at least one modification selected from the group consisting of:
  (a) substitution of P227G and P228G;
  (b) substitution of P230G;
  (c) substitution of C229S;
  (d) substitution of C226S;
  (e) insertion of at least one G between P227 and P228;
  (f) deletion of P227 and P228; and
  (g) substitution of P227W and P228W utilizing the EU index numbering system set forth in Kabat.

68. A polypeptide comprising an Fc region, said Fc region comprising a modified hinge region, said modified hinge region comprising at least one amino acid residue selected from the group consisting of: 216G, 216A, 216P, 217G, 217A, 218G, 218P, 218W, 218F, 221G, 221A, 221C, 221W, 221F, (no EU number, Kabat number 233)D, (no EU number, Kabat number 233)E, (no EU number, Kabat number 233)S, (no EU number, Kabat number 233)T, (no EU number, Kabat number 234)G, (no EU number, Kabat number 234)A, (no EU number, Kabat number 234)P, (no EU number, Kabat number 234)C, (no EU number, Kabat number 234)S, (no EU number, Kabat number 234)T, (no EU number, Kabat number 234)D, (no EU number, Kabat number 234)E, (no EU number, Kabat number 234)W, (no EU number, Kabat number 234)F, 222G, 222A, 222P, 222W, 222F, 223G, 223A, 223C, 223P, 223W, 223F, 224G, 224A, 224P, 224C, 224W, 224F, 225G, 225A, 225C, 225P, 226S, 226T, 227G, 227A, 227W, 227F, 228G, 228A, 228W, 228F, 229S, 229T, 230G and 230A.

69. A polypeptide comprising an Fc region, said Fc region comprising a modified hinge region, said modified hinge region comprising at least one amino acid residue selected from the group consisting of:
(a) 216G, 217G, 218G, 221G;
(b) (no EU number, Kabat number 234)G, 222G, 223G, 224G and 225G;
(c) 227G and 228G;
(d) 230G;
(e) "GGG" inserted between (no EU number, Kabat number 234) and 222;
(f) "GGG" inserted between 227 and 228;
(g) "PPP" inserted between (no EU number, Kabat number 234) and 222;
(h) "PPP" inserted between 227 and 228;
(i) 229S;
(j) 226S;
(k) 223T;
(l) 224C and 225T;
(m) (no EU number, Kabat number 234)P, 222P, 223P, 224P and 225P;
(n) 216P, 218P and 221P;
(o) 222W or 223W;
(p) 222W and 223W;
(q) 221C and (no EU number, Kabat number 233)S;
(r) (no EU number, Kabat number 233)D or (no EU number, Kabat number 234)C;
(s) (no EU number, Kabat number 233)D and (no EU number, Kabat number 234)C;
(t) (no EU number, Kabat number 233)D, (no EU number, Kabat number 234)C, 222W and 223W;
(u) 222W;
(v) 223W;
(w) 224W;
(x) 222F and 223F;
(y) 222W, 223W and 224W;
(z) (no EU number, Kabat number 234)W and 222W; and
(aa) 218W and 221W,
utilizing the EU index numbering system set forth in Kabat except where indicated.

70. The polypeptide of embodiment 68 or 69, wherein said polypeptide binds at least one FcγR with an altered affinity relative to a polypeptide having the same amino acid sequence except having a wild type hinge.

71. The polypeptide of embodiment 70, wherein said FcγR is FcγRIIIA.

72. The polypeptide of embodiment 71, wherein the affinity is increased.

73. The polypeptide of embodiment 72, wherein the affinity is increased between about 10% and 100%.

74. The polypeptide of embodiment 72, wherein the affinity is increased between about 2-fold and 100-fold.

75. The polypeptide of embodiment 71, 72, 73 or 74, wherein said polypeptide has ADCC activity that is increased between about 2-fold and 100-fold, relative to a polypeptide having the same amino acid sequence except having a wild type hinge.

76. The polypeptide of embodiment 71, wherein said affinity is decreased.

77. The polypeptide of embodiment 75, wherein the affinity is decreased between about 10% and 100%.

78. The polypeptide of embodiment 75, wherein the affinity is decreased between about 2-fold and 100-fold.

79. The polypeptide of embodiment 76, 77 or 78, wherein said polypeptide has ADCC activity that is decreased between about 2-fold and 100-fold, relative to a polypeptide having the same amino acid sequence except having a wild type hinge.

80. The polypeptide of embodiment 68 or 69, wherein said polypeptide binds at least C1q with an altered affinity relative to a polypeptide having the same amino acid sequence except having a wild type hinge.

81. The polypeptide of embodiment 80, wherein the affinity is increased.

82. The polypeptide of embodiment 81, wherein the affinity is increased between about 10% and 100%.

83. The polypeptide of embodiment 81, wherein the affinity is increased between about 2-fold and 100-fold.

84. The polypeptide of embodiment 81, 82 or 83, wherein said polypeptide has CDC activity that is increased between about 2-fold and 100-fold, relative to a polypeptide having the same amino acid sequence except having a wild type hinge.

85. The polypeptide of any of the preceding embodiments, wherein the polypeptide further comprises an antigen binding domain.

86. The polypeptide of any of the preceding embodiments, wherein the polypeptide is an antibody.

87. The polypeptide of any of the preceding embodiments, wherein the Fc region further comprises additional modifications.

88. A composition comprising the polypeptide of any of the preceding embodiments.

89. A nucleic acid sequence encoding the polypeptide of any of embodiments 1 to 87.

90. A cell engineered to contain the nucleic acid sequence of embodiment 89.

91. A method of producing a polypeptide comprising a modified hinge, said method comprising expressing the nucleotide sequence encoding the polypeptide in the cell of embodiment 90.

92. A method of altering the binding affinity for an Fc ligand of a polypeptide comprising an Fc region, wherein said Fc region comprises a hinge region, said method comprising introducing a modification into the hinge region.

93. The method of embodiment 92, wherein the Fc ligand is C1q.

94. The method of embodiment 93, wherein the binding affinity is increased.

95. The method of embodiment 94, wherein the affinity is increased between about 10% and 100%.

96. The method of embodiment 94, wherein the affinity is increased between about 2-fold and 100-fold.

97. The method of embodiment 94, 95 or 96, wherein the modification is at least one amino acid substitution selected from the group comprising:
(a) C(no EU number, Kabat number 233)D and D(no EU number, Kabat number 234)C or C(no EU number, Kabat number 233)E and D(no EU number, Kabat number 234)C;
(b) K222 and T223, wherein each residue is substituted with W or F;
(c) C(no EU number, Kabat number 233), D(no EU number, Kabat number 234)C, K222 and T223, wherein C(no EU number, Kabat number 233) is substituted with D or E and wherein K222 and T223 are each substituted with W or F;
(d) K222W or K222F;
(e) T223W or T223F;
(f) K222, T223 and H224, wherein each residue is substituted with W or F; and
(g) D(no EU number, Kabat number 234) and K222, wherein each residue is substituted with W or F,
utilizing the EU index numbering system set forth in Kabat except where noted.

98. The method of embodiment 94, 95 or 96, wherein the modification is at least one amino acid substitution selected from the group comprising:
  (a) C(no EU number, Kabat number 233)D and D(no EU number, Kabat number 234)C;
  (b) K222W and T223W
  (c) C(no EU number, Kabat number 233)D, D(no EU number, Kabat number 234)C, K222W and T223W;
  (d) K222W;
  (e) T223W;
  (f) K222W, T223W and H224W; and
  (g) D(no EU number, Kabat number 234)W and K222W, utilizing the EU index numbering system set forth in Kabat except where noted.

99. The method of embodiment 93, wherein the binding affinity is decreased.

100. The method of embodiment, 99, wherein the affinity is increased between about 10% and 100%

101. The method of embodiment 99, wherein the affinity is increased between about 2-fold and 100-fold 102. The method of embodiment 99, 100 or 101, wherein said modification is selected from the group consisting of:
  (a) substitution of at least one amino acid residue at position(s) C226, P227 P228, C229, P230;
  (b) insertion of at least one amino acid between P227 and P228; and
  (c) deletion of at least one amino acid residue at positions P227 and/or P228; utilizing the EU index numbering system set forth in Kabat.

103. The method of embodiment 102, wherein said substitution is the substitution of at least one amino acid residue selected from the group consisting of: C226S, C226T, P227G, P227A, P227W, P227F, P228G, P228A, P228W, P228F, C229S, C229T, P230G and P230A, utilizing the EU index numbering system set forth in Kabat.

104. The method of embodiment 102, wherein the amino acid insertion is the insertion of between 1 and 5 amino acid residues.

105. The method of embodiment 102 or 104, wherein the amino acid insertion is selected from the group consisting of: at least one A residue; at least one G residue and at least one A residues and at least one G residue.

106. The method of embodiment 102, 104 or 105, wherein the amino acid insertion is inserted between P227 and P228, utilizing the EU index numbering system set forth in Kabat.

107. The method of embodiment 99, 100 or 101, wherein said modification is selected from the group consisting of:
  (a) substitution of P227G and P228G;
  (b) substitution of P230G;
  (c) substitution of C229S;
  (d) substitution of C226S;
  (e) insertion of at least one to three G residues between P227 and P228;
  (f) deletion of P227 and P228; and
  (g) substitution of P227W and P228W utilizing the EU index numbering system set forth in Kabat.

108. A method of altering the CDC activity of a polypeptide comprising an Fc region, wherein said Fc region comprises a hinge region, said method comprising introducing a modification into the hinge region.

109. The method of embodiment 108, wherein CDC activity is increased.

110. The method of embodiment 109, wherein the modification is at least one amino acid substitution selected from the group consisting of:
  (a) C(no EU number, Kabat number 233)D and D(no EU number, Kabat number 234)C or C(no EU number, Kabat number 233)E and D(no EU number, Kabat number 234)C;
  (b) K222 and T223, wherein each residue is substituted with W or F;
  (c) C(no EU number, Kabat number 233), D(no EU number, Kabat number 234)C, K222 and T223, wherein C(no EU number, Kabat number 233) is substituted with D or E and wherein K222 and T223 are each substituted with W or F;
  (d) K222W or K222F;
  (e) T223W or T223F;
  (f) K222, T223 and H224, wherein each residue is substituted with W or F; and
  (g) D(no EU number, Kabat number 234) and K222, wherein each residue is substituted with W or F, utilizing the EU index numbering system set forth in Kabat except where noted.

111. The method of embodiment 109, wherein the modification is at least one amino acid substitution selected from the group consisting of:
  (a) C(no EU number, Kabat number 233)D and D(no EU number, Kabat number 234)C;
  (b) K222W and T223W;
  (c) C(no EU number, Kabat number 233)D, D(no EU number, Kabat number 234)C, K222W and T223W;
  (d) K222W;
  (e) T223W;
  (f) K222W, T223W and H224W; and
  (g) D (no EU number, Kabat number 234)W and K222W, utilizing the EU index numbering system set forth in Kabat except where noted.

112. The method of embodiment 108, wherein CDC activity is decreased.

113. The method of embodiment 112, wherein said modification is selected from the group consisting of:
  (a) substitution of at least one amino acid residue at position(s) C226, P227 P228, C229, P230;
  (b) insertion of at least one amino acid between P227 and P228; and
  (c) deletion of at least one amino acid residue at positions P227 and/or P228; utilizing the EU index numbering system set forth in Kabat.

114. The method of embodiment 113, wherein said substitution is the substitution of at least one amino acid residue selected from the group consisting of: C226S, C226T, P227G, P227A, P227W, P227F, P228G, P228A, P228W, P228F, C229S, C229T, P230G and P230A, utilizing the EU index numbering system set forth in Kabat.

115. The method of embodiment 113, wherein the amino acid insertion is the insertion of between 1 and 5 amino acid residues.

116. The method of embodiment 113 or 115, wherein the amino acid insertion is selected from the group consisting of: at least one A residue; at least one G residue and at least one A residues and at least one G residue.

117. The method of embodiment 113, 115 or 116, wherein the amino acid insertion is inserted between P227 and P228, utilizing the EU index numbering system set forth in Kabat.

118. The method of embodiment 113, wherein said modification is selected from the group consisting of:
  (a) substitution of P227G and P228G;
  (b) substitution of P230G;
  (c) substitution of C229S;
  (d) substitution of C226S;

(e) insertion of at least one to three G residues between P227 and P228;
(f) deletion of P227 and P228; and
(g) substitution of P227W and P228W
utilizing the EU index numbering system set forth in Kabat.

119. The method of any of embodiments 91 to 118, wherein the polypeptide further comprises an antigen binding domain.

120. The method of any of embodiments 91 to 119, wherein the polypeptide is an antibody.

121. The method of any of embodiments 91 to 120, wherein the Fc region further comprises additional modifications.

9. EXAMPLES

The invention is now described with reference to the following examples. These examples are provided for the purpose of illustration only and the invention should in no way be construed as being limited to these examples but rather should be construed to encompass any and all variations which become evident as a result of the teachings provided herein.

9.1 Construction and Expression of Novel Fc Variants

A human monoclonal antibody (referred to thereafter as mAb 12G3H11, see FIG. 1) directed against the human receptor tyrosine kinase EphA2 (Kinch et al., 2003, *Clin. Exp. Metastasis* 20: 59-68) was used as model. The amino acid sequences of the variable light ($V_L$) and variable heavy ($V_H$) genes of mAb 12G3H11 are shown in FIG. 1 (SEQ ID NOS. 1 and 2, respectively). The variable regions of 12G3H11 were individually cloned into mammalian expression vectors encoding a human cytomegalovirus major immediate early (hCMVie) enhancer, promoter and 5'-untranslated region (Boshart et al., 1985, *Cell* 41: 521-530). In this system, a human γ1 chain is secreted along with a human lc chain (Johnson et al., 1997, *J. Infect. Dis.* 176: 1215-1224). Modifications which altered the length, flexibility and conformation of the hinge (see Table 2) were generated and characterized for their binding to several Fc ligands. Several hinge modifications were identified which had a dramatic affect on the binding to one or more Fc ligand (see below for discussion).

9.1.1 Materials and Methods

Generation of the Fc variant antibody constructs: Various hinge modifications (designated "1-CD Invert", "2-SC Invert", "3-C to S low", "4-C to S Middle", "5-GGG Insert Low", "6-GGG Insert High", "7-P to G Low", "8-PP to GG Low", "9-DKTHT to GGGGG", "10-EPKS to GGGG", "11-4 AA Delete", "12-2 AA Delete Low", "13-2 AA Delete Mid", "14-T to C Middle", "15-PPP Insert Low", "16-PPP Insert High", "17-DKTHT to PPPPP", "18-EPKS to PPPP", "19-PP to WW Low", "20-KT to WW Mid" and "21-HT to CC Middle" and also referred to simply by the number designations 1-21, respectively) were introduced into the hinge region of the heavy chain of the anti-EphA2 mAb 12G3H11. This was carried out by site-directed mutagenesis using PCR by overlap extension (Ho et al., 1989, *Gene* 77: 51-59) and the oligonucleotides listed in Table 6 (all shown in the 5' to 3' orientation, sequence followed by primer name. The full amino acid sequences of the hinge region for each Fc variant (1-21) are listed in Table 2.

TABLE 6

| SEQ ID NO. | PRIMER | Name |
|---|---|---|
| 3 | GAGAGTTGAGCCCAAATCTgactgtAAAACTCACACATGCCCAC | 1 |
| 4 | GATCAATGAATTCGCGGCCGCTCA | 2 |
| 5 | GTGGGCATGTGTGAGTTTTACAGTCAGATTTGGGCTCAACTCTC | 3 |
| 6 | GCCTCCACCAAGGGCCCATCGGTCTTCC | 4 |
| 7 | GATCAATGAATTCGCGGCCGCTCA | 5 |
| 8 | GCCTCCACCAAGGGCCCATCGGTCTTCC | 6 |
| 9 | CAAGAGAGTTGAGCCCAAAtgttctGACAAAACTCACACATGC | 7 |
| 10 | GATCAATGAATTCGCGGCCGCTCA | 8 |
| 11 | GCATGTGTGAGTTTTGTCAGAACATTTGGGCTCAACTCTCTTG | 9 |
| 12 | GCCTCCACCAAGGGCCCATCGGTCTTCC | 10 |
| 13 | GATCAATGAATTCGCGGCCGCTCA | 11 |
| 14 | GCCTCCACCAAGGGCCCATCGGTCTTCC | 12 |
| 15 | TGTGACAAAACTCACACAAgcCCACCGTGCCCAGCACCTG | 13 |
| 16 | GATCAATGAATTCGCGGCCGCTCA | 14 |
| 17 | CAGGTGCTGGGCACGGTGGGCTTGTGTGAGTTTTGTCACA | 15 |
| 18 | GCCTCCACCAAGGGCCCATCGGTCTTCC | 16 |
| 19 | GATCAATGAATTCGCGGCCGCTCA | 17 |
| 20 | GCCTCCACCAAGGGCCCATCGGTCTTCC | 18 |
| 21 | ACTCACACATGCCCACCGagcCCAGCACCTGAACTCCTGG | 19 |
| 22 | GATCAATGAATTCGCGGCCGCTCA | 20 |
| 23 | CCAGGAGTTCAGGTGCTGGGCTCGGTGGGCATGTGTGAGT | 21 |
| 24 | GCCTCCACCAAGGGCCCATCGGTCTTCC | 22 |
| 25 | GATCAATGAATTCGCGGCCGCTCA | 23 |
| 26 | GCCTCCACCAAGGGCCCATCGGTCTTCC | 24 |
| 27 | CAAAACTCACACATGCCCAggaggcggtCCGTGCCCAGCACCTGAAC | 25 |
| 28 | GATCAATGAATTCGCGGCCGCTCA | 26 |
| 29 | GTTCAGGTGCTGGGCACGGACCGCCTCCTGGGCATGTGTGAGTTTTG | 27 |
| 30 | GCCTCCACCAAGGGCCCATCGGTCTTCC | 28 |
| 31 | GATCAATGAATTCGCGGCCGCTCA | 29 |
| 32 | GCCTCCACCAAGGGCCCATCGGTCTTCC | 30 |

TABLE 6-continued

Primers

| SEQ ID NO. | PRIMER | Name |
|---|---|---|
| 33 | GAGCCCAAATCTTGTGACggaggcggtAAAACTCACACATGCCCAC | 31 |
| 34 | GATCAATGAATTCGCGGCCGCTCA | 32 |
| 35 | GTGGGCATGTGTGAGTTTTACCGCCTCCGTCACAAGATTTGGGCTC | 33 |
| 36 | GCCTCCACCAAGGGCCCATCGGTCTTCC | 34 |
| 37 | GATCAATGAATTCGCGGCCGCTCA | 35 |
| 38 | GCCTCCACCAAGGGCCCATCGGTCTTCC | 36 |
| 39 | CACACATGCCCACCGTGCggaGCACCTGAACTCCTGGGG | 37 |
| 40 | GATCAATGAATTCGCGGCCGCTCA | 38 |
| 41 | CCCCAGGAGTTCAGGTGCTCCGCACGGTGGGCATGTGTG | 39 |
| 42 | GCCTCCACCAAGGGCCCATCGGTCTTCC | 40 |
| 43 | GATCAATGAATTCGCGGCCGCTCA | 41 |
| 44 | GCCTCCACCAAGGGCCCATCGGTCTTCC | 42 |
| 45 | GACAAAACTCACACATGCggcggaTGCCCAGCACCTGAACTC | 43 |
| 46 | GATCAATGAATTCGCGGCCGCTCA | 44 |
| 47 | GAGTTCAGGTGCTGGGCATCCGCCGCATGTGTGAGTTTTGTC | 45 |
| 48 | GCCTCCACCAAGGGCCCATCGGTCTTCC | 46 |
| 49 | GATCAATGAATTCGCGGCCGCTCA | 47 |
| 50 | GCCTCCACCAAGGGCCCATCGGTCTTCC | 48 |
| 51 | GTTGAGCCCAAATCTTGTGgCggggggaggtggaTGCCCACCGTGCCCAGC | 49 |
| 52 | GATCAATGAATTCGCGGCCGCTCA | 50 |
| 53 | GCTGGGCACGGTGGGCATCCACCTCCCCCCGCCACAAGATTTGGGCTCAAC | 51 |
| 54 | GCCTCCACCAAGGGCCCATCGGTCTTCC | 52 |
| 55 | GATCAATGAATTCGCGGCCGCTCA | 53 |
| 56 | GCCTCCACCAAGGGCCCATCGGTCTTCC | 54 |
| 57 | AAGGTGGACAAGAGAGTTGgGggcggaggtTGTGACAAAACTCACACATG | 55 |
| 58 | GATCAATGAATTCGCGGCCGCTCA | 56 |
| 59 | CATGTGTGAGTTTTGTCACAACCTCCGCCCCAACTCTCTTGTCCACCTT | 57 |
| 60 | GCCTCCACCAAGGGCCCATCGGTCTTCC | 58 |
| 61 | GATCAATGAATTCGCGGCCGCTCA | 59 |
| 62 | GCCTCCACCAAGGGCCCATCGGTCTTCC | 60 |
| 63 | GCCCAAATCTTGTGACAAAACATGCTGCCCAGCACCTGAACTCCTG | 61 |
| 64 | GATCAATGAATTCGCGGCCGCTCA | 62 |
| 65 | CAGGAGTTCAGGTGCTGGGCAGCATGTTTTGTCACAAGATTTGGGC | 63 |
| 66 | GCCTCCACCAAGGGCCCATCGGTCTTCC | 64 |
| 67 | GATCAATGAATTCGCGGCCGCTCA | 65 |
| 68 | GCCTCCACCAAGGGCCCATCGGTCTTCC | 66 |
| 69 | GACAAAACTCACACATGCTGCCCAGCACCTGAACTC | 67 |
| 70 | GATCAATGAATTCGCGGCCGCTCA | 68 |
| 71 | GAGTTCAGGTGCTGGGCAGCATGTGTGAGTTTTGTC | 69 |
| 72 | GCCTCCACCAAGGGCCCATCGGTCTTCC | 70 |
| 73 | GATCAATGAATTCGCGGCCGCTCA | 71 |
| 74 | GCCTCCACCAAGGGCCCATCGGTCTTCC | 72 |
| 75 | CCCAAATCTTGTGACAAAACATGCCCACCGTGCCCAG | 73 |
| 76 | GATCAATGAATTCGCGGCCGCTCA | 74 |
| 77 | CTGGGCACGGTGGGCATGTTTTGTCACAAGATTTGGG | 75 |
| 78 | GCCTCCACCAAGGGCCCATCGGTCTTCC | 76 |
| 79 | GATCAATGAATTCGCGGCCGCTCA | 77 |
| 80 | GCCTCCACCAAGGGCCCATCGGTCTTCC | 78 |
| 81 | CCCAAATCTTGTGACAAAtgtCACACATGCCCACCGTGC | 79 |
| 82 | GATCAATGAATTCGCGGCCGCTCA | 80 |
| 83 | GCACGGTGGGCATGTGTGACATTTGTCACAAGATTTGGG | 81 |
| 84 | GCCTCCACCAAGGGCCCATCGGTCTTCC | 82 |
| 85 | GATCAATGAATTCGCGGCCGCTCA | 83 |
| 86 | GCCTCCACCAAGGGCCCATCGGTCTTCC | 84 |
| 87 | CAAAACTCACACATGCCCAccccccgccaCCGTGCCCAGCACCTGAAC | 85 |
| 88 | GATCAATGAATTCGCGGCCGCTCA | 86 |
| 89 | GTTCAGGTGCTGGGCACGGTGGCGGGGGTGGGCATGTGTGAGTTTTG | 87 |
| 90 | GCCTCCACCAAGGGCCCATCGGTCTTCC | 88 |
| 91 | GATCAATGAATTCGCGGCCGCTCA | 89 |
| 92 | GCCTCCACCAAGGGCCCATCGGTCTTCC | 90 |
| 93 | GAGCCCAAATCTTGTGACcccccgccaAAAACTCACACATGCCCACCG | 91 |
| 94 | GATCAATGAATTCGCGGCCGCTCA | 92 |
| 95 | CGGTGGGCATGTGTGAGTTTTGGCGGGGGGTCACAAGATTTGGGCTC | 93 |
| 96 | GCCTCCACCAAGGGCCCATCGGTCTTCC | 94 |
| 97 | GATCAATGAATTCGCGGCCGCTCA | 95 |

TABLE 6-continued

Primers

| SEQ ID NO. | PRIMER | Name |
|---|---|---|
| 98 | GCCTCCACCAAGGGCCCATCGGTCTTCC | 96 |
| 99 | GAGAGTTGAGCCCAAATCTTGTccccgccacctcccTGCCCACCGTGCCCAGCACCTG | 97 |
| 100 | GATCAATGAATTCGCGGCCGCTCA | 98 |
| 101 | CAGGTGCTGGGCACGGTGGGCAGGGAGGTGGCGGGGACAAGATTTGGGCTCAACTCTC | 99 |
| 102 | GCCTCCACCAAGGGCCCATCGGTCTTCC | 100 |
| 103 | GATCAATGAATTCGCGGCCGCTCA | 101 |
| 104 | GCCTCCACCAAGGGCCCATCGGTCTTCC | 102 |
| 105 | AAGGTGGACAAGAGAGTTccgCCccctccaTGTGACAAAACTCACACATGC | 103 |
| 106 | GATCAATGAATTCGCGGCCGCTCA | 104 |
| 107 | GCATGTGTGAGTTTTGTCACATGGAGGGGGCGGAACTCTCTTGTCCACCTT | 105 |
| 108 | GCCTCCACCAAGGGCCCATCGGTCTTCC | 106 |
| 109 | GATCAATGAATTCGCGGCCGCTCA | 107 |
| 110 | GCCTCCACCAAGGGCCCATCGGTCTTCC | 108 |
| 111 | GACAAAACTCACACATGCtggtggTGCCCAGCACCTGAACTC | 109 |
| 112 | GATCAATGAATTCGCGGCCGCTCA | 110 |
| 113 | GAGTTCAGGTGCTGGGCACCACCAGCATGTGTGAGTTTTGTC | 111 |
| 114 | GCCTCCACCAAGGGCCCATCGGTCTTCC | 112 |
| 115 | GATCAATGAATTCGCGGCCGCTCA | 113 |
| 116 | GCCTCCACCAAGGGCCCATCGGTCTTCC | 114 |
| 117 | GAGCCCAAATCTTGTGACtggtggCACACATGCCCACCGTGC | 115 |
| 118 | GATCAATGAATTCGCGGCCGCTCA | 116 |
| 119 | GCACGGTGGGCATGTGTGCCACCAGTCACAAGATTTGGGCTC | 117 |
| 120 | GCCTCCACCAAGGGCCCATCGGTCTTCC | 118 |
| 121 | GATCAATGAATTCGCGGCCGCTCA | 119 |
| 122 | GCCTCCACCAAGGGCCCATCGGTCTTCC | 120 |
| 123 | CAAATCTTGTGACAAAACTgttgcTGCCCACCGTGCCCAGCAC | 121 |
| 124 | GATCAATGAATTCGCGGCCGCTCA | 122 |
| 125 | GTGCTGGGCACGGTGGGCAGCAACAAGTTTTGTCACAAGATTTG | 123 |
| 126 | GCCTCCACCAAGGGCCCATCGGTCTTCC | 124 |
| 127 | GATCAATGAATTCGCGGCCGCTCA | 125 |
| 128 | GCCTCCACCAAGGGCCCATCGGTCTTCC | 126 |
| 129 | TCCACAGGTGTCCACTCCCGGACTGAAGATCTCCCAAAG | EA1 |
| 130 | GGGAGAATTCCGCGGCCGCTTATTTGTCATCGTCATCTTTGTAGTCATGGTGATGGTGATGGTGTGCGCCTGCCAAACCTTGAGTGATGGT | EA2 |
| 131 | AAGCTTCGGTCCGCCACCATGGCAACTGAAGATCTCCCAAAG | A1 |
| 132 | GTCTGCCGAACCGCTGCCTGCCAAACCTTGAGTGATGGT | A2 |
| 133 | GGCAGCGGTTCGGCAGACCCCTCCAAGGAC | SA1 |
| 134 | CAGGGGCTAGCTTACTGCTGAACGGCGTCGAGCGG | SA2 |
| 135 | AGAGTTGAGCCCAAATCTGACTGTTGGTGGCACACATGCCCACCGTGC | 127 |
| 136 | GATCAATGAATTCGCGGCCGCTCA | 128 |
| 137 | GCACGGTGGGCATGTGTGCCACCAACAGTCAGATTTGGGCTCAACTCT | 129 |
| 138 | GCCTCCACCAAGGGCCCATCGGTCTTCC | 130 |
| 139 | GATCAATGAATTCGCGGCCGCTCA | 131 |
| 140 | GCCTCCACCAAGGGCCCATCGGTCTTCC | 132 |
| 141 | GAGCCCAAATCTTGTGACTGGACTCACACATGCCCACCG | 133 |
| 142 | GATCAATGAATTCGCGGCCGCTCA | 134 |
| 143 | CGGTGGGCATGTGTGAGTCCAGTCACAAGATTTGGGCTC | 135 |
| 144 | GCCTCCACCAAGGGCCCATCGGTCTTCC | 136 |
| 145 | GATCAATGAATTCGCGGCCGCTCA | 137 |
| 146 | GCCTCCACCAAGGGCCCATCGGTCTTCC | 138 |
| 147 | CCCAAATCTTGTGACAAATGGCACACATGCCCACCGTGC | 139 |
| 148 | GATCAATGAATTCGCGGCCGCTCA | 140 |
| 149 | GCACGGTGGGCATGTGTGCCATTTGTCACAAGATTTGGG | 141 |
| 150 | GCCTCCACCAAGGGCCCATCGGTCTTCC | 142 |
| 151 | GATCAATGAATTCGCGGCCGCTCA | 143 |
| 152 | GCCTCCACCAAGGGCCCATCGGTCTTCC | 144 |
| 153 | GAGCCCAAATCTTGTGACTTTTTTCACACATGCCCACCGTGC | 145 |
| 154 | GATCAATGAATTCGCGGCCGCTCA | 146 |
| 155 | GCACGGTGGGCATGTGTGAAAAAAGTCACAAGATTTGGGCTC | 147 |
| 156 | GCCTCCACCAAGGGCCCATCGGTCTTCC | 148 |
| 157 | GATCAATGAATTCGCGGCCGCTCA | 149 |
| 158 | GCCTCCACCAAGGGCCCATCGGTCTTCC | 150 |
| 159 | GAGCCCAAATCTTGTGACTGGTGGTGGACATGCCCACCGTGCCCAG | 151 |
| 160 | GATCAATGAATTCGCGGCCGCTCA | 152 |

TABLE 6-continued

Primers

| SEQ ID NO. | PRIMER | Name |
|---|---|---|
| 161 | CTGGGCACGGTGGGCATGTCCACCACCAGTCACAAGATTTGGGCTC | 153 |
| 162 | GCCTCCACCAAGGGCCCATCGGTCTTCC | 154 |
| 163 | GATCAATGAATTCGCGGCCGCTCA | 155 |
| 164 | GCCTCCACCAAGGGCCCATCGGTCTTCC | 156 |
| 165 | GTTGAGCCCAAATCTTGTTGGTGGACTCACACATGCCCACCG | 157 |
| 166 | GATCAATGAATTCGCGGCCGCTCA | 158 |
| 167 | CGGTGGGCATGTGTGAGTCCACCAACAAGATTTGGGCTCAAC | 159 |
| 168 | GCCTCCACCAAGGGCCCATCGGTCTTCC | 160 |
| 169 | GATCAATGAATTCGCGGCCGCTCA | 161 |
| 170 | GCCTCCACCAAGGGCCCATCGGTCTTCC | 162 |
| 171 | GACAAGAGAGTTGAGCCCTGGTGGTGTGACAAAACTCACACATG | 163 |
| 172 | GATCAATGAATTCGCGGCCGCTCA | 164 |
| 173 | CATGTGTGAGTTTTGTCACACCACCAGGGCTCAACTCTCTTGTC | 165 |
| 174 | GCCTCCACCAAGGGCCCATCGGTCTTCC | 166 |
| 175 | GATCAATGAATTCGCGGCCGCTCA | 167 |
| 176 | GCCTCCACCAAGGGCCCATCGGTCTTCC | 168 |

More precisely, the following oligonucleotide (see Table 6 for sequence information and corresponding SEQ ID NOS.) combinations were used for the PCR reactions:

1/2 and 3/4 separately (using the 12G3H11/heavy chain-encoding mammalian expression vector described above as a template) and then 5/6 (using the PCR fragments generated by the 1/2 and 3/4 oligonucleotides combinations as templates) to generate the "1-CD Invert" final PCR fragment. See Table 2 for the amino acid sequence of this Fc variant.

7/8 and 9/10 separately (using the 12G3H11/heavy chain-encoding mammalian expression vector described above as a template) and then 11/12 (using the PCR fragments generated by the 7/8 and 9/10 oligonucleotides combinations as templates) to generate the "2-SC Invert" final PCR fragment. See Table 2 for the amino acid sequence of this Fc variant.

13/14 and 15/16 separately (using the 12G3H11/heavy chain-encoding mammalian expression vector described above as a template) and then 17/18 (using the PCR fragments generated by the 13/14 and 15/16 oligonucleotides combinations as templates) to generate the "3-C to S low" final PCR fragment. See Table 2 for the amino acid sequence of this Fc variant.

19/20 and 21/22 separately (using the 12G3H11/heavy chain-encoding mammalian expression vector described above as a template) and then 23/24 (using the PCR fragments generated by the 19/20 and 21/22 oligonucleotides combinations as templates) to generate the "4-C to S Middle" final PCR fragment. See Table 2 for the amino acid sequence of this Fc variant.

25/26 and 27/28 separately (using the 12G3H11/heavy chain-encoding mammalian expression vector described above as a template) and then 29/30 (using the PCR fragments generated by the 25/26 and 27/28 oligonucleotides combinations as templates) to generate the "5-GGG Insert Low" final PCR fragment. See Table 2 for the amino acid sequence of this Fc variant.

31/32 and 33/34 separately (using the 12G3H11/heavy chain-encoding mammalian expression vector described above as a template) and then 35/36 (using the PCR fragments generated by the 31/32 and 33/34 oligonucleotides combinations as templates) to generate the "6-GGG Insert High" final PCR fragment. See Table 2 for the amino acid sequence of this Fc variant.

37/38 and 39/40 separately (using the 12G3H11/heavy chain-encoding mammalian expression vector described above as a template) and then 41/42 (using the PCR fragments generated by the 37/38 and 39/40 oligonucleotides combinations as templates) to generate the "7-P to G Low" final PCR fragment. See Table 2 for the amino acid sequence of this Fc variant.

43/44 and 45/46 separately (using the 12G3H11/heavy chain-encoding mammalian expression vector described above as a template) and then 47/48 (using the PCR fragments generated by the 43/44 and 45/46 oligonucleotides combinations as templates) to generate the "8-PP to GG Low" final PCR fragment. See Table 2 for the amino acid sequence of this Fc variant.

49/50 and 51/52 separately (using the 12G3H11/heavy chain-encoding mammalian expression vector described above as a template) and then 53/54 (using the PCR fragments generated by the 49/50 and 51/52 oligonucleotides combinations as templates) to generate the "9-DKTHT to GGGGG" final PCR fragment. See Table 2 for the amino acid sequence of this Fc variant.

55/56 and 57/58 separately (using the 12G3H11/heavy chain-encoding mammalian expression vector described above as a template) and then 59/60 (using the PCR fragments generated by the 55/56 and 57/58 oligonucleotides combinations as templates) to generate the "10-EPKS to GGGG" final PCR fragment. See Table 2 for the amino acid sequence of this Fc variant.

61/62 and 63/64 separately (using the 12G3H11/heavy chain-encoding mammalian expression vector described above as a template) and then 65/66 (using the PCR fragments generated by the 61/62 and 63/64 oligonucleotides combinations as templates) to generate the "11-4 AA Delete" final PCR fragment. See Table 2 for the amino acid sequence of this Fc variant.

67/68 and 69/70 separately (using the 12G3H11/heavy chain-encoding mammalian expression vector described above as a template) and then 71/72 (using the PCR fragments generated by the 67/68 and 69/70 oligonucleotides combinations as templates) to generate the "12-2 AA Delete Low" final PCR fragment. See Table 2 for the amino acid sequence of this Fc variant.

73/74 and 75/76 separately (using the 12G3H11/heavy chain-encoding mammalian expression vector described above as a template) and then 77/78 (using the PCR fragments generated by the 73/74 and 75/76 oligonucleotides combinations as templates) to generate the "13-2 AA Delete Mid" final PCR fragment. See Table 2 for the amino acid sequence of this Fc variant.

79/80 and 81/82 separately (using the 12G3H11/heavy chain-encoding mammalian expression vector described above as a template) and then 83/84 (using the PCR fragments generated by the 79/80 and 81/82 oligonucleotides combinations as templates) to generate the "14-T to C Middle" final PCR fragment. See Table 2 for the amino acid sequence of this Fc variant.

85/86 and 87/88 separately (using the 12G3H11/heavy chain-encoding mammalian expression vector described above as a template) and then 89/90 (using the PCR fragments generated by the 85/86 and 87/88 oligonucleotides combinations as templates) to generate the "15-PPP Insert Low" final PCR fragment. See Table 2 for the amino acid sequence of this Fc variant.

91/92 and 93/94 separately (using the 12G3H11/heavy chain-encoding mammalian expression vector described above as a template) and then 95/96 (using the PCR fragments generated by the 91/92 and 93/94 oligonucleotides combinations as templates) to generate the "16-PPP Insert High" final PCR fragment. See Table 2 for the amino acid sequence of this Fc variant.

97/98 and 99/100 separately (using the 12G3H11/heavy chain-encoding mammalian expression vector described above as a template) and then 101/102 (using the PCR fragments generated by the 97/98 and 99/100 oligonucleotides combinations as templates) to generate the "17-DKTHT to PPPPP" final PCR fragment. See Table 2 for the amino acid sequence of this Fc variant.

103/104 and 105/106 separately (using the 12G3H11/ heavy chain-encoding mammalian expression vector described above as a template) and then 107/108 (using the PCR fragments generated by the 103/104 and 105/ 106 oligonucleotides combinations as templates) to generate the "18-EPKS to PPPP" final PCR fragment. See Table 2 for the amino acid sequence of this Fc variant.

109/110 and 111/112 separately (using the 12G3H11/ heavy chain-encoding mammalian expression vector described above as a template) and then 113/114 (using the PCR fragments generated by the 109/110 and 111/ 112 oligonucleotides combinations as templates) to generate the "19-PP to WW Low" final PCR fragment. See Table 2 for the amino acid sequence of this Fc variant.

115/116 and 117/118 separately (using the 12G3H11/ heavy chain-encoding mammalian expression vector described above as a template) and then 119/120 (using the PCR fragments generated by the 115/116 and 117/ 118 oligonucleotides combinations as templates) to generate the "20-KT to WW Mid" final PCR fragment. See Table 2 for the amino acid sequence of this Fc variant.

121/122 and 123/124 separately (using the 12G3H11/ heavy chain-encoding mammalian expression vector described above as a template) and then 125/126 (using the PCR fragments generated by the 121/122 and 123/ 124 oligonucleotides combinations as templates) to generate the "21-HT to CC Middle" final PCR fragment. See Table 2 for the amino acid sequence of this Fc variant.

These 21 final PCR fragments were then individually cloned into the 12G3H11/heavy chain-encoding mammalian expression vector described above. This resulted in the replacement of the wild type heavy chain constant portion of 12G3H11 by the 21 different hinge-modified counterparts. The sequences were verified using an ABI 3100 sequencer.

Expression and purification of the various Fc variant antibodies: Human embryonic kidney (HEK) 293 cells were transiently transfected with the various antibody constructs (see above) in 90 mm dishes using Lipofectamine and standard protocols. Supernatants were harvested twice at 72 and 144 hours post-transfection and pooled. The secreted, soluble human IgG1s were purified from the conditioned media directly on 1 ml HiTrap protein A or protein G columns according to the manufacturer's instructions (APBiotech, Inc., Piscataway, N.J.). Purified human IgG1s (typically >95% homogeneity, as judged by SDS-PAGE) were dialyzed against phosphate buffered saline (PBS), flash frozen and stored at −70° C.

Cloning, expression and purification of the FLAG-tagged human FcγRIIIA construct: The FLAG-tagged extra cellular domain of human FcγRIIIA was cloned and expressed as follows: briefly, the EA1/EA2 (see Table 6) oligonucleotides combination was used to PCR amplify the extracellular domain of human FcγRIIIA using a cDNA library of human bone marrow (Clontech, CA) as the template. The PCR product was then cloned into the mammalian cell expression vector described above as an XbaI/NotI fragment. Human embryonic kidney (HEK) 293 cells were transiently transfected with this construct using Lipofectamine and standard protocols. Supernatants were harvested thrice at 72, 144 and 216 hours post-transfection and pooled. The secreted, soluble human FLAG-tagged FcγRIIIA was purified from the conditioned media directly on an anti-FLAG M2 agarose column according to the manufacturer's instructions (Sigma). The FLAG-tagged FcγRIIIA was then dialyzed against phosphate buffered saline (PBS) and stored at −70° C.

Cloning, expression and purifiction of a human FcγRIIIA/ streptavidin fusion protein: The extra cellular domain of human FcγRIIIA fused with streptavidin was cloned and expressed as follows: briefly, the SA1/SA2 and A1/A2 (see Table 6) oligonucleotides combinations were used to PCR amplify the streptavidin and extra cellular domains of human FcγRIII, respectively. A cDNA library of human bone marrow (Clontech, CA) and the genomic DNA of *Streptomyces avidinii* (ATCC, VA) were used as the templates for the amplification of FcγRIIIA and streptavidin, respectively. An overlapping PCR using the A1/SA2 oligonucleotides combination was then used to assemble the FcγRIII/streptavidin fusion protein which was subsequently cloned into the pET-28a expression vector (Novagen, CA) as an NcoI/NheI fragment. The FcγRIII/streptavidin fusion protein was expressed and refolded as described (Gao et al, 1997, Proc. Natl. Acad. Sci. USA 94: 11777-82). The refolded material was then purified using an immunobiotin column according to manufacturer's instructions (Pierce, Ill.), dialyzed against phosphate buffered saline (PBS) and stored at −70° C.

9.2 Binding Analysis of Fc variants to Fc ligands

The ability of each Fc variant to bind to two different Fc ligands, FcγRIIIA (F158 allotype) and C1q, was assessed. For many of the Fc variants both ELISA and BIAcore analysis was performed.

Figure 2:
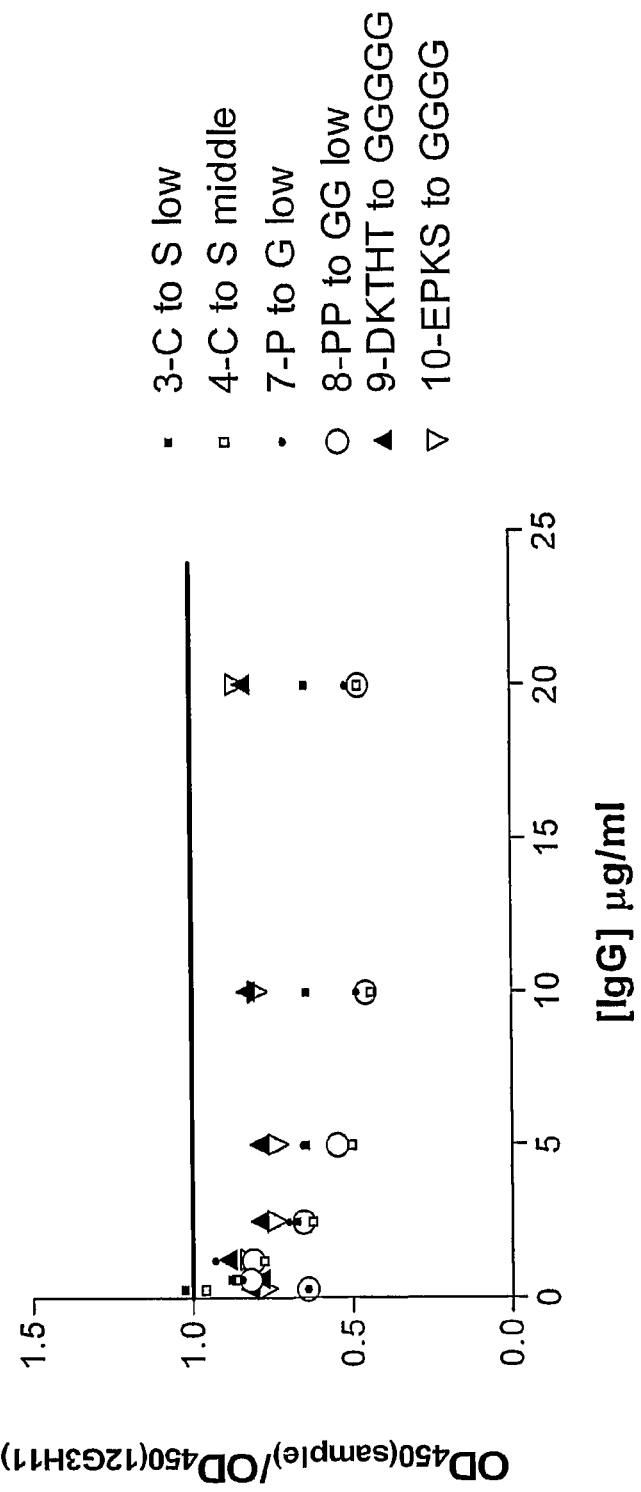
Figure 3:
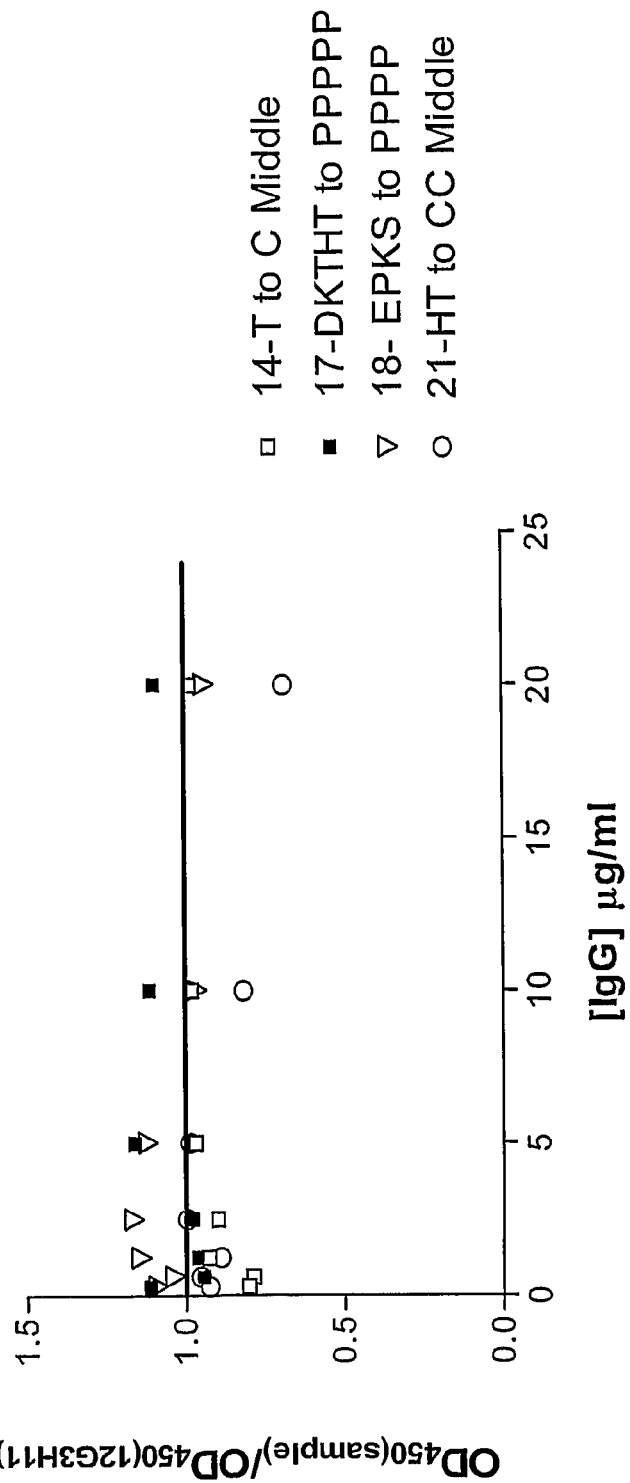

The effect of the various hinge modifications on the binding of the Fc variants to C1q are summarized here and shown in FIGS. 2-7. The consequences of increasing the flexibility of the hinge region are shown in FIG. 2. They vary from slightly (Fc variants 9, 10) to very (Fc variants 3, 4, 7, 8) detrimental. The consequences of decreasing the flexibility of the hinge region (shown in FIG. 3) vary from slightly reducing the binding (21) to no effect (14) to slightly improving the binding (Fc variants 17, 18).

Figure 4:
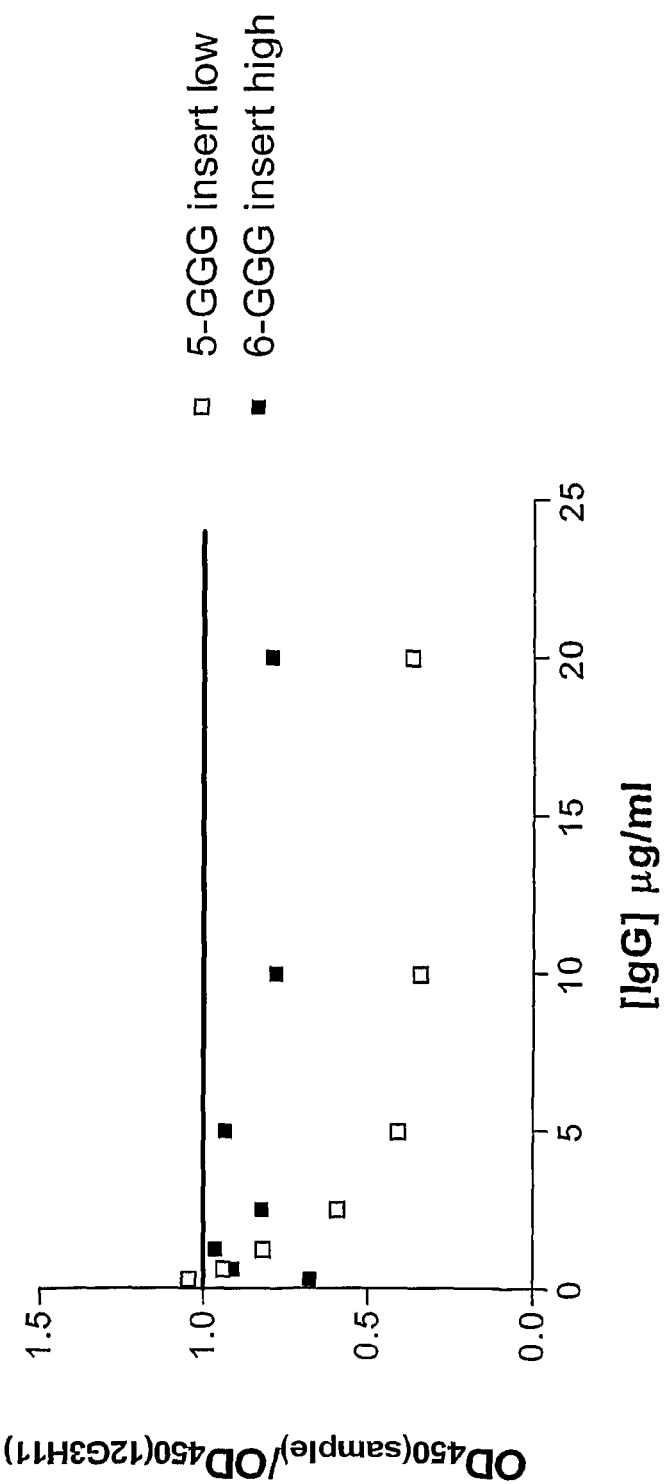
Figure 5:
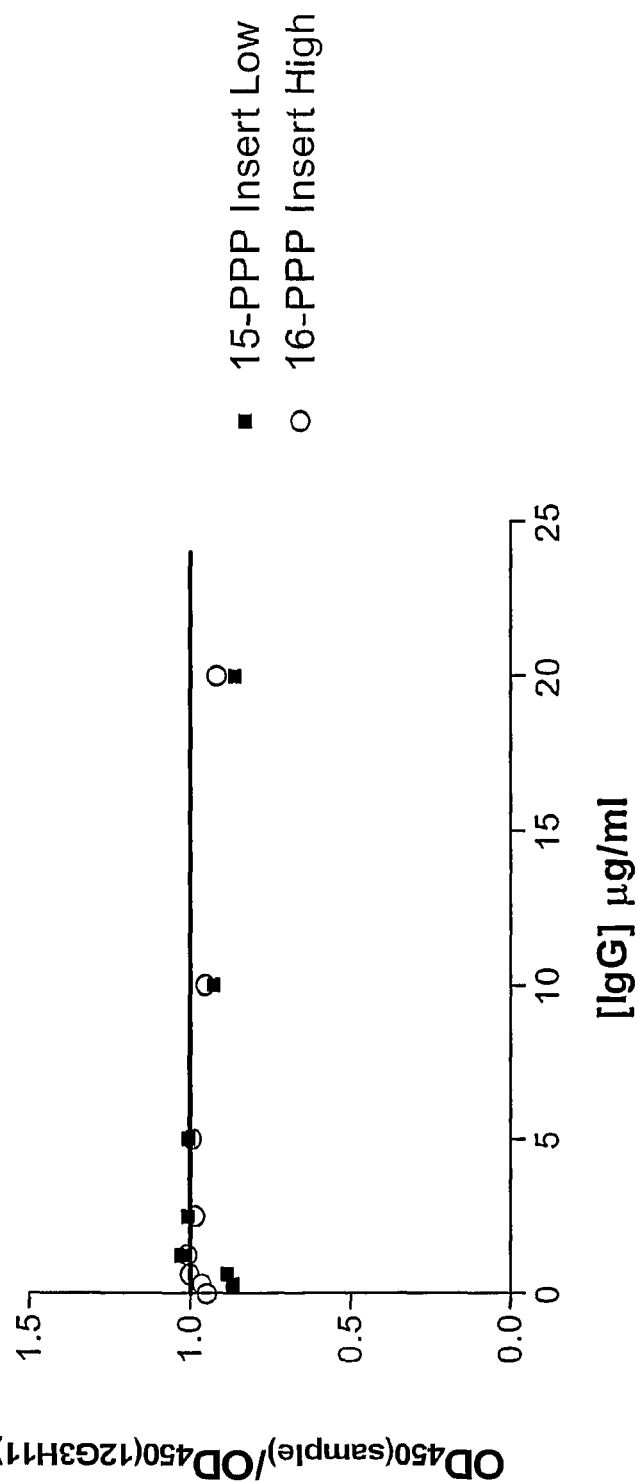

The effects on C1q binding of increasing the length of the hinge in conjunction with alterations in the flexibility of the hinge are shown in FIGS. 4 and 5. Increasing the length of the hinge region has a dramatic negative effect only when it is in conjunction with an increase in the overall flexibility of its middle portion (see Fc variant 5, FIG. 4). When the additional flexibility component is grafted in the hinge higher portion (see Fc variant 6, FIG. 4), the negative effect is still seen but is significantly attenuated. An increase in length coupled with a decrease in flexibility of the hinge region (Fc variants 15, 16, FIG. 5) did not have significant consequences regardless of where the additional rigidity component is introduced.

Figure 6:
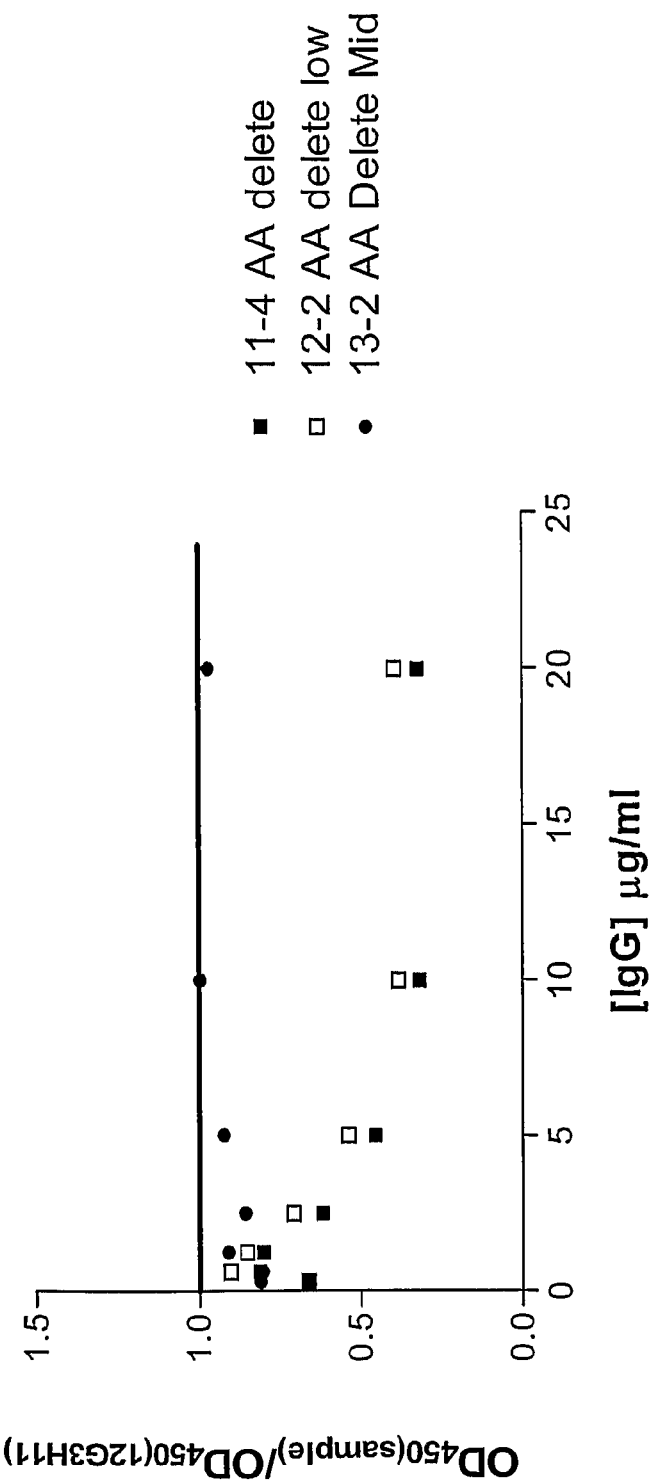

Decreasing the length of the hinge region has different effects depending on where the deletion is made (see FIG. 6). More precisely, a two amino acid deletion in the middle part of the hinge (Fc variant 12) results in knocking out binding to C1q whereas a two amino acids deletion in the upper part of the hinge did not have a significant effect on C1q binding (Fc variant 13). A two amino acid deletion in both the upper and medium parts of the hinge (Fc variant 11) has roughly the same effect on C1q binding than a two amino acid deletion in the middle part of the hinge alone (Fc variant 12).

Figure 7:
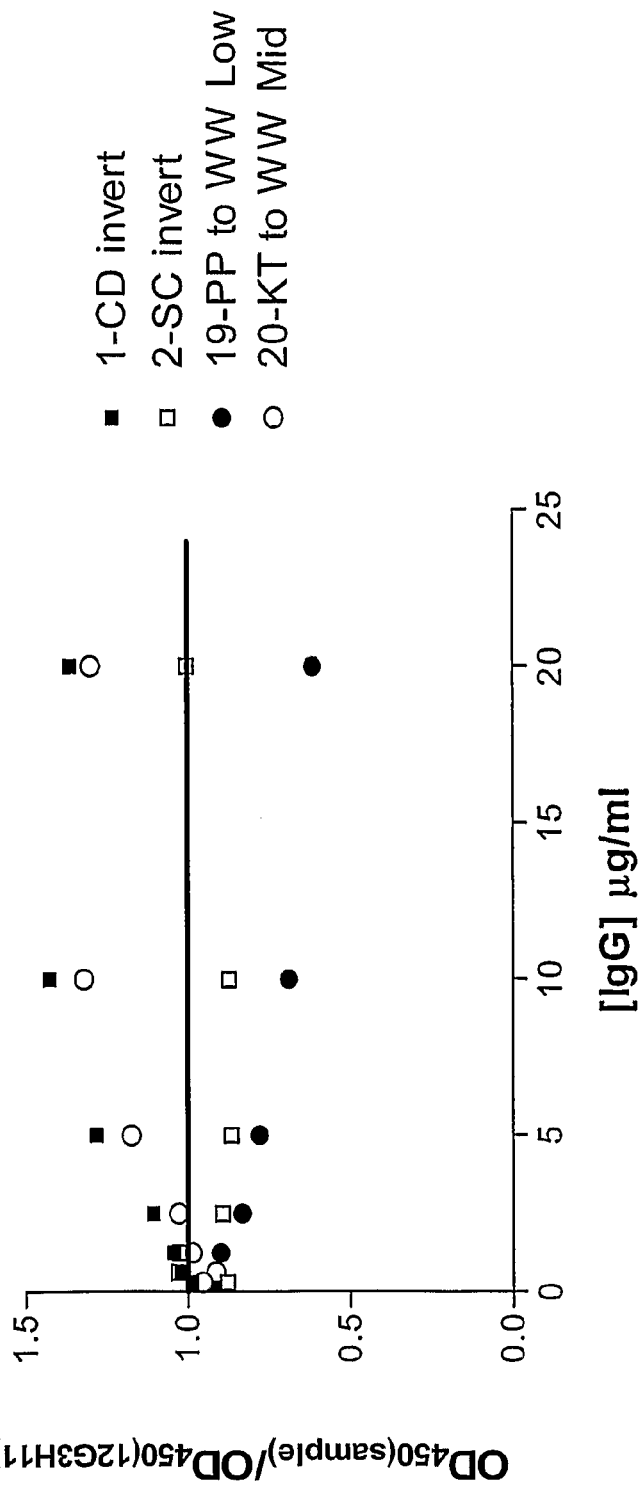
Figure 8:
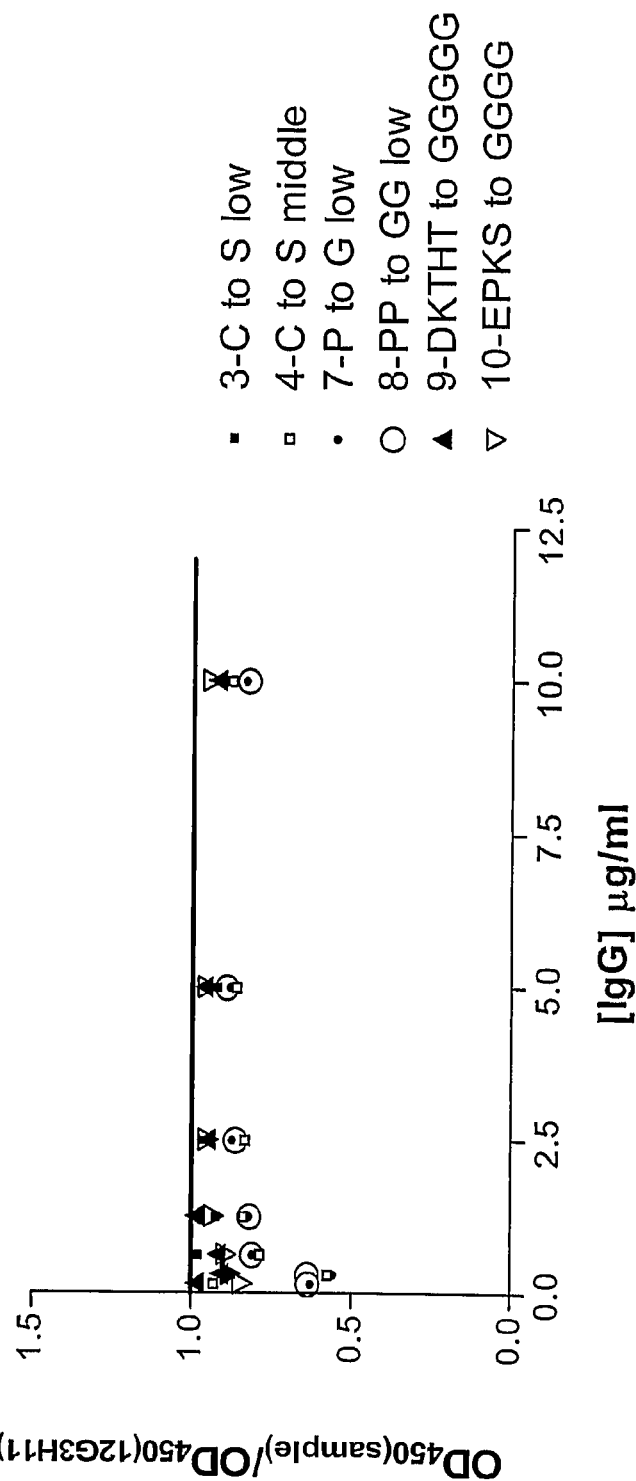
Figure 9:
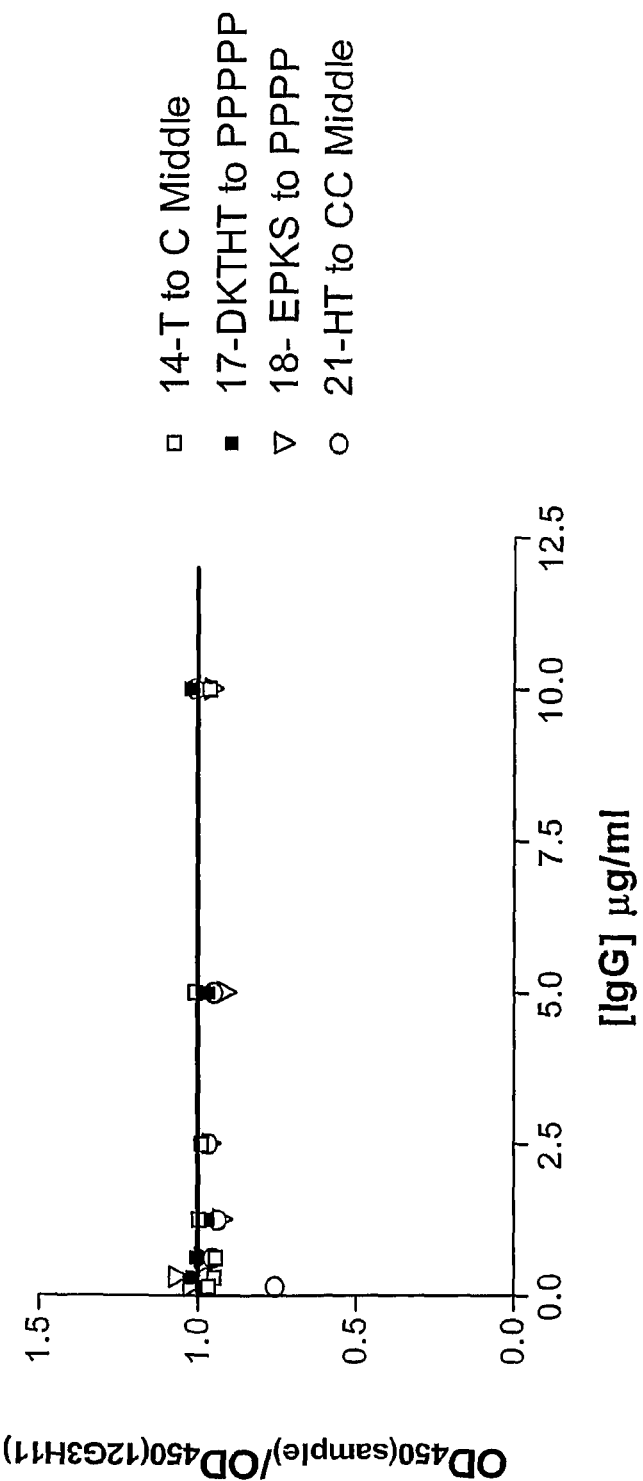

FIG. 7 shows the effect of hinge modification that alter the overall conformation of the hinge region. These hinge modifications have a more uncertain effect on the properties of the hinge region and result in either a strong negative (Fc variant 19), positive (Fc variants 1, 20) or insignificant (Fc variant 2) effect. If one compares the effect of introducing identical amino acid substitutions by hydrophotic and bulky tryptophan in either the upper or middle part of the hinge region, it is interesting to note that binding to C1q is negatively affected by modifications in the latter (compare Fc variants 19 and 20).

C1q binding of several Fc variants (1, 5, 8, 11, 17, 18, 19 and 20) was analyzed by BIAcore. The $K_D$s determined are reported in Table 7 and are generally in good agreement with the ELISA data. Variant 11, whose loss of binding to C1q was one of the most profound as determined by ELISA, exhibited a −7-fold reduction in binding affinity to C1q when compared with its wild-type counterpart (12G3H11). Variant 5, whose ELISA signal was comparable to variant 11, showed a loss in binding affinity to C1q of only ~3-fold. This difference is likely attributable to the different format of the assays. Unlike what was seen by ELISA and in the CDC assays (see below), "enhanced" variant 1 did not exhibit a significant increase in C1q binding when compared with 12G3H11 using BIAcore (Table 7). Here again, this probably reflected a difference in the assay format and/or sensitivity.

TABLE 7

Binding Affinity of Fc variants to C1q and human FcγRIIIA.

| Hinge Fc Variant | C1q-Dissociation Constant ($K_D$) (nM)[a] | FcγRIIIA-Dissociation Constant ($K_D$) (nM)[a] |
|---|---|---|
| Wild type (12G3H11) | 89 ± 21 | 6050 ± 950 |
| 1-CD Invert | 92 ± 21 | N.D. |
| 5-GGG Insert Low | 282 ± 66 | 42400 ± 6660 |
| 8-PP to GG Low | 155 ± 36 | 6400 ± 1000 |
| 11-4 AA Delete | 607 ± 141 | 12300 ± 1930 |
| 17-DKTHT to PPPPP | 91 | N.D. |
| 18-EPKS to PPPP | 75 | N.D. |
| 19-PP to WW Low | 274 ± 64 | N.D. |
| 20-KT to WW Mid | 61 ± 14 | N.D. |

N.D.: not determined.

[a]Errors in the binding measurements were estimated from the standard deviations of three (variant/C1q pair) and two (variant/FcγRIIIA pair) independent determinations.

The effect of the various hinge modifications on the binding of the Fc variants to FcγIIIA is summarized here and shown in FIGS. 8-13. The consequences of increasing the flexibility of the hinge region (shown in FIG. 8) seem to vary from slightly detrimental (Fc variants 4, 7, 8) to no effect (Fc variants 3, 9, 10). The consequences of decreasing the flexibility of the hinge region (see FIG. 9, Fc variants 14, 17, 18, 21) does not seem to have a significant effect as far as FcγRIII binding is concerned.

Increasing the length of the hinge region has a dramatic "knock out" effect on FcγRIII binding only when it is in conjunction with an increase in its overall flexibility of its middle portion (Fc variant 5, FIG. 10). When the additional flexibility component is grafted in the hinge higher portion (Fc variant 6, FIG. 10), the negative effect on FcγRIII binding is reduced almost back to normal. An increase in length coupled with a decrease in flexibility (Fc variants 15, 16, FIG. 11) does not have significant consequences for FcγRIII binding regardless of where the additional rigidity component is introduced.

The effect on FcγRIII binding of decreasing the length of hinge is shown in FIG. 12. Decreasing the length of the hinge region has different effects in function of where the deletion is made. More precisely, a two amino acid deletion in the middle part of the hinge (Fc variant 12) results in a small decrease for binding to FcγRIII whereas a two amino acids deletion in the upper part of the hinge does not have a significant effect on FcγRIII binding (Fc variant 13). A two amino acid deletion in both the upper and middle parts of the hinge (Fc variant 11) has roughly the same effect than a two amino acid deletion in the middle part of the hinge alone (Fc variant 12).

As was seen for C1q binding, modifications which alter the overall conformation of the hinge have a more uncertain effect on FcγRIII binding (FIG. 13). These types of hinge modifications result in either a strong negative (Fc variant 19) or insignificant (Fc variants 1, 2, 20) effect on FcγRIII binding. If one compares the effect of introducing identical amino acid substitutions in either the upper or middle part of the hinge region, it is interesting to note that binding to FcγRIII is affected to a larger extent by modifications in the latter (compare Fc variants 19 and 20).

FcγRIIIA binding of several Fc variants (5, 8 and 11) were analyzed by BIAcore to determine the $K_D$s (Table 7). The dissociation constants determined by BIAcore are in agreement with the ELISA data. Variant 5 exhibited the most dramatic reduction in binding to FcγRIIIA by ELISA, translating to an ~7-fold reduction in binding affinity to FcγRIIIA when compared with its wild-type counterpart. Also as expected from the ELISA measurements, variant 11 exhibited a slight reduction in binding affinity to FcγRIIIA (~2-fold) whereas variant 8 did not see its binding properties significantly changed.

Fcγ

9.2.1 Materials and Methods

Analysis of human C1q binding to 12G3H11 and Fc variants thereof by ELISA: In order to characterize the binding of the different human IgG1 Fc variants listed in Table 2 to human C1q, the following ELISA was carried out: briefly, individual wells of a 96-well Maxisorp Immunoplate were coated overnight at 4° C. with 50 μl of 2-fold serially diluted samples (purified 12G3H11 or hinge Fc variants thereof, see above) at concentrations ranging from 20 to 0.31 μg/ml and then blocked with 3% BSA/PBS for 2 h at 37° C. 12G3H11 "wild type" was systematically coated on each individual assay plate. Plates were then successively incubated with 100 μl of 2 μg/ml human C1q (Quidel, CA) for 1 h at 37° C. and sheep anti-human C1q (BioDesign, ME; 1/1000 dilution) for 1 h at 37° C. Incubation with a donkey anti-sheep IgG horseradish peroxydase conjugate (Serotec, NC; 1/10000 dilution) for 1 h at room temperature then followed. Horseradish peroxydase activity was detected with TMB substrate (KPL, MD) and the reaction quenched with 1% H2504. Plates were read at 450 nm. For each human IgG1 concentration, the ratio of the sample's average OD450 over the average OD450 exhibited by 12G3H11 "wild type" on the same plate was calculated. Typical results of at least two independent series of experiments are shown in FIGS. 2, 3, 4, 5, 6, 722 and 23.

Analysis of human FcγRIIIA binding to 12G3H11 and Fc variants Thereof by ELISA: In order to characterize the binding of the different human IgG1 Fc variants listed in Table 2 to human FcγRIII, the following ELISA was carried out: briefly, individual wells of a 96-well Maxisorp Immunoplate were coated overnight at 4° C. with 25 ng of Protein A/G (Pierce, Ill.), blocked with 3% BSA/PBS for 2 h at 37° C. and incubated with 50 μl of 2-fold serially diluted samples (purified 12G3H11 or hinge Fc variants thereof, see above) at concentrations ranging from 10 to 0.156 μg/ml for 1 hour at 37° C. 12G3H11 "wild type" was systematically loaded on each individual assay plate. Plates were then successively incubated with 100 μl of 2.5 μg/ml human FcγRIII/streptavidin (see above) and biotin horseradish peroxidase conjugate (Pierce, IL; 1/1000 dilution) for 1 h at 37° C. Horseradish peroxidase activity was detected with TMB substrate (KPL, MD) and the reaction quenched with 1% $H_2SO_4$. Plates were read at 450 nm. For each human IgG1 concentration, the ratio of the sample's average OD450 over the average OD450 exhibited by 12G3H11 "wild type" on the same plate was calculated. Typical results of at least two independent series of experiments are shown in FIGS. 8, 9, 10, 11, 12, 13, 24 and 25.

Analysis of human C1q binding to 12G3H11 and Fc variants thereof by BIAcore: The interaction of soluble human C1q (Quidel, CA) with immobilized 12G3H11 ("Wild type"), "1-CD Invert", "5-GGG Insert Low", "8-PP to GG Low", "11-4 AA Delete", "17-DKTHT to PPPPP", "18-EPKS to PPPP", "19-PP to WW Low" and "20-KT to WW Mid" hinge Fc variants was monitored by surface plasmon resonance detection using a BIAcore 3000 instrument (Pharmacia Biosensor, Uppsala, Sweden). Protein concentrations were calculated by the bicinchoninic acid methods. The different human IgG1s were coupled to the dextran matrix of a CM5 sensor chip (Pharmacia Biosensor) using an Amine Coupling Kit as described (Johnsson et al., 1991, Anal. Biochem. 198: 268-77) at a surface density of between 4830 and 9221 RU. Excess reactive esters were quenched by injection of 70 μl of 1.0 M ethanolamine hydrochloride, pH 8.5. Human C1q was buffer-exchanged against phosphate buffered saline (PBS) buffer and used in equilibrium binding experiments at concentrations ranging from 750 to 12 nM at a flow rate of 5-10 μL/min. Dilutions and binding experiments were carried out in 50 mM HBS buffer containing 0.01M HEPES pH 7.4, 0.15 M NaCl, 3 mM EDTA and 0.005% P-20. Data were collected for about 50 min, and two 1-min pulse of 1M NaCl/ 50 mM NaOH were used to regenerate the surfaces. Human C1q was allowed to flow over an uncoated cell, and the sensorgrams from these blank runs subtracted from those obtained with IgG1-coupled chips. Dissociation constants ($K_D$s) were determined by fitting the binding isotherms to a one site binding model using GraphPad Prism (GraphPad Software, Inc., CA) and are recorded in Table 7.

Analysis of human FcγRIIIA binding to 12G3H11 and Fc variants thereof by BIAcore: The interaction of soluble human FcγRIIIA with immobilized 12G3H11 ("wild type"), "5-GGG Insert Low", "8-PP to GG Low" and "11-4 AA Delete" hinge Fc variants was monitored by surface plasmon resonance detection using a BIAcore 3000 instrument (Pharmacia Biosensor, Uppsala, Sweden). Protein concentrations were calculated by the bicinchoninic acid methods. The different human IgG1s were coupled to the dextran matrix of a CM5 sensor chip (Pharmacia Biosensor) using an Amine Coupling Kit as described (Johnsson et al., 1991, Anal. Biochem. 198: 268-77) at a surface density of between 7765 and 8385 RU. Excess reactive esters were quenched by injection of 70 μl of 1.0 M ethanolamine hydrochloride, pH 8.5. Flag-tagged Human FcγRIIIA (see above) was used in equilibrium binding experiments at concentrations ranging from 20000 to 9.8 nM at a flow rate of 5-10 μL/min. Dilutions and binding experiments were carried out in 50 mM HBS buffer containing 0.01M HEPES pH 7.4, 0.15 M NaCl, 3 mM EDTA and 0.005% P-20. Data were collected for about 50 min, and one 30 sec pulse of 5 mM HCl was used to regenerate the surfaces. Flag-tagged human FcγRIIIA was allowed to flow over an uncoated cell, and the sensorgrams from these blank runs subtracted from those obtained with IgG1-coupled chips. Dissociation constants ($K_D$s) were determined by fitting the binding isotherms to a one site binding model using GraphPad Prism (GraphPad Software, Inc., CA) and are recorded in Table 7.

9.3 Effector Function of Fc Variants

Based on the binding data described above, several Fc variants were chosen for further analysis. The ADCC and/or CDC activity of the variants was determined as described below.

Figure 14:
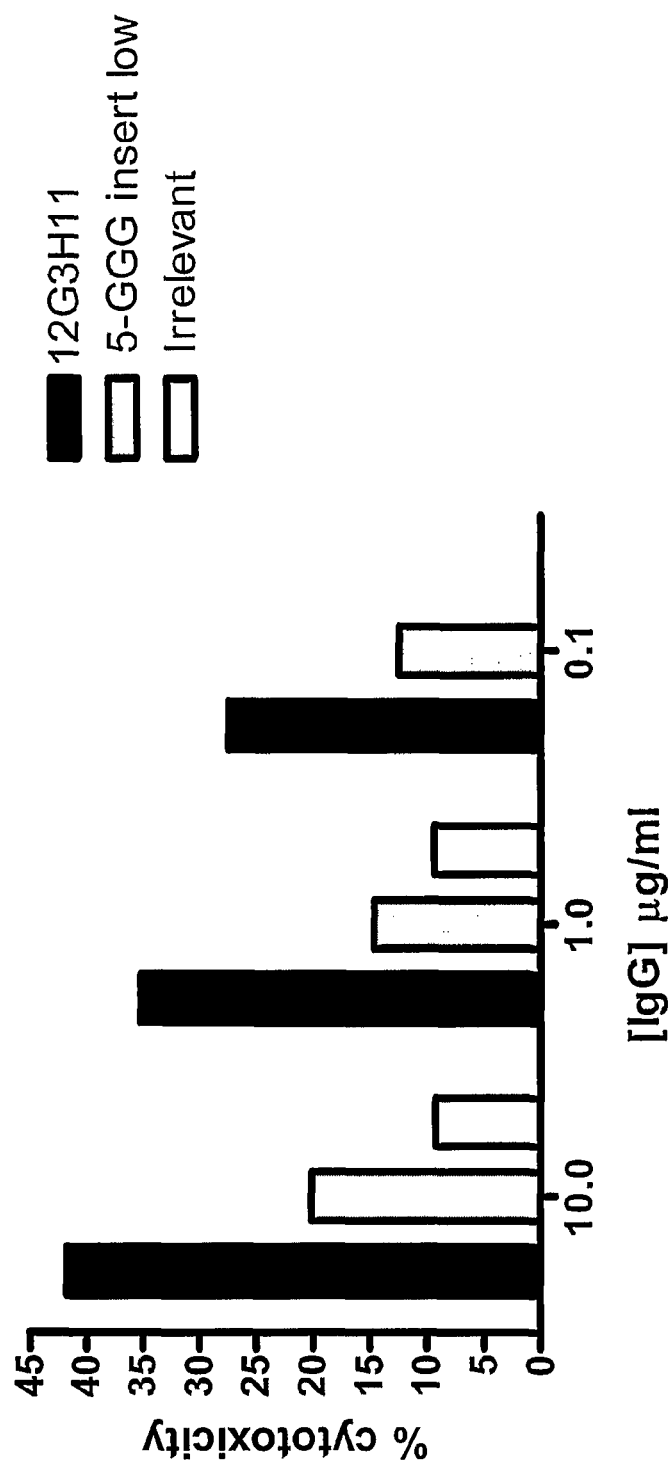
Figure 15:
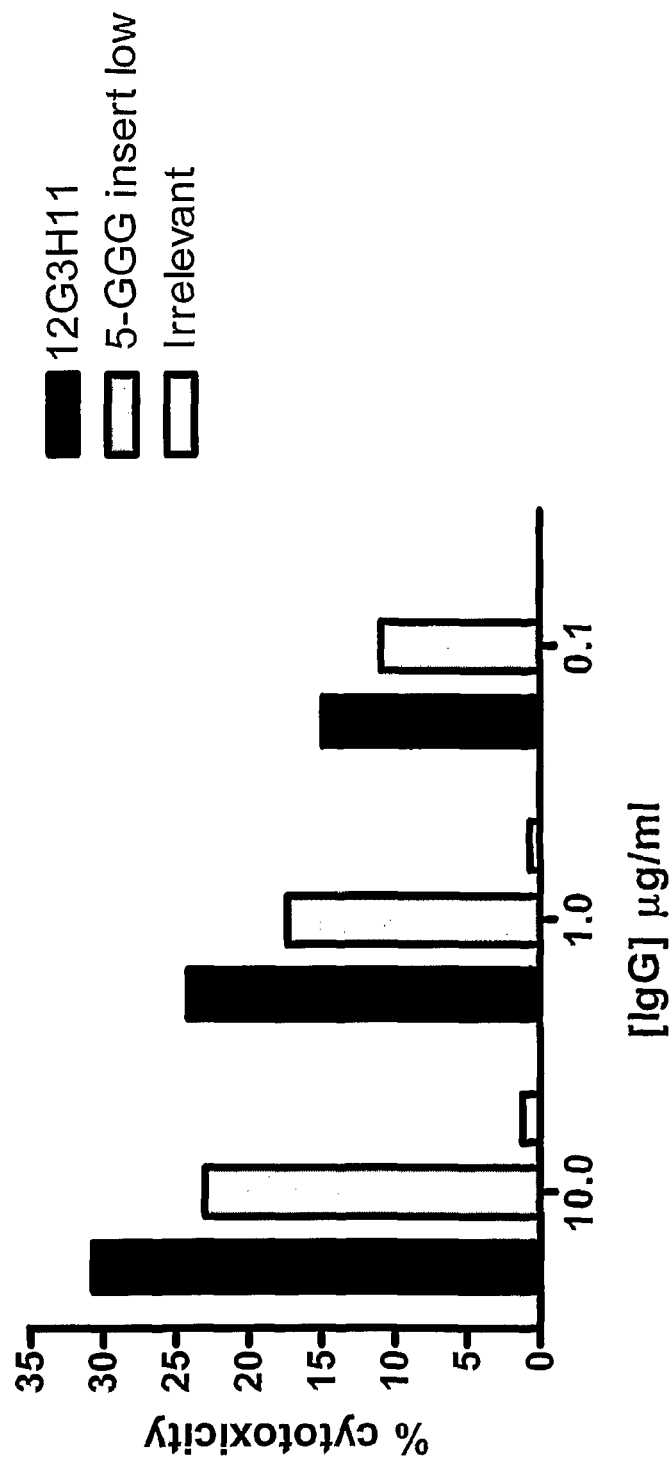
Figure 16:
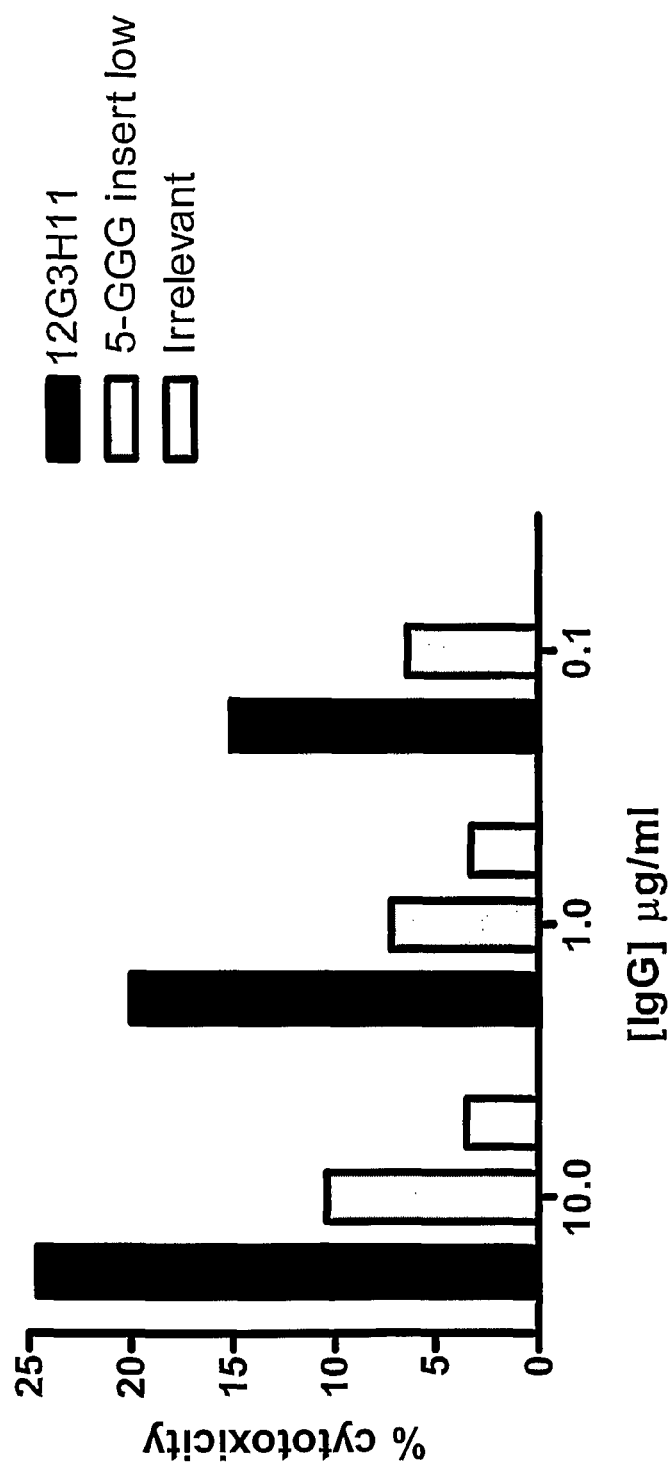

Fc variant "5-GGG insert low" consistently exhibited a significantly reduced ADCC activity when compared with its wild type counterpart (12G3H11). Representative data from three independent donors are shown in FIGS. 14, 15 and 16. This is in agreement with the corresponding binding data (Table 7, FIG. 10).

Figure 17:
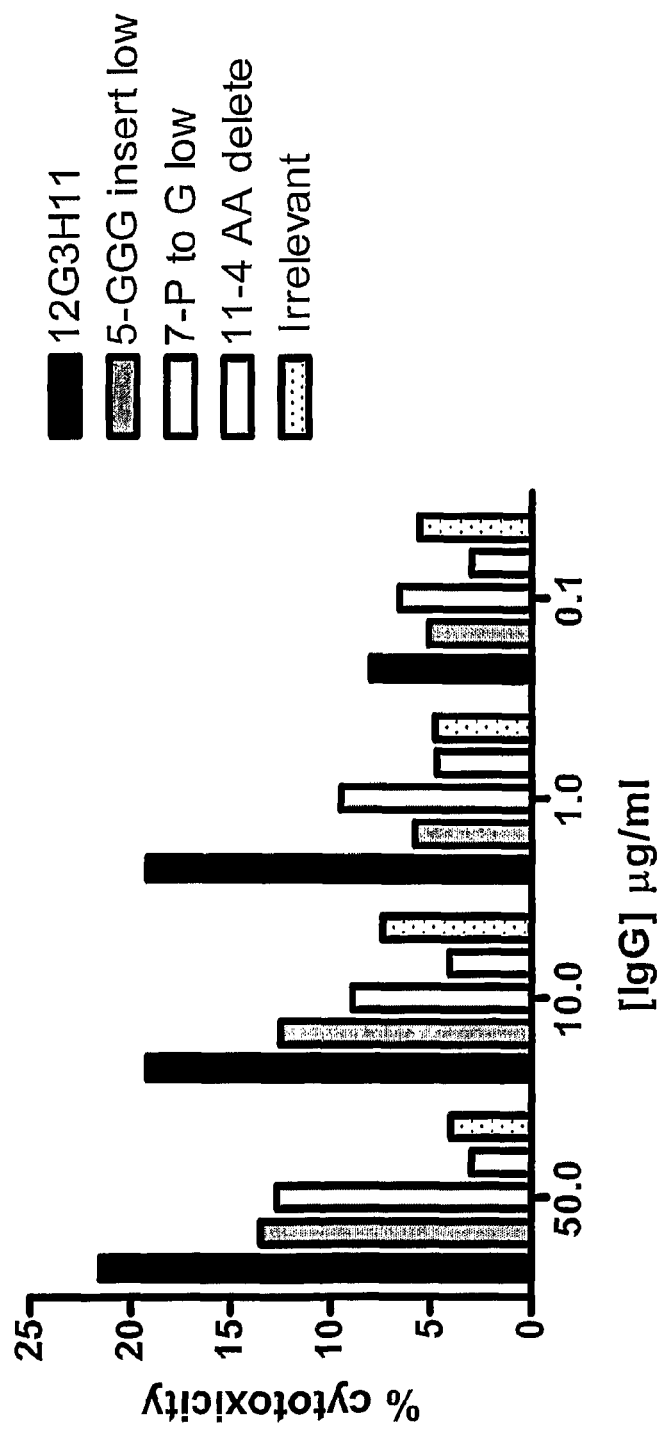
FIG. 17 shows the CDC activity against human EphA2-transfected CT26 cells of wild type 12G3H11 antibody, an irrelevant control antibody and several Fc variants (5, 7 and 11) all of which show reduced CDC activity. The same result was seen for EphA2-transfected KATOIII cells (see FIG. 18).
Figure 18:
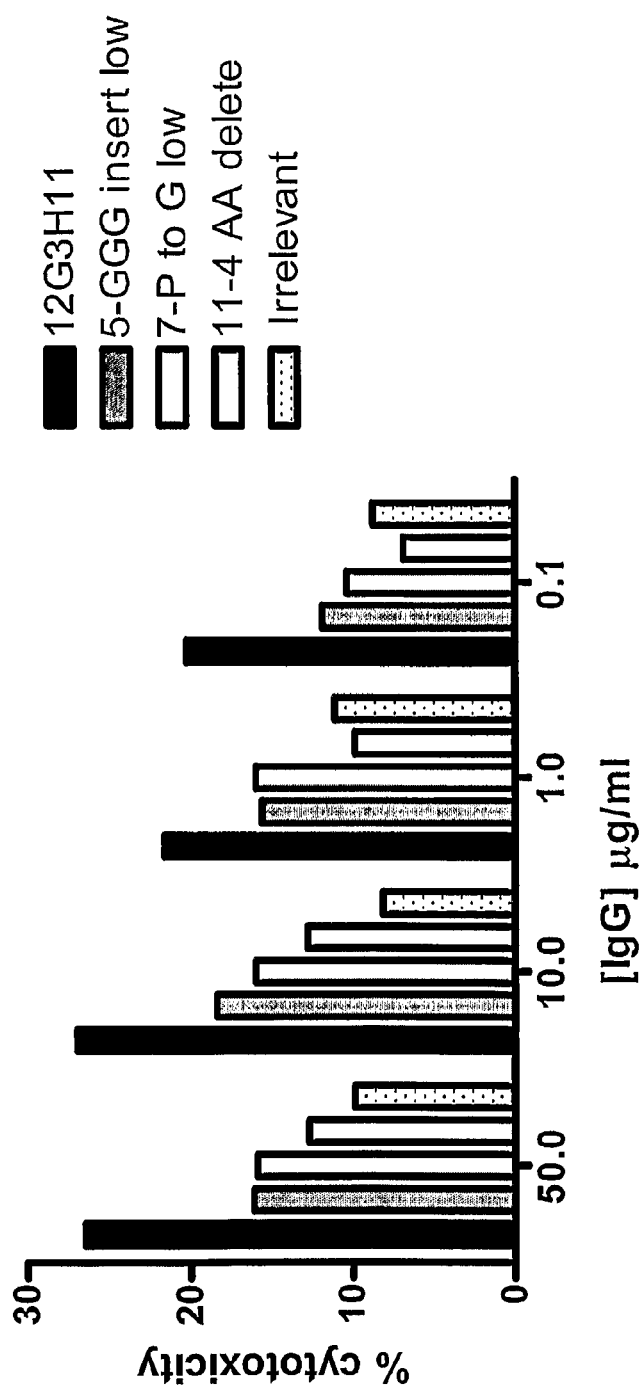
FIG. 18 shows the CDC activity against human EphA2-transfected KATOIII cells of wild type 12G3H11 antibody, an irrelevant control antibody and several Fc variants (5, 7 and 11) all of which show reduced CDC activity. The same result was seen for EphA2-transfected CT26 cells (see FIG. 17).

Fc variants "5-GGG insert low", "7-P to G low" and "11-4AA delete" consistently exhibited a significantly reduced CDC activity on both human EphA2-transfected CT26 cells and human EphA2-transfected KATO III cells when compared with their wild type counterpart (12G3H11). Representative data are shown in FIGS. 17 and 18, respectively. These data agree with the corresponding binding data (Table 7, FIGS. 2, 4 and 6).

Figure 19:
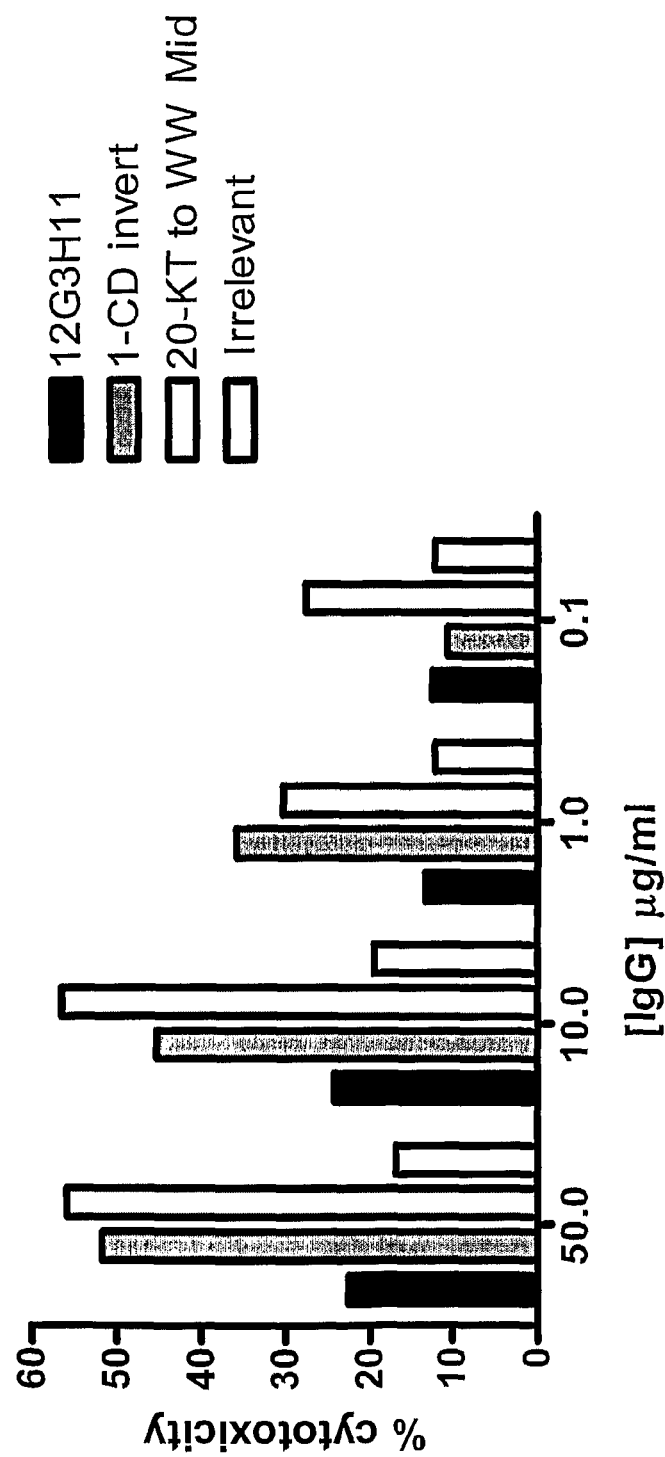
FIG. 19 shows the CDC activity against human EphA2-transfected CT26 cells of wild type 12G3H11 antibody, an irrelevant control antibody and two Fc variants (1 and 20) which show significantly increased CDC activity. The same result was seen for EphA2-transfected KATOIII cells and untransfected KATOIII cells (see FIGS. 20 and 21).
Figure 20:
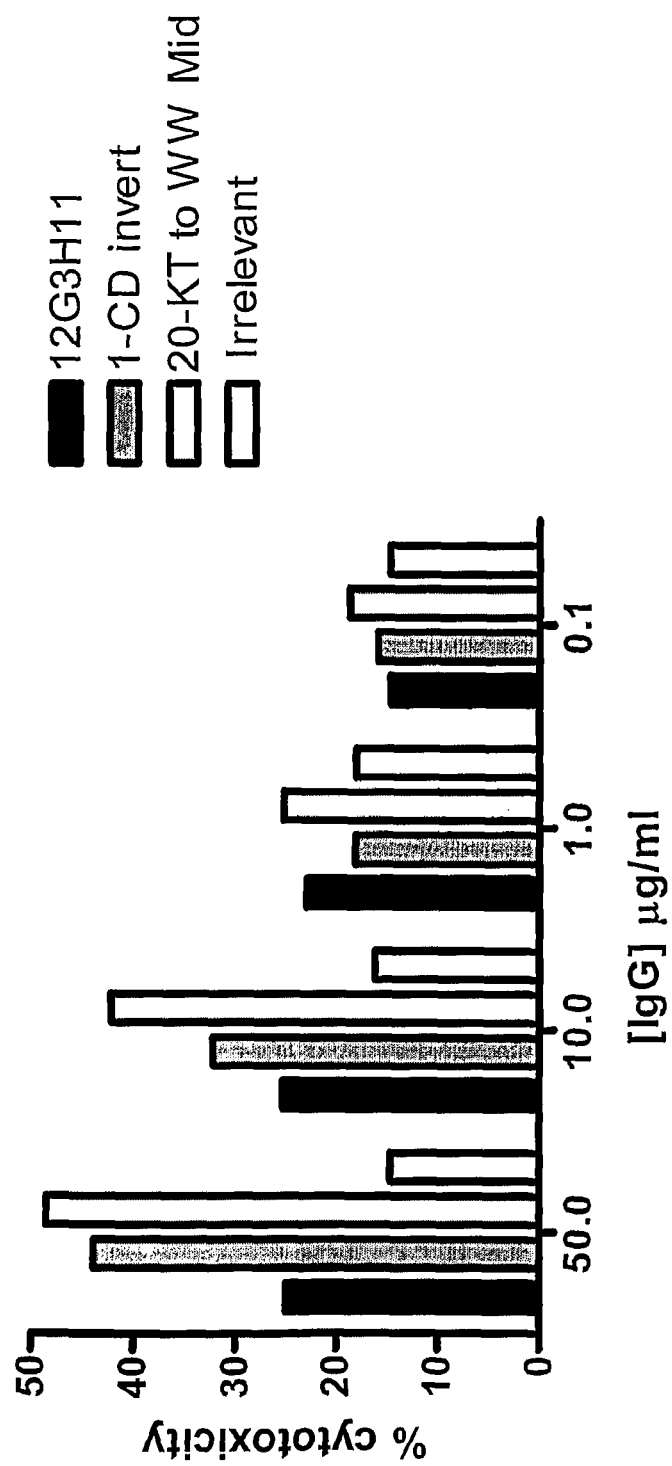
FIG. 20 shows the CDC activity against human EphA2-transfected KATOIII cells of wild type 12G3H11 antibody, an irrelevant control antibody and two Fc variants (1 and 20) which show significantly increased CDC activity. The same result was seen for EphA2-transfected CT26 cells and untransfected KATOIII cells (see FIGS. 19 and 21).
Figure 21:
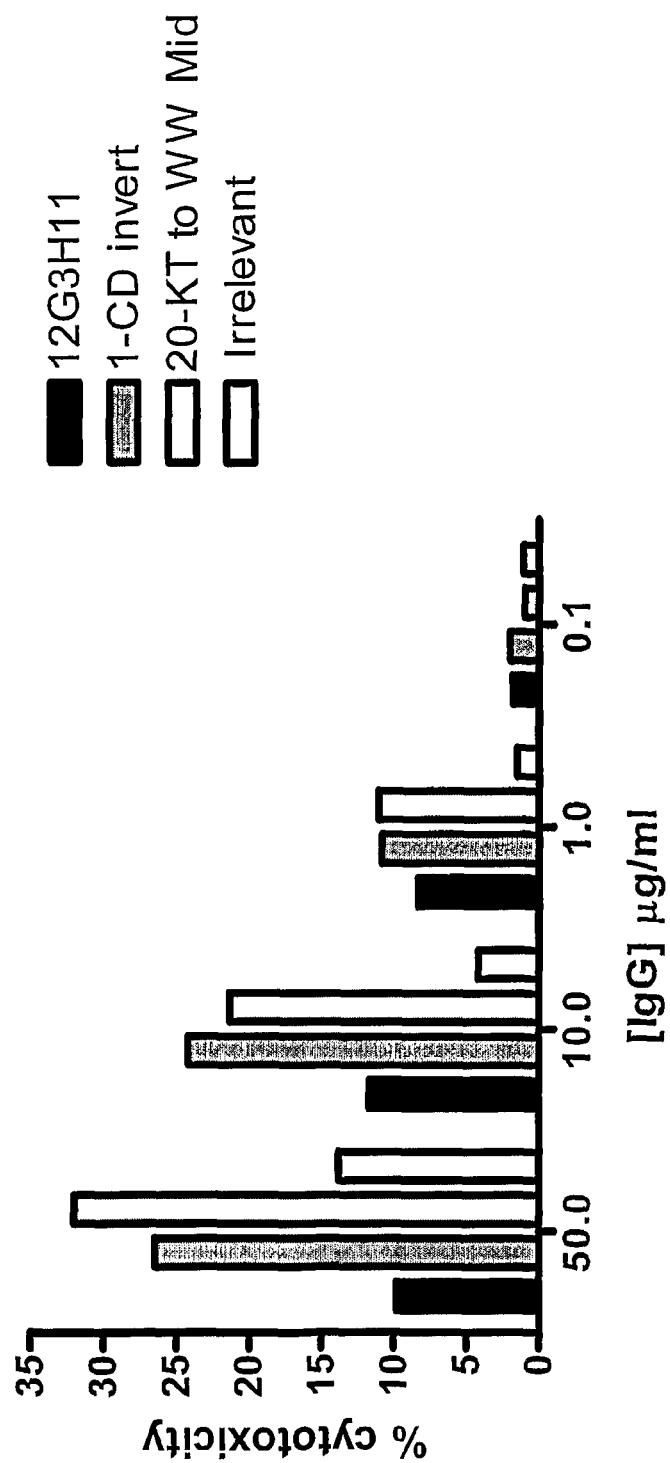
FIG. 21 shows the CDC activity against untransfected KATOIII cells of wild type 12G3H11 antibody, an irrelevant control antibody and two Fc variants (1 and 20) which show significantly increased CDC activity. The same result was seen for EphA2-transfected KATOIII and CT26 cells (see FIGS. 19 and 20).

Fc variants "1-CD invert" and "20-KT to WW mid" consistently exhibited a significantly enhanced CDC activity on both human EphA2-transfected CT26 cells and human EphA2-transfected KATO III cells when compared with their wild type counterpart (12G3H11). Representative data are shown in FIGS. 19 and 20, respectively (also see below). Interestingly, Fc variants "1-CD invert" and "20-KT to WW mid" also exhibited a significantly enhanced CDC activity on non-transfected KATO III cells, in conditions where their wild type counterpart (12G3H11) only exhibited marginal activity. Representative data are shown in FIG. 21. Here again, these data are in agreement with the corresponding binding experiments (Table 7, FIG. 7).

9.3.1 Materials and Methods

ADCC activity of 12G3H11 and of the different hinge variants: human blood samples were collected from eight independent healthy volunteers (not genotyped for their FcγRIIIA allotype) using heparinized syringes, diluted with twice the volume of phosphate buffered saline (PBS), layered onto a Lymphoprep gradient (ICN, Irvine, Calif.), and centrifuged at 400 g for 30 minutes at room temperature. Peripheral blood mononuclear cells (PBMCs) were harvested from the interface, washed 3 times with PBS, and resuspended in Roswell Park Memorial Institute (RPMI) 1640 medium with L-glutamine (Invitrogen, Carlsbad, Calif.) supplemented with 10% fetal bovine serum (FBS). 40 ng/ml of recombinant human IL-2 (R&D Systems, Minneapolis, Minn.) was then added to the PBMCs. Overnight incubation at 37° C. in T-175 flasks (BD Biosciences, Bedford, Mass.) then followed. Cultured A549 (human lung carcinoma) cells were harvested the following day and re-suspended in RPMI 1640 supplemented with 5% FBS (assay buffer) at a density of $2\times10^5$ cells/ml. These were then added to a 96-well round bottom tissue culture plate (BD Biosciences, Bedford, Mass.) at 50 µl/well along with various concentrations of antibody at 50 µl/well in assay buffer (see above) and pre-incubated at 37° C. for 30 minutes. PBMCs were then harvested from their overnight incubation and resuspended at $5\times10^6$ cells/ml (for an Effector (E):Target (T) ratio of 50:1) and $2.5\times10^6$/ml (for an E:T ratio of 25:1) in assay buffer (see above) and added at 100 µl/well to the assay plate. 25 µl/well of 9% Triton X-100 (Promega, Madison, Wis.) was added as a control for complete lysis. The plates were centrifuged at 300×g for 3 minutes and incubation at 37° C. was continued for 4 hours. Plates were then centrifuged at 300×g for 10 minutes and 50 µl of supernatant from each well was transferred to MaxiSorp 96-well plates (BD Biosciences, Bedford, Mass.). 50 µl of reconstituted substrate mix (CytoTox 96 Non-Radioactive Cytotoxicity Assay kit, Promega, Madison, Wis.) was then added to all wells and incubated in the dark at room temperature for 30 minutes. 50 µl of Stop solution (Promega, Madison, Wis.) was added to each well and lactate dehydrogenase (LDH) release was quantified by measuring the absorbance at 490 nm. % cytotoxicity was calculated using the following equation:

% cytotoxicity=(Experimental−Effector Spontaneous−Target Spontaneous)/(Target Maximum−Target Spontaneous)×100, where:

"Experimental" corresponds to the signal measured in one of the condition of interest described above, "Effector Spontaneous" corresponds to the signal measured in the presence of PBMCs alone, "Target Spontaneous" corresponds to the signal measured in the presence of A549 cells alone and "Target Maximum" corresponds to the signal measured in the presence of detergent-lysed A549 cells.

CDC activity of 12G3H11 and of the different hinge variants Three different cell lines were used to assess the CDC activity of 12G3H11 and of the different hinge variants: (i) KATO III (human gastric carcinoma) cells, (ii) KATO III cells transiently (lipofectamine) transfected with human EphA2, (iii) CT-26 (mouse colon carcinoma) cells stably transfected with human EphA2 (MedImmune, Inc), (iv) chinese hamster ovary (CHO) cells transiently transfected with human EphA2 using Lipofectamine (Invitrogen, Carlsbad, Calif.) and standard protocols and (v) chinese hamster ovary (CHO) cells stably transfected with Cynomolgus monkey EphA2. Typically, these cells were individually harvested using enzyme-free cell dissociation buffer (Invitrogen, Carlsbad, Calif.), and plated at 50,000 cells/well in 50 µl/well assay buffer (RPMI/0.1% bovine serum albumin (BSA)/20 mM HEPES) in a 96-well plate. Cells were then incubated with 50 µl/well of the various concentrations of antibody (0.1, 1.0, 10, or 50 µg/ml) for one hour on ice. 25 µl/well of 9% Triton X-100 (Promega, Madison, Wis.) was added as a control for complete lysis. Normal human serum complement (Quidel, San Diego, Calif.) was diluted in assay buffer (see above) at 1:5 for transfected and non-transfected KATO III cells and at 1:3 for CT-26 cells. 50 µl/well of diluted serum was added to the cells. Incubation for 2 hours at 37° C. then followed. Next, 50 µl/well of Alamar Blue (BioSource, Camarillo, Calif.) was added and the incubation was continued overnight. Fluorescence was read using a SpectraMax Fluorometer with the excitation and emissions wavelengths set at 530 and 590 nm, respectively. % cytotoxicity was calculated using a linear regression between 0 (cells, serum, no antibody) and 100% (cells, serum, no antibody, Triton X-100).

9.4 Combinatorial and Alternative Fc Variants

Based on the characterization of the Fc variants described above, several additional Fc variants (designated "22-Combo 1+20", "23-F2", "24-W3", "25-W2 variant", "26-WW upper", "27-W first" and "28-W second" and also referred to by the number designations 22-28, respectively) were generated by combining modifications already generated or by making alternative modifications of several upper hinge positions already examined (see Table 2, section entitled "Combinatorial and Alternative Modifications"). The ability of these variants to bind effector molecules (e.g., C1q and FcγRIIIA) was examined and the CDC activity of these variants was determined as described above.

Fc variants 22, 24, 25, 27 and 28 exhibited increased binding to C1q (see FIGS. 22 and 23) whereas Fc variants 26 and 23 did not have their C1q binding ability significantly altered (FIG. 23). However, the combination of Fc variant 1 and 20 (Fc variant 22) did not yield additive or synergistic effects, resulting in a molecule exhibiting C1q binding properties similar to variants 19 and 21 (compare FIGS. 7 and 22).

Fc variant 28 exhibited a slight increase in binding to human FcγRIIIA (see FIG. 24) whereas Fc variants 22, 23, 24, 25, 26 and 27 only exhibited a slight increase or decrease or no change in FcγRIIIA binding (FIGS. 24 and 25).

Fc variants 1, 20, 22, 24 and 25 consistently exhibited a significantly enhanced CDC activity on KATO III cells, human EphA2-transfected CT26 cells and Cynomolgus monkey EphA2-transfected CHO cells when compared with their wild type counterpart (12G3H11). Representative data are shown in FIGS. 26, 27 and 28, respectively. When human EphA2-transfected KATO III and human EphA2-transfected CHO cells were used, Fc variants 1, 20, 22, 24 and 25 still consistently exhibited a significantly increased CDC activity (FIGS. 29 and 30, respectively). As was previously seen, these data are in agreement with the corresponding binding experiments (Table 7, FIGS. 7, 22 and 23).

9.4.1 Materials and Methods

Generation of Combinatorial and Alternative Fc variant antibody constructs: Various hinge modifications (listed in Table 2, section entitled "Combinatorial and Alternative Modifications") were introduced into the hinge region of the heavy chain of mAb 12G3H11 by site-directed mutagensis using PCR by overlap extension essentially as described above. The following oligonucleotide (see Table 6 for sequence information and corresponding SEQ ID NOS.) combinations were used for the PCR reactions:

127/128 and 129/130 separately (using the 12G3H11/heavy chain-encoding mammalian expression vector described above as a template) and then 131/132 (using the PCR fragments generated by the 127/128 and 129/130 oligonucleotides combinations as templates) to generate the "22-Combo 1+20" final PCR fragment. See Table 2 for the amino acid sequence of this mutation.

145/146 and 147/148 separately (using the 12G3H11/heavy chain-encoding mammalian expression vector described above as a template) and then 149/150 (using the PCR fragments generated by the 145/146 and 147/148 oligonucleotides combinations as templates) to generate the "23-F2" final PCR fragment. See Table 2 for the amino acid sequence of this mutation.

151/152 and 153/154 separately (using the 12G3H11/heavy chain-encoding mammalian expression vector described above as a template) and then 155/156 (using the PCR fragments generated by the 151/152 and 153/154 oligonucleotides combinations as templates) to generate the "24-W3" final PCR fragment. See Table 2 for the amino acid sequence of this mutation.

157/158 and 159/160 separately (using the 12G3H11/ heavy chain-encoding mammalian expression vector described above as a template) and then 161/162 (using the PCR fragments generated by the 157/158 and 159/160 oligonucleotides combinations as templates) to generate the "25-W2 variant" final PCR fragment. See Table 2 for the amino acid sequence of this mutation.

163/164 and 165/166 separately (using the 12G3H11/ heavy chain-encoding mammalian expression vector described above as a template) and then 167/168 (using the PCR fragments generated by the 163/164 and 165/166 oligonucleotides combinations as templates) to generate the "26-WW-upper" final PCR fragment. See Table 2 for the amino acid sequence of this mutation.

133/134 and 135/136 separately (using the 12G3H11/ heavy chain-encoding mammalian expression vector described above as a template) and then 137/138 (using the PCR fragments generated by the 133/134 and 135/136 oligonucleotides combinations as templates) to generate the "27-W first" final PCR fragment. See Table 2 for the amino acid sequence of this mutation.

139/140 and 141/142 separately (using the 12G3H11/ heavy chain-encoding mammalian expression vector described above as a template) and then 143/144 (using the PCR fragments generated by the 139/140 and 141/142 oligonucleotides combinations as templates) to generate the "28-W second" final PCR fragment. See Table 2 for the amino acid sequence of this mutation.

These 7 final PCR fragments were then individually cloned into the 12G3H11/heavy chain-encoding mammalian expression vector as described above. This resulted in the replacement of the heavy chain constant portion of 12G3H11 by these 7 different Fc variant counterparts. The sequences were verified using an ABI 3100 sequencer.

9.5 Ligand Binding

The hinge variants that exhibited a significant change in C1q/FcγRIIIA binding (see above) had similar apparent binding affinity to their cognate antigen (human EphA2) as 12G3H11 (data not shown). Of these variants, those which also showed a decrease in their effector functions were more accurately characterized using a KinExa instrument, as their apparent dissociations rates were near or over BIAcore's sensitivity limit ($\sim 5 \times 10^{-6}$ s$^{-1}$). Again the corresponding affinities to human EphA2 were very similar to 12G3H11 (Table 8). This, along with the ability of these IgGs to be purified by protein A or G (see Materials and Methods), indicated that these effects on effector functions were not caused by major structural changes.

TABLE 8

Affinity measurements for the binding of different hinge-mutated human IgG1s to human EphA2[a].

| Hinge Variant | $K_D$ (pM) |
|---|---|
| Wild type (12G3H11) | 1.1 ± 0.9 |
| 3 | 2.8 ± 2.1 |
| 4 | 5.2 ± 3.5 |
| 5 | 0.8 ± 0.6 |
| 6 | 2.7 ± 2.0 |
| 11 | ≤1[b] |
| 13 | 1.7 ± 0.8 |
| 14 | 7.2 ± 4.3 |
| 18 | 1.5 ± 0.1 |

[a]Dissociation constants ($K_D$) were determined using a KinExa instrument as described in Materials and Methods. Errors in the binding measurements were estimated from the standard deviations of two independent determinations.
[b]The signal strength and KinExa's sensitivity limit precluded a more accurate determination. In all cases, the residual error between the fitted and theoretical curves was ≤6%.

Analysis of human EphA2 binding to 12G3H11 and its hinge variants by KinExa: The interaction of immobilized human EphA2-Fc with soluble 12G3H11, variants 3, 4, 5, 6, 11, 13, 14 and 18 was monitored using a KinExA 3000 instrument (Sapidyne Instruments, Boise, Id.). Protein concentrations were calculated by the BCA method. Typically, human EphA2-Fc was coated onto Azlactone beads at a concentration of 100 g/mL in 0.05 M NaHCO$_3$, pH 9.0, for 1-2 days at 4° C. according to the manufacturer's instructions (Sapidyne Instruments, Boise, Id.). Coated beads were then separated from unreacted EphA2-Fc using a gentle pulse spin and blocked for approximately 2 h at room temperature with 1M Tris, pH 8.0, bovine serum albumin 10 mg/mL. Beads were then resuspended in 30 mL of run buffer (PBS, pH 7.4-0.02% NaN$_3$) and packed into a column. Typically, human IgGs were prepared at concentrations of 10, 25 and/or 50 μM. Human EphA2-Fc was then titrated across these IgG solutions at concentrations ranging from 39 fM-80 μM and 156 fM-400 μM, respectively, and incubated for 3-7 days at room temperature. The amount of free IgG in the samples was derived from the fluorescence signal obtained after the passing of Cy5-labeled goat anti-human IgG F(ab')$_2$ (typically 0.5-2 μg/ml; Jackson ImmunoResearch Laboratories, West Grove, Pa.) through the column. Dissociation constants ($K_D$s) were determined by fitting the individual equilibrium titration data to a 1:1 binding model using the KinExA Pro 1.0.3. software.

9.6 Structural Analysis—Chain Pairing

Except for Fc variants 27 and 28, the variants described in Table 2 were further characterized by SDS-PAGE under reducing or non reducing conditions Under reducing conditions, all variants migrated as two main bands of about 60 and 30 kDa corresponding to their heavy and light polypeptide chains, respectively (FIG. 31, top panels and data not shown). Under non reducing conditions, variants 4, 5, 8, 11, 12 and 19 migrated as two main bands of about 200 and 100 kDa (FIG. 31, bottom left panel). The 200 kDa band corresponded to full length IgG. The 100 kDa band, present at significantly higher levels when compared with 12G3H11, corresponded to a dimeric half-structure consisting of covalently bound heavy and light chains indicative of an increased proportion of non covalently bound heavy chains. A range in the relative proportions of these two species was observed, varying from mostly half-IgG (variants 5 and 19), to similar amounts of full length- and half-IgG (variants 11 and 12), to mostly full length-IgG (variants 4 and 8). All other Fc variants did not exhibit a significantly greater proportion of the 100 kDa species when compared with 12G3H11 and showed a band corresponding to the full length IgG at about 200 kDa. While it is possible that at least some of the effect seen on CDC activity for these Fc variants is the direct consequence of differential interactions between both heavy chains, size exclusion chromatography of variants 4, 5, 7 and 8 did not reveal any significant dissociation (data not shown). Additionally, no significant amount of unpaired light chain was observed for Fc variants 1, 2, 20, 22, 23, 24, 25 and 26 under non reducing conditions, indicating that the upper hinge-mediated covalent bond was still forming in all cases.

Chain Pairing: Each variant was characterized by SDS-PAGE under reducing (FIG. 31 top panels) or non reducing conditions (FIG. 31 bottom panels).

Whereas, particular embodiments of the invention have been described above for purposes of description, it will be appreciated by those skilled in the art that numerous variations of the details may be made without departing from the invention as described in the appended claims.

All publications, patents and patent applications mentioned in this specification are herein incorporated by reference into the specification to the same extent as if each individual publication, patent or patent application was specifically and individually indicated to be incorporated herein by reference. In addition, U.S. Provisional Application Nos. 60/674,674 filed Apr. 26, 2005, 60/713,711 filed Sep. 6, 2005 and 60/735,169 filed Nov. 10, 2005 are incorporated by reference herein in their entirety for all purposes.

The invention claimed is:

1. A method of producing a polypeptide having increased binding affinity for C1q, wherein said polypeptide comprises an Fc region and said Fc region comprises a hinge region, said method comprising introducing an amino acid substitution into the hinge region selected from the group consisting of:
   (a) C233D (not EU number, Kabat number);
   (b) C233D (not EU number, Kabat number) and D234C (not EU number, Kabat number);
   (c) K222W and T223W;
   (d) C233D (not EU number, Kabat number), D234C (not EU number, Kabat number), K222W and T223W;
   (e) K222W, T223W and H224W; and
   (f) D234W (not EU number, Kabat number) and K222W, utilizing the EU index numbering system set forth in Kabat except where indicated.

2. The method of claim 1, wherein said polypeptide has CDC activity that is increased at least 10%, relative to a polypeptide having the same amino acid sequence except having an unmodified hinge region.

3. The method of claim 1, wherein said substitution is C233D (not EU number, Kabat number) and D234C (not EU number, Kabat number).

4. The method of claim 1, wherein said substitution is K222W and T223W.

5. The method of claim 1, wherein said substitution is C233D (not EU number, Kabat number), D234C (not EU number, Kabat number), K222W and T223W.

6. The method of claim 1, wherein said substitution is K222W, T223W and H224W.

7. The method of claim 1, wherein said substitution is D234W (not EU number, Kabat number) and K222W.

8. The method of claim 1, wherein said substitution is C233D (not EU number, Kabat number).

9. The method of claim 1, wherein the polypeptide is an antibody.

10. The method of claim 1, wherein the polypeptide is an Fc fusion protein.

* * * * *

```
                            SEQUENCE LISTING

<160> NUMBER OF SEQ ID NOS: 176

<210> SEQ ID NO 1
<211> LENGTH: 107
<212> TYPE: PRT
<213> ORGANISM: Artificial
<220> FEATURE:
<223> OTHER INFORMATION: recombinant antibody light chain variable
      region

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu His Trp Tyr Gln Gln Lys Pro Gly Lys Ala Pro Lys Leu Leu Ile
        35                  40                  45

Lys Tyr Ala Phe Gln Ser Ile Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Ala Asn Ser Trp Pro Leu
                85                  90                  95

Thr Phe Gly Gly Gly Thr Lys Val Glu Ile Lys
            100                 105

<210> SEQ ID NO 2
<211> LENGTH: 120
<212> TYPE: PRT
<213> ORGANISM: Artificial
<220> FEATURE:
<223> OTHER INFORMATION: recombinant antibody heavy chain variable
      region

<400> SEQUENCE: 2

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Asp Asp Tyr
            20                  25                  30

Ser Met Asn Trp Val Arg Gln Ala Arg Gly Gln Arg Leu Glu Trp Ile
        35                  40                  45

Gly Phe Ile Arg Asn Lys Ala Asn Asp Tyr Thr Thr Glu Tyr Ala Asp
    50                  55                  60

Ser Val Lys Gly Arg Val Thr Ile Thr Arg Asp Met Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Tyr Pro Arg His His Ala Met Asp Ser Trp Gly Gln
            100                 105                 110

Gly Thr Ser Val Thr Val Ser Ser
        115                 120
```

```
<210> SEQ ID NO 3
<211> LENGTH: 44
<212> TYPE: DNA
<213> ORGANISM: Artificial
<220> FEATURE:
<223> OTHER INFORMATION: primer

<400> SEQUENCE: 3
gagagttgag cccaaatctg actgtaaaac tcacacatgc ccac           44

<210> SEQ ID NO 4
<211> LENGTH: 24
<212> TYPE: DNA
<213> ORGANISM: Artificial
<220> FEATURE:
<223> OTHER INFORMATION: primer

<400> SEQUENCE: 4
gatcaatgaa ttcgcggccg ctca                                 24

<210> SEQ ID NO 5
<211> LENGTH: 44
<212> TYPE: DNA
<213> ORGANISM: Artificial
<220> FEATURE:
<223> OTHER INFORMATION: primer

<400> SEQUENCE: 5
gtgggcatgt gtgagtttta cagtcagatt tgggctcaac tctc           44

<210> SEQ ID NO 6
<211> LENGTH: 28
<212> TYPE: DNA
<213> ORGANISM: Artificial
<220> FEATURE:
<223> OTHER INFORMATION: primer

<400> SEQUENCE: 6
gcctccacca agggcccatc ggtcttcc                             28

<210> SEQ ID NO 7
<211> LENGTH: 24
<212> TYPE: DNA
<213> ORGANISM: Artificial
<220> FEATURE:
<223> OTHER INFORMATION: primer

<400> SEQUENCE: 7
gatcaatgaa ttcgcggccg ctca                                 24

<210> SEQ ID NO 8
<211> LENGTH: 28
<212> TYPE: DNA
<213> ORGANISM: Artificial
<220> FEATURE:
<223> OTHER INFORMATION: primer

<400> SEQUENCE: 8
gcctccacca agggcccatc ggtcttcc                             28

<210> SEQ ID NO 9
<211> LENGTH: 43
<212> TYPE: DNA
<213> ORGANISM: Artificial
<220> FEATURE:
<223> OTHER INFORMATION: primer
```

<400> SEQUENCE: 9
caagagagtt gagcccaaat gttctgacaa aactcacaca tgc         43

<210> SEQ ID NO 10
<211> LENGTH: 24
<212> TYPE: DNA
<213> ORGANISM: Artificial
<220> FEATURE:
<223> OTHER INFORMATION: primer

<400> SEQUENCE: 10
gatcaatgaa ttcgcggccg ctca         24

<210> SEQ ID NO 11
<211> LENGTH: 43
<212> TYPE: DNA
<213> ORGANISM: Artificial
<220> FEATURE:
<223> OTHER INFORMATION: primer

<400> SEQUENCE: 11
gcatgtgtga gttttgtcag aacatttggg ctcaactctc ttg         43

<210> SEQ ID NO 12
<211> LENGTH: 28
<212> TYPE: DNA
<213> ORGANISM: Artificial
<220> FEATURE:
<223> OTHER INFORMATION: primer

<400> SEQUENCE: 12
gcctccacca agggcccatc ggtcttcc         28

<210> SEQ ID NO 13
<211> LENGTH: 24
<212> TYPE: DNA
<213> ORGANISM: Artificial
<220> FEATURE:
<223> OTHER INFORMATION: primer

<400> SEQUENCE: 13
gatcaatgaa ttcgcggccg ctca         24

<210> SEQ ID NO 14
<211> LENGTH: 28
<212> TYPE: DNA
<213> ORGANISM: Artificial
<220> FEATURE:
<223> OTHER INFORMATION: primer

<400> SEQUENCE: 14
gcctccacca agggcccatc ggtcttcc         28

<210> SEQ ID NO 15
<211> LENGTH: 40
<212> TYPE: DNA
<213> ORGANISM: Artificial
<220> FEATURE:
<223> OTHER INFORMATION: primer

<400> SEQUENCE: 15
tgtgacaaaa ctcacacaag cccaccgtgc ccagcacctg         40

```
<210> SEQ ID NO 16
<211> LENGTH: 24
<212> TYPE: DNA
<213> ORGANISM: Artificial
<220> FEATURE:
<223> OTHER INFORMATION: primer

<400> SEQUENCE: 16
gatcaatgaa ttcgcggccg ctca                                              24

<210> SEQ ID NO 17
<211> LENGTH: 40
<212> TYPE: DNA
<213> ORGANISM: Artificial
<220> FEATURE:
<223> OTHER INFORMATION: primer

<400> SEQUENCE: 17
caggtgctgg gcacggtggg cttgtgtgag ttttgtcaca                              40

<210> SEQ ID NO 18
<211> LENGTH: 28
<212> TYPE: DNA
<213> ORGANISM: Artificial
<220> FEATURE:
<223> OTHER INFORMATION: primer

<400> SEQUENCE: 18
gcctccacca agggcccatc ggtcttcc                                           28

<210> SEQ ID NO 19
<211> LENGTH: 24
<212> TYPE: DNA
<213> ORGANISM: Artificial
<220> FEATURE:
<223> OTHER INFORMATION: primer

<400> SEQUENCE: 19
gatcaatgaa ttcgcggccg ctca                                              24

<210> SEQ ID NO 20
<211> LENGTH: 28
<212> TYPE: DNA
<213> ORGANISM: Artificial
<220> FEATURE:
<223> OTHER INFORMATION: primer

<400> SEQUENCE: 20
gcctccacca agggcccatc ggtcttcc                                           28

<210> SEQ ID NO 21
<211> LENGTH: 40
<212> TYPE: DNA
<213> ORGANISM: Artificial
<220> FEATURE:
<223> OTHER INFORMATION: primer

<400> SEQUENCE: 21
actcacacat gcccaccgag cccagcacct gaactcctgg                              40

<210> SEQ ID NO 22
<211> LENGTH: 24
<212> TYPE: DNA
<213> ORGANISM: Artificial
<220> FEATURE:
<223> OTHER INFORMATION: primer
```

```
<400> SEQUENCE: 22
gatcaatgaa ttcgcggccg ctca                                          24

<210> SEQ ID NO 23
<211> LENGTH: 40
<212> TYPE: DNA
<213> ORGANISM: Artificial
<220> FEATURE:
<223> OTHER INFORMATION: primer

<400> SEQUENCE: 23
ccaggagttc aggtgctggg ctcggtgggc atgtgtgagt                          40

<210> SEQ ID NO 24
<211> LENGTH: 28
<212> TYPE: DNA
<213> ORGANISM: Artificial
<220> FEATURE:
<223> OTHER INFORMATION: primer

<400> SEQUENCE: 24
gcctccacca agggcccatc ggtcttcc                                      28

<210> SEQ ID NO 25
<211> LENGTH: 24
<212> TYPE: DNA
<213> ORGANISM: Artificial
<220> FEATURE:
<223> OTHER INFORMATION: primer

<400> SEQUENCE: 25
gatcaatgaa ttcgcggccg ctca                                          24

<210> SEQ ID NO 26
<211> LENGTH: 28
<212> TYPE: DNA
<213> ORGANISM: Artificial
<220> FEATURE:
<223> OTHER INFORMATION: primer

<400> SEQUENCE: 26
gcctccacca agggcccatc ggtcttcc                                      28

<210> SEQ ID NO 27
<211> LENGTH: 47
<212> TYPE: DNA
<213> ORGANISM: Artificial
<220> FEATURE:
<223> OTHER INFORMATION: primer

<400> SEQUENCE: 27
caaaactcac acatgcccag gaggcggtcc gtgcccagca cctgaac                 47

<210> SEQ ID NO 28
<211> LENGTH: 24
<212> TYPE: DNA
<213> ORGANISM: Artificial
<220> FEATURE:
<223> OTHER INFORMATION: primer

<400> SEQUENCE: 28
gatcaatgaa ttcgcggccg ctca                                          24
```

```
<210> SEQ ID NO 29
<211> LENGTH: 47
<212> TYPE: DNA
<213> ORGANISM: Artificial
<220> FEATURE:
<223> OTHER INFORMATION: primer

<400> SEQUENCE: 29
gttcaggtgc tgggcacgga ccgcctcctg ggcatgtgtg agttttg                           47

<210> SEQ ID NO 30
<211> LENGTH: 28
<212> TYPE: DNA
<213> ORGANISM: Artificial
<220> FEATURE:
<223> OTHER INFORMATION: primer

<400> SEQUENCE: 30
gcctccacca agggcccatc ggtcttcc                                               28

<210> SEQ ID NO 31
<211> LENGTH: 24
<212> TYPE: DNA
<213> ORGANISM: Artificial
<220> FEATURE:
<223> OTHER INFORMATION: primer

<400> SEQUENCE: 31
gatcaatgaa ttcgcggccg ctca                                                   24

<210> SEQ ID NO 32
<211> LENGTH: 28
<212> TYPE: DNA
<213> ORGANISM: Artificial
<220> FEATURE:
<223> OTHER INFORMATION: primer

<400> SEQUENCE: 32
gcctccacca agggcccatc ggtcttcc                                               28

<210> SEQ ID NO 33
<211> LENGTH: 46
<212> TYPE: DNA
<213> ORGANISM: Artificial
<220> FEATURE:
<223> OTHER INFORMATION: primer

<400> SEQUENCE: 33
gagcccaaat cttgtgacgg aggcggtaaa actcacacat gcccac                           46

<210> SEQ ID NO 34
<211> LENGTH: 24
<212> TYPE: DNA
<213> ORGANISM: Artificial
<220> FEATURE:
<223> OTHER INFORMATION: primer

<400> SEQUENCE: 34
gatcaatgaa ttcgcggccg ctca                                                   24

<210> SEQ ID NO 35
<211> LENGTH: 46
<212> TYPE: DNA
<213> ORGANISM: Artificial
<220> FEATURE:
<223> OTHER INFORMATION: primer
```

<400> SEQUENCE: 35
gtgggcatgt gtgagtttta ccgcctccgt cacaagattt gggctc     46

<210> SEQ ID NO 36
<211> LENGTH: 28
<212> TYPE: DNA
<213> ORGANISM: Artificial
<220> FEATURE:
<223> OTHER INFORMATION: primer

<400> SEQUENCE: 36
gcctccacca agggcccatc ggtcttcc     28

<210> SEQ ID NO 37
<211> LENGTH: 24
<212> TYPE: DNA
<213> ORGANISM: Artificial
<220> FEATURE:
<223> OTHER INFORMATION: primer

<400> SEQUENCE: 37
gatcaatgaa ttcgcggccg ctca     24

<210> SEQ ID NO 38
<211> LENGTH: 28
<212> TYPE: DNA
<213> ORGANISM: Artificial
<220> FEATURE:
<223> OTHER INFORMATION: primer

<400> SEQUENCE: 38
gcctccacca agggcccatc ggtcttcc     28

<210> SEQ ID NO 39
<211> LENGTH: 39
<212> TYPE: DNA
<213> ORGANISM: Artificial
<220> FEATURE:
<223> OTHER INFORMATION: primer

<400> SEQUENCE: 39
cacacatgcc caccgtgcgg agcacctgaa ctcctgggg     39

<210> SEQ ID NO 40
<211> LENGTH: 24
<212> TYPE: DNA
<213> ORGANISM: Artificial
<220> FEATURE:
<223> OTHER INFORMATION: primer

<400> SEQUENCE: 40
gatcaatgaa ttcgcggccg ctca     24

<210> SEQ ID NO 41
<211> LENGTH: 39
<212> TYPE: DNA
<213> ORGANISM: Artificial
<220> FEATURE:
<223> OTHER INFORMATION: primer

<400> SEQUENCE: 41
ccccaggagt tcaggtgctc cgcacggtgg gcatgtgtg     39

```
<210> SEQ ID NO 42
<211> LENGTH: 28
<212> TYPE: DNA
<213> ORGANISM: Artificial
<220> FEATURE:
<223> OTHER INFORMATION: primer

<400> SEQUENCE: 42
gcctccacca agggcccatc ggtcttcc                                          28

<210> SEQ ID NO 43
<211> LENGTH: 24
<212> TYPE: DNA
<213> ORGANISM: Artificial
<220> FEATURE:
<223> OTHER INFORMATION: primer

<400> SEQUENCE: 43
gatcaatgaa ttcgcggccg ctca                                              24

<210> SEQ ID NO 44
<211> LENGTH: 28
<212> TYPE: DNA
<213> ORGANISM: Artificial
<220> FEATURE:
<223> OTHER INFORMATION: primer

<400> SEQUENCE: 44
gcctccacca agggcccatc ggtcttcc                                          28

<210> SEQ ID NO 45
<211> LENGTH: 42
<212> TYPE: DNA
<213> ORGANISM: Artificial
<220> FEATURE:
<223> OTHER INFORMATION: primer

<400> SEQUENCE: 45
gacaaaactc acacatgcgg cggatgccca gcacctgaac tc                          42

<210> SEQ ID NO 46
<211> LENGTH: 24
<212> TYPE: DNA
<213> ORGANISM: Artificial
<220> FEATURE:
<223> OTHER INFORMATION: primer

<400> SEQUENCE: 46
gatcaatgaa ttcgcggccg ctca                                              24

<210> SEQ ID NO 47
<211> LENGTH: 42
<212> TYPE: DNA
<213> ORGANISM: Artificial
<220> FEATURE:
<223> OTHER INFORMATION: primer

<400> SEQUENCE: 47
gagttcaggt gctgggcatc cgccgcatgt gtgagttttg tc                          42

<210> SEQ ID NO 48
<211> LENGTH: 28
<212> TYPE: DNA
<213> ORGANISM: Artificial
<220> FEATURE:
<223> OTHER INFORMATION: primer
```

```
<400> SEQUENCE: 48
gcctccacca agggcccatc ggtcttcc                                      28

<210> SEQ ID NO 49
<211> LENGTH: 24
<212> TYPE: DNA
<213> ORGANISM: Artificial
<220> FEATURE:
<223> OTHER INFORMATION: primer

<400> SEQUENCE: 49
gatcaatgaa ttcgcggccg ctca                                          24

<210> SEQ ID NO 50
<211> LENGTH: 28
<212> TYPE: DNA
<213> ORGANISM: Artificial
<220> FEATURE:
<223> OTHER INFORMATION: primer

<400> SEQUENCE: 50
gcctccacca agggcccatc ggtcttcc                                      28

<210> SEQ ID NO 51
<211> LENGTH: 50
<212> TYPE: DNA
<213> ORGANISM: Artificial
<220> FEATURE:
<223> OTHER INFORMATION: primer

<400> SEQUENCE: 51
gttgagccca aatcttgtgg cgggggaggt ggatgcccac cgtgcccagc              50

<210> SEQ ID NO 52
<211> LENGTH: 24
<212> TYPE: DNA
<213> ORGANISM: Artificial
<220> FEATURE:
<223> OTHER INFORMATION: primer

<400> SEQUENCE: 52
gatcaatgaa ttcgcggccg ctca                                          24

<210> SEQ ID NO 53
<211> LENGTH: 50
<212> TYPE: DNA
<213> ORGANISM: Artificial
<220> FEATURE:
<223> OTHER INFORMATION: primer

<400> SEQUENCE: 53
gctgggcacg gtgggcatcc acctcccccg ccacaagatt tgggctcaac              50

<210> SEQ ID NO 54
<211> LENGTH: 28
<212> TYPE: DNA
<213> ORGANISM: Artificial
<220> FEATURE:
<223> OTHER INFORMATION: primer

<400> SEQUENCE: 54
gcctccacca agggcccatc ggtcttcc                                      28
```

```
<210> SEQ ID NO 55
<211> LENGTH: 24
<212> TYPE: DNA
<213> ORGANISM: Artificial
<220> FEATURE:
<223> OTHER INFORMATION: primer

<400> SEQUENCE: 55
gatcaatgaa ttcgcggccg ctca                                          24

<210> SEQ ID NO 56
<211> LENGTH: 28
<212> TYPE: DNA
<213> ORGANISM: Artificial
<220> FEATURE:
<223> OTHER INFORMATION: primer

<400> SEQUENCE: 56
gcctccacca agggcccatc ggtcttcc                                      28

<210> SEQ ID NO 57
<211> LENGTH: 50
<212> TYPE: DNA
<213> ORGANISM: Artificial
<220> FEATURE:
<223> OTHER INFORMATION: primer

<400> SEQUENCE: 57
aaggtggaca agagagttgg gggcggaggt tgtgacaaaa ctcacacatg              50

<210> SEQ ID NO 58
<211> LENGTH: 24
<212> TYPE: DNA
<213> ORGANISM: Artificial
<220> FEATURE:
<223> OTHER INFORMATION: primer

<400> SEQUENCE: 58
gatcaatgaa ttcgcggccg ctca                                          24

<210> SEQ ID NO 59
<211> LENGTH: 50
<212> TYPE: DNA
<213> ORGANISM: Artificial
<220> FEATURE:
<223> OTHER INFORMATION: primer

<400> SEQUENCE: 59
catgtgtgag ttttgtcaca acctccgccc ccaactctct tgtccacctt              50

<210> SEQ ID NO 60
<211> LENGTH: 28
<212> TYPE: DNA
<213> ORGANISM: Artificial
<220> FEATURE:
<223> OTHER INFORMATION: primer

<400> SEQUENCE: 60
gcctccacca agggcccatc ggtcttcc                                      28

<210> SEQ ID NO 61
<211> LENGTH: 24
<212> TYPE: DNA
<213> ORGANISM: Artificial
<220> FEATURE:
<223> OTHER INFORMATION: primer
```

-continued

<400> SEQUENCE: 61
gatcaatgaa ttcgcggccg ctca                                    24

<210> SEQ ID NO 62
<211> LENGTH: 28
<212> TYPE: DNA
<213> ORGANISM: Artificial
<220> FEATURE:
<223> OTHER INFORMATION: primer

<400> SEQUENCE: 62
gcctccacca agggcccatc ggtcttcc                                28

<210> SEQ ID NO 63
<211> LENGTH: 46
<212> TYPE: DNA
<213> ORGANISM: Artificial
<220> FEATURE:
<223> OTHER INFORMATION: primer

<400> SEQUENCE: 63
gcccaaatct tgtgacaaaa catgctgccc agcacctgaa ctcctg            46

<210> SEQ ID NO 64
<211> LENGTH: 24
<212> TYPE: DNA
<213> ORGANISM: Artificial
<220> FEATURE:
<223> OTHER INFORMATION: primer

<400> SEQUENCE: 64
gatcaatgaa ttcgcggccg ctca                                    24

<210> SEQ ID NO 65
<211> LENGTH: 46
<212> TYPE: DNA
<213> ORGANISM: Artificial
<220> FEATURE:
<223> OTHER INFORMATION: primer

<400> SEQUENCE: 65
caggagttca ggtgctgggc agcatgtttt gtcacaagat ttgggc            46

<210> SEQ ID NO 66
<211> LENGTH: 28
<212> TYPE: DNA
<213> ORGANISM: Artificial
<220> FEATURE:
<223> OTHER INFORMATION: primer

<400> SEQUENCE: 66
gcctccacca agggcccatc ggtcttcc                                28

<210> SEQ ID NO 67
<211> LENGTH: 24
<212> TYPE: DNA
<213> ORGANISM: Artificial
<220> FEATURE:
<223> OTHER INFORMATION: primer

<400> SEQUENCE: 67
gatcaatgaa ttcgcggccg ctca                                    24

```
<210> SEQ ID NO 68
<211> LENGTH: 28
<212> TYPE: DNA
<213> ORGANISM: Artificial
<220> FEATURE:
<223> OTHER INFORMATION: primer

<400> SEQUENCE: 68
gcctccacca agggcccatc ggtcttcc                                      28

<210> SEQ ID NO 69
<211> LENGTH: 36
<212> TYPE: DNA
<213> ORGANISM: Artificial
<220> FEATURE:
<223> OTHER INFORMATION: primer

<400> SEQUENCE: 69
gacaaaactc acacatgctg cccagcacct gaactc                             36

<210> SEQ ID NO 70
<211> LENGTH: 24
<212> TYPE: DNA
<213> ORGANISM: Artificial
<220> FEATURE:
<223> OTHER INFORMATION: primer

<400> SEQUENCE: 70
gatcaatgaa ttcgcggccg ctca                                          24

<210> SEQ ID NO 71
<211> LENGTH: 36
<212> TYPE: DNA
<213> ORGANISM: Artificial
<220> FEATURE:
<223> OTHER INFORMATION: primer

<400> SEQUENCE: 71
gagttcaggt gctgggcagc atgtgtgagt tttgtc                             36

<210> SEQ ID NO 72
<211> LENGTH: 28
<212> TYPE: DNA
<213> ORGANISM: Artificial
<220> FEATURE:
<223> OTHER INFORMATION: primer

<400> SEQUENCE: 72
gcctccacca agggcccatc ggtcttcc                                      28

<210> SEQ ID NO 73
<211> LENGTH: 24
<212> TYPE: DNA
<213> ORGANISM: Artificial
<220> FEATURE:
<223> OTHER INFORMATION: primer

<400> SEQUENCE: 73
gatcaatgaa ttcgcggccg ctca                                          24

<210> SEQ ID NO 74
<211> LENGTH: 28
<212> TYPE: DNA
<213> ORGANISM: Artificial
<220> FEATURE:
<223> OTHER INFORMATION: primer
```

-continued

```
<400> SEQUENCE: 74
gcctccacca agggcccatc ggtcttcc                                    28

<210> SEQ ID NO 75
<211> LENGTH: 37
<212> TYPE: DNA
<213> ORGANISM: Artificial
<220> FEATURE:
<223> OTHER INFORMATION: primer

<400> SEQUENCE: 75
cccaaatctt gtgacaaaac atgcccaccg tgcccag                          37

<210> SEQ ID NO 76
<211> LENGTH: 24
<212> TYPE: DNA
<213> ORGANISM: Artificial
<220> FEATURE:
<223> OTHER INFORMATION: primer

<400> SEQUENCE: 76
gatcaatgaa ttcgcggccg ctca                                        24

<210> SEQ ID NO 77
<211> LENGTH: 37
<212> TYPE: DNA
<213> ORGANISM: Artificial
<220> FEATURE:
<223> OTHER INFORMATION: primer

<400> SEQUENCE: 77
ctgggcacgg tgggcatgtt ttgtcacaag atttggg                          37

<210> SEQ ID NO 78
<211> LENGTH: 28
<212> TYPE: DNA
<213> ORGANISM: Artificial
<220> FEATURE:
<223> OTHER INFORMATION: primer

<400> SEQUENCE: 78
gcctccacca agggcccatc ggtcttcc                                    28

<210> SEQ ID NO 79
<211> LENGTH: 24
<212> TYPE: DNA
<213> ORGANISM: Artificial
<220> FEATURE:
<223> OTHER INFORMATION: primer

<400> SEQUENCE: 79
gatcaatgaa ttcgcggccg ctca                                        24

<210> SEQ ID NO 80
<211> LENGTH: 28
<212> TYPE: DNA
<213> ORGANISM: Artificial
<220> FEATURE:
<223> OTHER INFORMATION: primer

<400> SEQUENCE: 80
gcctccacca agggcccatc ggtcttcc                                    28
```

```
<210> SEQ ID NO 81
<211> LENGTH: 39
<212> TYPE: DNA
<213> ORGANISM: Artificial
<220> FEATURE:
<223> OTHER INFORMATION: primer

<400> SEQUENCE: 81
cccaaatctt gtgacaaatg tcacacatgc ccaccgtgc                              39

<210> SEQ ID NO 82
<211> LENGTH: 24
<212> TYPE: DNA
<213> ORGANISM: Artificial
<220> FEATURE:
<223> OTHER INFORMATION: primer

<400> SEQUENCE: 82
gatcaatgaa ttcgcggccg ctca                                             24

<210> SEQ ID NO 83
<211> LENGTH: 39
<212> TYPE: DNA
<213> ORGANISM: Artificial
<220> FEATURE:
<223> OTHER INFORMATION: primer

<400> SEQUENCE: 83
gcacggtggg catgtgtgac atttgtcaca agatttggg                             39

<210> SEQ ID NO 84
<211> LENGTH: 28
<212> TYPE: DNA
<213> ORGANISM: Artificial
<220> FEATURE:
<223> OTHER INFORMATION: primer

<400> SEQUENCE: 84
gcctccacca agggcccatc ggtcttcc                                         28

<210> SEQ ID NO 85
<211> LENGTH: 24
<212> TYPE: DNA
<213> ORGANISM: Artificial
<220> FEATURE:
<223> OTHER INFORMATION: primer

<400> SEQUENCE: 85
gatcaatgaa ttcgcggccg ctca                                             24

<210> SEQ ID NO 86
<211> LENGTH: 28
<212> TYPE: DNA
<213> ORGANISM: Artificial
<220> FEATURE:
<223> OTHER INFORMATION: primer

<400> SEQUENCE: 86
gcctccacca agggcccatc ggtcttcc                                         28

<210> SEQ ID NO 87
<211> LENGTH: 47
<212> TYPE: DNA
<213> ORGANISM: Artificial
<220> FEATURE:
<223> OTHER INFORMATION: primer
```

-continued

```
<400> SEQUENCE: 87
caaaactcac acatgcccac ccccgccacc gtgcccagca cctgaac            47

<210> SEQ ID NO 88
<211> LENGTH: 24
<212> TYPE: DNA
<213> ORGANISM: Artificial
<220> FEATURE:
<223> OTHER INFORMATION: primer

<400> SEQUENCE: 88
gatcaatgaa ttcgcggccg ctca                                     24

<210> SEQ ID NO 89
<211> LENGTH: 47
<212> TYPE: DNA
<213> ORGANISM: Artificial
<220> FEATURE:
<223> OTHER INFORMATION: primer

<400> SEQUENCE: 89
gttcaggtgc tgggcacggt ggcggggtg ggcatgtgtg agttttg              47

<210> SEQ ID NO 90
<211> LENGTH: 28
<212> TYPE: DNA
<213> ORGANISM: Artificial
<220> FEATURE:
<223> OTHER INFORMATION: primer

<400> SEQUENCE: 90
gcctccacca agggcccatc ggtcttcc                                 28

<210> SEQ ID NO 91
<211> LENGTH: 24
<212> TYPE: DNA
<213> ORGANISM: Artificial
<220> FEATURE:
<223> OTHER INFORMATION: primer

<400> SEQUENCE: 91
gatcaatgaa ttcgcggccg ctca                                     24

<210> SEQ ID NO 92
<211> LENGTH: 28
<212> TYPE: DNA
<213> ORGANISM: Artificial
<220> FEATURE:
<223> OTHER INFORMATION: primer

<400> SEQUENCE: 92
gcctccacca agggcccatc ggtcttcc                                 28

<210> SEQ ID NO 93
<211> LENGTH: 48
<212> TYPE: DNA
<213> ORGANISM: Artificial
<220> FEATURE:
<223> OTHER INFORMATION: primer

<400> SEQUENCE: 93
gagcccaaat cttgtgaccc cccgccaaaa actcacacat gcccaccg            48
```

```
<210> SEQ ID NO 94
<211> LENGTH: 24
<212> TYPE: DNA
<213> ORGANISM: Artificial
<220> FEATURE:
<223> OTHER INFORMATION: primer

<400> SEQUENCE: 94
gatcaatgaa ttcgcggccg ctca                                          24

<210> SEQ ID NO 95
<211> LENGTH: 48
<212> TYPE: DNA
<213> ORGANISM: Artificial
<220> FEATURE:
<223> OTHER INFORMATION: primer

<400> SEQUENCE: 95
cggtgggcat gtgtgagttt ttggcggggg gtcacaagat ttgggctc                48

<210> SEQ ID NO 96
<211> LENGTH: 28
<212> TYPE: DNA
<213> ORGANISM: Artificial
<220> FEATURE:
<223> OTHER INFORMATION: primer

<400> SEQUENCE: 96
gcctccacca agggcccatc ggtcttcc                                      28

<210> SEQ ID NO 97
<211> LENGTH: 24
<212> TYPE: DNA
<213> ORGANISM: Artificial
<220> FEATURE:
<223> OTHER INFORMATION: primer

<400> SEQUENCE: 97
gatcaatgaa ttcgcggccg ctca                                          24

<210> SEQ ID NO 98
<211> LENGTH: 28
<212> TYPE: DNA
<213> ORGANISM: Artificial
<220> FEATURE:
<223> OTHER INFORMATION: primer

<400> SEQUENCE: 98
gcctccacca agggcccatc ggtcttcc                                      28

<210> SEQ ID NO 99
<211> LENGTH: 59
<212> TYPE: DNA
<213> ORGANISM: Artificial
<220> FEATURE:
<223> OTHER INFORMATION: primer

<400> SEQUENCE: 99
gagagttgag cccaaatctt gtcccccgcc acctccctgc ccaccgtgcc cagcacctg    59

<210> SEQ ID NO 100
<211> LENGTH: 24
<212> TYPE: DNA
<213> ORGANISM: Artificial
<220> FEATURE:
<223> OTHER INFORMATION: primer
```

```
<400> SEQUENCE: 100
gatcaatgaa ttcgcggccg ctca                                          24

<210> SEQ ID NO 101
<211> LENGTH: 59
<212> TYPE: DNA
<213> ORGANISM: Artificial
<220> FEATURE:
<223> OTHER INFORMATION: primer

<400> SEQUENCE: 101
caggtgctgg gcacggtggg cagggaggtg gcgggggaca agatttgggc tcaactctc    59

<210> SEQ ID NO 102
<211> LENGTH: 28
<212> TYPE: DNA
<213> ORGANISM: Artificial
<220> FEATURE:
<223> OTHER INFORMATION: primer

<400> SEQUENCE: 102
gcctccacca agggcccatc ggtcttcc                                      28

<210> SEQ ID NO 103
<211> LENGTH: 24
<212> TYPE: DNA
<213> ORGANISM: Artificial
<220> FEATURE:
<223> OTHER INFORMATION: primer

<400> SEQUENCE: 103
gatcaatgaa ttcgcggccg ctca                                          24

<210> SEQ ID NO 104
<211> LENGTH: 28
<212> TYPE: DNA
<213> ORGANISM: Artificial
<220> FEATURE:
<223> OTHER INFORMATION: primer

<400> SEQUENCE: 104
gcctccacca agggcccatc ggtcttcc                                      28

<210> SEQ ID NO 105
<211> LENGTH: 51
<212> TYPE: DNA
<213> ORGANISM: Artificial
<220> FEATURE:
<223> OTHER INFORMATION: primer

<400> SEQUENCE: 105
aaggtggaca agagagttcc gcccctcca tgtgacaaaa ctcacacatg c              51

<210> SEQ ID NO 106
<211> LENGTH: 24
<212> TYPE: DNA
<213> ORGANISM: Artificial
<220> FEATURE:
<223> OTHER INFORMATION: primer

<400> SEQUENCE: 106
gatcaatgaa ttcgcggccg ctca                                          24
```

```
<210> SEQ ID NO 107
<211> LENGTH: 51
<212> TYPE: DNA
<213> ORGANISM: Artificial
<220> FEATURE:
<223> OTHER INFORMATION: primer

<400> SEQUENCE: 107
gcatgtgtga gttttgtcac atggaggggg cggaactctc ttgtccacct t            51

<210> SEQ ID NO 108
<211> LENGTH: 28
<212> TYPE: DNA
<213> ORGANISM: Artificial
<220> FEATURE:
<223> OTHER INFORMATION: primer

<400> SEQUENCE: 108
gcctccacca agggcccatc ggtcttcc                                      28

<210> SEQ ID NO 109
<211> LENGTH: 24
<212> TYPE: DNA
<213> ORGANISM: Artificial
<220> FEATURE:
<223> OTHER INFORMATION: primer

<400> SEQUENCE: 109
gatcaatgaa ttcgcggccg ctca                                          24

<210> SEQ ID NO 110
<211> LENGTH: 28
<212> TYPE: DNA
<213> ORGANISM: Artificial
<220> FEATURE:
<223> OTHER INFORMATION: primer

<400> SEQUENCE: 110
gcctccacca agggcccatc ggtcttcc                                      28

<210> SEQ ID NO 111
<211> LENGTH: 42
<212> TYPE: DNA
<213> ORGANISM: Artificial
<220> FEATURE:
<223> OTHER INFORMATION: primer

<400> SEQUENCE: 111
gacaaaactc acacatgctg gtggtgccca gcacctgaac tc                      42

<210> SEQ ID NO 112
<211> LENGTH: 24
<212> TYPE: DNA
<213> ORGANISM: Artificial
<220> FEATURE:
<223> OTHER INFORMATION: primer

<400> SEQUENCE: 112
gatcaatgaa ttcgcggccg ctca                                          24

<210> SEQ ID NO 113
<211> LENGTH: 42
<212> TYPE: DNA
<213> ORGANISM: Artificial
<220> FEATURE:
<223> OTHER INFORMATION: primer
```

```
<400> SEQUENCE: 113
gagttcaggt gctgggcacc accagcatgt gtgagttttg tc                              42

<210> SEQ ID NO 114
<211> LENGTH: 28
<212> TYPE: DNA
<213> ORGANISM: Artificial
<220> FEATURE:
<223> OTHER INFORMATION: primer

<400> SEQUENCE: 114
gcctccacca agggcccatc ggtcttcc                                              28

<210> SEQ ID NO 115
<211> LENGTH: 24
<212> TYPE: DNA
<213> ORGANISM: Artificial
<220> FEATURE:
<223> OTHER INFORMATION: primer

<400> SEQUENCE: 115
gatcaatgaa ttcgcggccg ctca                                                  24

<210> SEQ ID NO 116
<211> LENGTH: 28
<212> TYPE: DNA
<213> ORGANISM: Artificial
<220> FEATURE:
<223> OTHER INFORMATION: primer

<400> SEQUENCE: 116
gcctccacca agggcccatc ggtcttcc                                              28

<210> SEQ ID NO 117
<211> LENGTH: 42
<212> TYPE: DNA
<213> ORGANISM: Artificial
<220> FEATURE:
<223> OTHER INFORMATION: primer

<400> SEQUENCE: 117
gagcccaaat cttgtgactg gtggcacaca tgcccaccgt gc                              42

<210> SEQ ID NO 118
<211> LENGTH: 24
<212> TYPE: DNA
<213> ORGANISM: Artificial
<220> FEATURE:
<223> OTHER INFORMATION: primer

<400> SEQUENCE: 118
gatcaatgaa ttcgcggccg ctca                                                  24

<210> SEQ ID NO 119
<211> LENGTH: 42
<212> TYPE: DNA
<213> ORGANISM: Artificial
<220> FEATURE:
<223> OTHER INFORMATION: primer

<400> SEQUENCE: 119
gcacggtggg catgtgtgcc accagtcaca agatttgggc tc                              42
```

```
<210> SEQ ID NO 120
<211> LENGTH: 28
<212> TYPE: DNA
<213> ORGANISM: Artificial
<220> FEATURE:
<223> OTHER INFORMATION: primer

<400> SEQUENCE: 120
gcctccacca agggcccatc ggtcttcc                                        28

<210> SEQ ID NO 121
<211> LENGTH: 24
<212> TYPE: DNA
<213> ORGANISM: Artificial
<220> FEATURE:
<223> OTHER INFORMATION: primer

<400> SEQUENCE: 121
gatcaatgaa ttcgcggccg ctca                                            24

<210> SEQ ID NO 122
<211> LENGTH: 28
<212> TYPE: DNA
<213> ORGANISM: Artificial
<220> FEATURE:
<223> OTHER INFORMATION: primer

<400> SEQUENCE: 122
gcctccacca agggcccatc ggtcttcc                                        28

<210> SEQ ID NO 123
<211> LENGTH: 44
<212> TYPE: DNA
<213> ORGANISM: Artificial
<220> FEATURE:
<223> OTHER INFORMATION: primer

<400> SEQUENCE: 123
caaatcttgt gacaaaactt gttgctgccc accgtgccca gcac                      44

<210> SEQ ID NO 124
<211> LENGTH: 24
<212> TYPE: DNA
<213> ORGANISM: Artificial
<220> FEATURE:
<223> OTHER INFORMATION: primer

<400> SEQUENCE: 124
gatcaatgaa ttcgcggccg ctca                                            24

<210> SEQ ID NO 125
<211> LENGTH: 44
<212> TYPE: DNA
<213> ORGANISM: Artificial
<220> FEATURE:
<223> OTHER INFORMATION: primer

<400> SEQUENCE: 125
gtgctgggca cggtgggcag caacaagttt tgtcacaaga tttg                      44

<210> SEQ ID NO 126
<211> LENGTH: 28
<212> TYPE: DNA
<213> ORGANISM: Artificial
<220> FEATURE:
<223> OTHER INFORMATION: primer
```

```
<400> SEQUENCE: 126
gcctccacca agggcccatc ggtcttcc                                         28

<210> SEQ ID NO 127
<211> LENGTH: 24
<212> TYPE: DNA
<213> ORGANISM: Artificial
<220> FEATURE:
<223> OTHER INFORMATION: primer

<400> SEQUENCE: 127
gatcaatgaa ttcgcggccg ctca                                             24

<210> SEQ ID NO 128
<211> LENGTH: 28
<212> TYPE: DNA
<213> ORGANISM: Artificial
<220> FEATURE:
<223> OTHER INFORMATION: primer

<400> SEQUENCE: 128
gcctccacca agggcccatc ggtcttcc                                         28

<210> SEQ ID NO 129
<211> LENGTH: 39
<212> TYPE: DNA
<213> ORGANISM: Artificial
<220> FEATURE:
<223> OTHER INFORMATION: primer

<400> SEQUENCE: 129
tccacaggtg tccactcccg gactgaagat ctcccaaag                             39

<210> SEQ ID NO 130
<211> LENGTH: 91
<212> TYPE: DNA
<213> ORGANISM: Artificial
<220> FEATURE:
<223> OTHER INFORMATION: primer

<400> SEQUENCE: 130
gggagaattc cgcggccgct tatttgtcat cgtcatcttt gtagtcatgg tgatggtgat      60
ggtgtgcgcc tgccaaacct tgagtgatgg t                                     91

<210> SEQ ID NO 131
<211> LENGTH: 42
<212> TYPE: DNA
<213> ORGANISM: Artificial
<220> FEATURE:
<223> OTHER INFORMATION: primer

<400> SEQUENCE: 131
aagcttcggt ccgccaccat ggcaactgaa gatctcccaa ag                         42

<210> SEQ ID NO 132
<211> LENGTH: 39
<212> TYPE: DNA
<213> ORGANISM: Artificial
<220> FEATURE:
<223> OTHER INFORMATION: primer

<400> SEQUENCE: 132
gtctgccgaa ccgctgcctg ccaaaccttg agtgatggt                             39
```

```
<210> SEQ ID NO 133
<211> LENGTH: 30
<212> TYPE: DNA
<213> ORGANISM: Artificial
<220> FEATURE:
<223> OTHER INFORMATION: primer

<400> SEQUENCE: 133
ggcagcggtt cggcagaccc ctccaaggac                                      30

<210> SEQ ID NO 134
<211> LENGTH: 35
<212> TYPE: DNA
<213> ORGANISM: Artificial
<220> FEATURE:
<223> OTHER INFORMATION: primer

<400> SEQUENCE: 134
caggggctag cttactgctg aacggcgtcg agcgg                                35

<210> SEQ ID NO 135
<211> LENGTH: 48
<212> TYPE: DNA
<213> ORGANISM: Artificial
<220> FEATURE:
<223> OTHER INFORMATION: primer

<400> SEQUENCE: 135
agagttgagc ccaaatctga ctgttggtgg cacacatgcc caccgtgc                  48

<210> SEQ ID NO 136
<211> LENGTH: 24
<212> TYPE: DNA
<213> ORGANISM: Artificial
<220> FEATURE:
<223> OTHER INFORMATION: primer

<400> SEQUENCE: 136
gatcaatgaa ttcgcggccg ctca                                            24

<210> SEQ ID NO 137
<211> LENGTH: 48
<212> TYPE: DNA
<213> ORGANISM: Artificial
<220> FEATURE:
<223> OTHER INFORMATION: primer

<400> SEQUENCE: 137
gcacggtggg catgtgtgcc accaacagtc agatttgggc tcaactct                  48

<210> SEQ ID NO 138
<211> LENGTH: 76
<212> TYPE: DNA
<213> ORGANISM: Artificial
<220> FEATURE:
<223> OTHER INFORMATION: primer

<400> SEQUENCE: 138
gcctccacca agggcccatc ggtcttccgc acggtgggca tgtgtgccac caacagtcag     60
atttgggctc aactct                                                     76

<210> SEQ ID NO 139
<211> LENGTH: 24
<212> TYPE: DNA
<213> ORGANISM: Artificial
<220> FEATURE:
<223> OTHER INFORMATION: primer
```

```
<400> SEQUENCE: 139
gatcaatgaa ttcgcggccg ctca                                              24

<210> SEQ ID NO 140
<211> LENGTH: 28
<212> TYPE: DNA
<213> ORGANISM: Artificial
<220> FEATURE:
<223> OTHER INFORMATION: primer

<400> SEQUENCE: 140
gcctccacca agggcccatc ggtcttcc                                          28

<210> SEQ ID NO 141
<211> LENGTH: 39
<212> TYPE: DNA
<213> ORGANISM: Artificial
<220> FEATURE:
<223> OTHER INFORMATION: primer

<400> SEQUENCE: 141
gagcccaaat cttgtgactg gactcacaca tgcccaccg                              39

<210> SEQ ID NO 142
<211> LENGTH: 24
<212> TYPE: DNA
<213> ORGANISM: Artificial
<220> FEATURE:
<223> OTHER INFORMATION: primer

<400> SEQUENCE: 142
gatcaatgaa ttcgcggccg ctca                                              24

<210> SEQ ID NO 143
<211> LENGTH: 39
<212> TYPE: DNA
<213> ORGANISM: Artificial
<220> FEATURE:
<223> OTHER INFORMATION: primer

<400> SEQUENCE: 143
cggtgggcat gtgtgagtcc agtcacaaga tttgggctc                              39

<210> SEQ ID NO 144
<211> LENGTH: 28
<212> TYPE: DNA
<213> ORGANISM: Artificial
<220> FEATURE:
<223> OTHER INFORMATION: primer

<400> SEQUENCE: 144
gcctccacca agggcccatc ggtcttcc                                          28

<210> SEQ ID NO 145
<211> LENGTH: 24
<212> TYPE: DNA
<213> ORGANISM: Artificial
<220> FEATURE:
<223> OTHER INFORMATION: primer

<400> SEQUENCE: 145
gatcaatgaa ttcgcggccg ctca                                              24
```

```
<210> SEQ ID NO 146
<211> LENGTH: 28
<212> TYPE: DNA
<213> ORGANISM: Artificial
<220> FEATURE:
<223> OTHER INFORMATION: primer

<400> SEQUENCE: 146
gcctccacca agggcccatc ggtcttcc                                      28

<210> SEQ ID NO 147
<211> LENGTH: 39
<212> TYPE: DNA
<213> ORGANISM: Artificial
<220> FEATURE:
<223> OTHER INFORMATION: primer

<400> SEQUENCE: 147
cccaaatctt gtgacaaatg gcacacatgc ccaccgtgc                          39

<210> SEQ ID NO 148
<211> LENGTH: 24
<212> TYPE: DNA
<213> ORGANISM: Artificial
<220> FEATURE:
<223> OTHER INFORMATION: primer

<400> SEQUENCE: 148
gatcaatgaa ttcgcggccg ctca                                          24

<210> SEQ ID NO 149
<211> LENGTH: 39
<212> TYPE: DNA
<213> ORGANISM: Artificial
<220> FEATURE:
<223> OTHER INFORMATION: primer

<400> SEQUENCE: 149
gcacggtggg catgtgtgcc atttgtcaca agatttggg                          39

<210> SEQ ID NO 150
<211> LENGTH: 28
<212> TYPE: DNA
<213> ORGANISM: Artificial
<220> FEATURE:
<223> OTHER INFORMATION: primer

<400> SEQUENCE: 150
gcctccacca agggcccatc ggtcttcc                                      28

<210> SEQ ID NO 151
<211> LENGTH: 24
<212> TYPE: DNA
<213> ORGANISM: Artificial
<220> FEATURE:
<223> OTHER INFORMATION: primer

<400> SEQUENCE: 151
gatcaatgaa ttcgcggccg ctca                                          24

<210> SEQ ID NO 152
<211> LENGTH: 28
<212> TYPE: DNA
<213> ORGANISM: Artificial
<220> FEATURE:
<223> OTHER INFORMATION: primer
```

```
<400> SEQUENCE: 152
gcctccacca agggcccatc ggtcttcc                                              28

<210> SEQ ID NO 153
<211> LENGTH: 42
<212> TYPE: DNA
<213> ORGANISM: Artificial
<220> FEATURE:
<223> OTHER INFORMATION: primer

<400> SEQUENCE: 153
gagcccaaat cttgtgactt ttttcacaca tgcccaccgt gc                              42

<210> SEQ ID NO 154
<211> LENGTH: 24
<212> TYPE: DNA
<213> ORGANISM: Artificial
<220> FEATURE:
<223> OTHER INFORMATION: primer

<400> SEQUENCE: 154
gatcaatgaa ttcgcggccg ctca                                                  24

<210> SEQ ID NO 155
<211> LENGTH: 42
<212> TYPE: DNA
<213> ORGANISM: Artificial
<220> FEATURE:
<223> OTHER INFORMATION: primer

<400> SEQUENCE: 155
gcacggtggg catgtgtgaa aaagtcaca agatttgggc tc                               42

<210> SEQ ID NO 156
<211> LENGTH: 28
<212> TYPE: DNA
<213> ORGANISM: Artificial
<220> FEATURE:
<223> OTHER INFORMATION: primer

<400> SEQUENCE: 156
gcctccacca agggcccatc ggtcttcc                                              28

<210> SEQ ID NO 157
<211> LENGTH: 24
<212> TYPE: DNA
<213> ORGANISM: Artificial
<220> FEATURE:
<223> OTHER INFORMATION: primer

<400> SEQUENCE: 157
gatcaatgaa ttcgcggccg ctca                                                  24

<210> SEQ ID NO 158
<211> LENGTH: 28
<212> TYPE: DNA
<213> ORGANISM: Artificial
<220> FEATURE:
<223> OTHER INFORMATION: primer

<400> SEQUENCE: 158
gcctccacca agggcccatc ggtcttcc                                              28
```

```
<210> SEQ ID NO 159
<211> LENGTH: 46
<212> TYPE: DNA
<213> ORGANISM: Artificial
<220> FEATURE:
<223> OTHER INFORMATION: primer

<400> SEQUENCE: 159
gagcccaaat cttgtgactg gtggtggaca tgcccaccgt gcccag            46

<210> SEQ ID NO 160
<211> LENGTH: 24
<212> TYPE: DNA
<213> ORGANISM: Artificial
<220> FEATURE:
<223> OTHER INFORMATION: primer

<400> SEQUENCE: 160
gatcaatgaa ttcgcggccg ctca                                    24

<210> SEQ ID NO 161
<211> LENGTH: 46
<212> TYPE: DNA
<213> ORGANISM: Artificial
<220> FEATURE:
<223> OTHER INFORMATION: primer

<400> SEQUENCE: 161
ctgggcacgg tgggcatgtc caccaccagt cacaagattt gggctc            46

<210> SEQ ID NO 162
<211> LENGTH: 28
<212> TYPE: DNA
<213> ORGANISM: Artificial
<220> FEATURE:
<223> OTHER INFORMATION: primer

<400> SEQUENCE: 162
gcctccacca agggcccatc ggtcttcc                                28

<210> SEQ ID NO 163
<211> LENGTH: 24
<212> TYPE: DNA
<213> ORGANISM: Artificial
<220> FEATURE:
<223> OTHER INFORMATION: primer

<400> SEQUENCE: 163
gatcaatgaa ttcgcggccg ctca                                    24

<210> SEQ ID NO 164
<211> LENGTH: 28
<212> TYPE: DNA
<213> ORGANISM: Artificial
<220> FEATURE:
<223> OTHER INFORMATION: primer

<400> SEQUENCE: 164
gcctccacca agggcccatc ggtcttcc                                28

<210> SEQ ID NO 165
<211> LENGTH: 42
<212> TYPE: DNA
<213> ORGANISM: Artificial
<220> FEATURE:
<223> OTHER INFORMATION: primer
```

<400> SEQUENCE: 165
gttgagccca aatcttgttg gtggactcac acatgcccac cg                              42

<210> SEQ ID NO 166
<211> LENGTH: 24
<212> TYPE: DNA
<213> ORGANISM: Artificial
<220> FEATURE:
<223> OTHER INFORMATION: primer

<400> SEQUENCE: 166
gatcaatgaa ttcgcggccg ctca                                                  24

<210> SEQ ID NO 167
<211> LENGTH: 42
<212> TYPE: DNA
<213> ORGANISM: Artificial
<220> FEATURE:
<223> OTHER INFORMATION: primer

<400> SEQUENCE: 167
cggtgggcat gtgtgagtcc accaacaaga tttgggctca ac                              42

<210> SEQ ID NO 168
<211> LENGTH: 28
<212> TYPE: DNA
<213> ORGANISM: Artificial
<220> FEATURE:
<223> OTHER INFORMATION: primer

<400> SEQUENCE: 168
gcctccacca agggcccatc ggtcttcc                                              28

<210> SEQ ID NO 169
<211> LENGTH: 24
<212> TYPE: DNA
<213> ORGANISM: Artificial
<220> FEATURE:
<223> OTHER INFORMATION: primer

<400> SEQUENCE: 169
gatcaatgaa ttcgcggccg ctca                                                  24

<210> SEQ ID NO 170
<211> LENGTH: 28
<212> TYPE: DNA
<213> ORGANISM: Artificial
<220> FEATURE:
<223> OTHER INFORMATION: primer

<400> SEQUENCE: 170
gcctccacca agggcccatc ggtcttcc                                              28

<210> SEQ ID NO 171
<211> LENGTH: 44
<212> TYPE: DNA
<213> ORGANISM: Artificial
<220> FEATURE:
<223> OTHER INFORMATION: primer

<400> SEQUENCE: 171
gacaagagag ttgagccctg gtggtgtgac aaaaactcaca catg                           44

```
<210> SEQ ID NO 172
<211> LENGTH: 24
<212> TYPE: DNA
<213> ORGANISM: Artificial
<220> FEATURE:
<223> OTHER INFORMATION: primer

<400> SEQUENCE: 172
gatcaatgaa ttcgcggccg ctca                                          24

<210> SEQ ID NO 173
<211> LENGTH: 44
<212> TYPE: DNA
<213> ORGANISM: Artificial
<220> FEATURE:
<223> OTHER INFORMATION: primer

<400> SEQUENCE: 173
catgtgtgag ttttgtcaca ccaccagggc tcaactctct tgtc                    44

<210> SEQ ID NO 174
<211> LENGTH: 28
<212> TYPE: DNA
<213> ORGANISM: Artificial
<220> FEATURE:
<223> OTHER INFORMATION: primer

<400> SEQUENCE: 174
gcctccacca agggcccatc ggtcttcc                                      28

<210> SEQ ID NO 175
<211> LENGTH: 24
<212> TYPE: DNA
<213> ORGANISM: Artificial
<220> FEATURE:
<223> OTHER INFORMATION: primer

<400> SEQUENCE: 175
gatcaatgaa ttcgcggccg ctca                                          24

<210> SEQ ID NO 176
<211> LENGTH: 28
<212> TYPE: DNA
<213> ORGANISM: Artificial
<220> FEATURE:
<223> OTHER INFORMATION: primer

<400> SEQUENCE: 176
gcctccacca agggcccatc ggtcttcc                                      28
```